(12) United States Patent
Haynes et al.

(10) Patent No.: US 11,161,895 B2
(45) Date of Patent: Nov. 2, 2021

(54) METHODS TO IDENTIFY IMMUNOGENS BY TARGETING IMPROBABLE MUTATIONS

(71) Applicant: Duke University, Durham, NC (US)

(72) Inventors: Barton F. Haynes, Durham, NC (US); Kevin J. Wiehe, Durham, NC (US); Mattia Bonsignori, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 16/337,264

(22) PCT Filed: Oct. 3, 2017

(86) PCT No.: PCT/US2017/054956
§ 371 (c)(1),
(2) Date: Mar. 27, 2019

(87) PCT Pub. No.: WO2018/067580
PCT Pub. Date: Apr. 12, 2018

(65) Prior Publication Data
US 2020/0031908 A1    Jan. 30, 2020

Related U.S. Application Data

(63) Continuation-in-part of application No. PCT/US2017/020823, filed on Mar. 3, 2017.

(60) Provisional application No. 62/489,250, filed on Apr. 24, 2017, provisional application No. 62/476,985, filed on Mar. 27, 2017, provisional application No. 62/403,649, filed on Oct. 3, 2016, provisional application No. 62/403,635, filed on Oct. 3, 2016.

(51) Int. Cl.
| | |
|---|---|
| *C07K 16/10* | (2006.01) |
| *A61K 39/00* | (2006.01) |
| *A61K 39/12* | (2006.01) |
| *A61K 39/395* | (2006.01) |
| *C07K 16/00* | (2006.01) |
| *A61K 39/21* | (2006.01) |
| *C12N 7/00* | (2006.01) |
| *G01N 33/569* | (2006.01) |

(52) U.S. Cl.
CPC .......... *C07K 16/1063* (2013.01); *A61K 39/21* (2013.01); *C12N 7/00* (2013.01); *G01N 33/56983* (2013.01); *C07K 2317/55* (2013.01); *C07K 2317/56* (2013.01); *C07K 2317/92* (2013.01); *C12N 2740/16034* (2013.01)

(58) Field of Classification Search
CPC ............ C07K 2317/76; C07K 16/1063; C07K 2317/565; C07K 2317/21; C07K 2317/92
See application file for complete search history.

(56) References Cited

U.S. PATENT DOCUMENTS

| | | | |
|---|---|---|---|
| 5,792,459 A | 8/1998 | Haigwood | |
| 7,951,377 B2 | 5/2011 | Korber et al. | |
| 8,071,107 B2 | 12/2011 | Haynes et al. | |
| 9,872,900 B2 | 1/2018 | Ciaramella et al. | |
| 2003/0147888 A1 | 8/2003 | Haynes et al. | |
| 2006/0051373 A1 | 3/2006 | Olson et al. | |
| 2009/0286852 A1 | 11/2009 | Kariko et al. | |
| 2010/0015218 A1 | 1/2010 | Jadhav et al. | |
| 2010/0041875 A1 | 2/2010 | Dey et al. | |
| 2011/0076298 A1 | 3/2011 | Olson et al. | |
| 2011/0250220 A1 | 10/2011 | Dey et al. | |
| 2011/0262488 A1 | 10/2011 | Phogat et al. | |
| 2012/0052090 A1 | 3/2012 | Tamamura et al. | |
| 2013/0111615 A1 | 5/2013 | Kariko et al. | |
| 2013/0197068 A1 | 8/2013 | Kariko et al. | |
| 2013/0261172 A1 | 10/2013 | Kariko et al. | |
| 2014/0328862 A1* | 11/2014 | Scheid ................... A61P 31/12 424/160.1 |
| 2015/0038558 A1 | 2/2015 | Kariko et al. | |
| 2016/0032316 A1 | 2/2016 | Weissman et al. | |
| 2016/0271244 A1* | 9/2016 | Haynes ................... A61P 31/18 |
| 2017/0043037 A1 | 2/2017 | Kariko et al. | |
| 2017/0233441 A1 | 8/2017 | Kwong et al. | |
| 2017/0327842 A1 | 11/2017 | Weissman et al. | |
| 2017/0369532 A1 | 12/2017 | Carfi et al. | |
| 2018/0028645 A1 | 2/2018 | Ciaramella et al. | |
| 2018/0072777 A1 | 3/2018 | Rutten et al. | |

FOREIGN PATENT DOCUMENTS

| | | |
|---|---|---|
| CA | 2944068 A1 | 10/2015 |
| EP | 0272858 A2 | 6/1988 |
| EP | 1466924 A1 | 10/2004 |
| EP | 1738764 A1 | 1/2007 |
| WO | WO-07/149491 A2 | 12/2007 |

(Continued)

OTHER PUBLICATIONS

"FASTX-Toolkit", downloaded from http://hannonlab.cshl.edu/fastx_toolkit, last retrieved Nov. 4, 2020 (2 total pages).
"Models of SHM Targeting and Substitution—SF5 Mutability Model dataset" last downloaded Feb. 2, 2021 from; http://clip.med.yale.edu/shm/download.php (2 total pages).
Alam, S. M., et al., "Antigenicity and Immunogenicity of RV144 Vaccine AIDSVAX Clade E Envelope Immunogen Is Enhanced by a gp120 N-Terminal Deletion," Journal of Virology, vol. 87, No. 3, pp. 1554-1568 (Feb. 2013).
Alam, S.M., et al., "Human Immunodeficiency Virus Type 1 gp41 Antibodies That Mask Membrane Proximal Region Epitopes: Antibody Binding Kinetics, Induction, and Potential for Regulation in Acute Infection," J. Virol., vol. 82, No. 1, pp. 115-125 (Jan. 2008).

(Continued)

*Primary Examiner* — Barry A Chestnut
(74) *Attorney, Agent, or Firm* — Wilmer Cutler Pickering Hale and Dorr LLP

(57) ABSTRACT

The invention is directed to methods to identify improbable mutations in the heavy or light chain variable domain of an antibody, methods to identify antigens which bind to antibodies comprising such improbable mutations, and methods of using such antigens to induce immune responses.

26 Claims, 113 Drawing Sheets

Specification includes a Sequence Listing.

(56) References Cited

FOREIGN PATENT DOCUMENTS

| WO | WO-10/031113 A1 | 3/2010 |
|---|---|---|
| WO | WO-2013/006688 A2 | 1/2013 |
| WO | WO-14/42669 A1 | 3/2014 |
| WO | WO-14/043386 A1 | 3/2014 |
| WO | WO-2014/172366 A1 | 10/2014 |
| WO | WO-2015/127108 A1 | 8/2015 |
| WO | WO-2015/153638 A1 | 10/2015 |
| WO | WO-16/037154 A1 | 3/2016 |
| WO | WO-2016/149695 A1 | 9/2016 |
| WO | WO-17/151801 A1 | 9/2017 |
| WO | WO-17/0152146 A2 | 9/2017 |
| WO | WO-18/067580 A1 | 4/2018 |
| WO | WO-18/161049 A1 | 9/2018 |
| WO | WO-19/169356 A1 | 9/2019 |
| WO | WO-20/72162 A1 | 4/2020 |
| WO | WO-20/72169 A1 | 4/2020 |

OTHER PUBLICATIONS

Alam, S.M., et al., "Mimicry of an Hiv broadly neutralizing antibody epitope with a synthetic glycopeptide," Sci. Transl. Med., vol. 9, No. 381, eaai7521 (Author Manucript—20 total pages—available in PMC Aug. 18, 2017).

Alam, S.M., et al., "Recognition of synthetic glycopeptides by HIV-1 broadly neutralizing antibodies and their unmutated ancestors," PNAS, vol. 110, No. 45, pp. 18214-18219 (Nov. 5, 2013)—last downloaded Oct. 6, 2020 from https://www.pnas.org/content/110/45/18214 (24 total pages).

Alam, S.M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," J. Immunol., vol. 178, pp. 4424-4435 (accepted for publication Jan. 12, 2007).

Alam, S. M., et al, "Role of HIV membrane in neutralization by two broadly neutralizing antibodies", PNAS, vol. 106, No. 48, pp. 20234-20239 (Dec. 1, 2009).

Alving, C.R., et al, "Adjuvants for human vaccines," Current Opinion in Immunology, vol. 24, No. 3, pp. 310-315, Author Manuscript—12 total pages, (Jun. 2012).

Andrabi, R., et al., "Identification of Common Features in Prototype Broadly Neutralizing Antibodies to HIV Envelope V2 Apex to Facilitate Vaccine Design," Immunity, vol. 43, No. 5, pp. 959-973 (Nov. 2015)—Author Manuscript (25 total pages).

Arnaoty, A., et al., "Novel Approach for the Development of New Antibodies Directed Against Transposase-Derived Proteins Encoded by Human Neogenes," Yves Bigot (ed.), Mobile Genetic Elements: Protocols and Genomic Applications, Methods in Molecular Biology, vol. 859, Chapter 17, pp. 293-305 (2012).

Arnaoty, Ahmed, et al., "Reliability of the nanopheres-DNA immunization technology to produce polyclonal antibodies directed against human neogenic proteins," Mol. Genet. Genomics, vol. 288, pp. 347-363 (2013).

Aussedat, B., et al., "Chemical synthesis of highly congested gp120 V1V2 N-glycopeptide antigens for potential HIV-1-directed vaccines," J. Am. Chem. Soc., vol. 135, No. 35, Sep. 2013 (Author Manuscript—16 total pages—available in PMC Sep. 4, 2014).

Bamrungsap, S. et al., "Nanotechnology in therapeutics: a focus on nanoparticles as a drug delivery system," Nanomedicine, vol. 7, No. 8, pp. 1253-1271 (2012).

Barouch, D. H., et al., "Mosaic HIV-1 Vaccines Expand the Breadth and Depth of Cellular Immune Responses in Rhesus Monkeys," Nature Medicine, vol. 16, No. 3, pp. 319-323, Mar. 2010 (Author Manuscript—15 total pages—available in PMC Sep. 1, 2010).

Batista, F.D., et al., "B cells extract and present immobilized antigen: implications for affinity discrimination," The EMBO Journal, vol. 19, No. 4, pp. 513-520 (2000).

Behrens, A.J., et al. "Composition and Antigenic Effects of Individual Glycan Sites of a Trimeric HIV-1 Envelope Glycoprotein," Cell Rep. vol. 14, pp. 2695-2706 (2016).

Betz, A G., "Passenger transgenes reveal intrinsic specificity of the antibody hypermutation mechanism: Clustering, polarity, and specific hot spots," Proceedings of the National Academy of Sciences of the United States of America, vol. 90, pp. 2385-2388 (Mar. 1993).

Bhattacharya, T., et al., "Founder Effects in the Assessment of HIV Polymorphisms and HLA Allele Associations," Science, vol. 315, No. 5818, pp. 1583-1586, Apr. 2007 (last downloaded Oct. 6, 2020 from https://www.researchgate.net/publication/6442933_Founder_Effects_in_the_Assessment_of_HIV_Polymorphisms_and_HLA_Allele_Associations—10 total pages).

Binley, J.M., et al., "Enhancing the Proteolytic Maturation of Human Immunodeficiency Virus Type 1 Envelope Glycoproteins," Journal of Virology, vol. 76, No. 6, pp. 2606-2616 (Mar. 2002).

Bonsignori, M., et al. "Staged induction of HIV-1 glycan-dependent broadly neutralizing antibodies" Sci Transl Med., vol. 9, No. 381, pp. 1-26—Author Manuscript (Mar. 2017).

Bonsignori, M., et al., "Analysis of a Clonal Lineage of HIV-1 Envelope V2/V3 Conformational Epitope-Specific Broadly Neutralizing Antibodies and Their Inferred Unmutated Common Ancestors," Journal of Virology, vol. 85, No. 19, pp. 9998-10009 (Oct. 2011).

Bonsignori, M., et al., "Maturation Pathway from Germline to Broad HIV-1 Neutralizer of a CD4-Mimic Antibody," Cell, vol. 165, pp. 449-463 (Apr. 7, 2016).

Bonsignori, M., et al., "Two distinct broadly neutralizing antibody specificities of different clonal lineages in a single HIV-1-infected donor: implications for vaccine design," Journal of Virology, vol. 86, No. 8, pp. 4688-4692 (published online Feb. 1, 2012).

Bosch, V., et al., "Mutational Analysis of the Human Immunodeficiency Virus Type 1 env Gene Product Proteolytic Cleavage Site," Journal of Virology, vol. 64, No. 5, pp. 2337-2344 (May 1990).

Bransteitter, R., et al., "Biochemical analysis of Hypermutational Targeting by Wild Type and Mutant Activation-induced Cytidine Deaminase," The Journal of Biological Chemistry, vol. 279, No. 49, pp. 51612-51621 (Dec. 3, 2004).

Burton D. R. , "Antibody responses to envelope glycoproteins in HIV-1 infection," Nature immunology, vol. 16, No. 6, pp. 571-576, Jun. 2015 (Author Manuscript—17 total pages—available in PMC Apr. 18, 2016).

Burton, D.R., et al. "Broadly Neutralizing Antibodies to HIV and Their Role in Vaccine Design," Annu Rev Immunol, vol. 34, pp. 635-659, May 2016 (Author Manuscript—31 total pages—available in PMC Jul. 6,2018).

Cany, J., et al., "AFP-specific immunotherapy impairs growth of autochthonous hepatocellular carcinoma in mice," Journal of Hepatology, vol. 54, pp. 115-121 (2011).

Center, R.J., et al., "Oligomeric structure of the human immunodeficiency virus type 1 envelope protein on the virion surface," Journal of Virology, vol. 76, No. 15, pp. 7863-7867 (Aug. 2002).

Chakrabarti, B.K., et al., "Modifications of the Human Immunodeficiency Virus Envelope Glycoprotein Enhance Immunogenicity for Genetic Immunization," Journal of Virology, vol. 76, No. 11, pp. 5357-5368 (Jun. 2002).

Churchyard, G.J., et al, A Phase IIa Randomized Clinical Trial of a Multiclade HIV-1 DNA Prime Followed by a Multiclade rAd5 HIV-1 Vaccine Boost in Healthy Adults (HVTN204), PLoS One, vol. 6, No. 8, e21225, Aug. 2011 (last downloaded on Jan. 19, 2021 from https://journals.plos.org/plosone/article?id=10.1371/journal.pone.0021225—10 total pages).

Cloanalyst Software, Boston University—Microbiology, Laboratory of Computation Immunology, downloaded from http://www.bu.edu/computationalimmunology/research/software (3 total pages) last retrieved Oct. 5, 2020.

Cowell, L. G. and Kepler, T.B., "The nucleotide-replacement spectrum under somatic hypermutation exhibits microsequence dependence that is strand-symmetric and distinct from that under germline mutation," Journal of Immunology, vol. 164, pp. 1971-1976 2000.

De Taeye, S. W., et al., "Immunogenicity of stabilized HIV-1 envelope trimers with reduced exposure of non-neutralizing epitopes," Cell., vol. 163, No. 7, pp. 1702-1715, Dec. 2015 (Author Manuscript—25 total pages—available in PMC Jan. 29, 2016).

(56) References Cited

OTHER PUBLICATIONS

DeCamp, A., et al. "Global panel of HIV-1 Env reference strains for standardized assessments of vaccine-elicited neutralizing antibodies," J Virol, vol. 88, No. 5, pp. 2489-2507 (Mar. 2014).
Dennison, S.M., et al., "Induction of Antibodies in Rhesus Macaques That Recognize a Fusion-Intermediate Conformation of HIV-1 gp41," Public Library of Science One, vol. 6, No. 11, pp. e27824, pp. 1-14 (Nov. 2011).
Dennison, S.M., et al., "Nonneutralizing HIV-1 gp4 I envelope cluster II human monoclonal antibodies show polyreactivity for binding to phospholipids and protein autoantigens," J Virol, vol. 85, No. 3, pp. 1340-1347 (Feb. 2011).
Dennison, S.M., et al., "Stable Docking of Neutralizing Human Immunodeficiency Virus Type 1 gp41 Membrane-Proximal External Region Monoclonal Antibodies 2F5 and 4E10 Is Dependent on the Membrane Immersion Depth of Their Epitope Regions," Journal of Virology, vol. 83., No. 19, pp. 10211-10223 (Oct. 2009).
Di Noia, J.M., et al., "Molecular mechanisms of antibody somatic hypermutation," Annu Rev Biochem, vol. 76, pp. 1-22 including TOC—25 total pages (published online Feb. 28, 2007).
Doores, K. J., et al., "Two Classes of Broadly Neutralizing Antibodies within a Single Lineage Directed to the High-Mannose Patch of HIV Envelope," Journal of Virology, vol. 89, No. 2, pp. 1105-1118 (Jan. 2015) with Author Correction, Journal of Virology, vol. 89, No. 12, p. 6525.
Doria-Rose, N.A., et al., "Developmental pathway for potent V1V2-directed HIV-neutralizing antibodies," Nature, vol. 509, No. 7498, pp. 55-62 (published online Mar. 2014)—Author Manuscript—33 total pages (published online Apr. 2015).
Easterhoff, D., et al. "Boosting of HIV envelope CD4 binding site antibodies with long variable heavy third complementarity determining region in the randomized double blind RV305 HIV-1 vaccine trial," PLoS Pathogens, vol. 13, No. 2, e1006182, pp. 1-21 (Feb. 2017).
Eroshkin, A.M., et al., "bNAber: database of broadly neutralizing HIV antibodies," Nucleic Acids Res, vol. 42, pp. D1133-D1139 (published online Nov. 7, 2013).
Fera, D. and Harrison, S.C., "92BR SOSIP.664 trimer in complex with DH270.1 Fab," EM Data Bank Accession No. EMD-8507 downloaded from EMDataResource https://www.emdataresource.org/EMD-8507 (6 total pages) last retrieved Nov. 3, 2020.
Fera, D., "Affinity maturation in an HIV broadly neutralizing B-cell lineage through reorientation of variable domains," Proceedings of the National Academy of Sciences of the United States of America, vol. 111, No. 28, pp. 10275-10280 (Jul. 15, 2014).
Gao, F. et al., "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao, F., et al., "Cooperation of B Cell Lineages in Induction of HIV-1-Broadly Neutralizing Antibodies," Cell, vol. 158, pp. 481-491 (Jul. 31, 2014).
Garces, F., et al., "Affinity maturation of a potent family of HIV antibodies is primarily focused on accommodating or avoiding glycans," Immunity, vol. 43, No. 6, pp. 1053-1063, Dec. 2015 (Author Manuscript—22 total pages—available in PMC Dec. 15, 2016).
Garces, F., et al., "Structural evolution of glycan recognition by a family of potent HIV antibodies," Cell, vol. 159, No. 1, pp. 69-79, Sep. 2014 (Author Manuscript—23 total pages—available in PMC Sep. 25, 2015).
GenBank with accession Nos. KY347498 through KY347701 downloaded from https://www.ncbi.nlm.nih.gov/ last retrieved on Nov. 4, 2020 (22 total pages).
GenBank with accession Nos. KY354938 through KY354963 downloaded from https://www.ncbi.nlm.nih.gov/ last retrieved on Nov. 4, 2020 (3 total pages).
Georgiev, I.S., et al., "Antibodies VRC01 and 10E8 neutralize HIV-1 with high breadth and potency even with Ig-framework regions substantially reverted to germline," Journal of Immunology, vol. 192, pp. 1100-1106 (published online Jan. 2014).
Gnanakaran, S., et al., "Genetic Signatures in the Envelope Glycoproteins of HIV-1 that Associate with Broadly Neutralizing Antibodies," PLoS Computational Biology, vol. 6, No. 10, e1000955, 26 total pages (published Oct. 7, 2010).
Go, E.P., et al., "Comparative Analysis of the Glycosylation Profiles of Membrane-Anchored HIV-1 Envelope Glycoprotein Trimers and Soluble gp140," Journal of Virology, vol. 89, No. 16, pp. 8245-8257 (Aug. 2015).
Goo, L., et al., "Early development of broadly neutralizing antibodies in HIV-I-infected infants," Nature Medicine, vol. 20, No. 6, pp. 655-658, Author Manuscript—14 total pages (Jun. 2014).
Gorman, J., et al., "Structures of HIV-1 Env V1V2 with broadly neutralizing antibodies reveal commonalities that enable vaccine design," Nature Structural and Molecular Biology, vol. 23, No. 1, pp. 81-90 (Jan. 2016)—Author Manuscript (34 total pages)—available in PMC Jun. 21, 2016).
Graham, B.S., et al., "DNA Vaccine Delivered by a Needle-Free Injection Device Improves Potency of Priming for Antibody and CD8+ T-Cell Responses after rAd5 Boost in a Randomized Clinical Trial," Public Library of Science ONE, vol. 8, No. 4, e59340, pp. 1-11 (Apr. 2013).
Gray, E.S., et al. "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray, E. S., et al., "The Neutralization Breadth of HIV-1 Develops Incrementally over Four Years and Is Associated with CD4+ T Cell Decline and High Viral Load during Acute Infection," Journal of Virology, vol. 85, No. 10, pp. 4828-4840 (May 2011).
Guo, H.-G., et al., "Characterization of an HIV-1 Point Mutant Blocked in Envelope Glycoprotein Cleavage," Virology, vol. 174, pp. 217-224 (1990).
Guttman, M., et al., "Antibody potency relates to the ability to recognize the closed, pre-fusion form of HIV Env," Nature Communications, vol. 6, No. 6144, pp. 1-11 (Feb. 5, 2015).
Haynes, B. F., et al., "B-cell-lineage immunogen design in vaccine development with HIV-1 as a case study," Nat. Biotechnol., vol. 30, No. 5, pp. 423-433 (May 2012).
Haynes, B.F., et al., "Developing an HIV vaccine," Science, vol. 355, No. 6330, pp. 1129-1130, Author Manuscript—5 total pages (Mar. 2017).
He, L., et al., "Presenting native-like trimeric HIV-1 antigens with self-assembling nanoparticles," Nature Communications, vol. 7, No. 12041, pp. 1-15 (Jun. 28, 2016).
Hraber, P., et al., "Prevalence of broadly neutralizing antibody responses during chronic HIV-1 infection," AIDS, vol. 28, No. 2, pp. 163-169 (Jan. 2014), Author Manuscript—9 total pages (Jan. 2015).
Hraber, P., et al., "Longitudinal Antigenic Sequences and Sites from Intra-Host Evolution (LASSIE) Identifies Immune-Selected HIV Variants," Viruses, vol. 7, pp. 5443-5475 (Oct. 21, 2015).
Hwang, J.K., et al., "Sequence Intrinsic Somatic Mutation Mechanisms Contribute to Affinity Maturation of VRC01-class HIV-1 Broadly Neutralizing Antibodies," Proceedings of the National Academy of Sciences of the United States of America, vol. 114, No. 32, pp. 8614-8619 (Aug. 2017).
International Search Report and Written Opinion dated Aug. 23, 2017 by U.S. Patent and Trademark Office as International Searching Authority for International Patent Application No. PCT/US2017/020823 (15 total pages).
International Search Report and Written Opinion dated Feb. 1, 2018 by U.S. Patent and Trademark Office as International Searching Authority for International Patent Application No. PCT/US2017/054956 (14 total pages).
Jardine, J.G., et al., "Minimally Mutated HIV-1 Broadly Neutralizing Antibodies to Guide Reductionist Vaccine Design," PLOS Pathogens, vol. 12, No. 8, e1005815, 33 total pages (Aug. 2016).
Julien, J.-P., et al., "Broadly Neutralizing Antibody PGT121 Allosterically Modulates CD4 Binding via Recognition of the HIV-1 gp120

(56) References Cited

OTHER PUBLICATIONS

V3 Base and Multiple Surrounding Glycans," Public Library of Science Pathogens, vol. 9, No. 5: e1003342, pp. 1-15 (May 2013).

Keele, B. F., et al., "Identification and characterization of transmitted and early founder virus envelopes in primary HIV-1 infection," Proceedings of the National Academy of Sciences of the United States of America, vol. 105, No. 21, pp. 7552-7557 (May 27, 2008).

Kelsoe, G., et al., "Host controls of HIV broadly neutralizing antibody development," Immunology Review, vol. 275, No. 1, pp. 79-88 (Jan. 2017), Author Manuscript—19 total pages—available in PMC Jun. 21, 2017.

Kepler, T.B., "Reconstructing a B-cell clonal lineage. I. Statistical inference of unobserved ancestors," F1000 Research 2013, vol. 2, No. 103, 12 total pages (last updated Jan. 22, 2014).

Kepler, T.B., et al., "Immunoglobulin gene insertions and deletions in the affinity maturation of HIV-1 broadly reactive neutralizing antibodies," Cell Host & Microbe, vol. 16, pp. 304-313 (Sep. 2014).

Kepler, T.B., et al., "Reconstructing a B-Cell Clonal Lineage. II. Mutation, Selection, and Affinity Maturation," Frontiers in Immunology, vol. 5, Article 170, pp. 1-10 (Apr. 2014).

Kibler, K. V., et al., "Improved NYVAC-based vaccine vectors," Public Library of Science One, vol. 6, No. 11: e25674, pp. 1-13, (Nov. 9, 2011).

Kirchherr, J. L., et al., "High throughput functional analysis of HIV-1 env genes without cloning," Journal of Virological Methods, vol. 143, No. 1, pp. 104-111, Jul. 2007 (Author Manuscript—18 total p——available in PMC Jul. 1, 2008).

Klein, F., et al., "Somatic Mutations of the Immunoglobulin Framework Are Generally Required for Broad and Potent HIV-1 Neutralization", Cell, vol. 153, pp. 126-138 (Mar. 2013).

Kong, L., et al., "Complete epitopes for vaccine design derived from a crystal structure of the broadly neutralizing antibodies PGT128 and 8ANC195 in complex with an HIV-1 Env trimer," Acta Crystallographica, Section D, Biological Crystallography, vol. D71, pp. 2099-2108 (2015).

Kong, L., et al., "Supersite of immune vulnerability on the glycosylated face of HIV-1 envelope glycoprotein gp120," Nature Structural Molecular Biology, vol. 20, No. 7, pp. 796-803, Jul. 2013 (Author Manuscript—22 total pages—available in PMC Jan. 1, 2014).

Kwon, Y.-D., et al., "Crystal structure, conformational fixation, and entry-related interactions of mature ligand-free HIV-1 Env," Nature Structural Molecular Biology, vol. 22, No. 7, pp. 522-531, Jul. 2015 (Author Manuscript—30 total pages—available in PMC Jan. 8, 2016).

Lee J. H., et al., "Model Building and Refinement of a Natively Glycosylated HIV-1 Env Protein by High-Resolution Cryoelectron Microscopy", Structure, vol. 23, pp. 1943-1951 (Oct. 6, 2015).

Li, M., et al., "Human Immunodeficiency Virus Type 1 env Clones from Acute and Early Subtype B Infections for Standardized Assessments of Vaccine-Elicited Neutralizing Antibodies," J. Virol., vol. 79, No. 16, pp. 10108-10125 (Aug. 2005).

Li, Y. et al., "Control of expression, glycosylation, and secretion of HIV-1 gp120 by homologous and heterologous signal sequences," Virology, vol. 204, pp. 266-278 (accepted Jun. 23, 1994).

Li, Y., et al., "Effects of inefficient cleavage of the signal sequence of HIV-1 gp120 on its association with calnexin, folding, and intracellular transport," Proceedings of the National Academy of Sciences of the United States of America, vol. 93, pp. 9606-9611 (Sep. 1996).

Liao, H.-X., et al., "A group M consensus envelope glycoprotein induces antibodies that neutralize subsets of subtype B and C HIV-1 primary viruses," Virology, vol. 353, pp. 268-282 (available online Jul. 7, 2006).

Liao, H.X., et al., "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 with Supplementary Materials—34 total pages (Apr. 2013).

Liao, H.X., et al., "Co-evolution of a broadly neutralizing HIV-1 antibody and founder virus," Nature, vol. 496, No. 7446, pp. 469-476, Apr. 2013 (Author Manuscript—25 total pages available in PMC Oct. 25, 2013).

Liao, H.X., et al., "Vaccine induction of antibodies against a structurally heterogeneous site of immune pressure within HIV-1 envelope protein variable regions 1 and 2," Immunity, vol. 38, No. 1, pp. 176-186, Jan. 2013 (Author Manuscript—21 total pages—available in PMC Jan. 24, 2014).

Loughran, G., et al., "Evidence of efficient stop codon readthrough in four mammalian genes," Nucleic Acids Research, vol. 42, No. 14, pp. 8928-8938 (published online Jul. 10, 2014).

Mascola, J. R. and Haynes, B.F., "HIV-1 neutralizing antibodies: understanding nature's pathways," Immunological Reviews, vol. 254, No. 1, pp. 225-244 Jul. 2013 (Author Manuscript 29 pages—available in PMC Jul. 1, 2014).

McCune, J.M., et al., "Endoproteolytic Cleavage of gp160 is Required for the Activation of Human Immunodeficiency Virus," Cell, vol. 53, pp. 55-67 (Apr. 8, 1988).

McGuire, A.T., et al., "Engineering HIV envelope protein to activate germline B cell receptors of broadly neutralizing anti-CD4 binding site antibodies", The Journal of Experimental Medicine, vol. 210, No. 4, pp. 655-663 (Mar. 2013).

Moody, M.A., et al., "Toll-Like Receptor 7 /8 (TLR7/8) and TLR9 Agonists Cooperate to Enhance HIV-1 Envelope Antibody Responses in Rhesus Macaques," J. Virol., vol. 88, No. 6, pp. 3329-3339 (Mar. 2014).

Moore, P. L. et al, "Evolution of an HIV glycan-dependent broadly neutralizing antibody epitope through immune escape," Nat. Med. vol. 18, No. 11, pp. 1688-1692 (Author Manuscript—12 total pages—available in PMC Nov. 9, 2012).

Mouquet, H., et al., "Complex-type N-glycan recognition by potent broadly neutralizing HIV antibodies," Proceedings of the National Academy of Sciences of the United States of America, vol. 109, No. 47, pp. E3268-E3277 (published online Oct. 30, 2012).

Muenchhoff, M., et al., "Non-progressing HIV-infected children share fundamental immunological features of non-pathogenic SIV infection," Sci Transl Med, vol. 8, No. 358ra125 (published Sep. 2016), Author Manuscript—25 total pages (available Aug. 2018).

Munro, J.B., et al., "Conformational dynamics of single HIV-1 envelope trimers on the surface of native virions," Science, vol. 346, Issue 6210, pp. 759-763, Nov. 7, 2014, with Supplementary Materials, 28 pages (34 total pages).

Neuberger, M.S., et al., "Monitoring and interpreting the intrinsic features of somatic hypermutation," Immunol. Rev., vol. 162, pp. 107-116 (1998).

Nickle D. C., Heath L, "HIV-Specific Probabilistic Models of Protein Evolution," PloS One, Issue 6, e503, pp. 1-11 (Jun. 2007).

Pancera, M., et al. "Structure and immune recognition of trimeric prefusion HIV-1 Env", Nature, vol. 514, No. 7523, pp. 455-461, Oct. 2014 (Author Manuscript—43 total pages—available in PMC Apr. 23, 2015).

Pancera, M., et al., "N332-Directed Broadly Neutralizing Antibodies Use Diverse Modes of HIV-1 recognition: Inferences from Heavy-Light Chain Complementation of Function," PloS One, vol. 8, No. 2, e55701, 11 total pages (published Feb. 19, 2013).

Parren, P.W.H.I., et al., "Antibody Neutralization-Resistant Primary Isolates of Human Immunodeficiency Virus Type 1," Journal of Virology, vol. 72, No. 12, pp. 10270-10274 (Dec. 1998).

Pejchal, R., et al., "A potent and broad neutralizing antibody recognizes and penetrates the HIV glycan shield," Science, vol. 334, No. 6059, pp. 1097-1103, Oct. 2011 (Author Manuscript—13 total pages—available in PMC Nov. 25, 2012).

Perreau, M., et al., "DNA/NYVAC Vaccine Regimen Induces HIV-Specific CD4 and CD8 T-Cell Responses in Intestinal Mucosa," Journal of Virology, vol. 85, No. 19, pp. 9854-9862 (Oct. 2011).

Poignard, P., et al., "Heterogeneity of envelope molecules expressed on primary human immunodeficiency virus type 1 particles as probed by the binding of neutralizing and nonneutralizing antibodies.," Journal of Virology, vol. 77, No. 1, pp. 353-365 (Jan. 2003).

(56) References Cited

OTHER PUBLICATIONS

Proft, T., et al., "Sortase-mediated protein ligation: an emerging biotechnology tool for protein modification and immobilisation," Biotechnol. Lett., vol. 32, pp. 1-10 (published online Sep. 1, 2009).
Protein Data Bank (PDB) ID 4LST, downloaded from https://www.rcsb.org/structure/4LST, last retrieved Nov. 4, 2020 (7 total pages).
Protein Data Bank (PDB) ID 4QHL, downloaded from https://www.rcsb.org/structure/4QHL, last retrieved Nov. 4, 2020 (4 total pages).
Protein Data Bank Accession Code 5TPL, downloaded from https://www.rcsb.org/structure/5TPL, last retrieved Feb. 2, 2021 (4 total pages).
Protein Data Bank Accession Code 5TPP, downloaded from https://www.rcsb.org/structure/5TPP, last retrieved Feb. 2, 2021 (4 total pages).
Protein Data Bank Accession Code 5TQA, downloaded from https://www.rcsb.org/structure/5TQA, last retrieved Feb. 2, 2021 (4 total pages).
Protein Data Bank Accession Code 5TRP, downloaded from https://www.rcsb.org/structure/5TRP, last retrieved Feb. 2, 2021 (4 total pages).
Protein Data Bank Accession Code 5U0R, downloaded from https://www.rcsb.org/structure/5U0R, last retrieved Feb. 2, 2021 (4 total pages).
Protein Data Bank Accession Code 5U0U, downloaded from https://www.rcsb.org/structure/5U0U, last retrieved Feb. 2, 2021 (4 total pages).
Protein Data Bank Accession Code 5U15, downloaded from https://www.rcsb.org/structure/5U15, last retrieved Feb. 2, 2021 (4 total pages).
Rerks-Ngam, S., et al., "Vaccination with ALVAC and AIDSVAX to prevent HIV-I infection in Thailand," The New England Journal of Medicine, vol. 361, pp. 2209-2220—22 total pages, (Dec. 2009).
Ringe, R.P., et al., "Influences on the Design and Purification of Soluble, Recombinant Native-Like HIV-1 Envelope Glycoprotein Trimers," Journal of Virology, vol. 89, No. 23, pp. 12189-12210 (Dec. 2015).
Salazar-Gonzalez, J F., et al., "Genetic identity, biological phenotype, and evolutionary pathways of transmitted/founder viruses in acute and early HIV-1 infection," The Journal of Experimental Medicine, vol. 206, No. 6, pp. 1273-1289 (2009).
Sanders, R.W., et al., "A Next-Generation Cleaved, Soluble HIV-1 Env Trimer, BG505 SOSIP.664 gp140, Expresses Multiple Epitopes for Broadly Neutralizing but Not Non-Neutralizing Antibodies," PLOS—Pathogens, vol. 9, No. 9, e1003618, pp. 1-20 (published Sep. 19, 2013).
Santra, S., et al., "Mosaic Vaccines Elicit CD8+ T lymphocyte Responses in Monkeys that Confer Enhanced Immune Coverage of Diverse HIV Strains," Nat. Med., vol. 16, No. 3, pp. 324-328, Mar. 2010 (Author Manuscript—13 total pages—available in PMC Sep. 1, 2010).
Sarzotti-Kelsoe, M., et al., "Optimization and validation of the TZM-bl assay for standardized assessments of neutralizing antibodies against HIV-1," J Immunol Methods (Jul. 2014), Author Manuscript—37 total pages (Jul. 2015).
Saunders, K.O., "Vaccine Elicitation of High Mannose-Dependent Neutralizing Antibodies against the V3-Glycan Broadly Neutralizing Epitope in Nonhuman Primates," Cell Rep. vol. 18, No. 9, pp. 2175-2188 (Feb. 2017), Author Manuscript—25 total pages (Apr. 2017).
Scheid, J.F., et al., "Sequence and structural convergence of broad and potent HIV antibodies that mimic CD4 binding," Science, vol. 333, No. 6049, pp. 1633-1637 (Sep. 16, 2011)—Author Manuscript available in PMC May 15, 2012 (11 total pages).
Schmohl, L., and Schwarzer, D., "Sortase-mediated ligations for the site-specific modification of proteins," Current Opinion in Chemical Biology, vol. 22, pp. 122-128 (available online Oct. 6, 2014).
Seaman, M. S., et al., "Tiered Categorization of a Diverse Panel of HIV-1 Env Pseudoviruses for Assessment of Neutralizing Antibodies," Journal of Virology, vol. 84, No. 3, pp. 1439-1452 (Feb. 2010).

Sharma, S. et al., "Cleavage-Independent HIV-1 Env Trimers Engineered as Soluble Native Spike Mimetics for Vaccine Design," Cell Reports, vol. 11, pp. 539-550 (Apr. 28, 2015).
Shaw, G.M. and Hunter, Eric, "HIV transmission," Cold Spring Harbor Perspectives in Medicine, vol. 2, a006965, pp. 1-23 (2012).
Sheng, Z., et al., "Gene-Specific Substitution Profiles Describe the Types and Frequencies of Amino Acid Changes during Antibody Somatic Hypermutation," Front. Immunol., vol. 8, No. 537, published online May 10, 2017, last downloaded Oct. 7, 2020 from <https://www.ncbi.nlm.nih.gov/pmc/articles/PMC5424261/>—27 total pages.
Simonich, C.A., et al., "HIV-1 Neutralizing Antibodies with Limited Hypermutation from an Infant," Cell, vol. 166, No. 1, pp. 77-87 (Jun. 2016), Author Manuscript—16 total pages (Jun. 2017).
Sliepen, K., et al., "Presenting native-like HIV-1 envelope ; trimers on ferritin nanoparticles improves their ; immunogenicity," Retrovirology, vol. 12, No. 82, 5 total pages (2015).
Sok, D., "Promiscuous glycan site recognition by antibodies to the high-mannose patch of gp120 broadens neutralization of HIV," Science Translational Medicine, vol. 6, No. 236, 236ra263, May 2014 (Author Manuscript—26 total pages—available in PMC Nov. 14, 2014).
Sok, D., "The effects of somatic hypermutation on neutralization and binding in the PGT121 family of broadly neutralizing HIV antibodies," PLoS—Pathogens, vol. 9, No. 11, e1003754, pp. 1-20 (published Nov. 21, 2013).
Steichen, J.M, et al., "HIV Vaccine Design to Target Germline Precursors of Glycan-Dependent Broadly Neutralizing Antibodies," Immunity, vol. 45, pp. 483-496 (Sep. 20, 2016).
Stewart-Jones, G.B., "Trimeric HIV-1-Env Structures Define Glycan Shields from Clades A, B, and G," Cell, vol. 165, pp. 813-826 (May 2016) with supplemental data—49 total pages.
Tabata, et al., "Development of a Sortase A—mediated Peptide-labeled Liposome Applicable to Drug-delivery Systems," Anticancer Research, vol. 35, pp. 4411-4417 (2015).
Teng, G., et al., "Immunoglobulin somatic hypermutation," Annu Rev Genet, vol. 41, pp. 107-120 (Jun. 2007).
Tomaras, G.D., et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia," Journal of Virology, vol. 82, No. 24, pp. 12449-12463 (Dec. 2008).
Tsukiji, S., et al., "Sortase-Mediated Ligation: A Gift from Gram-Positive Bacteria to Protein Engineering," ChemBioChem, vol. 10, pp. 787-798 (published online Feb. 6, 2009).
Wagh, K., et al., "Optimal Combinations of Broadly Neutralizing Antibodies for Prevention and Treatment of HIV-1 Clade C Infection," Public Library of Science Pathogens, vol. 12, No. 3: e1005520, pp. 1-27 (Mar. 30, 2016).
Walker, L.M., et al., "Broad and potent neutralizing antibodies from an African donor reveal a new HIV-1 vaccine target," Science, vol. 326, pp. 285-289 (Oct. 9, 2009) with correction dated Feb. 19, 2010.
Walker, L.M., et al., "Broad neutralization coverage of HIV by multiple highly potent antibodies," Nature, vol. 477, No. 7365, pp. 466-470, Sep. 2011 (Author Manuscript—10 total pages—available in PMC Jul. 10, 2012).
West, Jr., A.P., et al., "Structural basis for germ-line gene usage of a potent class of antibodies targeting the CD4-binding site of HIV-1 gp120", Proceedings of the National Academy of Sciences, vol. 109, No. 30, pp. E2083-E2090 (Jun. 2012).
Williams, W. B., et al., "Diversion of HIV-1 vaccine-induced immunity by gp41-microbiota cross-reactive antibodies," Science, vol. 349, No. 6249, aab1253, Aug. 2015 (Author Manuscript—23 total pages—available in PMC Aug. 14, 2016).
Wu, X., et al., "Maturation and Diversity of the VRC01—Antibody Lineage over 15 Years of Chronic HIV-1 Infection," Cell, vol. 161, No. 3, pp. 470-485 (Apr. 23, 2015)—Author Manuscript (31 total pages).
Yaari, G. et al., "Models of Somatic Hypermutation Targeting and Substitution Based on Synonymous Mutations from High-Throughput Immunoglobulin Sequencing Data," Frontiers in Immunology, vol. 4, No. 358, pp. 1-11 (published online Nov. 15, 2013.

(56) References Cited

OTHER PUBLICATIONS

Yang. X., et al., "Antibody binding is a dominant determinant of the efficiency of human immunodeficiency virus type 1 neutralization," Journal of Virology, vol. 80, No. 22, pp. 11404-11408 (Nov. 2006).
Yeap, L.-S., et al., "Sequence-intrinsic mechanisms that target AID mutational outcomes on antibody genes," Cell, vol. 163, No. 5, pp. 1124-1137, Nov. 2015 (Author Manuscript—26 total pages—available in PMC Nov. 19, 2016).
Yoon, H., et al., "CATNAP: a tool to compile, analyze and tally neutralizing antibody panels," Nucleic Acids Res., vol. 43 (Web Server issue), pp. W213-W219—10 total pages (Jun./Jul. 2015).
Yu, J.-S., et al., "Generation of Mucosal Anti-Human Immunodeficiency Virus Type 1 T-Cell Responses by Recombinant *Mycobacterium smegmatis*," Clinical and Vaccine Immunology, vol. 13, No. 11, pp. 1204-1211 (Nov. 2006).
Yu, J.-S., et al., "Recombinant Mycobacterium bovis Bacillus Calmette-Guerin Elicits Human Immunodeficiency Virus Type 1 Envelope-Specific T Lymphocytes at Mucosal Sites," Clinical and Vaccine Immunology, vol. 14, No. 7, pp. 886-893 (Jul. 2007).
Yu, L., et al., "Immunologic Basis for Long HCDR3s in Broadly Neutralizing Antibodies Against HIV-1," Front Immunol., vol. 5, No. 250, pp. 1-15 (published online Jun. 2014).
Zhou, T, et al., "Multi-donor analysis reveals structural elements, genetic determinants, and maturation pathway for HIV-1 neutralization by VRCO1-class antibodies," Immunity, vol. 39, pp. 245-258, Aug. 2013 (Author Manuscript—26 total pages—available in PMC Apr. 14, 2014).
Zhou, T., et al., "Structural basis for broad and potent neutralization of HIV-1 by antibody VRC01," Science, vol. 329, No. 5993, pp. 811-817 (Aug. 2010)—Author Manuscript (19 total pages).
Sanders, R.W., et al., "HIV-1 neutralizing antibodies induced by native-like envelope trimers," Science, vol. 349, Issue 6244, pp. 154, aac4223-1-aac4223-10 (Jul. 10, 2015).
Afonine, P.V., et al., "Real-space refinement in PHENIX for cryo-EM and crystallography," Acta Crystallographica Section D, Structural Biology, vol. 74, pp. 531-544 (Jun. 1, 2018).
Altschul, Stephen F., et al., "Basic Local Alignment Search Tool," J. Mol. Biol., vol. 215, pp. 403-410 (1990).
Altschul, Stephen F., et al., "Issues in searching molecular sequence databases", Nature Genetics, vol. 6, pp. 119-129 (Feb. 1994).
Barad, B.A., et al., "EMRinger: side chain-directed model and map validation for 3D Electron Cryomicroscopy," Nature Methods, vol. 12, No. 10. pp. 943-946 (Oct. 12, 2015)—Author Manuscript available in PMC Apr. 1, 2016 (13 total pages).
Barnes, C.O., et al., "Structural characterization of a highly-potent V3-glycan broadly neutralizing antibody bound to natively-glycosylated HIV-1 envelope," Nature Communications, vol. 9, No. 1251, pp. 1-12 (2018).
Bartesaghi, A., et al., "Atomic Resolution Cryo-EM Structure of β-Galactosidase," Structure, vol. 26, pp. 848-856 with pp. e1-e3 (Jun. 5, 2018).
Cao, J., et al., "Effects of amino acid changes in the extracellular domain of the human immunodeficiency virus type 1 gp41 envelope glycoprotein," Journal of virology 67, 2747-2755 (1993).
Cao, L., et al., "Differential processing of HIV envelope glycans on the virus and soluble recombinant trimer," Nature Communications, vol. 9, No. 3693, pp. 1-14 (Sep. 12, 2018).
Chan, D.C., et al., "HIV Entry and Its Inhibition," Cell 93, vol. 3, No. 5, pp. 681-684 (May 29, 1998).
Chen, V.B., et al., "MolProbity: all-atom structure validation for macromolecular crystallography," Acta Crystallographica Section D, Biological Crystallography, vol. 66, pp. 12-21 (2010).
Chuang, G.-Y., et al., "Structure-Based Design of a Soluble Prefusion-Closed HIV-1 Env Trimer with Reduced CD4 Affinity and Improved Immunogenicity," Journal of Virology, vol. 91, No. 10, e02268-16, pp. 1-18 (May 2017).
Corpet, Florence, "Multiple sequence alignment with hierarchical clustering," Nucleic Acids Research, vol. 16, No. 22, p. 10881-10890 (1988).

Cowell, L.G., et al., "The Nucleotide-Replacement Spectrum Under Somatic Hypermutation Exhibits Microsequence Dependence That is Strand-Symmetric and Distinct from That Under Germline Mutation," Journal of Immunology, vol. 164, pp. 1971-1976 (2000).
Crooks, E.T., et al., "Vaccine-Elicited Tier 2 HIV-1 Neutralizing Antibodies Bind to Quaternary Epitopes Involving Glycan-Deficient Patches Proximal to the CD4 Binding Site," Public Library of Science Pathogens, vol. 11, No. 5, e1004932, pp. 1-34 (May 29, 2015).
De Taeye, SW et al., HIV-1 envelope trimer design and immunization strategies to induce broadly neutrailizing antibodies, Trends in Immunology, vol. 37, No. 3, pp. 221-232 (Mar. 2016)—Author Manuscript available in PMC Jun. 2, 2017 (19 total pages).
Ding, S., et al., "A Highly Conserved gp120 Inner Domain Residue Modulates Env Conformation and Trimer Stability," Journal of Virology, vol. 90, No. 19, pp. 8395-8409 (Oct. 1, 2016).
Dingens, A.S., et al., "Complete functional mapping of infection- and vaccine-elicited antibodies against the fusion peptide of HIV," Public Library of Science Pathogens, vol. 14, No. 7, e7159, pp. 1-16 (Jul. 5, 2018).
Doran, R.C., et al., "Characterization of a monoclonal antibody to a novel glycan-dependent epitope in the V1/V2 domain of the HIV-1 envelope protein, gp120," Molecular Immunology, vol. 62, No. 1, pp. 219-226 (Jul. 11, 2014).
Doria-Rose, N.A., "A short segment of the HIV-1 gp120 V1/V2 region is a major determinant of resistance to V1/V2 neutralizing antibodies," Journal of Virology. vol. 86, No. 15, pp. 8319-8323 (Aug. 2012).
Emsley, P., et al., "Features and development of Coot," Acta Crystallographica Section D, Biological Crystallography, vol. D66, pp. 486-501 (2010).
Finzi, A., et al., "Topological Layers in the HIV-1 gp120 Inner Domain Regulate gp41 Interaction and CD4-Triggered Conformational Transitions," Molecular Cell, vol. 37, No. 5, pp. 656-667 (Mar. 12, 2010).
Gardner, M.R., et al., "AAV-expressed eCD4-Ig provides durable protection from multiple SHIV challenges," Nature, vol. 519, No. 7541, pp. 87-91 (Mar. 5, 2015)—Author Manuscript available in PMC Sep. 5, 2016 (30 total page).
Grant, T., et al., "Measuring the optimal exposure for single particle cryo-EM using a 2.6 Å reconstruction of rotavirus VP6," eLife, vol. 4, No. e06980, pp. 1-19 (May 29, 2015).
Grant, T., et al., "cisTEM, user-friendly software for single-particle image processing," eLife, vol. 7, No. e35383, pp. 1-24 (Mar. 7, 2018).
Gristick, H.B., et al., "Natively glycosylated HIV-1 Env structure reveals new mode for antibody recognition of the CD4-binding site," Nature Structural & Molecular Biology, vol. 23, No. 10, pp. 906-915 (Oct. 23, 2016)—Author Manuscript available in PMC Apr. 1, 2017 (24 total pages).
Grupping, K., et al., "MiniCD4 protein resistance mutations affect binding to the HIV-1 gp120 CD4 binding site and decrease entry efficiency," Retrovirology, vol. 9, No. 36, pp. 1-16 (May 2, 2012).
Harrison, S.C., "Viral membrane fusion," Nature Structural & Molecular Biology, vol. 15, No. 7, pp. 690-698 (Jul. 2008).
He, L., et al., "HIV-1 vaccine design through minimizing envelope metastability," Science Advances, vol. 4, No. 11, pp. 1-19 (Nov. 21, 2018).
Herschhorn, A., et al., "The β20-β21 of gp120 is a regulatory switch for HIV-1 Env conformational transitions," Nature Communications, vol. 8, No. 1049, pp. 1-12 (Oct. 19, 2017).
Higgins, D.G. and Sharp, P.M., "CLUSTAL: a package for performing multiple sequence alignment on a microcomputer," Gene, vol. 73, pp. 237-244 (1988).
Higgins, D.G., et al., "Fast and sensitive multiple sequence alignments on a microcomputer," CABIOS Communications, vol. 5, No. 2, pp. 151-153 (1989).
Huang, J., et al., "Identification of a CD4-Binding-Site Antibody to HIV that Evolved Near-Pan Neutralization Breadth," Immunity, vol. 45, No. 5, pp. 1108-1121 (Nov. 15, 2016).
Humphrey, W., et al., "VMD: Visual molecular dynamics," Journal of Molecular Graphics, vol. 14, pp. 33-38 (Feb. 1996).

(56) References Cited

OTHER PUBLICATIONS

Ingale, J., et al., "High-Density Array of Well-Ordered HIV-1 Spikes on Synthetic Liposomal Nanoparticles Efficiently Activate B Cells," Cell Reports, vol. 15, No. 9, pp. 1986-1999 (May 31, 2016).
International Search Report and Written Opinion issued by U.S. Patent and Trademark Office as International Application No. PCT/US18/20788 dated Jul. 2, 2018 (14 total pages).
International Search Report and Written Opinion issued by U.S. Patent and Trademark Office as International Application No. PCT/US2019/049431 dated Feb. 4, 2020 (11 total pages).
International Search Report and Written Opinion issued by U.S. Patent and Trademark Office as International Application No. PCT/US2019/049662 dated Feb. 11, 2020 (17 total pages).
International Search Report and Written Opinion issued by U.S. Patent and Trademark Office as International Application No. PCT/US2019/020436 dated Jul. 22, 2019 (12 total pages).
Juette, M.F., et al., "Single-molecule imaging of non-equilibrium molecular ensembles on the millisecond timescale," Nature Methods, vol. 13, No. 4, pp. 341-344 (Apr. 2016)—Author Manuscript available in PMC Aug. 15, 2016 (14 total pages).
Kong, L., et al., "Uncleaved prefusion-optimized gp140 trimers derived from analysis of HIV-1 envelope metastability," Nature Communications, vol. 7, No. 12040, pp. 1-15 (Jun. 28, 2016).
Korber, B., et al., "Polyvalent vaccine approaches to combat HIV-1 diversity," Immunological Reviews, vol. 275, No. 1, pp. 230-244 (Jan. 30, 2017).
Kulp, D.W., et al., "Structure-based design of native-like HIV-1 envelope trimers to silence non-neutralizing epitopes and eliminate CD4 binding," Nature Communications, vol. 8, No. 1655, pp. 1-14 (Nov. 21, 2017).
Kwong, P.D., et al., "Structure of an HIV gp120 envelope glycoprotein in complex with the CD4 receptor and a neutralizing human antibody," Nature, vol. 393, No. 6686, pp. 648-659 (Jun. 18, 1998)—Author Manuscript available in PMC Oct. 6, 2017 (29 total pages).
Langley, D.R., et al., "Homology Models of the HIV-1 Attachment Inhibitor BMS-626529 Bound to gp120 Suggest a Unique Mechanism of Action," Proteins, vol. 83, pp. 331-350 (2015).
Lee, J.H., et al., "A Broadly Neutralizing Antibody Targets the Dynamic HIV Envelope Trimer Apex via a Long, Rigidified, and Anionic β-Hairpin Structure," Immunity, vol. 46, pp. 690-702, (Apr. 18, 2017).
Lee, J.H., et al., "Cryo-EM structure of a native, fully glycosylated, cleaved HIV-1 envelope trimer," Science, vol. 351, No. 6277, pp. 1043-1048 (Mar. 4, 2016).
Lemmin, T., et al., "Microsecond Dynamics and Network Analysis of the HIV-1 SOSIP Env Trimer Reveal Collective Behavior and Conserved Microdomains of the Glycan Shield," Structure, vol. 25, No. 10, pp. 1631-1639 with pp. e1-e2 (Oct. 3, 2017).
Liu, J., et al., "Molecular architecture of native HIV-1 gp120 trimers," Nature, vol. 455, pp. 109-113 with "Methods" (6 total pages) Sep. 4, 2008.
Liu, Q., et al., "Quaternary contact in the initial interaction of CD4 with the HIV-1 envelope trimer," Nature Structural & Molecular Biology, vol. 24, No. 4, Apr. 2017, pp. 370-378 with "Online Methods" and "Corrigendum: Quaternary contact in the initial interaction of CD4 with the HIV-1 envelope trimer," published online Feb. 20, 2017; corrected after print Apr. 27, 2017 (13 total pages).
Lu, M., et al., "Associating HIV-1 envelope glycoprotein structures with states on the virus observed by smFRET," Nature, vol. 568, No. 7752, pp. 415-419 (Apr. 10, 2019) available in PMI Oct. 19, 2019 (36 total pages).
Ma, B.J., et al., "Envelope Deglycosylation Enhances Antigenicity of HIV1 gp41 Epitopes for Both Broad Neutralizing Antibodies and Their Unmutated Ancestor Antibodies," Public Library of Science Pathogens, vol. 7, No. 9, e1002200, pp. 1-16 (Sep. 1, 2011).
Ma, X., et al., "HIV-1 Env trimer opens through an asymmetric intermediate in which individual protomers adopt distinct conformations," eLife, vol. 7, No. e34271, pp. 1-18 (Mar. 21, 2018).

Martinez-Murillo, P., et al., "Particulate Array of Well-Ordered HIV Clade C Env Trimers Elicits Neutralizing Antibodies that Display a Unique V2 Cap Approach," Immunity, vol. 46, No. 5, pp. 804-817 with pp. e1-e7 (May 16, 2017).
McLellan, J.S., et al., "Structure of HIV-1 gp120 V1/V2 domain with broadly neutralizing antibody PG9," Nature, vol. 480, No. 7377, pp. 336-343 with "Methods" (10 total pages) Dec. 15, 2011.
Meanwell, N.A., et al., "Inhibitors of HIV-1 Attachment: The Discovery and Development of Temsavir and its Prodrug Fostemsavir," Journal of Medicinal Chemistry, vol. 61, pp. 62-80 (2018).
Mo, H., et al., "Conserved residues in the coiled-coil pocket of human immunodeficiency virus type 1 gp41 are essential for viral replication and interhelical interaction," Virology, vol. 329, pp. 319-327 (available online Sep. 25, 2004).
Munro, J.B., et al., "Structure and Dynamics of the Native HIV-1 Env Trimer," Journal of Virology, vol. 89, No. 11, pp. 5752-5755 (Jun. 2015).
Munro, S. et al. "Use of peptide tagging to detect proteins expressed from cloned genes: deletion mapping functional domains of Drosophila hsp70", The EMBO Journal, vol. 3, No. 13, pp. 3087-3093 (1984).
Needleman, S.B., et al. "A General Method Applicable to the Search for Similarities in the Amino Acid Sequence of Two Proteins" J. Mol. Biol., vol. 48, pp. 443-453 (1970).
Ozorowski, G., et al., "Open and closed structures reveal allostery and pliability in the HIV-1 envelope spike," Nature, vol. 547, pp. 360-363 with "Methods" (16 total pages), Jul. 20, 2017.
Pancera, M., et al., "Crystal structures of trimeric HIV envelope with entry inhibitors BMS-378806 and BMS-626529," Nature Chemical Biology, vol. 13, No. 10, pp. 1115-1122 (Oct. 2017)—Author Manuscript available in PMC Feb. 21, 2018 (24 total pages).
Pancera, M., et al., "Structure of HIV-1 gp 120 with gp41-interactive region reveals layered envelope architecture and basis of conformational mobility," Proceedings of the National Academy of Sciences of the United States of America, vol. 107, No. 3, pp. 1166-1171 (Jan. 19, 2010).
Pancera, M., et.al., "Structure and immune recognition of trimeric pre-fusion HIV-1 Env," Nature, vol. 514, No. 7523, pp. 455-461 (Oct. 23, 2014)—Author Manuscript available in PMC Apr. 23, 2015 (43 total pages).
Pearson, W. R., et al., "Improved tools for biological sequence comparison." Proc. Natl. Acad. Sci. U.S.A., vol. 85, pp. 2444-2448 (Apr. 1988).
Pettersen, E.F., et al., "UCSF Chimera—A Visualization System for Exploratory Research and Analysis," Journal of Computational Chemistry, vol. 25, No. 13, pp. 1605-1612 (2004).
Powell, R.L.R., et al., "Plasticity and Epitope Exposure ofthe HIV-1 Envelope Trimer," Journal of Virology, vol. 91, No. 17, e00410-417, pp. 1-17 (Sep. 2017).
Pritz, S., et al., "Synthesis of Biologically Active Peptide Nucleic Acid—Peptide Conjugates by Sortase-Mediated Ligation," Journal of Organic Chemistry, vol. 72, No. 10, pp. 3909-3912 (published on Web Apr. 14, 2007).
Pugach, P., et al., "A Native-Like SOSIP.664 Trimer Based on an HIV-1 Subtype B env Gene," Journal of Virology, vol. 89, No. 6, pp. 3380-3395 (Mar. 2015).
Punjani, A., et al., "cryoSPARC: algorithms for rapid unsupervised cryo-EM structure determination," Nature Methods, vol. 14, No. 3, pp. 290-296 with "Online Methods" (8 total pages), Mar. 2017.
Rantalainen, K., et al., "Co-evolution of HIV Envelope and Apex-Targeting Neutralizing Antibody Lineage Provides Benchmarks for Vaccine Design," Cell Reports, vol. 23, No. 11, pp. 3249-3261 (Jun. 12, 2018).
Rohou, A., et al., "CTFFIND4: Fast and accurate defocus estimation from electron micrographs," Journal of Structural Biology, vol. 192, No. 2, pp. 216-221, (Nov. 2015)—Author Manuscript available in PMC Sep. 25, 2019 (18 total pages).
Saunders, K.O., et al., "Vaccine Induction of Heterologous Tier 2 HIV-1 Neutralizing Antibodies in Animal Models," Cell Reports, vol. 21, No. 13, pp. 3681-3690 (Dec. 26, 2017).
Scharf, L., et al., "Broadly Neutralizing Antibody 8ANC195 Recognizes Closed and Open States of HIV-1 Env," Cell, vol. 162, No. 6, pp. 1379-1390 (Sep. 10, 2015).

(56) References Cited

OTHER PUBLICATIONS

Shaik, M.M., et al., "Structural basis of coreceptor recognition by HIV-1 envelope spike," Nature, vol. 565, No. 7739, pp. 318-323 (Jan. 2019)—Author Manuscript available In PMC Jun. 12, 2019 (34 total pages).
Smith, T. F., et al., "Comparison of Biosequences," Adv. Appl. Math., vol. 2, pp. 482-489 (1981).
Stamatatos, L., et al., "An Envelope Modification That Renders a Primary, Neutralization-Resistant Clade B Human immunodeficiency Virus Type 1 Isolate Highly Susceptible to Neutralization by Sera from Other Clades," Journal of Virology, vol. 72, No. 10, pp. 7840-7845 (Oct. 1, 1998).
Tang, G., et al., "EMAN2: An Extensible Image Processing Suite for Electron Microscopy," Journal of Structural Biology, Article in Press: 2006 (accepted May 31.2006), doi:10.1016/j.jsb.2006.05.009, pp. 1-9.
Torrents de la Peña, A., et al., "Improving the Immunogenicity of Native-like HIV-1 Envelope Trimers by Hyperstabilization," Cell Reports, vol. 20, No. 8, pp. 1805-1817 (Aug. 22, 2017).
Tran, E.E.H., et al., "Structural Mechanism of Trimeric HIV-1 Envelope Glycoprotein Activation," Public Library of Science Pathogens, vol. 8, No. 7, e1002797, pp. 1-18 (Jul. 12, 2012).
Tria, G., et al., "Advanced ensemble modelling of flexible macromolecules using X-ray solution scattering," International Union of Crystallography Journal, vol. 2, No. 2, pp. 207-217 (accepted Jan. 30, 2015).
Voss, J.E., et al., "Elicitation of Neutralizing Antibodies Targeting the V2 Apex of the HIV Envelope Trimer in a Wild-Type Animal Model," Cell Reports, vol. 21, No. 1, pp. 222-235 (Oct. 3, 2017).
Wagh, K., et al., "Completeness of HIV-1 Envelope Glycan Shield at Transmission Determines Neutralization Breadth," Cell Reports, vol. 25, No. 4 pp. 893-908 with pp. e1-e7 (Oct. 23, 2018).
Wang, H., et al., "Cryo-EM structure of a CD4-bound open HIV-1 envelope trimer reveals structural rearrangements of the gp120 V1V2 loop," Proceedings of the National Academy of Sciences of the Unites States for America, vol. 113, No. 46, pp. E7151-E7158 (Oct. 31, 2016).
Wang, H., et al., "Partially Open HIV-1 Envelope Structures Exhibit Conformational Changes Relevant for Coreceptor Binding and Fusion," Cell Host & Microbe, vol. 24, No. 4, pp. 579-592 with pp. e1-e4 (Oct. 10, 2018).
Wang, R.Y.-R., et al., "Automated structure refinement of macromolecular assemblies from cryo-EM maps using Rosetta," eLife, vol. 5, No. e17219, pp. 1-22 (Sep. 26, 2016).
Wang, W., et al., "A systematic study of the N-glycosylation sites of HIV-1 envelope protein on infectivity and antibody-mediated neutralization," Retrovirology, vol. 10, No. 14, pp. 1-14 (Feb. 6, 2013).
Ward, A.B., et al., "Insights Into the Trimeric HIV-1 Envelope Glycoprotein Structure," Trends in Biochemical Sciences, vol. 40, No. 2, pp. 101-107 (Feb. 1, 2015)—Author Manuscript available in PMC Feb. 1, 2016 (16 total pages).
Ward, A.B., et al., "The HIV-1 envelope glycoprotein structure: nailing down a moving target," Immunological Reviews, vol. 275, No. 1, pp. 21-32 (Jan. 30, 2017).
Weissenhorn, W., et al., "Atomic structure of the ectodomain from HIV-1 gp41," Nature, 387, pp. 426-430 (May 22, 1997).
Xu, K., et al., "Epitope-based vaccine design yields fusion peptide-directed antibodies that neutralize diverse strains ofHIV-1," Nature Medicine, vol. 24, No. 6, Jun. 4, 2018, pp. 857-867 with "Methods" and "Nature Research: Life Sciences Reporting Summary—Jun. 2017" (19 total pages).
Zhang, P., et al., "Interdomain Stabilization Impairs CD4 Binding and Improves Immunogenicity of the HIV-1 Envelope Trimer," Cell Host & Microbe, vol. 23, No. pp. 832-844 and pp. e1-e6 (Jun. 13, 2018).
Zhou, T., et al., "Quantification of the Impact of the HIV-1-Glycan Shield on Antibody Elicitation," Cell Reports, vol. 19, No. 4, pp. 719-732 (Apr. 25, 2017).
Zolla-Pazner, S., et al., "Structure/Function Studies Involving the V3 Region of the HIV-1 Envelope Delineate Multiple Factors That Affect Neutralization Sensitivity," Journal of Virology, vol. 90, No. 2, pp. 636-649 (accepted and posted online Oct. 21, 2015).

\* cited by examiner

Figure 2D
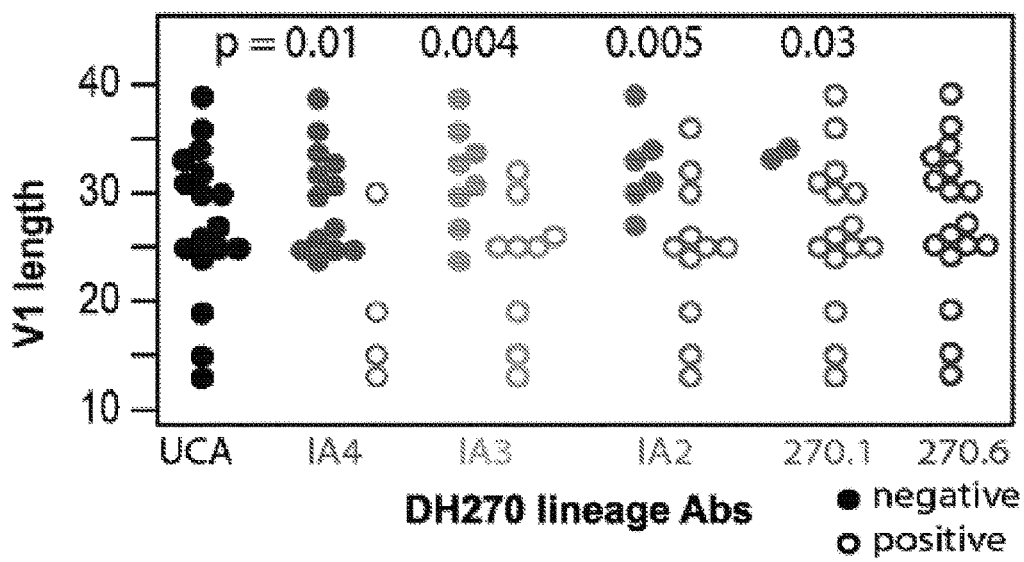
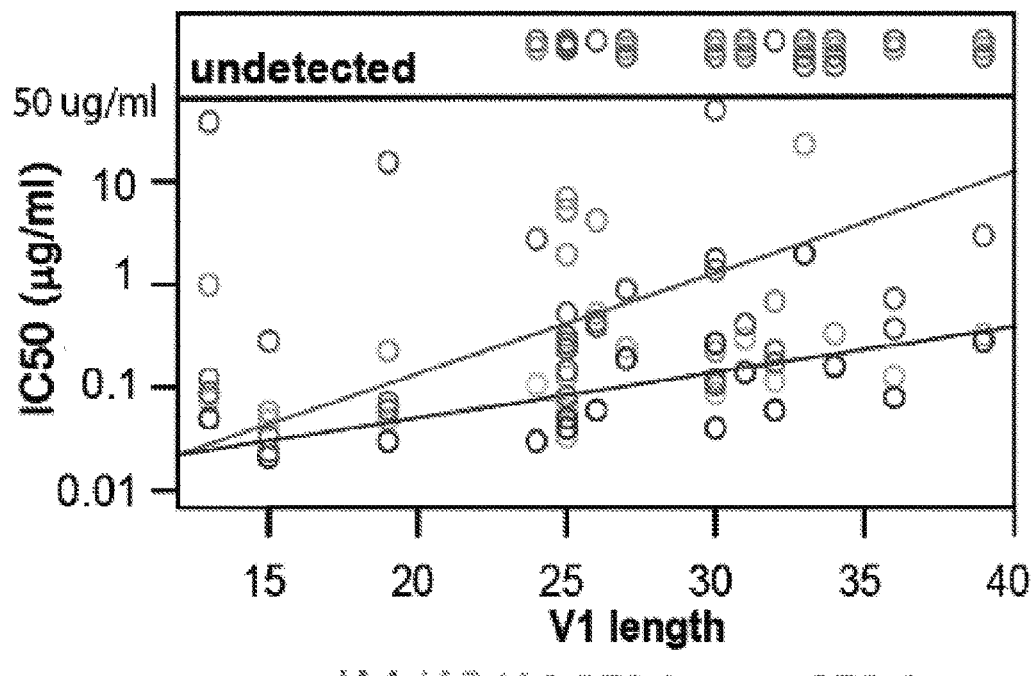

B

| CH0848.d0274.30.07 | DH475 | DH270.1 |
|---|---|---|
| WT | | |
| d134-143+D185N+N413Y+d463-464 | | ▓ |
| d134-143+N413Y+d463-464 | | ▓ |
| d134-143+N413Y | | ▓ |
| d134-143+D185N+N413Y | | ▓ |
| d134-143 | ▒ | ▓ |
| d134-143 + d463-464 | ░ | ▓ |
| D185N | ▒ | |
| N413Y | | |

C

| CH0848.d0274.30.07 | DH272 | DH270.1 |
|---|---|---|
| WT | ▓ | |
| d134-143+D185N+N413Y+d463-464 | | ▒ |
| d134-143+D185N+N413Y | | ▒ |
| N413Y + d134-143 + d463-464 | | ▓ |
| d134-143 + d463-464 | | ▓ |
| N413Y + d134-143 | | ▓ |
| d134-143 | | ▓ |
| N413Y | | ▓ |
| D185N | | |

$IC_{50}$ µg/ml

Figure 6A continued
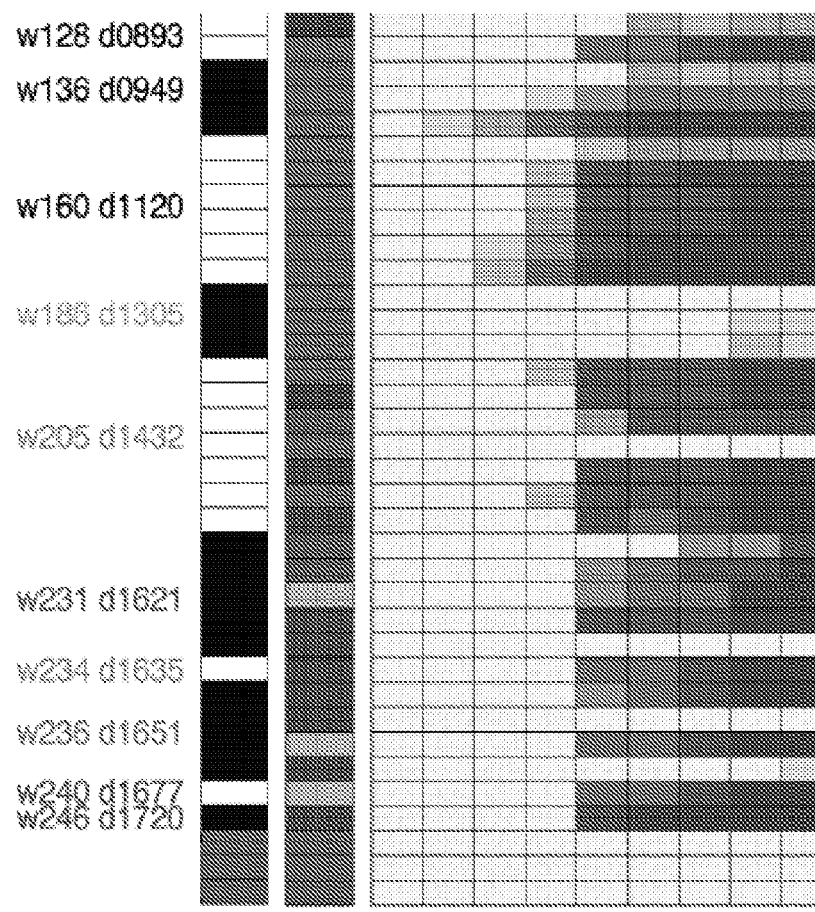
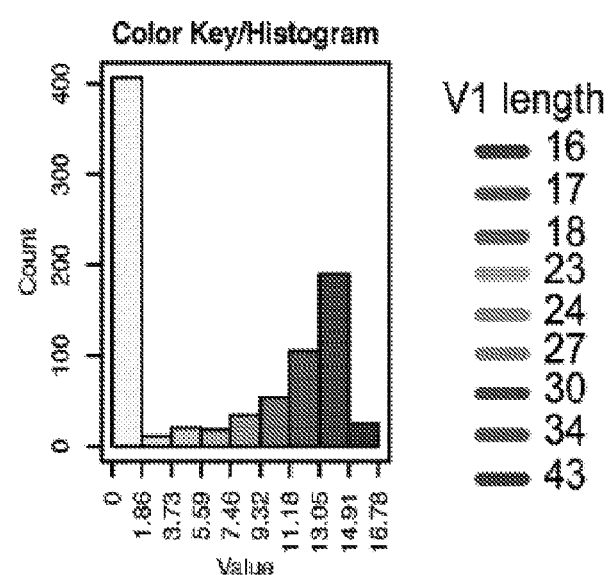

Figure 7A

| Antibody ID | VH | D | JH | VH | Mutation frequency VH/DH nt | VH/DH aa | CDRH3 length | VL | JL | VL | Mutation frequency VL/JL nt | VL/JL aa | CDRL3 length | Week of isolation | Insertions/ deletions |
|---|---|---|---|---|---|---|---|---|---|---|---|---|---|---|---|
| DH270.UCA | 1-2*02 | 3-22*01 | 4*02 | 0.0% | 0/381 (0%) | 0 (0%) | 20 | 2-23*02 | 2*01 | 0.0% | 0/330 (0%) | 0 (0%) | 10 | - | none |
| DH270.IA4 | 1-2*02 | 3-22*01 | 4*02 | 1.4% | 4/381 (1.0%) | 4/127 (3.1%) | 20 | 2-23*02 | 2*01 | 0.7% | 2/330 (0.6%) | 1/110 (0.9%) | 10 | - | none |
| DH270.IA2 | 1-2*02 | 3-22*01 | 4*02 | 2.1% | 7/381 (1.8%) | 7/127 (5.5%) | 20 | 2-23*02 | 2*01 | 2.1% | 6/330 (1.8%) | 3/110 (2.7%) | 10 | - | none |
| DH270.IA3 | 1-2*02 | 3-22*01 | 4*02 | 3.5% | 16/381 (4.2%) | 11/127 (8.7%) | 20 | 2-23*02 | 2*01 | 1.4% | 4/330 (1.2%) | 2/110 (1.8%) | 10 | - | none |
| DH270.1 | 1-2*02 | 3-22*01 | 4*02 | 5.6% | 21/381 (5.5%) | 18/127 (14.2%) | 20 | 2-23*02 | 2*01 | 5.2% | 21/330 (6.3%) | 11/110 (10.0%) | 10 | 205 | none |
| DH270.IA1 | 1-2*02 | 3-22*01 | 4*02 | 8.3% | 33/381 (8.7%) | 22/127 (17.3%) | 20 | 2-23*02 | 2*01 | 6.9% | 26/330 (7.9%) | 14/110 (12.7%) | 10 | - | none |
| DH270.2 | 1-2*02 | 3-22*01 | 4*02 | 10.8% | 46/381 (12.1%) | 27/127 (21.3%) | 20 | 2-23*02 | 2*01 | 3.8% | 13/330 (3.9%) | 7/110 (6.4%) | 10 | 232 | none |
| DH270.3 | 1-2*02 | 3-22*01 | 4*02 | 11.8% | 48/381 (12.6%) | 27/127 (21.3%) | 20 | 2-23*02 | 2*01 | 8.3% | 27/330 (8.2%) | 16/110 (14.5%) | 10 | 205 | none |
| DH270.4 | 1-2*02 | 3-22*01 | 4*02 | 11.5% | 44/381 (11.6%) | 28/127 (22.0%) | 20 | 2-23*02 | 2*01 | 8.0% | 29/330 (8.8%) | 16/110 (14.5%) | 10 | 232 | none |
| DH270.5 | 1-2*02 | 3-22*01 | 4*02 | 11.1% | 45/381 (11.8%) | 26/127 (20.5%) | 20 | 2-23*02 | 2*01 | 11.5% | 41/330 (12.4%) | 22/110 (20.0%) | 10 | 232 | none |
| DH270.6 | 1-2*02 | 3-22*01 | 4*02 | 12.9% | 47/381 (12.3%) | 28/127 (22.0%) | 20 | 2-23*02 | 2*01 | 7.6% | 39/330 (11.8%) | 17/110 (15.5%) | 10 | 234 | none |

Amino Acid Sequence Alignment of DH270 Lineage Antibodies V$_H$DJ$_H$ rearrangements

D

Amino Acid Sequence Alignment of DH270 Lineage Antibodies V$_L$J$_L$ rearrangements

Figure 8A

Neutralization IC$_{50}$ μg/ml

| A | AC13.8 | | PVO.4 | | TRO.11 | | AC10.029 | | RHPA.4259 | |
|---|---|---|---|---|---|---|---|---|---|---|
| | wt | N332A | wt | N332A | wt | N332A | wt | N332A | wt | N332A |
| DH270.UCA | >50 | >50 | >50 | >50 | >50 | >50 | >50 | >50 | >50 | >50 |
| DH270.IA4 | >50 | >50 | 42 | >50 | 43 | >50 | >50 | >50 | >50 | >50 |
| DH270.IA3 | >50 | >50 | >50 | >50 | 0.2 | >50 | >50 | >50 | 6.6 | >50 |
| DH270.IA2 | >50 | >50 | >50 | >50 | 0.1 | >50 | >50 | >50 | 6.4 | >50 |
| DH270.1 | >50 | >50 | 0.2 | >50 | 0.08 | >50 | 1.9 | >50 | 0.2 | >50 |
| DH270.IA1 | >50 | >50 | 0.07 | >50 | 0.05 | 32.4 | <0.02 | >50 | 0.04 | >50 |
| DH270.2 | 21 | >50 | 0.3 | >50 | 0.06 | >50 | 0.3 | >50 | 0.1 | >50 |
| DH270.3 | >50 | >50 | 23 | >50 | 0.3 | >50 | 43 | >50 | 42 | >50 |
| DH270.4 | 15 | >50 | 0.1 | >50 | 0.04 | 14 | <0.02 | >50 | 0.05 | >50 |
| DH270.5 | 41 | >50 | 0.1 | >50 | 0.07 | >50 | <0.02 | >50 | 0.04 | >50 |
| DH270.6 | 1.4 | >50 | 0.03 | >50 | 0.02 | >50 | <0.02 | >50 | <0.02 | >50 |

Figure 9B

| Antibody ID | $V_H$ | D | $J_H$ | $V_H$ mutation frequency | CDRH3 length | $V_L$ | $J_L$ | κ/λ | $V_L$ mutation frequency | CDRL3 length | Week of isolation | Insertions/ deletions |
|---|---|---|---|---|---|---|---|---|---|---|---|---|
| DH475 | 3-23*01 | 2-8*02 | 3*01 | 10.1% | 19 | 4-69*02 | 1*01 | λ | 10.9% | 9 | 232 | none |
| DH272 | 1-2*02 | 3-3*01 | 4*02 | 14.9% | 17 | 2-30*02 | 2*02 | κ | 5.1% | 9 | 205 | -6 FRH3 |

Figure 14

Env positions < 8.5 Å from PGT128

```
UCA1_HC    QVQLVQSGAEVKKPGASVKVSCKASGYTFTGYYMHWVRQAPGQGLEWMGWINPNSGGTNY
UCA3_HC    QVQLVQSGAEVKKPGASVKVSCKASGYTFTGYYMHWVRQAPGQGLEWMGWINPNSGGTNY
UCA4_HC    QVQLVQSGAEVKKPGASVKVSCKASGYTFTGYYMHWVRQAPGQGLEWMGWINPNSGGTNY
           ************************************************************

UCA1_HC    AQKFQGRVTMTRDTSISTAYMELSRLRSDDTAVYYCATGGWIGLYDSSGYPNFDYWGQG
UCA3_HC    AQKFQGRVTMTRDTSISTAYMELSRLRSDDTAVYYCARGGWISLYDSSGYPNFDYWGQG
UCA4_HC    AQKFQGRVTMTRDTSISTAYMELSRLRSDDTAVYYCARGGWIGLYDSSGYPNFDYWGQG
           **********************************.*****:******************

UCA1_HC    TLVTVS
UCA3_HC    TLVTVS
UCA4_HC    TLVTVS
           ******
```

B

```
UCA3_LC    QSALTQPASVSGSPGQSITTSCTGTSSDVGSYNLVSWYQQHPGKAPKLMIYEVSKRPSGV
UCA1_LC    QSALTQPASVSGSPGQSITTSCTGTSSDVGSYNLVSWYQQHPGKAPKLMIYEVSKRPSGV
           ************************************************************

UCA3_LC    SNRFSGSKSGNTASLTISGLQAEDEADYYCCSYAGSSTVIFGGGTKLTVL
UCA1_LC    SNRFSGSKSGNTASLTISGLQAEDEADYYCCSYAGSSILEGGGTKLTVL
           *************************************::*********
```

| Boost | Subject.day.clone | gp120 Binding AUC | | | | | | | | Neutralization IC50 | | | | | | | V1 loop length |
|---|---|---|---|---|---|---|---|---|---|---|---|---|---|---|---|---|---|
| | | UCA | IA4 | IA3 | IA2 | i | IA1 | 4 | 5 | 6 | UCA | IA4 | IA3 | IA2 | i | IA1 | 4 | 5 | |
| i. | CH848.0949.10.17 | 0 | | 6.3 | 9.4 | | | | | | >50 | 0.64 | 0.2 | 0.14 | 0.18 | | | 0.5 | 17 |
| ii. | CH848.0836.10.31 | 0 | 0.0 | 4.9 | 9.4 | | | | | | >50 | | | | | | | | 17 |
| iii. | CH848.0358.80.06 | 0 | 0.0 | 0.0 | 0.3 | 11.2 | | | | | >50 | >50 | >50 | >50 | 1.3 | | | | 24 |
| iii. | CH848.1432.5.41 | 0 | 0.0 | 0.0 | 0.8 | 11.7 | | | | | >50 | >50 | >50 | >50 | 2.6 | 0.33 | 0.26 | 0.21 | 30 |
| iii. | CH848.0526.25.02 | 0 | 0.0 | 0.0 | 0.0 | 8.8 | 12.0 | | | | >50 | >50 | >50 | >50 | | 1.4 | 1.1 | 1.6 | 34 |

| Epitope | Type | HIV BNAb | Antibody Characteristics | | | | Neutralization | |
|---|---|---|---|---|---|---|---|---|
| | | | # Improbable Mutations[a] | #AA Muts[b] | # Indels[c] | CDR3 Length[d] | Geo Mean Potency[e] | Breadth[f] |
| CD4 | CD4 mimicking VH1-46 derived | CH235.12 | 22 | 67 | 0 | 21 | 0.69 | 100% |
| | | 8ANC131 | 17 | 69 | 3 | 25 | 10.23 | 100%* |
| | | 1B2530 | 13 | 60 | 0 | 27 | 2.74 | 100%* |
| | CD4 mimicking VH1-2 derived | VRC01 | 23 | 71 | 3 | 17 | 0.59 | 92% |
| | | VRC-CH31 | 15 | 70 | 9 | 18 | 0.20 | 92% |
| | | 3BNC117 | 16 | 68 | 8 | 15 | 0.29 | 92% |
| | | N6 | 19 | 75 | 0 | 18 | 0.08 | 100%* |
| | CDRH3 Binder | CH103 | 9 | 49 | 3 | 23 | 3.11 | 80%* |
| | | DH270.6 | 11 | 34 | 0 | 28 | 0.59 | 67% |
| | | BF520.1 | 12 | 24 | 0 | 29 | 5.28 | 82%* |
| Glycan-V3 | | PGT128 | 7 | 53 | 11 | 29 | 0.04 | 83% |
| | | PGT121 | 15 | 55 | 3 | 36 | 0.30 | 64% |
| | | PGT135 | 18 | 64 | 5 | 27 | 9.36 | 50%*+ |

Figure 31A

|  |  |  |  |  |  |  |
|---|---|---|---|---|---|---|
| Glycan-V1V2 | PG9 | 14 | 28 | 0 | 38 | 0.17 | 92% |
|  | CH01 | 16 | 44 | 0 | 33 | 2.26 | 75% |
|  | PGT145 | 12 | 52 | 0 | 40 | 0.05 | 86%* |
|  | CAP256-VRC26.25 | 8 | 27 | 0 | 48 | 0.01 | 78%* |
|  | PGDM1400 | 14 | 67 | 0 | 41 | 0.02 | 100%* |
| MPER | 2F5 | 10 | 31 | 0 | 31 | 17.40 | 50% |
|  | 4E10 | 10 | 30 | 0 | 27 | 3.09 | 100% |
|  | DH511.2 | 19 | 46 | 0 | 32 | 0.25 | 100% |
|  | 10E8 | 14 | 45 | 0 | 32 | 0.21 | 100% |
| gp120-gp41 Interface | PGT151 | 17 | 41 | 0 | 35 | 0.26 | 83% |
|  | 35022 | 23 | 78 | 8 | 24 | 2.50 | 58% |
|  | N123-VRC34 | 10 | 37 | 0 | 22 | 7.49 | 42% |
|  | 8ANC195 | 20 | 77 | 8 | 29 | 1.60 | 83% | a Probability of mutations in the absence of selection estimated by the ARMADiLLO program. Due to inconsistent certainity in the inference of the CDRH3 region between BNAbs, only mutations outside the CDR3 were used.
b Number of total amino acids mutations
c Number of amino acids inserted or deleted relative to UCA d Sum of heavy and light chain CDR3 length e Geometric mean neutralization potency of BNAb against a standard 12 tier-2 virus global panel f Neutralization breadth of BNAb against a standard 12 tier-2 virus global panel

* The number of viruses run in panel was <12

Figure 31A continued

| T | L | V | T | V | S | S |
|---|---|---|---|---|---|---|
| 121 | 122 | 123 | 124 | 125 | 126 | 127 |
| A 1.33 / C 0.31 | T 1.04 / G 0.30 | G 0.40 / T 0.44 | A 0.86 / C 0.42 | T 0.46 / | T 0.66 / C 0.31 / C 0.62 | T 0.41 / C N/A / A N/A |

| T | L | V | T | V | S | S |
|---|---|---|---|---|---|---|
| 121 | 122 | 123 | 124 | 125 | 126 | 127 |
| A 1.33 / C 0.31 | T 1.04 / G 0.30 | G 0.40 / T 0.44 | A 0.86 / C 0.42 | T 0.46 / | T 0.66 / C 0.31 / C 0.62 | T 0.41 / C N/A / A N/A |
| 0.80675 | 0.92978 | 0.94982 | 0.92201 | 0.95430 | 0.94151 | 0.95291 |

| | Probability‡ | CH505 T/F† | DU156.12 | JR-FL | Q23 | TRO.11* | 246-F3_C10_2* | X1632_S2_B10* |
|---|---|---|---|---|---|---|---|---|
| CH235 | - | 0.572 | 18.385 | 2.438 | 1.927 | 11.933 | 3.649 | 8.907 |
| T19K | 0.0116 | 0.888 | >50 | 1.635 | 7.39 | >50 | 6.148 | >25 |
| L47W | 0.00864 | 0.699 | NT | NT | NT | >25 | >25 | >25 |
| W55G | 0.00017 | 1.663 | NT | NT | NT | >25 | >25 | >25 |
| Q23K | 0.01612 | 0.398 | NT | NT | NT | 19.869 | 2.641 | 11.821 |
| Q46E | 0.01847 | 0.41 | NT | NT | NT | 12.142 | 2.178 | 7.125 |
| R57S | 0.22522 | 6.102 | NT | NT | NT | >25 | >25 | >25 |
| T19N | 0.033 | 23.249 | >50 | 20.289 | >50 | >50 | NT | NT |
| T19R | 0.021 | 0.587 | 35.681 | 2.175 | 3.715 | 40.392 | NT | NT |
| CH01+CH31 | - | | 3.078 | | | | | |

| | Probability‡ | JR-FL | TRO.11* | 246-F3_C10_2* | X1632_S2_B10* | 398-F1-F6_20* | CNE8* | X2278_C2_B6* |
|---|---|---|---|---|---|---|---|---|
| BF520.1 | - | 1.315 | 1.866 | NT | >50 | 0.39 | >50 | 0.467 |
| A52N | 0.0005 | 12.81 | >50 | NT | >50 | 1.247 | >50 | 2.238 |
| CH01+CH31 | - | | 0.38 | NT | | 0.108 | 0.183 | |

| | 398-F1-F6_20* | CNE8* | X2278_C2_B6* | CNE55* | CH119.10* | BJOX00 2000.03.2* | 25710-2.43* | Ce70301 0217* | Ce1176_A3* | SVA |
|---|---|---|---|---|---|---|---|---|---|---|
| CH235 | >25 | >25 | >25 | >25 | >25 | >25 | >25 | >25 | >25 | >25 |
| T19K | >25 | >25 | >25 | >25 | >25 | >25 | >25 | >25 | >25 | >25 |
| L47W | >25 | >25 | >25 | >25 | >25 | >25 | >25 | >25 | >25 | >25 |
| W55G | >25 | >25 | >25 | >25 | >25 | >25 | >25 | >25 | >25 | >25 |
| Q23K | >25 | >25 | >25 | >25 | >25 | >25 | >25 | >25 | >25 | >25 |
| Q46E | >25 | >25 | >25 | >25 | >25 | >25 | >25 | >25 | >25 | >25 |
| R57S | >25 | >25 | >25 | >25 | >25 | >25 | >25 | >25 | >25 | >25 |
| T19N | NT | NT | NT | NT | NT | NT | NT | NT | NT | >25 |
| T19R | NT | NT | NT | NT | NT | NT | NT | NT | NT | >25 |
| CH01+CH31 | 0.069 | 0.059 | 0.075 | 0.035 | 0.468 | 0.977 | 0.16 | 0.041 | 0.016 | >25 |

BF520.1

| | CNE55* | CH119.10* | BJOX00 2000.03.2* | 25710-2.43* | Ce70301 0217* | Ce1176_A3* | SVA |
|---|---|---|---|---|---|---|---|
| BF520.1 | >50 | 3.894 | 0.598 | 40.449 | 1.901 | 1.472 | >50 |
| A52N | >50 | 22.203 | 3.971 | >50 | 13.288 | 3.634 | >50 |
| CH01+CH31 | 0.113 | 2.29 | 10.806 | 0.895 | 0.102 | 0.11 | >50 |

Figure 38 continued

| | | Neutralization (IC50 μg/ml) |  |
|---|---|---|---|
| | | 50 to 1 | 1 to 1 |
| | | | 6.1 |

| | | Probability‡ | JR-FL | 45_01dG 5† | RHPA42 59 | SVA |
|---|---|---|---|---|---|---|
| VRC01 | VRC01 | - | 0.04 | 0.036 | 0.034 | >10 |
| | VK_W68S | 0.0007 | 0.215 | 0.036 | 0.069 | >10 |
| | VK_Y72F | 0.009 | 2.095 | 0.057 | 0.109 | >10 |
| | VK_N73T | 0.0085 | 0.261 | 0.025 | 0.086 | >10 |
| | VH_E28T | 0.0009 | 0.141 | 0.019 | 0.069 | >10 |
| | VH_E16A | 0.0012 | 0.12 | 0.022 | 0.042 | >10 |
| | VH_P63K | 0.007 | 0.209 | 0.038 | 0.133 | >10 |
| | VK_I21L | 0.0095 | 0.196 | 0.040 | 0.121 | >10

| bnAb | #AA mutations[A] | AA mut freq | # Improbable Mutations (M)[B] | Expected Frequency of >=M[C] | Counts |
|---|---|---|---|---|---|
| CH235.12* | 45 | 42.1% | 16 | 0.20% | 2/985 |
| 8ANC195* | 44 | 39.3% | 13 | 2.34% | 23/981 |
| N6* | 43 | 40.2% | 12 | 4.35% | 43/989 |
| VRC01* | 43 | 40.2% | 12 | 3.75% | 37/986 |
| 8ANC131* | 41 | 38.3% | 12 | 3.67% | 36/980 |
| VRC-CH31* | 29 | 33.6% | 12 | 1.43% | 14/981 |
| CH01* | 29 | 27.1% | 11 | 0.71% | 7/985 |
| DH511.2* | 28 | 25.7% | 11 | 0.51% | 5/981 |
| PGT151* | 27 | 25.2% | 11 | 0.62% | 6/974 |
| 35O22* | 34 | 29.6% | 11 | 1.32% | 13/984 |
| 3BNC117 | 36 | 32.4% | 10 | 5.28% | 52/985 |
| 10E8* | 27 | 24.8% | 9 | 4.54% | 45/991 |
| PGDM1400 | 45 | 42.1% | 9 | 36.59% | 360/984 |
| 1B2530 | 40 | 37.4% | 9 | 25.43% | 249/979 |
| PG9* | 18 | 16.8% | 9 | 1.63% | 16/983 |
| PGT135 | 32 | 28.3% | 8 | 15.96% | 157/984 |
| PGT121 | 25 | 23.6% | 8 | 8.61% | 85/987 |
| 2F5* | 16 | 14.8% | 8 | 4.47% | 44/984 |
| PGT145 | 29 | 27.1% | 7 | 25.96% | 256/986 |

Figure 39A

| bnAb | #AA mutations[A] | AA mut freq | # Improbable Mutations (M)[B] | Expected Frequency of >=M[C] | Counts |
|---|---|---|---|---|---|
| VRC34 | 25 | 23.4% | 6 | 32.21% | 315/978 |
| VRC26.25 | 15 | 14.0% | 6 | 23.71% | 234/987 |
| DH270.6 | 23 | 21.5% | 6 | 29.67% | 292/984 |
| CH103 | 26 | 24.5% | 5 | 56.58% | 559/988 |
| 4E10 | 19 | 17.8% | 5 | 46.97% | 465/990 |
| PGT128 | 32 | 28.1% | 4 | 82.36% | 808/981 |
| BF520.1 | 12 | 11.2% | 3 | 84.37% | 831/985 |

A Number of amino acid mutations, excluding CDRH3 region

B The number of improbable mutations M (at <2% cutoff) identified for the BNAb using ARMADiLLO C The expected frequency of M or greater improbable mutations (at <2% cutoff) from simulations of SHM at the BNAb's AA mutation frequency
* Number of improbable mutations in this bnAb exceeds number expected by chance (cutoff=.05) given the mutation frequency of this bnAb

Figure 39A continued

| Epitope | Type | HIV BNAb | Estimated Number of Improbable Mutations[a] | | | | Heavy Chain | | | |
|---|---|---|---|---|---|---|---|---|---|---|
| | | | <2%[b] | <1%[b] | <.1%[b] | <.01%[b] | #AA Muts[c] | # Muts[d] | # Indels[e] | CDR3 Len[f] |
| CD4 | CD4 mimicking VH1-46 derived | CH235.12 | 16 | 10 | 3 | 0 | 45 | 78 | 0 | 13 |
| | | 8ANC131 | 12 | 6 | 1 | 0 | 42 | 79 | 1 | 16 |
| | | 1B2530 | 9 | 6 | 1 | 0 | 40 | 82 | 0 | 16 |
| | | VRC01 | 12 | 3 | 1 | 0 | 43 | 95 | 0 | 12 |
| | CD4 mimicking VH1-2 derived | VRC-CH31 | 12 | 8 | 1 | 0 | 48 | 78 | 9 | 13 |
| | | 3BNC117 | 10 | 8 | 2 | 0 | 40 | 79 | 4 | 10 |
| | | N6 | 12 | 5 | 0 | 0 | 43 | 98 | 0 | 13 |
| | CDRH3 Binder | CH103 | 5 | 2 | 0 | 0 | 26 | 52 | 0 | 13 |
| Glycan-V3 | | DH270.6 | 6 | 4 | 0 | 0 | 23 | 39 | 0 | 18 |
| | | BF520.1 | 3 | 1 | 1 | 0 | 12 | 20 | 0 | 18 |
| | | PGT128 | 4 | 2 | 0 | 0 | 38 | 69 | 6 | 19 |
| | | PGT121 | 8 | 5 | 1 | 0 | 25 | 60 | 0 | 24 |
| | | PGT135 | 8 | 4 | 0 | 0 | 37 | 63 | 5 | 18 |
| Glycan-V1V2 | | PG9 | 9 | 7 | 3 | 0 | 18 | 44 | 0 | 28 |
| | | CH01 | 11 | 6 | 0 | 0 | 29 | 50 | 0 | 24 |
| | | PGT145 | 7 | 4 | 1 | 0 | 29 | 54 | 0 | 31 |
| | | CAP256-VRC26.25 | 6 | 6 | 3 | 1 | 15 | 35 | 0 | 36 |
| | | PGDM1400 | 9 | 5 | 0 | 0 | 45 | 79 | 0 | 32 |
| MPER | | 2F5 | 8 | 6 | 0 | 0 | 16 | 42 | 0 | 22 |
| | | 4E10 | 5 | 3 | 0 | 0 | 19 | 20 | 0 | 18 |
| | | DH511.2 | 11 | 3 | 0 | 0 | 28 | 62 | 0 | 21 |
| | | 10E8 | 9 | 5 | 1 | 0 | 27 | 64 | 0 | 20 |
| gp120-gp41 Interface | | PGT151 | 11 | 7 | 0 | 0 | 27 | 64 | 0 | 26 |
| | | 35022 | 11 | 5 | 0 | 0 | 42 | 74 | 8 | 14 |
| | | N123-VRC34 | 6 | 4 | 2 | 0 | 25 | 45 | 0 | 13 |
| | | 8ANC195 | 13 | 9 | 1 | 0 | 51 | 86 | 7 | 20 |

Figures 39B

| | | | Estimated Number of Improbable Mutations[a] | | | | | | | |
|---|---|---|---|---|---|---|---|---|---|---|
| | | | Light Chain | | | | | | | |
| Epitope | Type | HIV BNAb | <2% [b] | <1% [b] | <.1% [b] | <.01% [b] | #AA Muts[c] | # Muts[d] | # Indels[e] | CDR3 Len[f] |
| CD4 | CD4 mimicking VH1-46 derived | CH235.12 | 6 | 2 | 0 | 0 | 22 | 41 | 0 | 8 |
| | | 8ANC131 | 5 | 2 | 0 | 0 | 27 | 51 | 2 | 9 |
| | | 1B2530 | 4 | 3 | 0 | 0 | 20 | 50 | 0 | 11 |
| | CD4 mimicking VH1-2 derived | VRC01 | 11 | 7 | 1 | 0 | 28 | 55 | 3 | 5 |
| | | VRC-CH31 | 3 | 3 | 2 | 1 | 22 | 42 | 0 | 5 |
| | | 3BNC117 | 6 | 4 | 1 | 0 | 28 | 45 | 4 | 5 |
| | | N6 | 7 | 5 | 2 | 1 | 32 | 66 | 0 | 5 |
| | CDRH3 Binder | CH103 | 4 | 3 | 0 | 0 | 23 | 33 | 3 | 10 |
| Glycan-V3 | | DH270.6 | 5 | 3 | 2 | 0 | 11 | 21 | 0 | 10 |
| | | BF520.1 | 9 | 6 | 2 | 0 | 12 | 15 | 0 | 11 |
| | | PGT128 | 3 | 2 | 0 | 0 | 15 | 21 | 5 | 10 |
| | | PGT121 | 7 | 6 | 2 | 1 | 30 | 48 | 3 | 12 |
| | | PGT135 | 10 | 6 | 2 | 0 | 27 | 45 | 0 | 9 |
| Glycan-V1V2 | | PG9 | 5 | 3 | 1 | 0 | 10 | 21 | 0 | 10 |
| | | CH01 | 5 | 5 | 1 | 0 | 15 | 30 | 0 | 9 |
| | | PGT145 | 5 | 2 | 0 | 0 | 23 | 47 | 0 | 9 |
| | | CAP256-VRC26.25 | 2 | 1 | 0 | 0 | 12 | 24 | 0 | 12 |
| | | PGDM1400 | 5 | 2 | 0 | 0 | 22 | 34 | 0 | 9 |
| MPER | | 2F5 | 2 | 2 | 0 | 0 | 15 | 33 | 0 | 9 |
| | | 4E10 | 5 | 4 | 1 | 0 | 11 | 12 | 0 | 9 |
| | | DH511.2 | 8 | 6 | 2 | 0 | 18 | 42 | 0 | 11 |
| | | 10E8 | 5 | 1 | 0 | 0 | 18 | 38 | 0 | 12 |
| gp120-gp41 Interface | | PGT151 | 6 | 2 | 1 | 0 | 14 | 35 | 0 | 9 |
| | | 35022 | 12 | 7 | 2 | 0 | 36 | 67 | 0 | 10 |
| | | N123-VRC34 | 4 | 3 | 3 | 0 | 12 | 23 | 0 | 9 |
| | | 8ANC195 | 7 | 4 | 0 | 0 | 26 | 44 | 1 | 9 |

Figures 39B continued

| Epitope | Type | HIV BNAb | Estimated Number of Improbable Mutations[a] | | | | Total | | # Indels[e] | CDR3 Len[f] |
|---|---|---|---|---|---|---|---|---|---|---|
| | | | <2%[b] | <1%[b] | <.1%[b] | <.01%[b] | #AA Muts[c] | # Muts[d] | | |
| CD4 | CD4 mimicking VH1-46 derived | CH235.12 | 22 | 12 | 3 | 0 | 67 | 119 | 0 | 21 |
| | | 8ANC131 | 17 | 8 | 1 | 0 | 69 | 130 | 3 | 25 |
| | | 1B2530 | 13 | 9 | 1 | 0 | 60 | 132 | 0 | 27 |
| | CD4 mimicking VH1-2 derived | VRC01 | 23 | 10 | 2 | 0 | 71 | 150 | 3 | 17 |
| | | VRC-CH31 | 15 | 11 | 3 | 1 | 70 | 120 | 9 | 18 |
| | | 3BNC117 | 16 | 12 | 3 | 0 | 68 | 124 | 8 | 15 |
| | | N6 | 19 | 10 | 2 | 1 | 75 | 164 | 0 | 18 |
| | CDRH3 Binder | CH103 | 9 | 5 | 0 | 0 | 49 | 85 | 3 | 23 |
| Glycan-V3 | | DH270.6 | 11 | 7 | 2 | 0 | 34 | 60 | 0 | 28 |
| | | BF520.1 | 12 | 7 | 3 | 0 | 24 | 35 | 0 | 29 |
| | | PGT128 | 7 | 4 | 0 | 0 | 53 | 90 | 11 | 29 |
| | | PGT121 | 15 | 11 | 3 | 1 | 55 | 108 | 3 | 36 |
| | | PGT135 | 18 | 10 | 2 | 0 | 64 | 108 | 5 | 27 |
| Glycan-V1V2 | | PG9 | 14 | 10 | 4 | 0 | 28 | 65 | 0 | 38 |
| | | CH01 | 16 | 11 | 1 | 0 | 44 | 80 | 0 | 33 |
| | | PGT145 | 12 | 6 | 1 | 0 | 52 | 101 | 0 | 40 |
| | | CAP256-VRC26.25 | 8 | 7 | 3 | 1 | 27 | 59 | 0 | 48 |
| | | PGDM1400 | 14 | 7 | 0 | 0 | 67 | 113 | 0 | 41 |
| MPER | | 2F5 | 10 | 8 | 0 | 0 | 31 | 75 | 0 | 31 |
| | | 4E10 | 10 | 7 | 1 | 0 | 30 | 32 | 0 | 27 |
| | | DH511.2 | 19 | 9 | 2 | 0 | 46 | 104 | 0 | 32 |
| | | 10E8 | 14 | 6 | 1 | 0 | 45 | 102 | 0 | 32 |
| gp120-gp41 Interface | | PGT151 | 17 | 9 | 1 | 0 | 41 | 99 | 0 | 35 |
| | | 35022 | 23 | 12 | 2 | 0 | 78 | 141 | 8 | 24 a Probability of mutations in the absence of selection estimated by the ARMADiLLO program. Due to inconsistent certainty in the inference of the CDRH3 region between BNAbs, only mutations outside the CDR3 were used.
b Improbable mutation count at probability cutoff of <2%, <1%, <0.1% or <.01%
c Number of amino acid mutations
d Number of nucleotide mutations
e Number of amino acids inserted or deleted relative to the unmutated common ancestor sequence
f CDR3 length (defined for heavy chain starting at 3rd residue after 2nd invariant CYS; defined for light chain starting at 1st residue after 2nd invariant CYS)
g Geometric mean potency of neutralization (IC50 ug/ml) with undetected neutralization set to 100
h Neutralization breadth in a 12-virus panel representative of the global HIV population
i Number of viruses in the global 12 virus panel for which neutralization was tested

| Epitope | Type | HIV BNAb | Neutralization | | # Tested in Global Panel[i] |
|---|---|---|---|---|---|
| | | | Geo Mean Potency[g] | Global12 Breadth[h] | |
| CD4 | CD4 mimicking VH1-46 derived | CH235.12 | 0.69 | 100% | 12 |
| | | 8ANC131 | 10.23 | 100% | 4 |
| | | 1B2530 | 2.74 | 100% | 3 |
| | CD4 mimicking VH1-2 derived | VRC01 | 0.59 | 92% | 12 |
| | | VRC-CH31 | 0.20 | 92% | 12 |
| | | 3BNC117 | 0.29 | 92% | 12 |
| | | N6 | 0.08 | 100% | 6 |
| | CDRH3 Binder | CH103 | 3.11 | 80% | 5 |
| Glycan-V3 | | DH270.6 | 0.59 | 67% | 12 |
| | | BF520.1 | 5.28 | 82% | 11 |
| | | PGT128 | 0.04 | 83% | 12 |
| | | PGT121 | 0.30 | 64% | 11 |
| | | PGT135 | 9.36 | 50% | 4 |
| Glycan-V1V2 | | PG9 | 0.17 | 92% | 12 |
| | | CH01 | 2.26 | 75% | 12 |
| | | PGT145 | 0.05 | 86% | 7 |
| | | CAP256-VRC26.25 | 0.01 | 78% | 9 |
| | | PGDM1400 | 0.02 | 100% | 7 |
| MPER | | 2F5 | 17.40 | 50% | 12 |
| | | 4E10 | 3.09 | 100% | 12 |
| | | DH511.2 | 0.25 | 100% | 12 |
| | | 10E8 | 0.21 | 100% | 12 |
| gp120-gp41 Interface | | PGT151 | 0.26 | 83% | 12 |
| | | 35O22 | 2.50 | 58% | 12 |
| | | N123-VRC34 | 7.49 | 42% | 12 |
| | | 8ANC195 | 1.60 | 83% | 12 |

Figures 39B continued

| Protein ID |
|---|
| CH848.3.D0949.10.17chim.6R.DS.SOSIP.664 |
| CH848.3.D0949.10.17chim.6R.DS.SOSIP.664_N301A |

> CH848.3.D0949.10.17chim.6R.DS.SOSIP.664
MGSLQPLATLYLLGMLVASVLAAENLWVTVYYGVPVWKEAKTTLFCASDARAYEKEVHNVWATHA
CVPTDPSPQELVLGNVTENFNMWKNDMVDQMHEDIISLWDQSLKPCVKLTPLCVTLICSNATVKNGT
VEEMKNCSFNTTTEIRDKEKKEYALFYKPDIVPLSETNNTSEYRLINCNTSACTQACPKVTFEPIPIHYCA
PAGYAILKCNDETFNGTGPCSNVSTVQCTHGIRPVVSTQLLLNGSLAEKEIVIRSENLTNNAKIIIVHLHT
PVEIVCTRPNNNTRKSVRIGPGQTFYATGDIIGDIKQAHCNISEEKWNDTLQKVGIELQKHFPNKTIKYN
QSAGGDMEITTHSFNCGGEFFYCNTSNLFNGTYNGTYISTNSSANSTSTITLQCRIKQIINMWQGVGRC
MYAPPIAGNITCRSNITGLLLTRDGGTNSNETETFRPAGGDMRDNWRSELYKYKVVKIEPLGVAPTRCK
RRVVGRRRRRAVGIGAVFLGFLGAAGSTMGAASMTLTVQARNLLSGIVQQQSNLLRAPEAQQHLLK
LTVWGIKQLQARVLAVERYLRDQQLLGIWGCSGKLICCTNVPWNSSWSNRNLSEIWDNMTWLQWDK
EISNYTQIIYGLLEESQNQQEKNEQDLLALD**

> CH848.3.D0949.10.17chim.6R.DS.SOSIP.664_N301A
MGSLQPLATLYLLGMLVASVLAAENLWVTVYYGVPVWKEAKTTLFCASDARAYEKEVHNVWATHA
CVPTDPSPQELVLGNVTENFNMWKNDMVDQMHEDIISLWDQSLKPCVKLTPLCVTLICSNATVKNGT
VEEMKNCSFNTTTEIRDKEKKEYALFYKPDIVPLSETNNTSEYRLINCNTSACTQACPKVTFEPIPIHYCA
PAGYAILKCNDETFNGTGPCSNVSTVQCTHGIRPVVSTQLLLNGSLAEKEIVIRSENLTNNAKIIIVHLHT
PVEIVCTRPNANTRKSVRIGPGQTFYATGDIIGDIKQAHCNISEEKWNDTLQKVGIELQKHFPNKTIKYN
QSAGGDMEITTHSFNCGGEFFYCNTSNLFNGTYNGTYISTNSSANSTSTITLQCRIKQIINMWQGVGRC
MYAPPIAGNITCRSNITGLLLTRDGGTNSNETETFRPAGGDMRDNWRSELYKYKVVKIEPLGVAPTRCK
RRVVGRRRRRAVGIGAVFLGFLGAAGSTMGAASMTLTVQARNLLSGIVQQQSNLLRAPEAQQHLLK
LTVWGIKQLQARVLAVERYLRDQQLLGIWGCSGKLICCTNVPWNSSWSNRNLSEIWDNMTWLQWDK
EISNYTQIIYGLLEESQNQQEKNEQDLLALD**

Figure 41

METHODS TO IDENTIFY IMMUNOGENS BY TARGETING IMPROBABLE MUTATIONS

This application claims the benefit of and priority to U.S. Application Ser. No. 62/403,635 filed Oct. 3, 2016, U.S. Application Ser. No. 62/476,985 filed Mar. 27, 2017, U.S. Application Ser. No. 62/489,250 filed Apr. 24, 2017, U.S. Application Ser. No. 62/403,649 filed Oct. 3, 2016, and International Application No. PCT/US17/20823 filed Mar. 3, 2017, published as WO/2017/152146 on Sep. 8, 2017, the entire content of each application is herein incorporated by reference.

GOVERNMENT SUPPORT

This invention was made with government support under Grant No. AI 100645 awarded by the National Institutes of Health. The government has certain rights in the invention.

TECHNICAL FIELD

The present invention relates, in general, to human immunodeficiency virus (HIV), and, in particular, to HIV-1 broadly neutralizing antibodies (bnAbs) and methods to define the probability of bnAb mutations and determine the functional significance of improbable mutations in bnAb development. The invention also relates to antibodies comprising such improbable mutation, antigens which bind to antibodies comprising such improbable mutations, and methods to identify such antigens. The invention also relates to immunogenic compositions comprising such antigens, and method for their use in vaccination regimens.

BACKGROUND

Development of an effective vaccine for prevention of HIV-1 infection is a global priority. To provide protection, an HIV-1 vaccine should induce broadly neutralizing antibodies (bnAbs). However, BnAbs have not been successfully induced by vaccine constructs thus far.

SUMMARY OF THE INVENTION

HIV-1 broadly neutralizing antibodies (bnAbs) require high levels of activation-induced cytidine deaminase (AID) catalyzed somatic mutations for optimal neutralization potency. Probable mutations occur at sites of frequent AID activity, while improbable mutations occur where AID activity is infrequent. One bottleneck for induction of bnAbs is the evolution of viral envelopes (Envs) that can select bnAb B cell receptors (BCR) with improbable mutations. The invention provides methods to define the probability of bnAb mutations and demonstrate the functional significance of improbable mutations in heavy and/or light antibody chains in bnAb development. In some aspects the invention provides that bnAbs are enriched for improbable mutations, thus elicitation of at least some improbable mutations will be critical for successful vaccine induction of potent bnAb B cell lineages.

In some aspects the invention provides a mutation-guided vaccine strategy for identification of Envs that can select B cells with BCRs with key improbable mutations required for bnAb development. The analysis described herein suggests that through generations of viral escape, Env trimers evolved to hide in low probability regions of antibody sequence space.

In some aspects the invention provides methods to determine the probability of any amino acid at any position at a given mutation frequency in heavy and light antibody chains during antibody maturation.

In one aspect the invention is directed to methods of identifying and targeting improbable mutations critical for BNAb development as a vaccine design strategy.

In certain aspects the invention is directed to methods to identify functionally important improbable mutations occurring during maturation of a broad neutralizing antibody clone. The invention is directed to methods to identify antigens which specifically or preferentially bind antibodies with these functionally important improbable mutation(s). Without being bound by theory, these improbable mutations are limiting steps in the maturation of antibodies. Identifying these functional mutations and antigens which bind to antibodies comprising such functional mutations is expected to provide a series of immunogens which start a lineage by targeting the B-cell receptor, and guide antibody maturation to desired functional characteristics, e.g. but not limited to antibody breadth, potency, etc.

The invention is directed to methods of identifying immunogens which induce broad neutralizing antibodies to a desired antigen, comprising: determining the probability of any amino acid at any position at a given mutation frequency in heavy and light antibody chains; identifying improbable mutations in a mature member of a broad neutralizing antibody lineage; making those antibody mutants; and functionally validating their importance by testing for effect in binding and neutralization breadth; identifying and selecting antigens, e.g. but not limited to HIV-1 envelopes, that preferentially bind those improbable and important mutations, wherein these selected antigens are used as immunogens, which are expected to direct maturation of an antibody clone for example but not limited to having broad neutralization properties.

In some aspects the invention is directed to methods to identify important mutations which drive affinity maturation of a desired antibody. The methods of the invention comprise:
 a. Identifying/providing a first/mature antibody with desired properties, e.g. but not limited to an HIV-1 bnAb; providing includes without limitation providing the amino acid and/or nucleic acid sequence of an antibody which has desired functional characteristics;
 b. Identifying or computationally deducing the unmutated common ancestor (UCA) and/or intermediates; wherein in some embodiments the UCA is deduced based on a single antibody with desired properties; where in some embodiments the UCA is deduced based on information of multiple intermediate antibody sequences, for example sequences organized in an antibody clonal tree;
 c. Identifying and ranking mutations in the first/mature antibody compared to the UCA the intermediates and, for example but not limited to % mutation and # of mutation in the mature antibody, and/or intermediates, in some embodiments mutations are improbable if their probability is less than 2%; in some embodiments these mutations are identified by a computations program called ARMADILLO;
 d. Determining which mutations are functionally important, e.g. for affinity binding and/or neutralization, or any other functional characteristics, by the antibody or intermediates against a panel of homologous and heterologous antigens (e.g. HIV envelopes and viruses);

e. Based on (d) identifying the one or more functional mutations which are important for the affinity maturation and/or development of neutralization breadth of the desired antibody;
f. Recombinantly expressing a UCA antibody(ies) and one or more antibody(ies) comprising a functional mutation(s); and
g. Identifying antigens which bind differentially to the UCA antibody(ies) and an antibody(ies) comprising functional mutation(s).

In certain aspects the invention provides methods to identifying antigens which bind preferentially to important antibody mutations, thereby selecting these important mutations and driving the maturation of the antibody lineage.

In certain aspects, the invention provides methods to induce an immune response comprising administering immunogens identified by the methods of the invention.

In certain aspects, the invention provides that improbable mutations to critical amino acids are potential bottlenecks in the development of breadth and/or potency in BNAb lineages. In certain aspects, the invention provides methods to identify these improbable mutations by simulating somatic hypermutation, and identifying functionally important improbable mutations. In certain aspects, the invention provides methods to select improbable mutations by identifying or designing immunogens that bind UCA or antibodies with these improbable mutations, wherein binding could be preferentially and/or with high specificity, affinity or avidity.

In certain aspects, the invention is directed methods for identifying improbable mutations in the heavy or light chains of a mature, non-germline, non-UCA antibody, wherein in some embodiments the non-germline antibody is broadly neutralizing anti-HIV-1 antibody comprising:
(a) identifying at least one rare/improbable somatic mutation in the heavy or light chain variable domain of a broadly neutralizing anti-HIV-1 antibody, wherein before/without/in the absence of antigenic selection the rare/improbable somatic mutation occurs at a frequency of less than 2% in the sequence of an unmutated common ancestor antibody of the broadly neutralizing anti-HIV-1 antibody;
(b) selecting the amino acid sequence of the broadly neutralizing anti-HIV-1 antibody of step (a) and reverting the at least one somatic mutation identified in step (a) to its germline-encoded amino acid(s) to thereby provide a reverted recombinant antibody;
(c) expressing the reverted recombinant antibody of step (b) and testing the reverted expressed recombinant antibody for neutralizing activity against an HIV-1 virus or for binding ability against the envelope of an HIV-1 virus, and
(d) determining whether the rare/improbable somatic mutation identified in step (a) is an improbable functional mutation, wherein the somatic mutation identified in step (a) is an improbable functional mutation if the expressed reverted recombinant antibody of step (c) exhibits a reduction of neutralizing activity or reduction of envelope binding as compared to an antibody with the same amino acid sequence but for the reverted amino acid sequence.

In certain aspects, the invention provides methods to identify HIV-1 vaccine antigens that specifically or preferentially bind an antibody with an improbable functional mutation comprising:
(a) identifying at least one somatic mutation in the heavy or light chain variable domain of a mature, non-germline, non-UCA antibody, wherein in some embodiments the non-germline antibody is broadly neutralizing anti-HIV-1 antibody, wherein before antigenic selection the somatic mutation occurs at a frequency of less than 2% in an ancestor antibody of the broadly neutralizing anti-HIV-1 antibody;
(b) selecting the amino acid sequence of the broadly neutralizing anti-HIV-1 antibody of step (a) and reverting the at least one somatic mutation identified in step (a) to its germline-encoded amino acid(s) to thereby provide a recombinant antibody;
(c) expressing the recombinant antibody of step (b) and testing the expressed recombinant antibody for neutralizing activity against an HIV-1 virus or for binding ability against the envelope of an HIV-1 virus;
(d) determining whether the somatic mutation identified in step (a) functionally significant by testing whether the expressed recombinant antibody of step (c) exhibits a reduction of neutralizing activity or reduction of envelope binding as compared to an antibody with the same amino acid sequence but for the reverted amino acid sequence; and
(e) testing whether an anti-HIV-1 antibody with the improbable mutation determined to be functionally significant in step (d) binds to an HIV-1 antigen with high affinity, wherein if the anti-HIV-1 antibody binds with high affinity to the HIV-1 antigen, then the antigen is identified as an HIV-1 vaccine antigen.

In certain embodiments of the methods, the HIV-1 vaccine antigen identified in step (e) is administered to a subject in an amount sufficient to induce the production of broadly neutralizing anti-HIV-1 antibodies in the subject. In certain aspects, the invention provides methods of inducing an immune response in a subject comprising administering the antigen identified in step (e) of the preceding claims, wherein the antigen is administered in an amount sufficient to effect such induction.

In certain embodiments of the methods, wherein before antigenic selection the improbable mutation occurs at a frequency of less than 1%, or 0.1% in an ancestor antibody of the broadly neutralizing anti-HIV-1 antibody lineage.

In certain embodiments of the methods, determining whether a mutation is improbable comprises antibody VH and/or VL sequence analysis with the ARMADiLLO program. In certain embodiments, the calculation of the frequency of the somatic mutation occurring in the ancestor antibody prior to antigenic selection is conducted with the ARMADiLLO program.

In certain embodiments, an anti-HIV-1 antibody comprising an improbable functional mutation(s) binds with high affinity or has differential binding to an HIV-1 envelope antigen. In certain embodiments, the antibody binds with a $K_D$ of least $10^{-8}$ or $10^{-9}$ to an HIV-1 envelope antigen.

In certain embodiments, testing the expressed recombinant antibody for neutralizing activity is conducted against a heterologous, difficult-to-neutralize HIV-1 virus. In certain embodiments, the rare/improbable somatic mutation identified by the methods is an improbable functional mutation if the expressed recombinant antibody of step (c) exhibits at least a 25% reduction of neutralizing activity as compared to an antibody with the same amino acid sequence but for the reverted amino acid sequence. In certain embodiments, the rare/improbable somatic mutation identified in step (a) is an improbable functional mutation if the expressed recombinant antibody of step (c) exhibits substantially no neutralizing activity as compared to an antibody with the same amino acid sequence but for the reverted amino acid sequence. In certain embodiments, the rare/improbable somatic mutation identified in step (a) is an improbable functional mutation if the expressed recombinant antibody of step (c) exhibits a reduction of envelope binding of least one order of magnitude of $K_D$ as compared to an antibody with the same amino acid sequence but for the reverted amino acid sequence. In certain embodiments, high affinity is a $K_D$ of at least $10^{-8}$ or $10^{-9}$.

In certain embodiments, the methods comprise isolating the mature non-germline antibody and determining the amino acid and/or nucleic acid sequence of the heavy or light chain variable domain(s). In certain embodiments, the methods comprising isolating and determining the amino acid and/or nucleic acid sequence of the heavy or light chain variable domain of at least one additional antibody clonally related to the non-germline antibody.

In certain embodiments, the methods comprise determining or inferring the sequence of the unmutated common ancestor antibody.

In certain embodiments, improbable somatic mutation is any one of the mutations described herein, including without limitations the improbable mutations in FIG. 36. In certain embodiments, the broad neutralizing antibody is any one of the antibodies in FIG. 36.

In certain embodiments, two non-limiting examples of antigens identified in step (e) are listed in FIG. 41.

In certain aspect the invention provides a recombinant heavy or light chain variable domain polypeptide of a mature antibody, which in some embodiment is a broadly neutralizing anti-HIV-1 antibody, wherein the sequence of at least the VH or the VL polypeptide, or both polypeptides, comprises at least one improbable mutation, and wherein the sequence of each polypeptide and the position of the improbable mutation are listed in FIG. 36. An antibody or a functional fragment thereof, wherein the antibody comprises a heavy and a light chain variable domain polypeptide of a broadly neutralizing anti-HIV-1 antibody, wherein the sequence of at least the VH or the VL polypeptide, or both polypeptides, comprises at least one improbable mutation, and wherein the sequence of each polypeptide of the broadly neutralizing anti-HIV-1 antibody and the position of the improbable mutation are listed in FIG. 36. FIGS. 39A and 39B show the estimated number of improbable mutation count at a probability cut off of less than 2%, less than 1%, less 0.1% or less than 0.01%.

In certain embodiments, the invention provides methods to identify an HIV-1 antigen which binds to an anti-HIV-1 antibody comprising: testing whether a first anti-HIV-1 antibody with an improbable functional mutation binds to an HIV-1 antigen with high or differential affinity compared to a second antibody which has the same sequence but for the improbable mutation(s), wherein the first anti-HIV-1 antibody comprises a heavy or light chain variable domain polypeptide with at least one improbable mutation, and wherein the sequence of each polypeptide and the position of the improbable mutation is listed in FIG. 36, and wherein if the anti-HIV-1 antibody with an improbable mutation binds with high or differential affinity to the HIV-1 antigen, then the antigen is identified as an HIV-1 vaccine antigen. The rare mutation position in the second "comparator" antibody could be occupied by any suitable amino acid. In certain embodiments the first antibody does not comprise all improbable mutations identified in the mature antibodies listed in FIG. 36. In certain embodiments, the first antibody does not comprise the combination(s) of improbable mutations present in intermediate antibodies which are members of known lineages of the broad neutralizing antibodies of FIG. 36.

BRIEF DESCRIPTION OF THE DRAWINGS

The patent or application file contains at least one drawing executed in color. To conform to the requirements for PCT patent applications, many of the figures presented herein are black and white representations of images originally created in color.

FIGS. 2A-D. Heterologous breadth in the DH270 lineage. (A) Neutralizing activity of DH270.1, DH270.5 and DH270.6 bnAbs (columns) for 207 tier 2 heterologous viruses (rows). Coloring is by neutralization $IC_{50}$ (µg/ml). The first column displays presence of a PNG site at position 332 (blue), N334 (orange) or at neither one (black). The second column indicates the Glade of each individual HIV-1 strain and is color coded as indicated: Glade A: green; Glade B: blue; Glade C: yellow; Glade D: purple; CRF01: pink; Glade G: cyan; others: gray. See also FIG. 33 of WO/2017/152146. (B). Heterologous neutralization of all DH270 lineage antibodies for a 24-virus panel. Color coding for presence of PNG sites, Glade and $IC_{50}$ is the same of panel A. See also FIGS. 7A-D; FIGS. 34-35 of WO/2017/152146. (C) Co-variation between $V_H$ mutation frequencies (x-axis), neutralization breadth (y-axis, top panels) and potency (y-axis, bottom panels) of individual antibodies against viruses with a PNG site at position N332 from the larger (left) and smaller (right) pseudovirus panels. (D) Correlation between viral V1 loop length and DH270 lineage antibody neutralization. Top panel: neutralization of 17 viruses (with N332 and sensitive to at least one DH270 lineage antibody) by selected DH270 lineage antibodies from UCA to mature bnAbs (x-axis). Viruses are identified by their respective V1 loop lengths (y-axis); for each virus, neutralization sensitivity is indicated by an open circle and resistance by a solid circle. The p-value is a Wilcoxon rank sum comparison of V1 length distributions between sensitive and resistant viruses. Bottom panel: regression lines ($IC_{50}$ for neutralization vs. V1 loop length) for DH270.1 and DH270.6, with a p-value based on Kendall's tau.

FIGS. 2A-D.

FIGS. 7A-D. Characteristics of DH270 lineage monoclonal antibodies. (A) Immunogenetics of DH270 lineage monoclonal antibodies. (B) Phylogenetic relationship of VHDJH rearrangements of the unmutated common ancestor (DH270.UCA) and maturation intermediates DH270.IA1 through DH270.IA4 inferred from mature antibodies DH270.1 through DH270.5. DH270.6 was not included and clusters close to DH270.4 and DH270.5 as shown in FIG. 1. (C) Amino acid alignment of the VHDJH rearrangements of the inferred UCA and intermediate antibodies and DH270.1 through DH270.6 mature antibodies. (D) Amino acid alignment of VLJL rearrangements of the inferred UCA and intermediate antibodies and DH270.1 through DH270.6 mature antibodies. For DH270.6, all experimental data presented in this manuscript were obtained using the light chain sequence reported here. The light chain sequence of DH270.6 was subsequently revised to amino acids Q and A in positions 1 and 3 (instead of T and L). This difference did not affect neutralization and binding of DH270.6.

FIGS. 8A-C. DH270 lineage displays a N332-dependent V3 glycan bnAb functional profile. (A) DH270 antibody lineage neutralization of five HIV-1 pseudoviruses and respective N332A mutants. Data are expressed as IC50 µg/ml. Positivity <10 µg/ml is shown in bold. (B, C) DH270.1 ability to compete gp120 Env binding of V3 glycan bnAbs PGT125 and PGT128. Inhibition by cold PGT125 or PGT128 (grey line) was used as control (see Methods).

FIGS. 9A-D. DH475 and DH272 are strain-specific, N332-glycan dependent antibodies. (A) Phylogenetic trees of DH475 (top) and DH272 (bottom) clonal lineages. External nodes (filled circles) representing VHDJH observed sequences retrieved from cultured and sorted memory B cells (labeled) or NGS antibody sequences (unlabeled) are colored according to time point of isolation. Internal nodes (open circles) represent inferred ancestral intermediate sequences. Branch length estimates units are nucleotide substitution per site. (B) Immunogenetics of DH475 and DH272 monoclonal antibodies; (C) Binding of DH475 (top) and DH272 (bottom) monoclonal antibodies to wild-type CH848TF gp120 Env (wild-type (wt), on the x-axis, and mutants with disrupted the 301 and/or 332 N-linked glycosylation sites. Results are expressed as LogAUC. (D) Heterologous neutralization profile of DH475 and DH272 monoclonal antibodies expressed as IC50 µg/ml on a multiclade panel of 24 viruses. White square indicates IC50>50 µg/ml, the highest antibody concentration tested. Clades are reported on the left and virus identifiers on the right. DH475 neutralized no heterologous viruses and DH272 neutralized one Tier 1 heterologous virus.

FIG. 14. Accumulation of amino acid mutations in CH848 virus over time. This figure shows all of the readily aligned positions near the contact site of V3 glycan antibodies in FIGS. 13A-B, (excluding amino acids that are embedded in the V1 hypervariable regions). The magenta 0 is a PNG site, whereas an N is an Asn that is not embedded in a glycosylation site. The logo plots represent the frequency of amino acids at each position, and the TF amino acid is left blank to highlight the differences over time.

FIGS. 21A-C. Sequence and structural comparison of DH270.UCA1 and DH270.UCA3. Sequence alignments of UCA3 and UCA1. (A) Heavy chains and (B) light chains, whose structures were obtained in this study, are aligned with UCA4, the germline antibody for the DH270 lineage (DH270.UCA). The UCA3 and UCA4 light chains are identical. Asterisks indicate positions in which the amino acids are the same. Colon ":", period "." and blanks " " correspond to strictly conserved, conserved and major differences, respectively. (C) Superposition of UCA3 (cyan) and UCA1 (gray). Structural differences in CDR regions are indicated with an arrow.

FIG. 28. Example of an immunization regimen derived from studies of virus-bnAb coevolution in CH848. An immunization strategy composed of the following steps: first, prime with an immunogen that binds the UCA and the boost with immunogens with the following characteristics: i. engagement of DH270.IA4-like antibodies and selection for the G57R mutation; ii. Selection of antibodies that favor recognition of trimeric Env and expand the variation in the autologous signature residue to potentially expand recognition of diversity in population; iii. Exposing maturing antibodies to viruses with longer loops, even though these viruses are not bound or neutralized as well as viruses with shorter V1 loops, as this is the main constrain on antibody heterologous population neutralization breadth.

FIGS. 31A-B. BnAbs are enriched for improbable antibody mutations. (A) Table of improbable mutations for a representative set of bnAbs (B) Histogram for the distributions of number of improbable mutations from antibody heavy chain sequences from three groups: "RV144-induced" antibodies were isolated from RV144 vaccinated subjects by antigenically sorting with RV144 immunogens (red shaded area); "Uninfected" antibodies correspond to duplicated NGS reads from IgG antibodies isolated from PBMC samples from 8 HIV-uninfected individuals (blue shaded area; see methods for details on sampling); a representative set of published bnAb antibody sequences are shown labeled above dotted lines that correspond to their number of improbable mutations (at the <2% level).

Figure 33A:
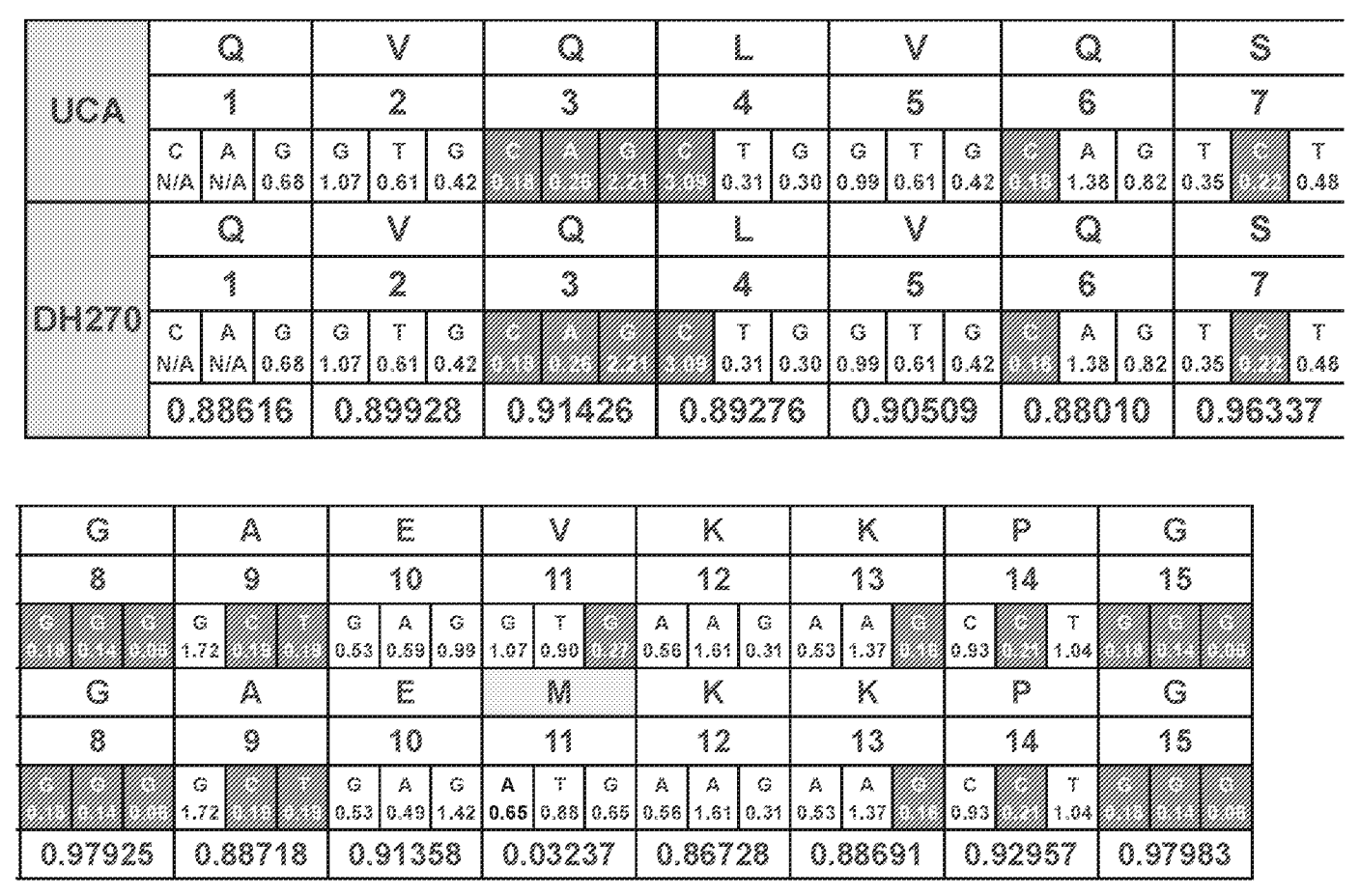
Figure 33A:
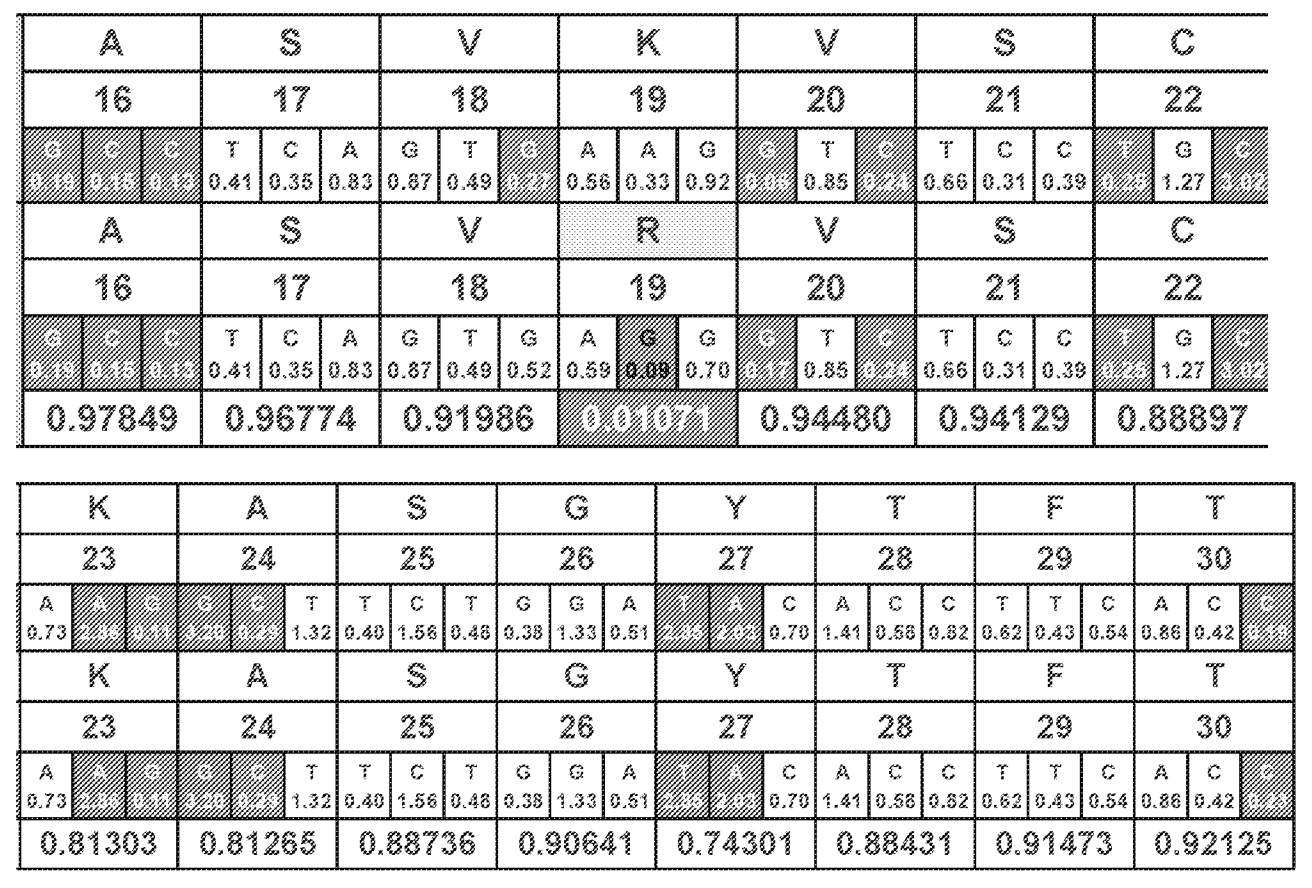
Figure 33A:
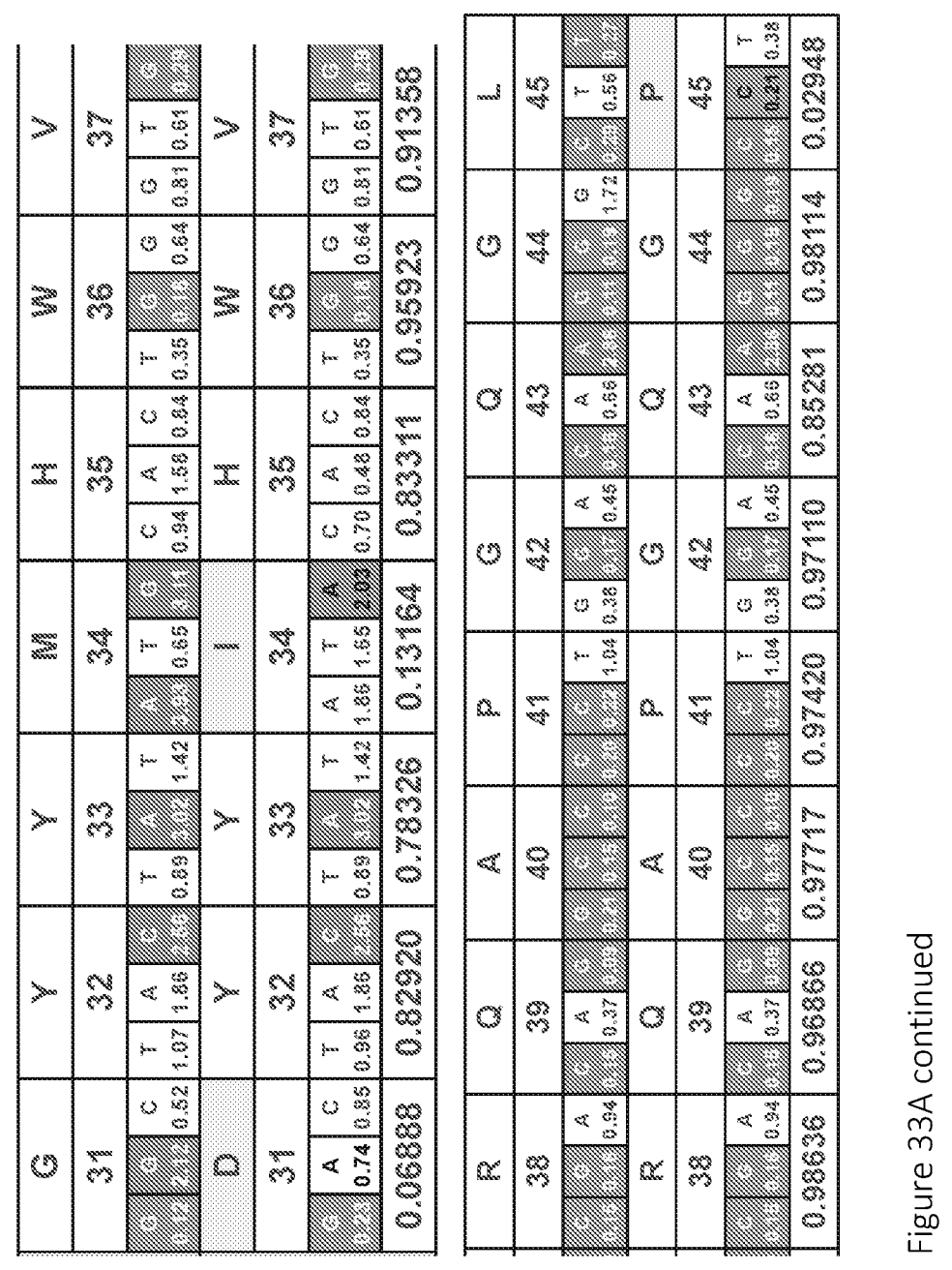
Figure 33A:
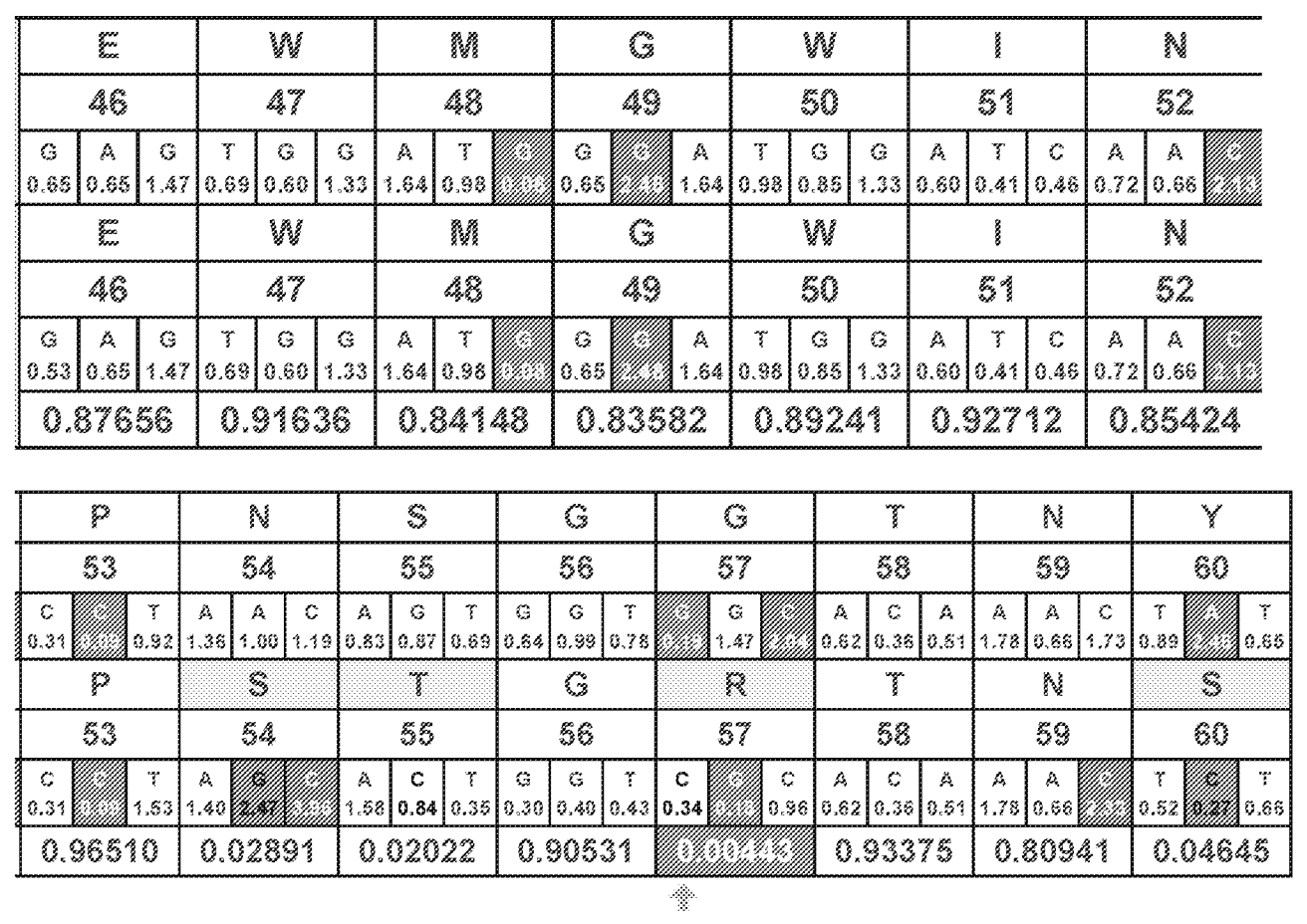
Figure 33A:
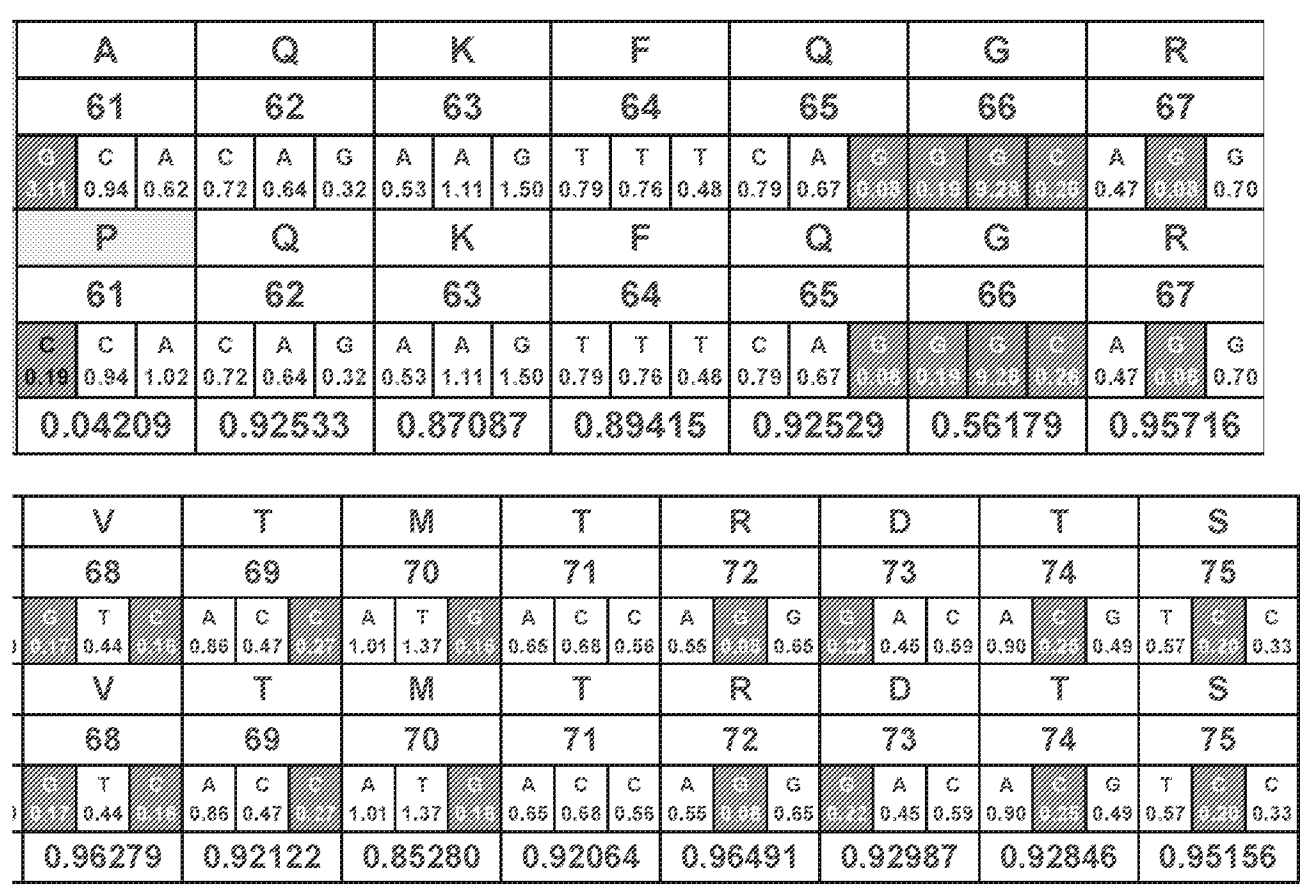
Figure 33A:
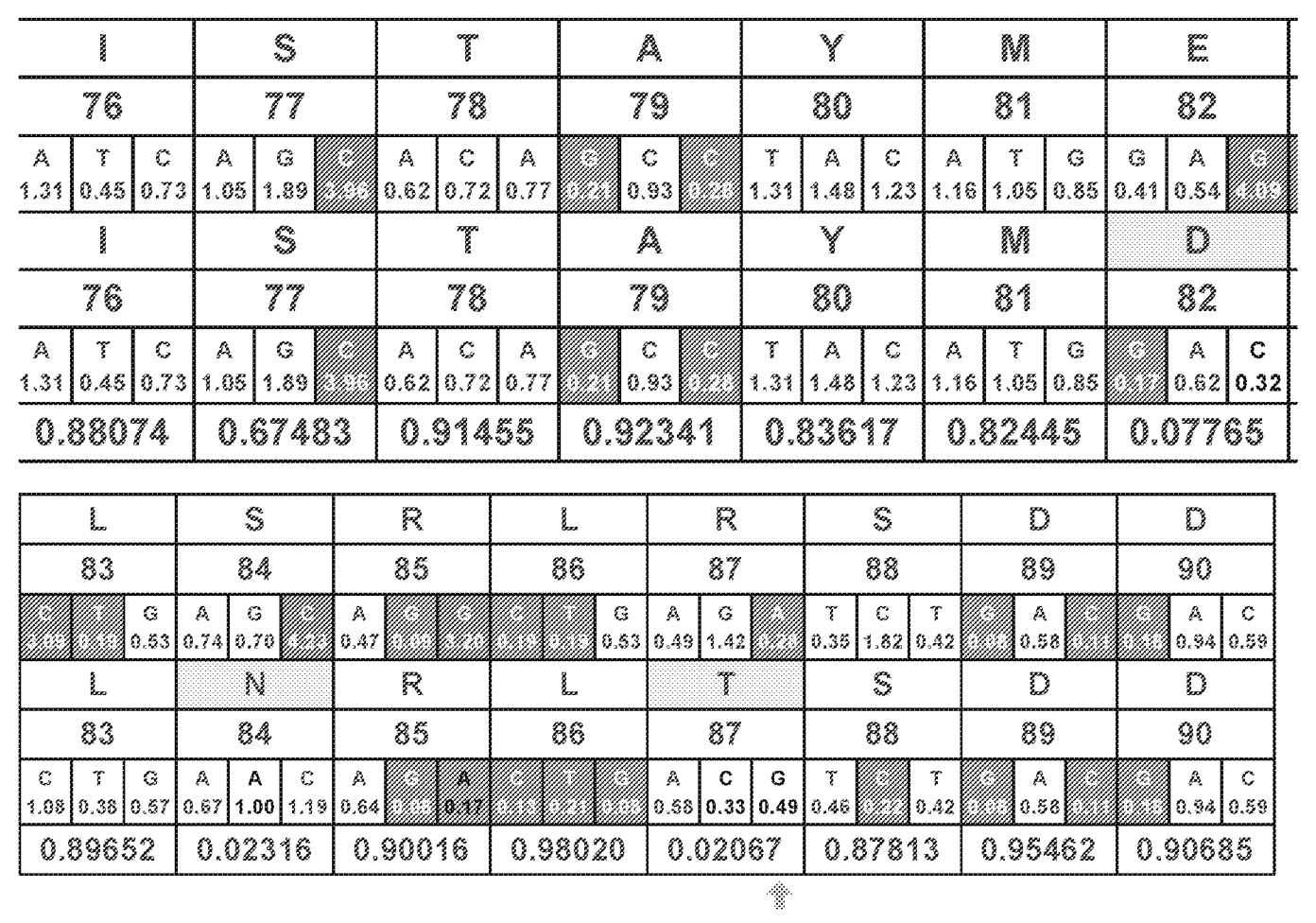
Figure 33A:
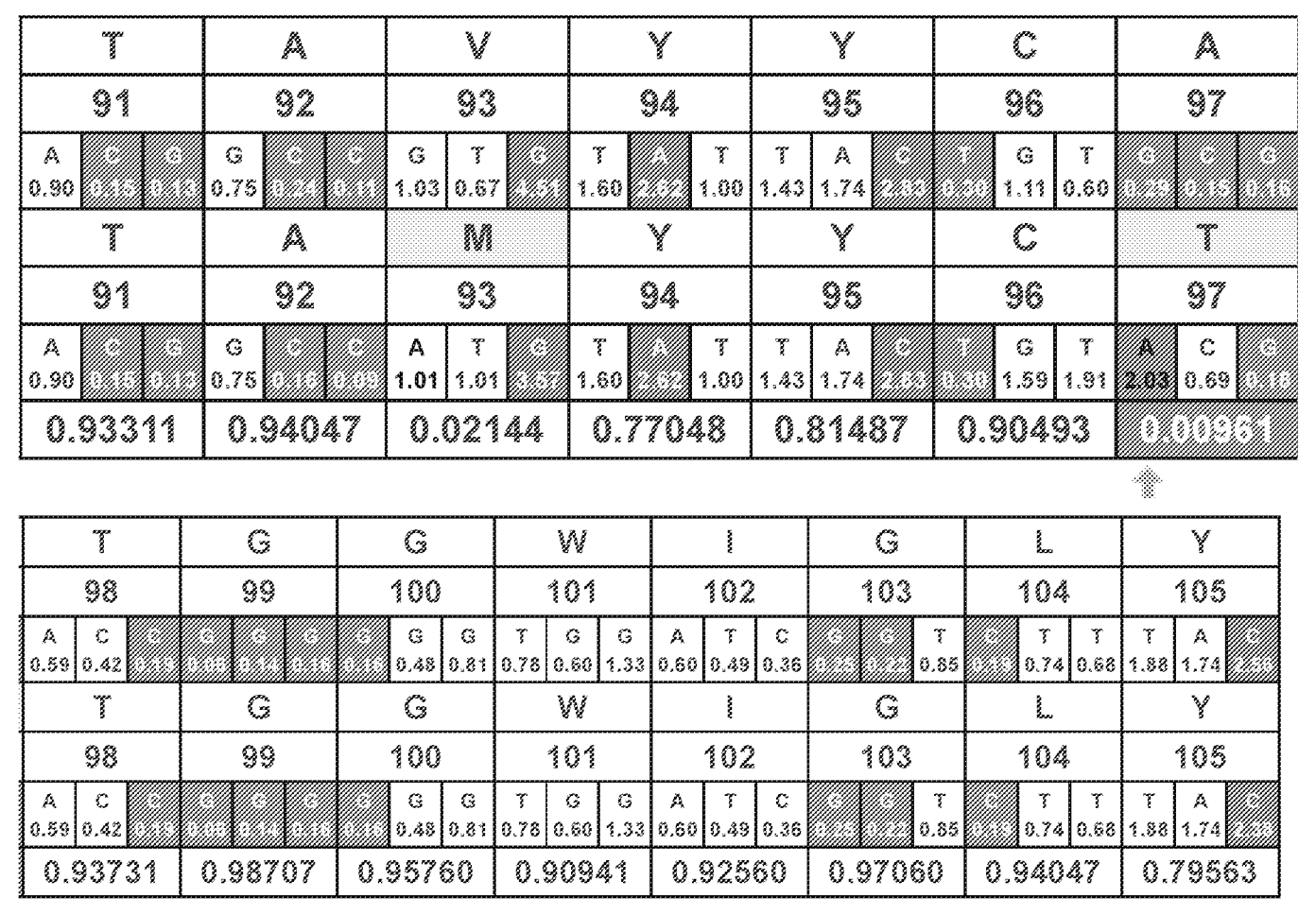
Figure 33A:
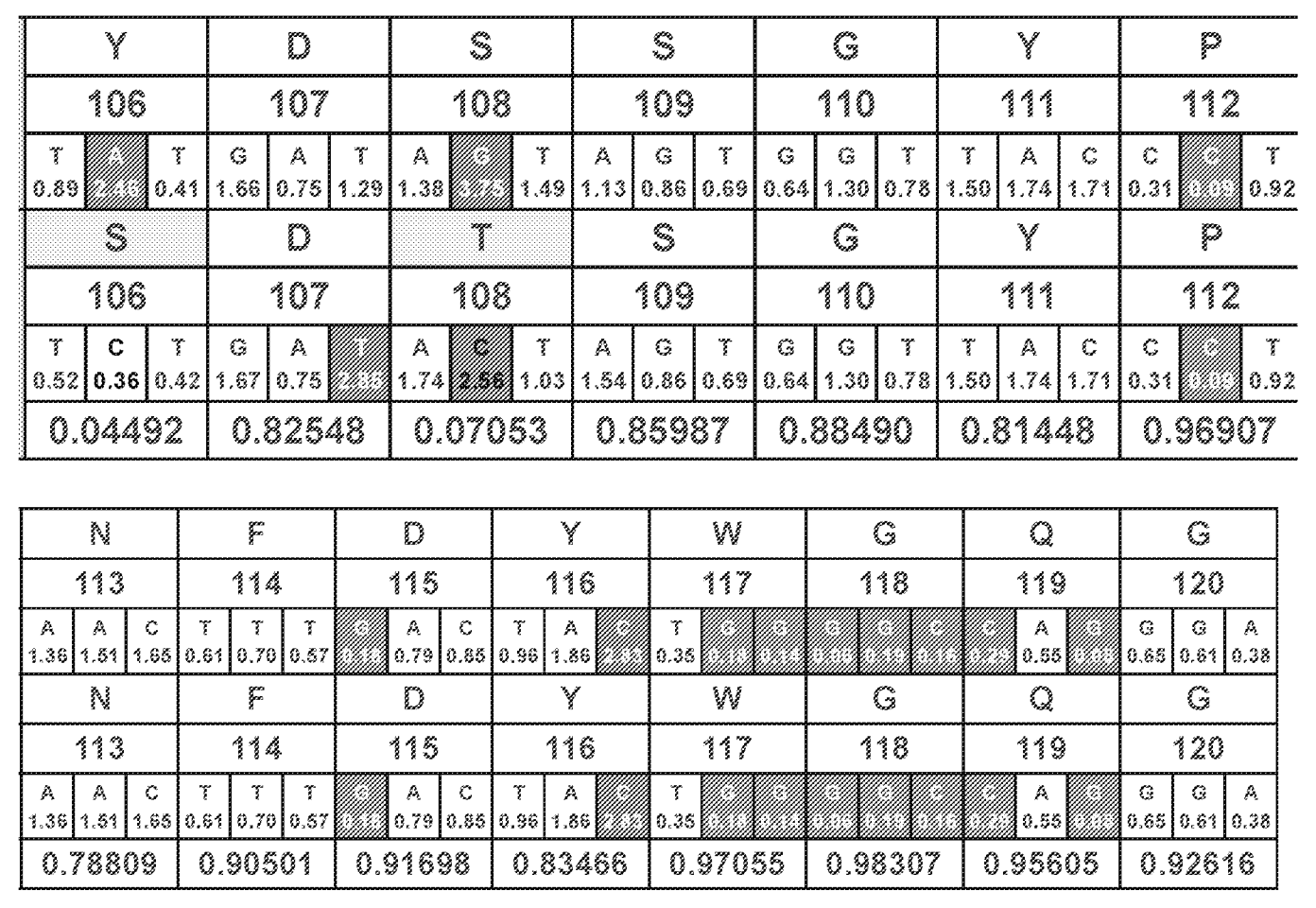
Figure 33B:
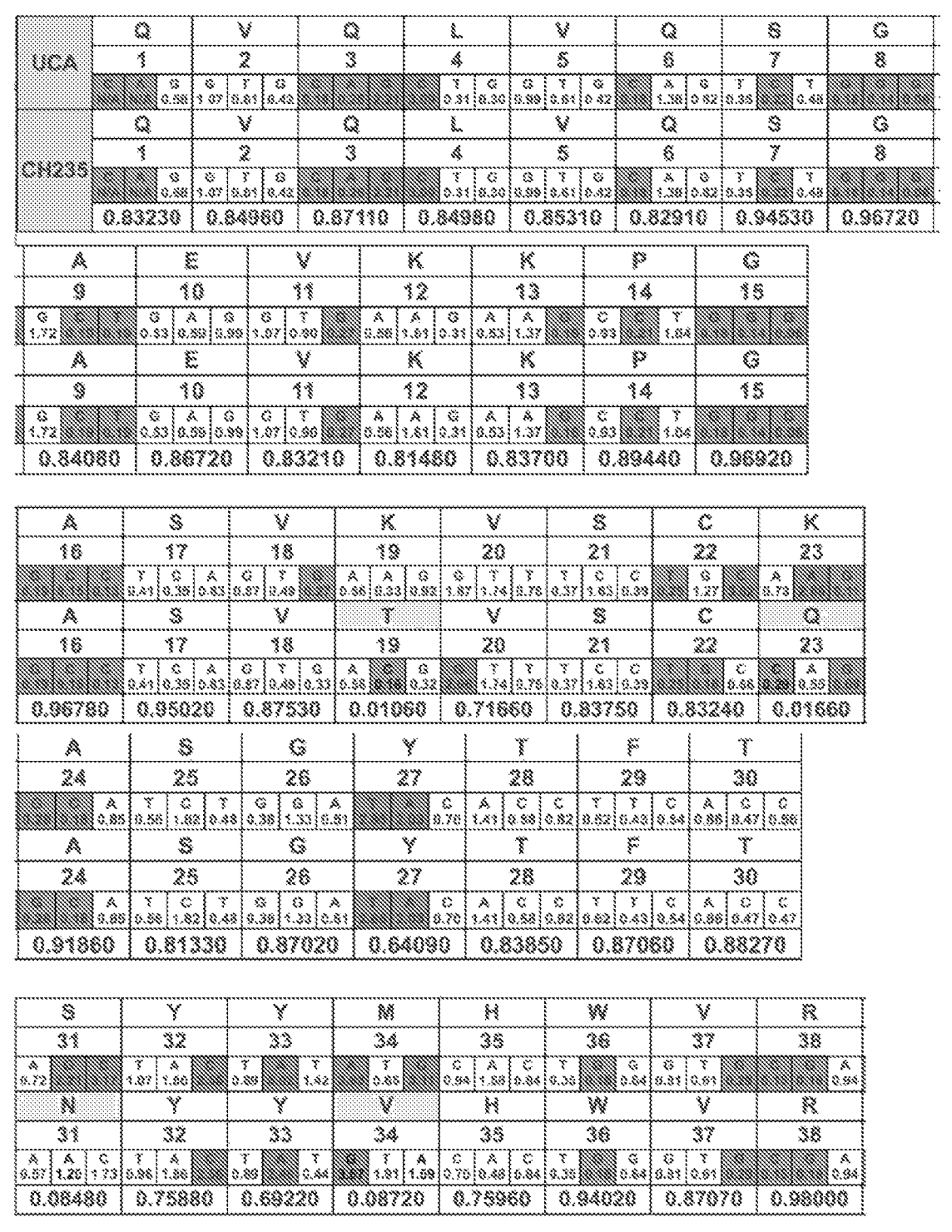
Figure 33B:
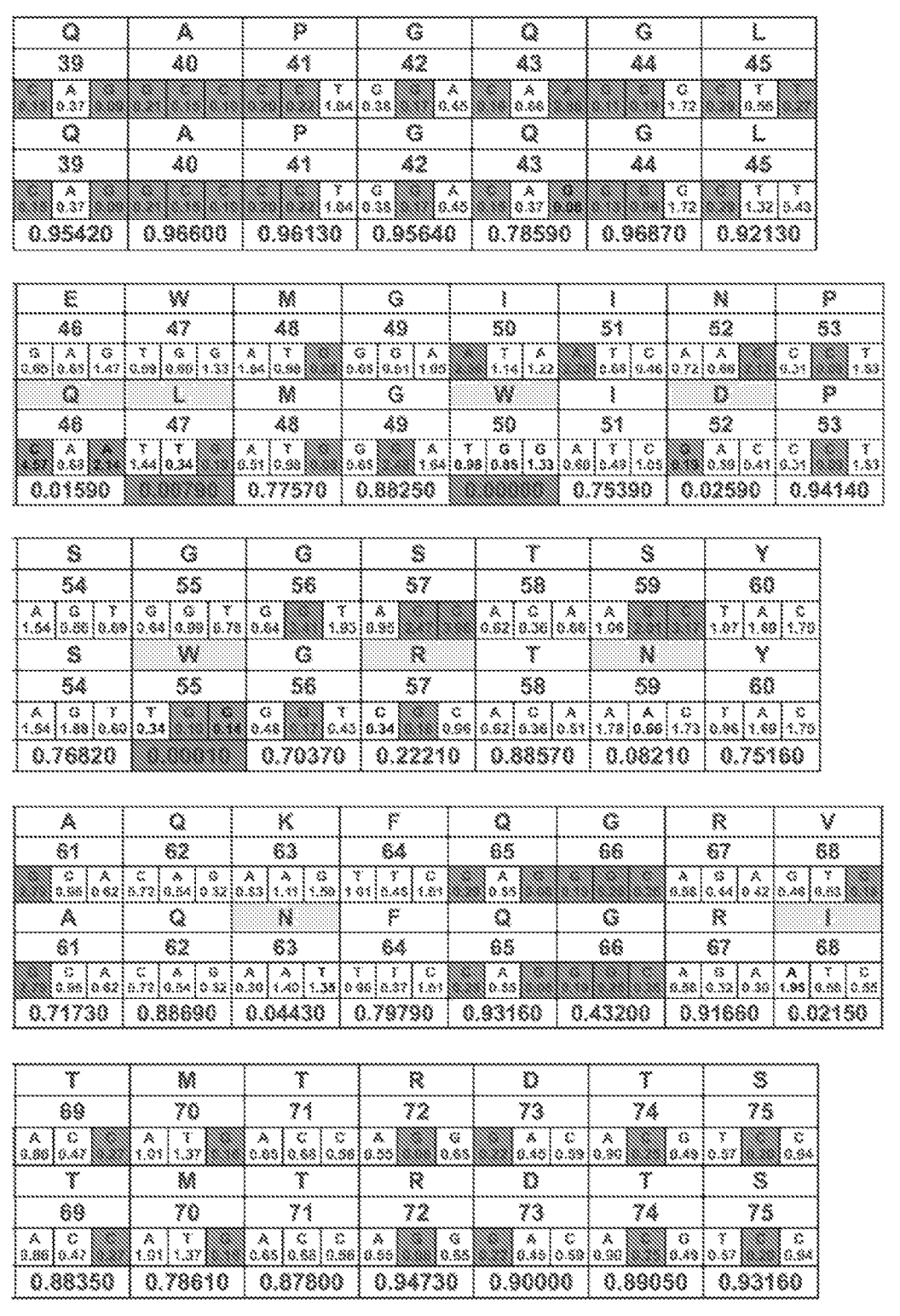
Figure 33B:
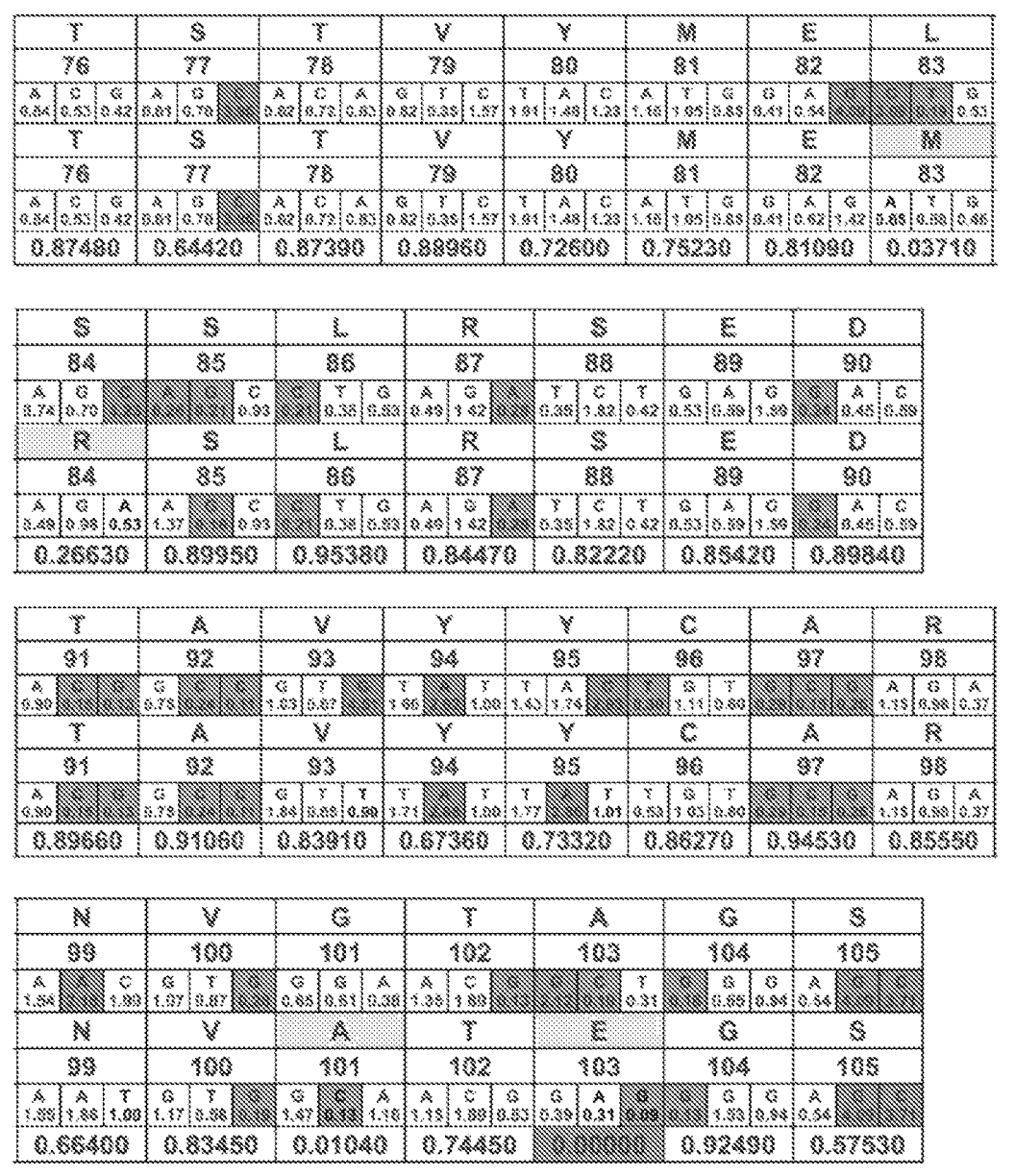
Figure 33B:
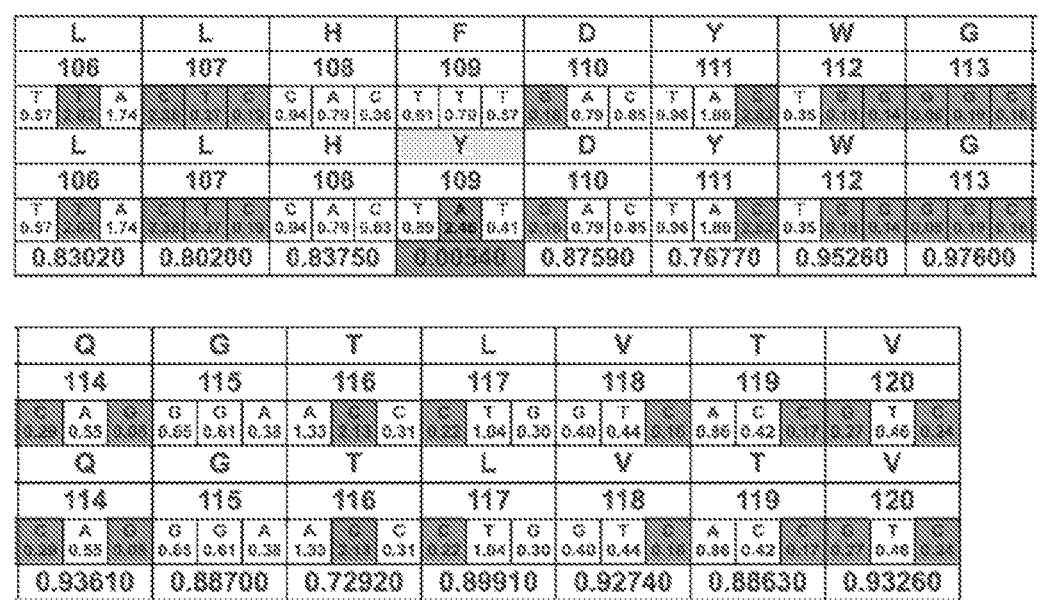

FIGS. 33A-B. ARMADiLLO output for DH270 heavy chain shows G57R mutation is improbable. (A) ARMADiLLO output for the DH270 heavy chain. The first three rows of each block corresponds to the DH270 UCA sequence and the following four rows correspond to the matured DH270 sequenced. The first row is the amino acid sequence for the DH270 UCA. The second row is the amino acid numbering (consecutively numbered starting at 1 for the first residue) for the DH270 UCA. The third row is the nucleotide sequence with each codon falling under the amino acid designated in row 1. The mutability score calculated with the S5F model is shown below the base in each box in this row. Each box is highlighted at AID hot spots (red; mutability score>2) and cold spots (blue; mutability score<0.3). Row 8 is the estimated probability of the amino acid observed in the matured sequence (see methods for how this is calculated). The formatting pattern of rows 1-3 is repeated for the matured DH270 in rows 4-7. Amino acid substitutions are highlighted in yellow in row 4. Nucleotide mutations are shown in dark red text. Nucleotide mutations that are the result of mutations at AID cold spots are shown with an arrow below. (B) ARMADiLLO output for the VH chain of antibody CH235.

FIGS. 35A-D. K19T mutation is conserved across all VH1-46 derived bnAb lineages and T19 position is proximal to N197 glycan site A) Amino acid multiple sequence alignment of the heavy chains of the three known VH1-46 gene segment-derived CD4 binding site bnAbs: 8ANC131, 1B2530, and the multiple member CH235 lineage aligned to the CH235 UCA. The K19T mutation (red) is observed in all three lineages suggesting convergence of this mutation in three distinct individuals. Dots denote an amino acid match with the CH235 UCA in that position. B) The T19 position (magenta) in the CH235/gp120 complex structure (PDB: 5F9W) is outside of the CH235 (heavy chain, blue; light chain, gray) binding site. The complex structure was determined with monomeric gp120 (green) and only minimal glycosylation (not shown) was resolved. C) Superposition of the CH235 complex onto a fully glycosylated SOSIP trimer (SFYL) revealed that T19 (magenta) is in close proximity (7A) to the N197 glycan base (red) resolved in the trimer structure (green). A longer Lys residue in the 19$^{th}$ position may sterically clash with longer glycans, providing a structural rationale for the conservation of the K19T mutation in VH1-46 derived CD4 binding site bnAbs. D) SPR sensorgrams for wildtype CH235 UCA and 5 UCA mutants containing improbable mutations show binding response to M5, a gp120 construct featuring a single amino acid mutation from the CH505 T/F that makes it more favorable for binding the CH235.UCA.

FIG. 36A shows Heavy chain sequences for a representative set of bnAbs are highlighted by their mutation probability as estimated by ARMADiLLO. UCA inference was performed with only the observed bnAb sequence as input and as such there may be substantial uncertainty in mutation calls within the CDR3s. FIG. 36B shows Kappa chain sequences for a representative set of bnAbs are highlighted by their mutation probability as estimated by ARMADiLLO. UCA inference was performed with only the observed bnAb sequence as input and as such there may be substantial uncertainty in mutation calls within the CDR3s. FIG. 36C shows Lambda chain sequences for a representative set of bnAbs are highlighted by their mutation probability as estimated by ARMADiLLO. UCA inference was performed with only the observed bnAb sequence as input and as such there may be substantial uncertainty in mutation calls within the CDR3s. FIGS. 36A, 36B and 36C use the following legend: Positions having black outline show mutations from the UCA sequences, and among these are mutations that are expected to occur frequently in the absence of selection (high probability mutations). Mutations that are expected to occur rarely in the absence of selection (improbable mutations) are colored in shades of gray: Black background, White Lettering: <0.1%; Gray background, White lettering: <1%; Gray background, Black lettering: <2%. Amino acids residing in CDRs are denoted with a line above them. The VH and VL sequences in FIG. 36 show a polypeptide sequence which comprises all improbable mutations with probability of less than 2%, less than 1%, or less than 0.1%. The invention contemplates embodiments, wherein the VH and VL polypeptide sequence(s) comprise any one of the improbable mutations, or any combination of the improbable mutations. In these embodiments wherein fewer than all improbable positions are changed to improbable mutation(s), any improbable mutation position could comprise an amino acid found in the UCA, or any other suitable amino acid, for example but not limited to an amino acid expected to occur frequently, or an amino acid which is found at the corresponding position of another lineage member.

FIG. 38 shows neutralization of bnAbs and mutants.

FIGS. 39A and 39B show the number of amino acid mutations and mutation frequencies.

FIG. 41 shows amino acid sequences of envelopes CH848.3.D0949.10.17chim.6R.DS.SOSIP.664 and CH848.3.D0949.10.17chim.6R.DS.SOSIP.664_N301A. The underlined sequence is the signal peptide in these envelopes. A skilled artisan can readily determine nucleic acid sequences which correspond to these amino acid sequences. These nucleic acid sequences could be optimized for expression is any suitable system.

DETAILED DESCRIPTION

Figure 1A:
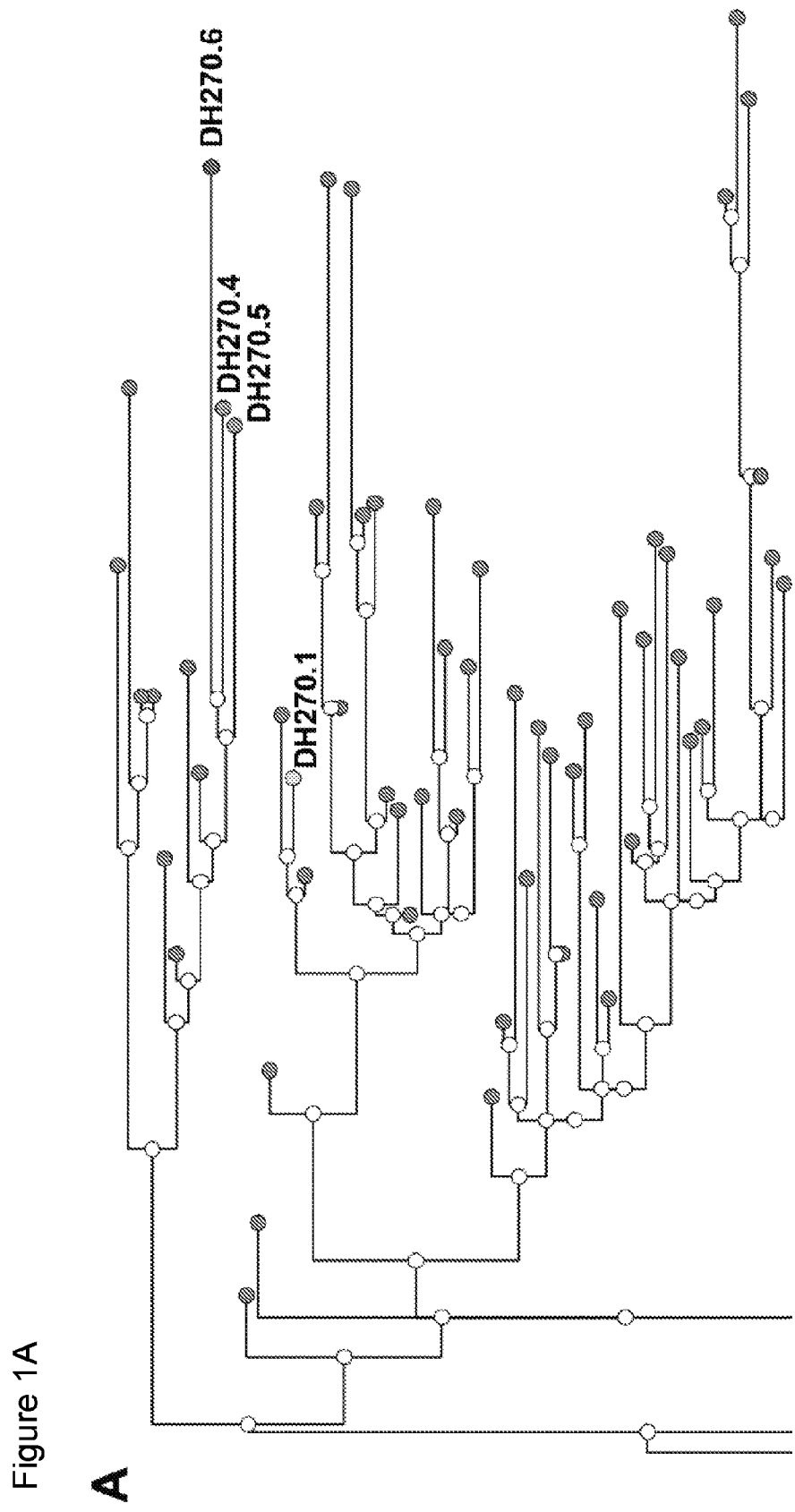
FIGS. 1A-B. DH270 lineage with time of appearance and neutralization by selected members. (A) Phylogenetic relationship of 6 mAbs and 93 NGS $V_H DJ_H$ sequence reads in the DH270 clonal lineage. External nodes (filled circles) represent $V_H DJ_H$ nucleotide sequences of either antibodies retrieved from cultured and sorted memory B cells (labeled) or a curated dataset of NGS $V_H DJ_H$ rearrangement reads (unlabeled). Coloring is by time of isolation. Samples from week 11, 19, 64, 111, 160, 186 and 240 were tested and time-points from which no NGS reads within the lineage were retrieved are reported in FIGS. 30A-C of WO/2017/152146. Internal nodes (open circles) represent inferred ancestral intermediate sequences. Units for branch-length estimates are nucleotide substitution per site. (B) Neutralization dendrograms display single mAb neutralization of a genetically diverse panel of 207 HIV-1 isolates. Coloring is by $IC_{50}$. See also FIG. 33 of WO/2017/152146.
Figure 1A:
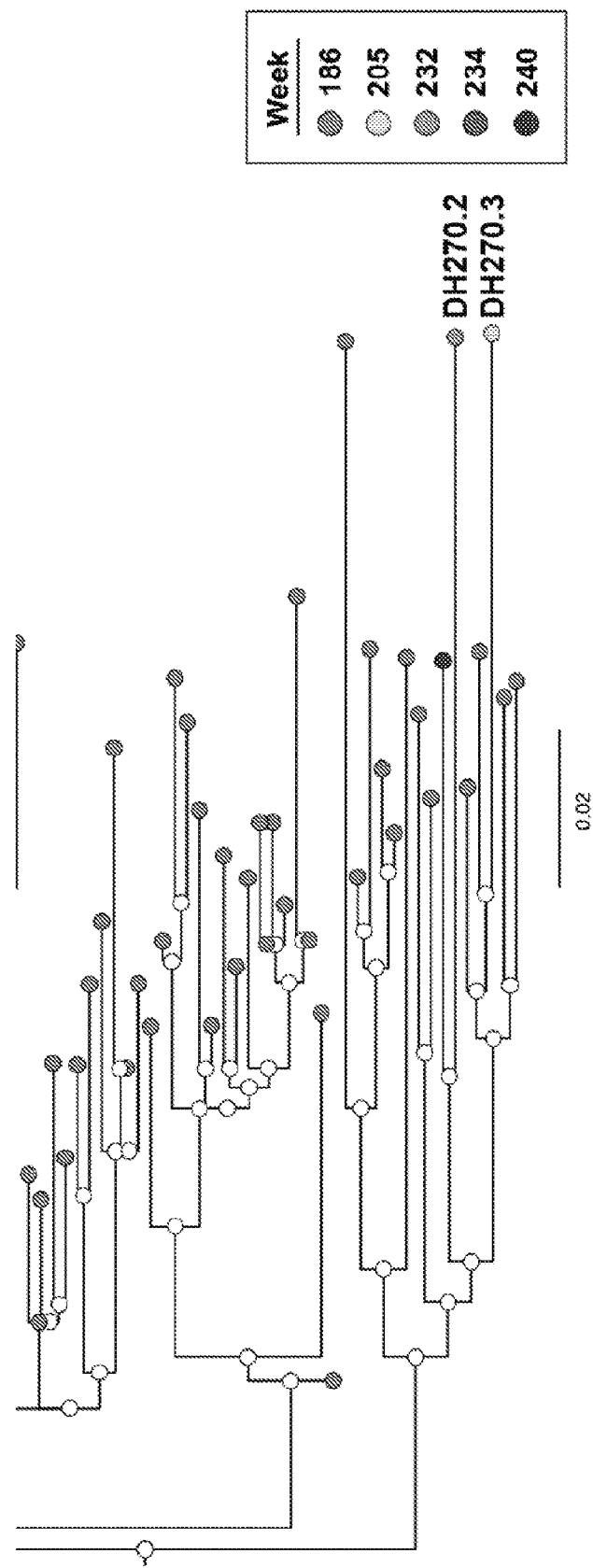

During the development of bnAbs, B-cells undergo an evolutionary process in order to achieve high specificity recognition of antigen and this process is called affinity maturation. As with all evolutionary processes, there is diversification and selection. There are two primary diversification methods in that process. The first is the initial V(D)J recombination event. This defines the starting point for a clonal lineage. The second is somatic hypermutation (SHM) which is discussed in more detail. Somatic hypermutation is the process which introduces mutations within the antibody gene.

Selection of the survival of B cells that have undergone somatic hypermutation is based on affinity to antigen. This manifests as a competition with other B-cells in the germinal center. Somatic Hypermutation is mediated by Activation-Induced Cytidine Deaminase or A.I.D.

Clonal lineages of antibodies trace the history of a clone as its members acquire mutations. Clonal lineages can be displayed as trees. Trees are rooted on the initial VDJ rearrangements and heavy and light chain pairing, which is referred as the unmutated common ancestor or UCA. A fundamental goal of HIV-1 vaccine development is to recapitulate the response infrequently observed in HIV-1 infection: that is the induction of exquisitely potent, broadly neutralizing antibodies.

To recapitulate the induction of a specific antibody lineage, at least two essential components are needed. First is to engage naïve B cells with the germline-encoded characteristics important for neutralization of the lineage. In some embodiments this is the same heavy and light pairing. In other embodiments, this is the same signature contact residues that are encoded in a V gene segment. In other embodiments, this is a similar CDR H3. In some embodiments, this is any combination of those germline-encoded features. After UCA is engaged, it is long way to go to becoming a broad neutralizing antibody (bnAb). In that process, the UCA must now traverse the mutational space to acquire breadth and potency.

Second, after a lineage is initiated, it must accrue the specific, critical somatic mutations that are necessary for that lineage to acquire desired characteristics, e.g. but not limited to neutralization breadth. The mutational space could be visualized as a maze, and the UCA and subsequent intermediates must make the correct turns through the maze, by making the right mutations. Many of the paths will be off-target and lead to dark alleys and dead ends. And there will be forces that can steer the clone into these dark alleys such as non-deletional modes of immune tolerance referred to as "affinity reversion" or "antibody redemption". Even when a successful path is found, it may represent a subdominant part of the lineage.

A clonal lineage tree, when available, thus acts as a map, defining the mutational pathway that leads a UCA to mature to a BNAb. Such maps could be used to recapitulate this phenomenon in the vaccine setting. A key question in evaluating vaccine induced lineages to determine if lineages are on the right path to becoming a BNAb. Related to that is to determine if maturation is going off-target towards a dead-end.

Traditionally this is done by assessing whether the vaccinated lineages share commonalities with known BNAb lineages; whether they share heavy and light chain gene segment usage; whether they share mutations at the same positions; whether these are positions at contact sites in the complex; whether the lineages share mutations at the same position, and whether the change is to the same exact amino acid. However, evaluating shared mutations does not take into account an important factor—namely that is the somatic hypermutation process is biased.

Figure 40:
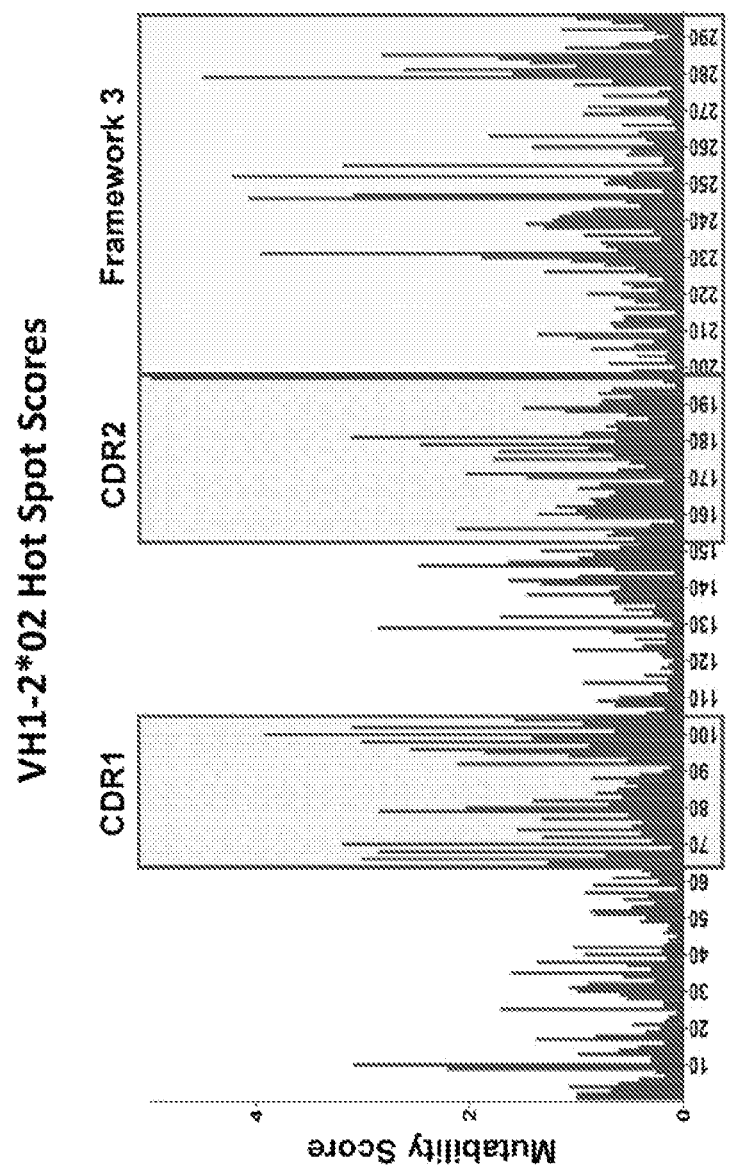
FIG. 40 shows that hot spots are not uniformly distributed.
Figure 42:
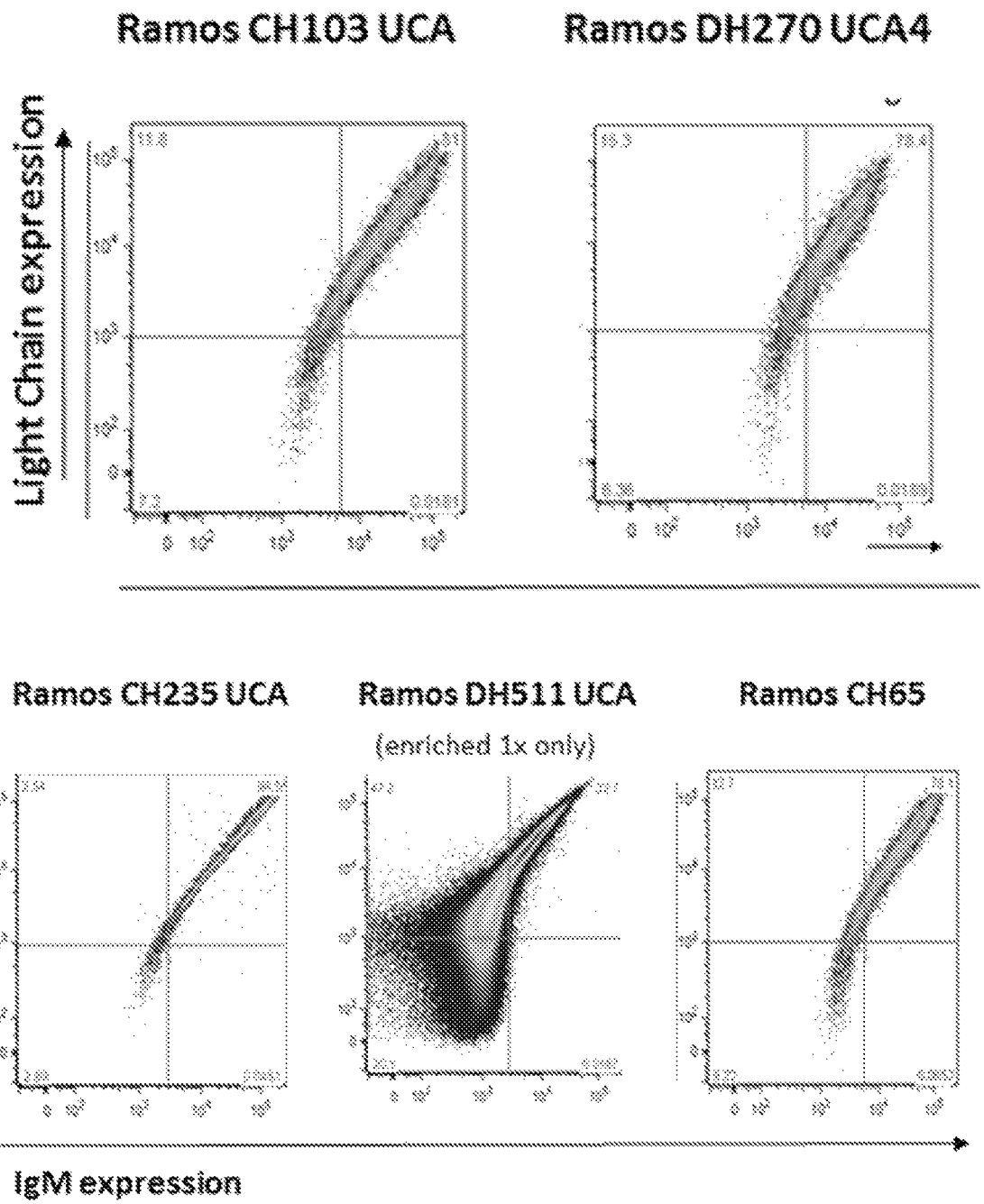
FIG. 42 shows Ramos B cells expressing broadly neutralizing antibody UCA B cell receptors.
Figure 42:
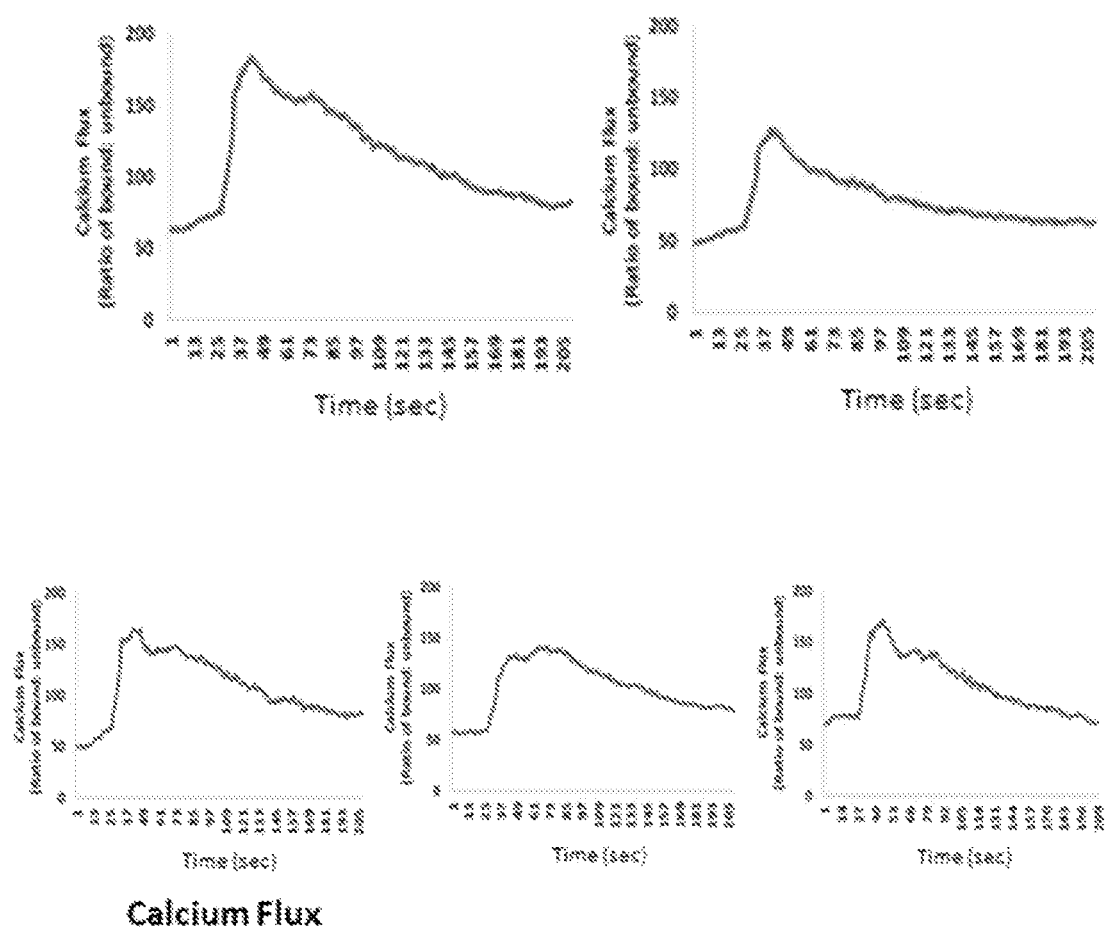

AID targeting is not uniformly random, it shows a preference towards certain microsequence motifs, called "hotspots", and away from other motifs called "coldspots". Base substitution is also dependent on the surrounding sequence. So this must be accounted for when comparing lineage members to BNAb sequences. Some mutations will occur in hot-spots and are more readily available prior to selection than mutations that occur in cold-spots. This bias is evident when the pattern of hot spots in V gene segments is analyzed. FIG. 40 shows a plot of mutability scores for VH1-2*02. This figure shows that the hot spots are not uniformly distributed. They occur in the CDR loop regions and mostly away from framework regions as expected. However, there are areas, especially in framework 3, that have more hot spots than one might expect. The result is that mutations tend to accrue where these hot spots are enriched. The figure shows the pattern plotted at the nucleotide level, but how that manifests at the codon level and how the hot spots may change as the antibody gene becomes more mutated, will have an effect on the pattern at the amino acid level as the clone matures.

For these analyses it would be useful to calculate the probability of individual amino acid mutations, not only for comparing lineages, but also for evaluating bottlenecks in BNAb developmental pathways. One such pathway is the one described in a lineage of HIV-1 bnAb referred to as DH270 lineage (Example 2).

To determine the probability of any amino acid at any position at a given mutation frequency three things are needed. We need the starting point, the UCA sequence; and the number of mutations in the observed mature sequence. This will define the number of opportunities the antibody has to get that specific mutation. Also needed is a method for simulating somatic hypermutation in the absence of selection. To do that simulation and that calculation, the invention provides a program called ARMADILLO, which stands for Antigen Receptor Mutation Analyzer for Detection of Low Likelihood Occurrences. ARMADILLO simulates the somatic hypermutation process using a statistical model of AID targeting and substitution, and estimates the probability of any observed amino acid mutation in a matured antibody sequence. It highlights those mutations that are improbable, prior to selection. Both heavy and light antibody chains could be analyzed by ARMADILLO. One statistical model of SHM is described by Yaari et al. in "Models of somatic hypermutation targeting and substitution based on synonymous mutations from high-throughput immunoglobulin sequencing data." In Front Immunol. 2013 Nov. 15; 4:358.

doi: 10.3389/fimmu.2013.00358. eCollection 2013. The model of Yaari et al. could be improved, and other models could also be used.

ARMADILLO can be used to retrospectively confirm an improbable, yet critical mutation. For a non-limiting embodiment see Example 2, and the output of the program for the V3 antibody DH270 (FIG. 33). Zooming in on the G57R mutation in the DH270.IA4 (Example 2), the top three rows show the UCA sequence. The program shows the amino acid Glycine (point) at position 57 (point) has the specific bases GGC in its codon (point) and highlights hotspots in red and cold spots in blue. The next three rows show the mature DH270 sequence, highlighting in yellow that an amino acid substitution to Arginine has occurred, and that was the result of a mutation at a base that was in a cold spot. The number in the last row, here highlighted in magenta is the probability of this mutation occurring in the absence of selection, and this probability is 0.5%. And as Example 2 shows, this improbable mutation was critical to the acquisition of heterologous breadth and occurred early in the DH270 lineage.

Figure 36A:
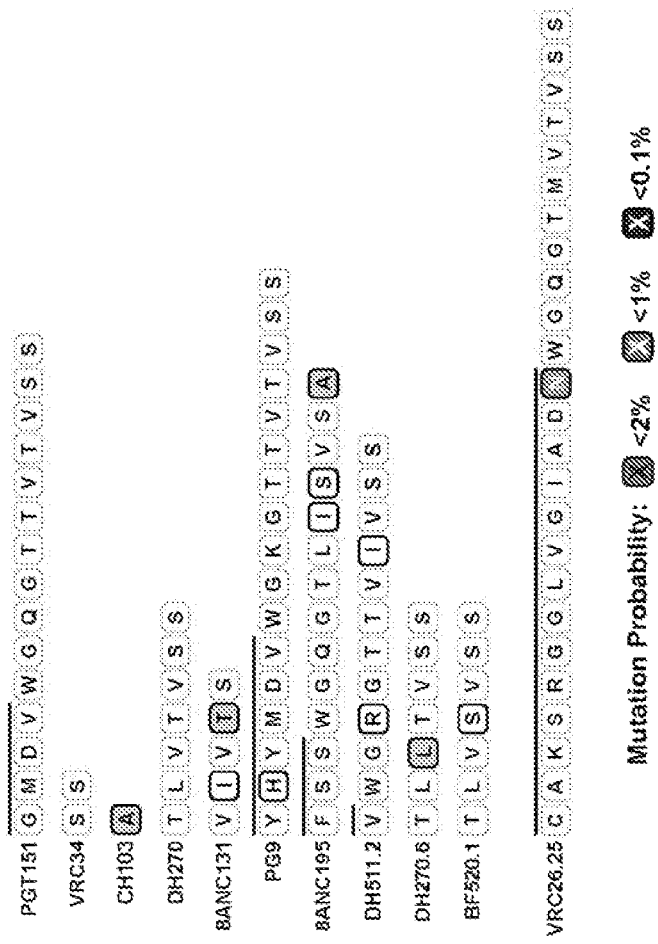
FIGS. 36A-C. Representative bnAb sequences colored by mutation probability.

Having confirmed that ARMADILLO can be used retrospectively at the DH270 lineage and identify and quantify an improbable mutation important for the development of that lineage, the next step was to use it prospectively to predict important mutations based on mutation probabilities. For that we turned to the CH235 lineage that is a CD4 binding site antibody lineage, and the mature antibody CH235.12 in that lineage (lineage is from patient CH505). See Gao et al. Cell (2014) Volume 158, Issue 3, 31 Jul. 2014, Pages 481-491 Bonsignori et al. Cell (2016) Volume 165, Issue 2, p449-463, 7 Apr. 2016. FIG. 36A shows the ARMADILLO output for the VH chain of antibody CH235.

FIG. 35 shows the mapping of the contact sites from the crystal structure of CH235.12 antibody. This figure shows that there was an improbable mutation that occurred in Framework 1 that was not in a contact site. This mutation was Lysine to Threonine, i.e. K to T. A sequence alignment of the CH235 clone with two other VH1-46 derived BNAbs that are also CD4 mimics, 8ANC131 and 1B2530, and showed, remarkably, that they both had the same exact, improbable mutation. And all but one member of the CH235 clone did as well. The CH235 structure showed that this amino acid T19, was far from the antigen binding site in the complex with monomeric gp120 core. However, when we superposed the CH235 complex into a recently solved glycosylated trimer structure, it revealed a different story. The K19T mutation position is very close to the N197 glycan, a glycan that occurs in the V2 that is missing in the gp120 core. That led us to ask whether the role of this mutation is to accommodate the N197 glycan. The reversion mutation, T19K, was made in CH235 and tested for neutralization. While it had only a marginal reduction in CH505 T/F neutralization, there was a loss of neutralization of two tier two viruses. So this single mutation reduced heterologous breadth. There was no effect with JRFL neutralization, likely because JFRL lacks the N197 glycan site. These results demonstrate that using the methods of the invention one can prospectively find functionally relevant, improbable mutations.

That we can estimate the probability of mutations along BNAb pathways, and successfully utilize that information to identify candidate mutations that are critical to the acquisition of breadth, leads us to propose the following immunization strategy. (1) First, identify the set of improbable mutations in the BNAb lineage that we are trying to recapitulate. (2) We then make those antibody mutants, and (3) functionally validate their importance in the lineage by testing for improvement in binding and neutralization breadth. (4) Then, we choose Envs that preferentially bind those improbable and important mutations. (5) Finally we immunize with those Envs in ascending order of the probability of mutations for which we want to select. These envelopes are expected to lead the clone to mature by specifically selecting for the hardest mutations to arise, while the clone makes the highly probable mutations.

In some embodiments of the invention, each mutation has a probability so ascending order of that probability is a ranking. In some embodiments, the methods identify the mutations that have an effect on binding or neutralization. In some embodiments, the methods first filter mutations by probability, wherein to test functionally 10 mutants one selects the ten lowest probability mutants. Without bound by theory, not every tested mutation is expected to have functional effect on neutralization and/or binding. In some embodiments, the mutations are picked for analyses in ascending order of probability. In some embodiments, if only few, e.g. 3, could be tested for practical reasons, use the lowest 3 of the 5 in order. In some embodiments the methods also weigh the probability score by the frequency observed in the clone if there are multiple clonal members isolated. In non-limited embodiments, timing of mutation (earliness/lateness of mutation) occurrence within a clone is associated with frequency/infrequency in the clone because of the way phylogenetic tree inference is constructed. In some embodiments the methods also weigh mutation occurrence in the phylogenetic tree.

In certain aspects, the invention provides methods of identifying and selecting antigens, e.g. but not limited to HIV-1 envelopes, that preferentially bind antibodies with identified improbable and important mutations, wherein these selected antigens are used as immunogens. which are expected to direct maturation of an antibody clone for example but not limited to having broad neutralization properties.

In certain embodiments an antibody or fragment thereof comprising functional mutation(s) binds specifically or preferentially to a particular target, peptide, or polysaccharide (such as an antigen present on the surface of a pathogen, for example gp120, gp41), even where the specific epitope may not be known, and do not bind in a significant amount to other proteins or polysaccharides present in the sample or subject. Specific binding between and antibody and an antigen can be determined by methods known in the art. Various binding and screening assays to isolate antigens which bind to an antibody with a functional mutation(s), including competitive binding assays, quantitative binding assays are known in the art. Non-limiting examples of such assays include phage display screening, ELISA, protein arrays, etc. Antigens can also be identified using phage display techniques. Such techniques can be used to isolate an initial antigen or to generate variants with altered specificity or avidity characteristics. Various techniques for making mutational, combinatorial libraries to generate diverse antigens are known in the art. Single chain Fv comprising the functional mutation(s) can also be used as is convenient. A skilled artisan appreciates that an antigen does not have to bind exclusively to an antibody with a specific functional mutation (e.g. X1), but that the antigen could bind preferentially or in some way detectably different to the antibody with mutation X1 compared to another antibody, for example to the UCA.

Antigens can be tested functionally for calcium flux, for example using Ramos cell lines expressing B cell receptors of desired specificity.

With reference to an antibody antigen complex, in certain embodiments specific binding of the antigen and antibody has a Kd of less than about $10^6$ Molar, such as less than about $10^6$ Molar, $10^7$ Molar, $10^8$ Molar, $10^9$, or even less than about $10^{10}$ Molar. With reference to an antibody antigen complex, in certain embodiments specific binding of the antigen and antibody has a detectably different Kd. Kd measurements of antibody binding to HIV-1 envelope, e.g. gp41 or any other suitable peptide for the MPER antibodies, will be determined by Surface Plasmon Resonance measurements, for example using Biacore, or any other suitable technology which permits detection of interaction between two molecules in a quantitative way.

The improbable mutation analysis is applicable to other antibodies other than HIV-1 antibodies. For example, the analysis was conducted for a neutralizing flu antibodies. Improbable mutations were identified, and these are tested to determine their effect on the neutralization of the reverted antibody A skilled artisan appreciates that the analysis identifying improbable mutations is applicable to other antibodies other than HIV-1 antibodies, for example but not limited to flu antibodies.

Antibody nomenclature and names: UCA4=DH270.UCA; IA4=DH270.IA4; IA3=DH270.IA3; IA2=DH270.IA2; IA1=DH270.IA1; DH270=DH270.1; DH473=DH270.2; DH391=DH270.3; DH429=DH270.4; DH471=DH270.5; DH542=DH270.6; DH542-L4 (comprising VH from DH542 and VL from DH429), DH542_QSA.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1: Functional Improbable Antibody Mutations Critical for HIV Broadly Neutralizing Antibody Development HIV-1 broadly neutralizing antibodies (bnAbs) require high levels of activation-induced cytidine deaminase (AID) catalyzed somatic mutations for optimal neutralization potency. Probable mutations occur at sites of frequent AID activity, while improbable mutations occur where AID activity is infrequent. One bottleneck for induction of bnAbs is the evolution of viral envelopes (Envs) that can select bnAb B cell receptors (BCR) with improbable mutations. Here we define the probability of bnAb mutations and demonstrate the functional significance of improbable mutations in bnAb development. We show that bnAbs are enriched for improbable mutations, thus their elicitation will be critical for successful vaccine induction of potent bnAb B cell lineages. We outline a mutation-guided vaccine strategy for identification of Envs that can select B cells with BCRs with key improbable mutations required for bnAb development. Our analysis suggests that through generations of viral escape, Env trimers evolved to hide in low probability regions of antibody sequence space.

The goal of HIV-1 vaccine development is the reproducible elicitation of potent, broadly neutralizing antibodies (bnAbs) that can protect against infection of transmitted/founder (TF) viruses (Haynes and Burton, 2017). While ~50% of HIV-infected individuals generate bnAbs (Hraber et al., 2014), bnAbs in this setting only arise after years of infection (Bonsignori et al., 2016; Doria-Rose et al., 2014; Liao et al., 2013b). BnAbs isolated from infected individuals have one or more unusual traits, including long third complementarity determining regions (CDR3s) (Yu and Guan, 2014), autoreactivity (Kelsoe and Haynes, 2017), large insertions and deletions (Kepler et al., 2014a), and high frequencies of somatic mutations (Burton and Hangartner, 2016). Somatic hypermutation of the B cell receptor (BCR) heavy and light chain genes is the primary diversification method during antibody affinity maturation—the evolutionary process that drives antibody development after initial BCR rearrangement and leads to high affinity antigen recognition (Teng and Papavasiliou, 2007). Not all somatic mutations acquired during antibody maturation are necessary for bnAb development; rather high mutational levels may reflect the length of time required to elicit bnAbs (Georgiev et al., 2014; Jardine et al., 2016). Therefore, shorter maturation pathways to neutralization breadth involving a critical subset of mutations is desirable, but vaccine design to achieve this goal requires a strategy to determine all key mutations (Haynes et al., 2012).

Mutation during antibody affinity maturation, like all evolutionary processes, occurs prior to selection and the principal mutational enzyme is activation-induced cytidine deaminase (AID) (Di Noia and Neuberger, 2007). AID preferentially targets nucleotide sequence motifs (referred to as "AID hot spots") or is shielded away from certain nucleotide motifs (referred to as "AID cold spots") (Betz et al., 1993; Yaari et al., 2013) and subsequent repair of DNA lesions results in a bias for which bases are substituted (Cowell and Kepler, 2000). The result of this non-uniformly random mutation process is that specific amino acid substitutions occur with varying frequencies prior to antigenic selection. Mutations at hot spots can occur frequently in the absence of antigen selection due to immune activation-associated AID activity (Bonsignori et al., 2016; Yeap et al., 2015). Improbable amino acid substitutions generally require strong antigenic selection to arise during maturation. Amino acid substitutions can be improbable prior to selection for two primary reasons: 1) base mutations must occur at AID cold spots, or 2) due to codon mapping, multiple base substitutions must occur for a specific amino acid change to take place. We have recently described a rare mutation in a bnAb unmutated common ancestor antibody (UCA) that only occurred when a virus bearing a distinct Env arose three years after HIV-1 infection (Bonsignori et al., 2017). Thus, the requirement for rare, functional bnAb mutations can be a key roadblock in HIV-1 bnAb development. Without being bound by theory, the invention provides that roadblocks are a general problem and thus a frequent barrier in the elicitation of bnAbs. Here we describe the identification of improbable mutations in multiple bnAb B cell lineages, determine the functional relevance of these mutations for development of bnAb potency, and outline a vaccine design strategy for choosing sequential Envelopes capable of selecting B cells with BCRs with improbable mutations.

Identification of Functional Improbable Antibody Mutations

Figure 29:
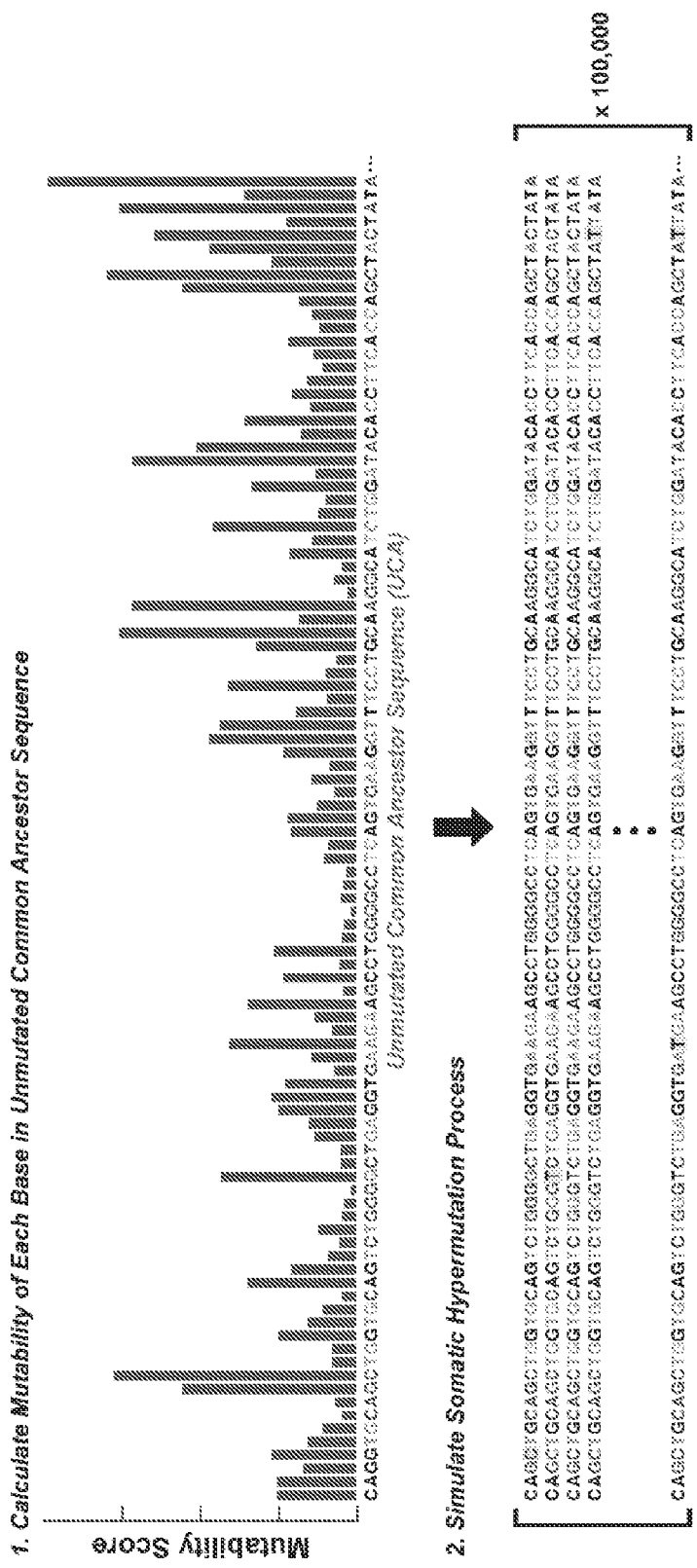
FIG. 29. Computational method for estimating the probability of antibody mutations. The probability of an amino acid substitution during B cell maturation in the absence of selection is estimated by simulating the somatic hypermutation process. 1) The inferred unmutated common ancestor sequence (UCA) of the antibody of interest is assigned mutability scores according to a statistical model of AID targeting. 2) Bases in the sequence are then drawn randomly according to these scores and mutated according to a base substitution model (see Example 1). Rounds of single base mutation continue for the number of mutations observed in the antibody of interest with mutability scores updated as the simulation proceeds. The simulation is then repeated 100,000 times to generate a set of synthetic matured sequences. 3) An amino acid positional frequency matrix is constructed from the simulated sequences and utilized to estimate the probability of amino acid substitutions. 4) The UCA and matured sequence are aligned and 5) the estimated probability of amino acid substitutions identified in the matured sequence are outputted.
Figure 29:
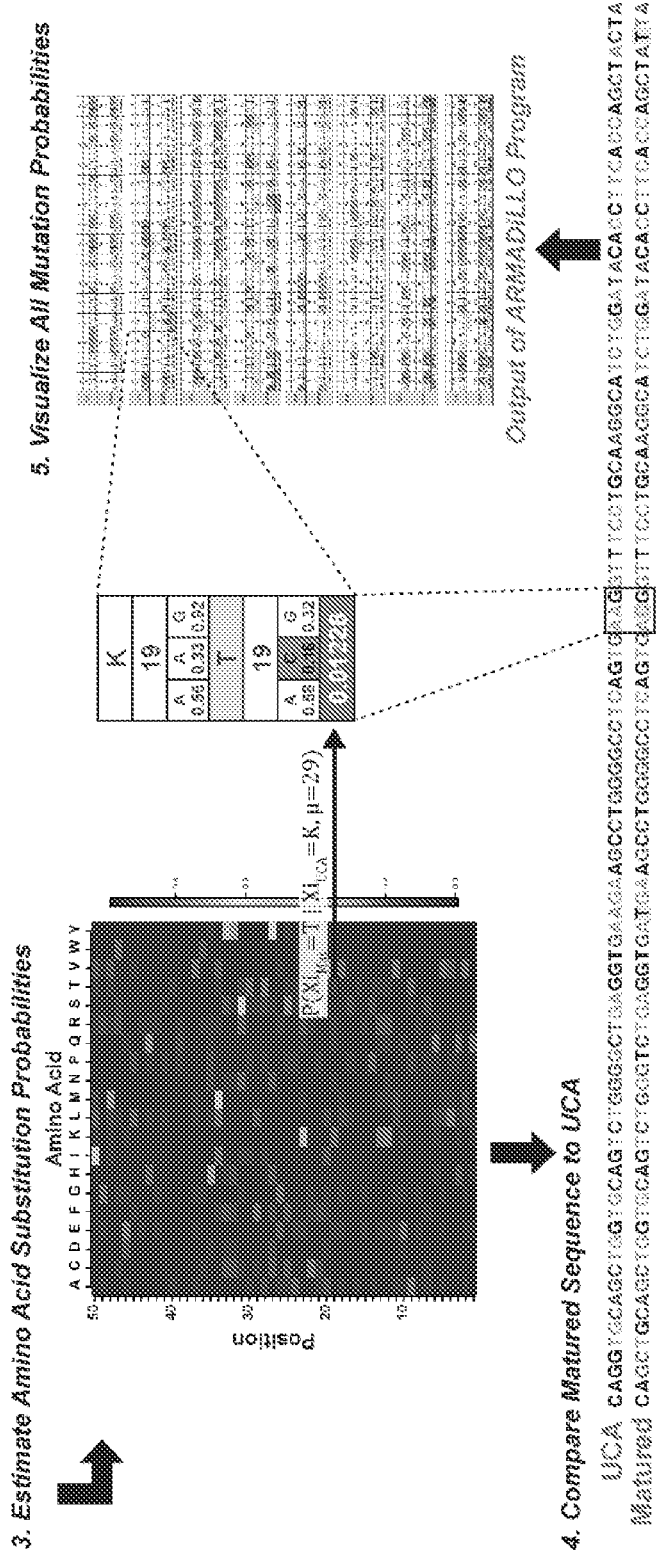

To determine the role of rare mutational events in bnAb development, we developed a computational program to identify improbable antibody mutations. Our program, Antigen Receptor Mutation Analyzer for Detection of Low Likelihood Occurrences (ARMADiLLO) simulates the somatic hypermutation process using a statistical model of AID targeting and base substitution via DNA repair (Yaari et al., 2013) and estimates the probability of any amino acid substitution in an antibody based on the frequencies observed in the computational simulation (FIG. 29).

First, we applied ARMADiLLO retrospectively to the analysis of a mutation in a bnAb lineage that occurred at an AID cold spot that we have previously shown was functionally important for neutralization (Bonsignori et al., 2017). The DH270 V3-glycan bnAb lineage developed a variable heavy chain ($V_H$) complementary determining region 2 (CDR H2) G57R mutation that when analyzed with the ARMADiLLO program was predicted to occur with <1% frequency prior to selection (FIG. 33). This mutation was functionally critical because reversion back to G57 in the DH270 bnAb lineage resulted in total loss of neutralization potency and breadth. See Example 2 and WO2017/152146, the contents of which is hereby incorporated by reference in its entirety; see also (Bonsignori et al., 2017). Thus, the ARMADiLLO program can identify a known, key improbable mutation.

All BCR mutations arise during the stochastic process of somatic hypermutation prior to antigenic selection. In HIV-1 infection, antibody heterologous breadth is not directly selected for during bnAb development because BCRs only interact with autologous virus Envs. Since improbable bnAb mutations can confer heterologous breadth, they represent critical events in bnAb development, and make compelling targets for focusing selection with immunogens. To test this hypothesis, we analyzed three bnAb lineages with ARMA-DiLLO to identify improbable mutations (in one non-limiting embodiment defined as <2% estimated probability of occurring prior to selection) and then tested for the effect of these mutations on bnAb neutralization during bnAb B cell lineage development. FIG. 39 shows the counts for different probability cut off values, e.g. a 1% probability cutoff and for 0.1%. If the cutoff is lowered, the counts are lowered. A skilled artisan appreciates that the cutoff doesn't change the overall strategy, but simply affects the number of mutations that would be considered functionally important. The goal is to select the mutations that are the most important (i.e. functional) for heterologous neutralization and least likely to occur. Without being bound by theory, the 2% cutoff was chosen as it is expected to include mutations that are functionally important. We chose three lineages that allowed for study of different levels of maturation in bnAb development: CH235, mid-stage bnAb development (Bonsignori et al., 2017); VRC01, late stage bnAb development (Wu et al., 2015); and BF520.1, early stage bnAb development in an infant (Simonich et al., 2016).

Figures 30A, 30B, 30C:
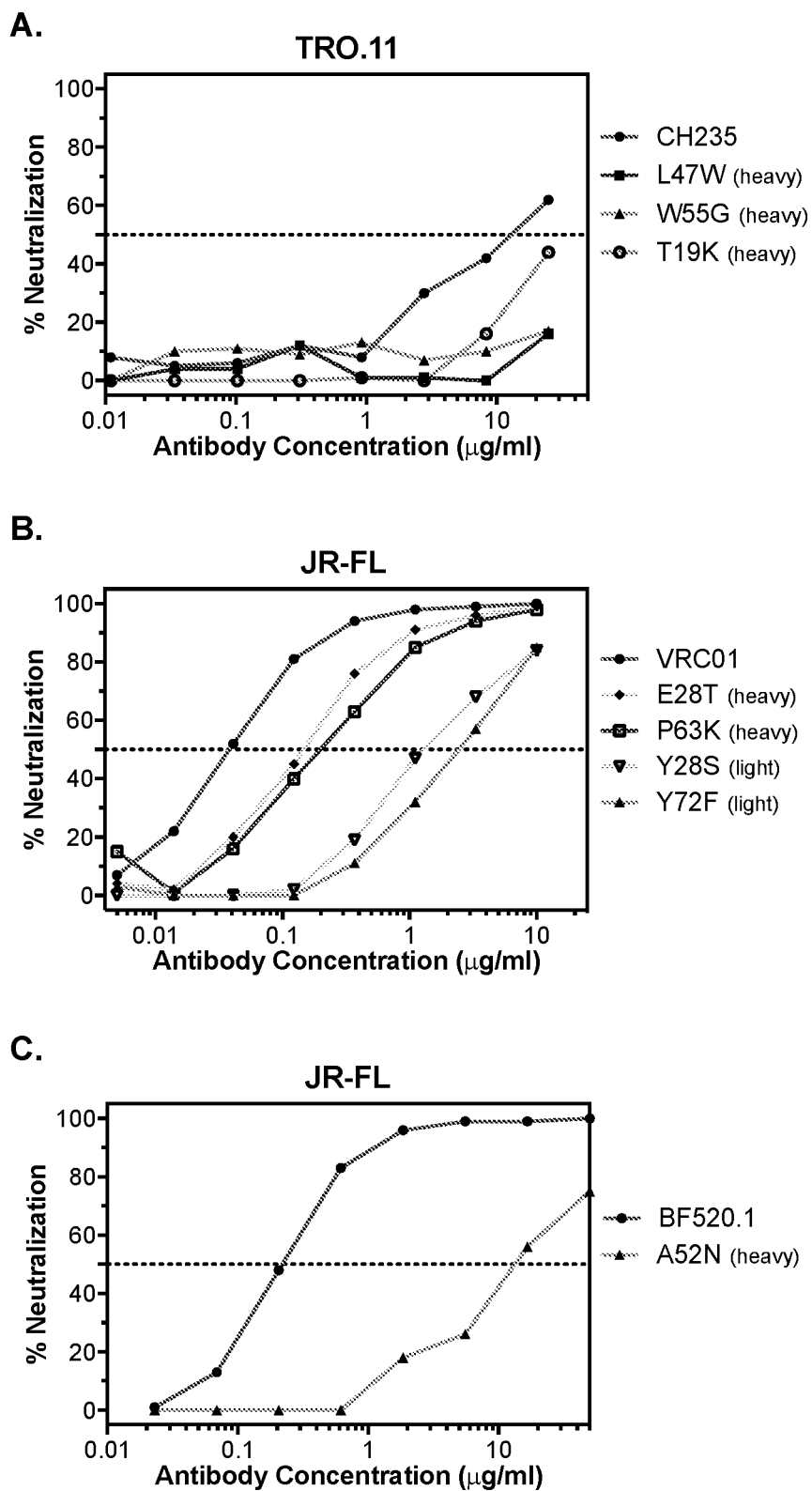
FIGS. 30A-C. Improbable mutations confer heterologous neutralization in bnAb development. BnAbs A) CH235, B) VRCO1 and C) BF520.1 and their corresponding mutants with reverted improbable mutations were tested for neutralization against heterologous viruses. The reversion of improbable mutations in all three bnAbs diminished neutralization potency.
Figure 34A:
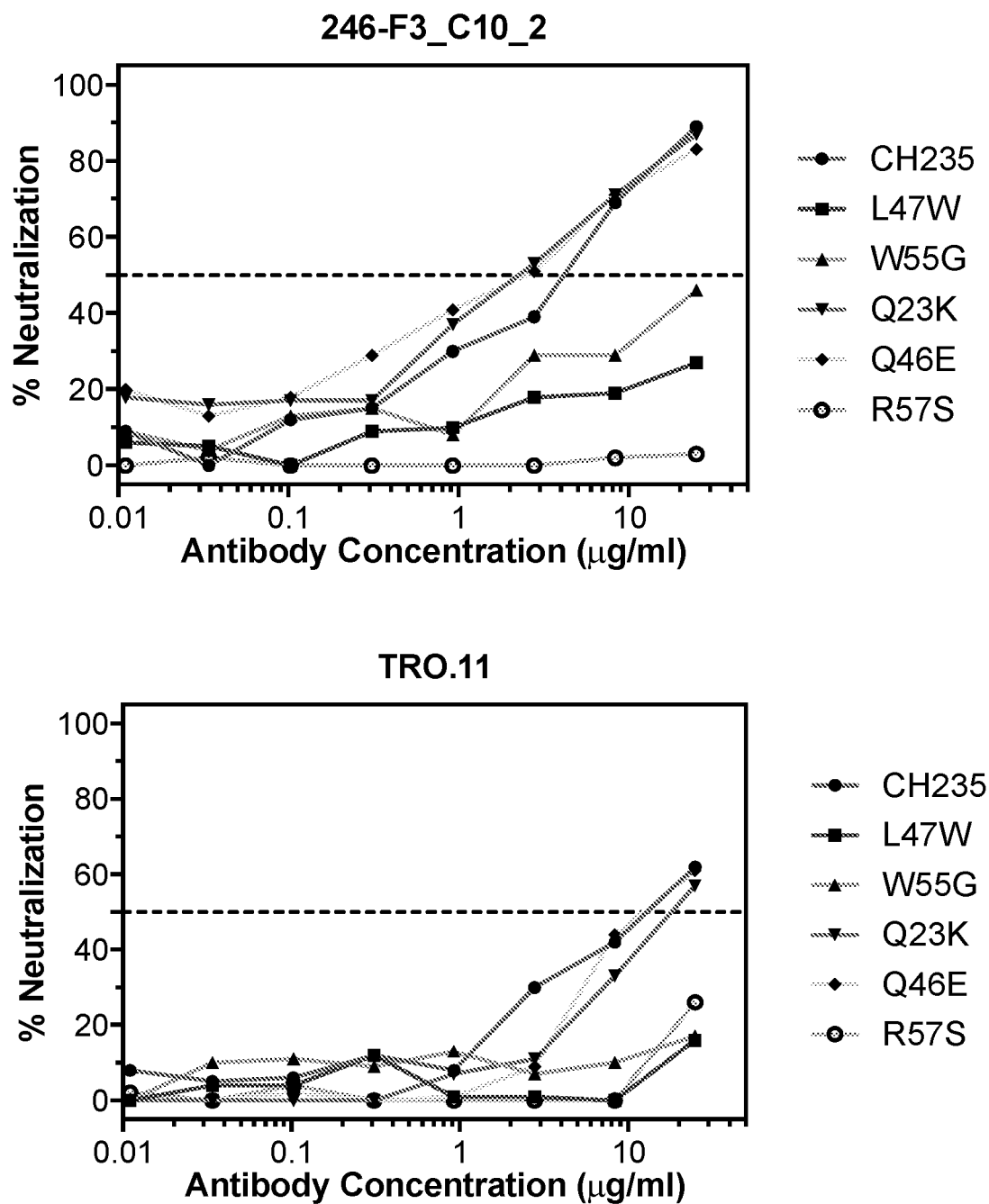
FIGS. 34A-C. Neutralization of improbable mutation reversion mutants for CH235, VRC01, and BF520.1. Curves of the percent neutralization of WT (red line) A) CH235 B) VRC01 and C) BF520.1 and mutants containing reversions of identified improbable mutations against heterologous and autologous (CH505 T/F and 4501dG5 for CH235 and VRC01, respectively) viruses. 50% neutralization is denoted by a dotted line.
Figure 34A:
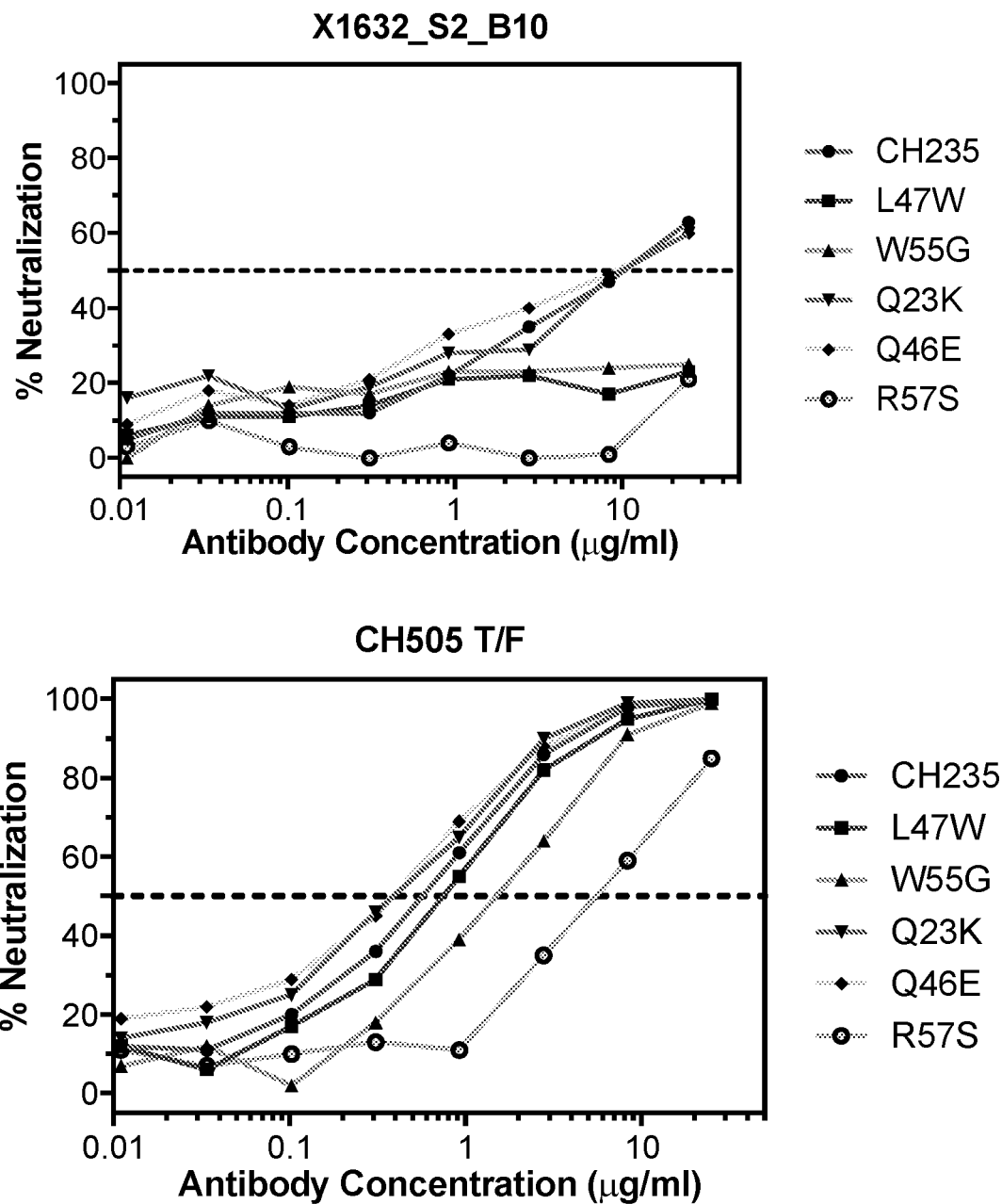

Improbable Mutations Confer Heterologous Neutralization in CD4 Binding Site bnAb Lineages CH235 is a CD4-binding site, CD4-mimicking (Gao et al., 2014) bnAb B cell lineage that evolved to 90% neutralization breadth and high potency over 5-6 years of infection and acquired 44 $V_H$ amino acid mutations (Bonsignori et al., 2016). We identified improbable mutations in the heavy chain of an early intermediate member of the lineage (also termed CH235), reverted each to their respective germline-encoded amino acid, and then tested each CH235 antibody mutant for neutralization against the heterologous, difficult-to-neutralize (tier 2) (Seaman et al., 2010) TRO.11 virus (FIG. 30A and FIG. 34A). Single amino acid reversion mutations resulted in either a reduction or total loss of heterologous HIV-1 TRO.11 neutralization for each of three improbable mutations, K19T, W47L and G55W demonstrating that improbable mutations in the CH235 lineage were indeed critical and could confer heterologous neutralization.

Figure 35A:
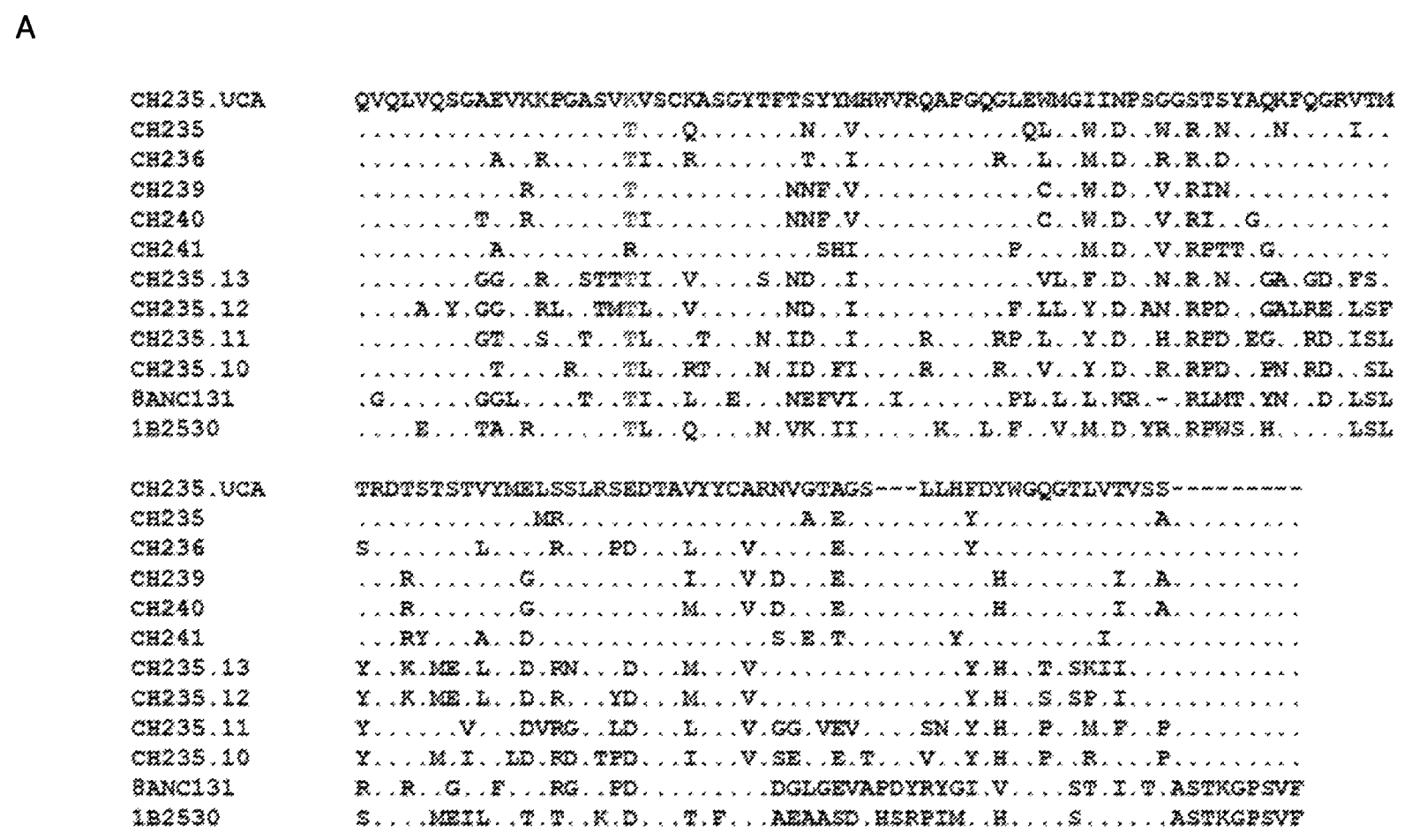
Figures 35B, 35C, 35D:
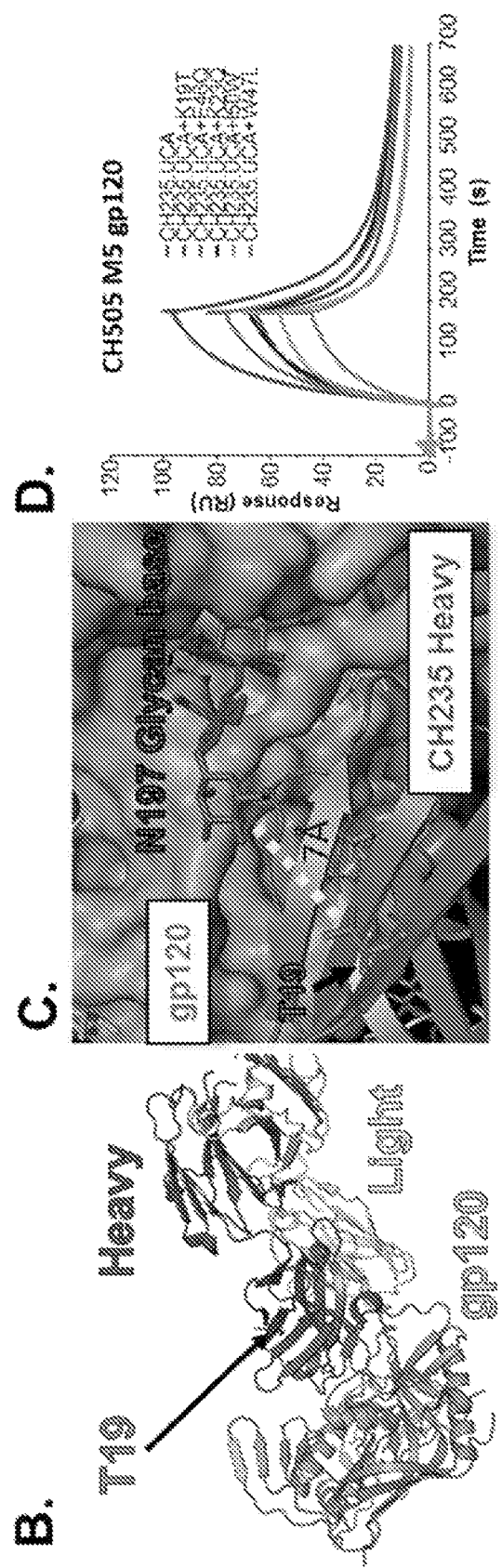

Identification of the K19T mutation was of particular interest because the mutation was observed in all but one member of the CH235 bnAb lineage and was also present in two other CD4-binding site bnAbs (Scheid et al., 2011) from different individuals that shared the same VH gene segment as CH235 (FIG. 35A). Superposition of the CH235 complex into a fully-glycosylated trimer (Stewart-Jones et al., 2016) showed that the K19T mutation position was in close proximity to the N197 glycan site on the Env trimer (FIGS. 35B and 35C). The K19T mutation shortened the amino acid at this position which could act to accommodate larger glycan forms at the heterogeneously glycosylated N197 position (Behrens et al., 2016) providing a structural rationale for the effect of this mutation on heterologous breadth. Consistent with this hypothesis, CH235 neutralization of JR-FL, a tier 2 heterologous virus lacking the N197 glycan site, was unaffected by the T19K reversion mutation (FIG. 38 and FIG. 34A). Moreover, we introduced the K19T mutation into the CH235 UCA and observed improved binding to an early autologous Env suggesting that the improbable K19T mutation may have been selected for by an early variant of the autologous virus (FIG. 35D).

Figure 34B:
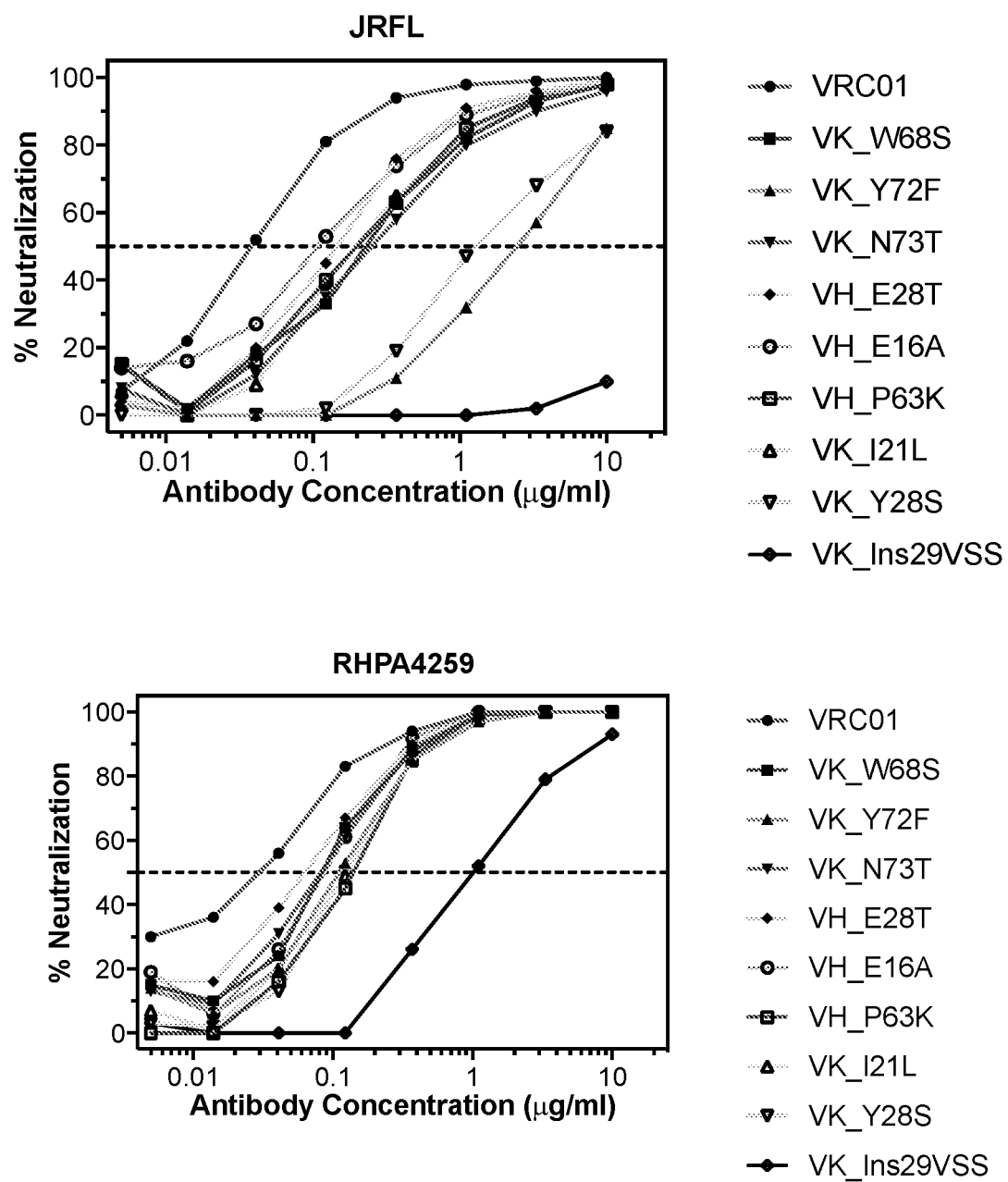
Figure 34B:
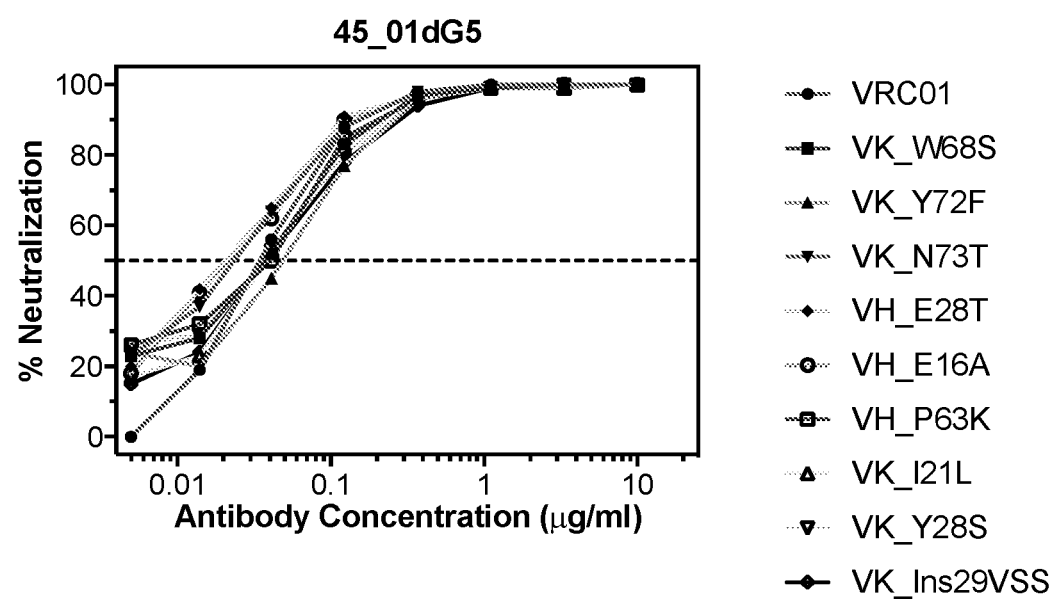

We next asked what role improbable mutations played in the maturation of a highly broad and potent second CD4 binding site-targeting bnAb lineage, termed VRC01, that acquired 43 $V_H$ amino acid mutations (Zhou et al., 2010). We reverted improbable mutations in the fully matured VRC01 and tested for their effects on neutralization of the heterologous tier 2 HIV-1 JR-FL (FIG. 30B). Reversion of improbable mutations reduced potency of heterologous neutralization of HIV-1 JRFL demonstrating that in the VRCO1 CD4 binding site B cell lineage, single improbable amino acid substitutions can also have functional consequences for heterologous neutralization capacity. Improbable mutations identified by ARMADiLLO in the VRCO1 light chain showed an even larger effect on reducing neutralization than heavy chain mutations (FIG. 38 and FIG. 34B), further underscoring, along with an atypically short CDRL3 and a critical CDRL1 deletion (Zhou et al., 2013), the importance of improbable events in the maturation of the VRCO1 bnAb lineage.

An Improbable Mutation Associated with Accelerated BnAb Development

Figure 34C:
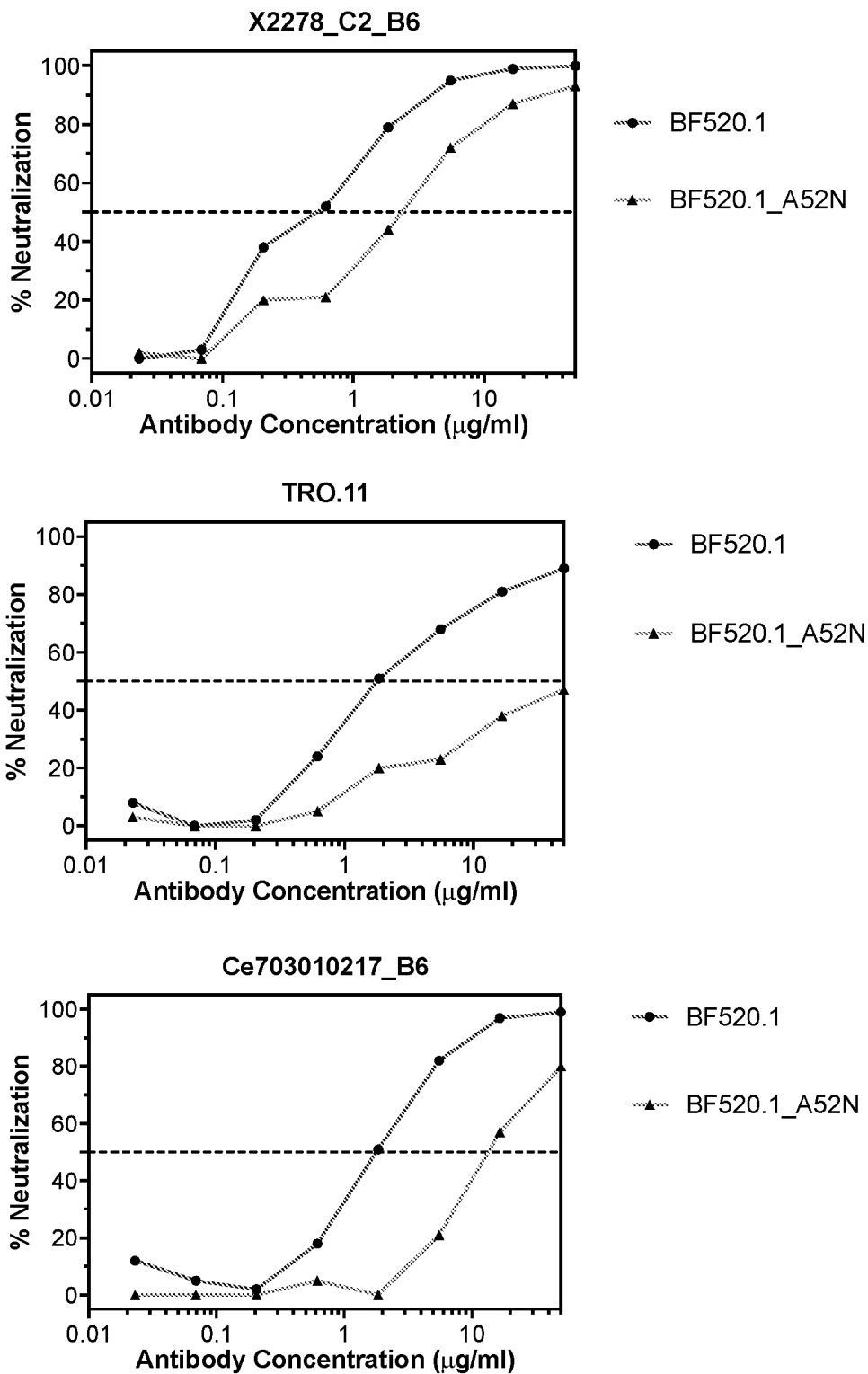
Figure 34C:
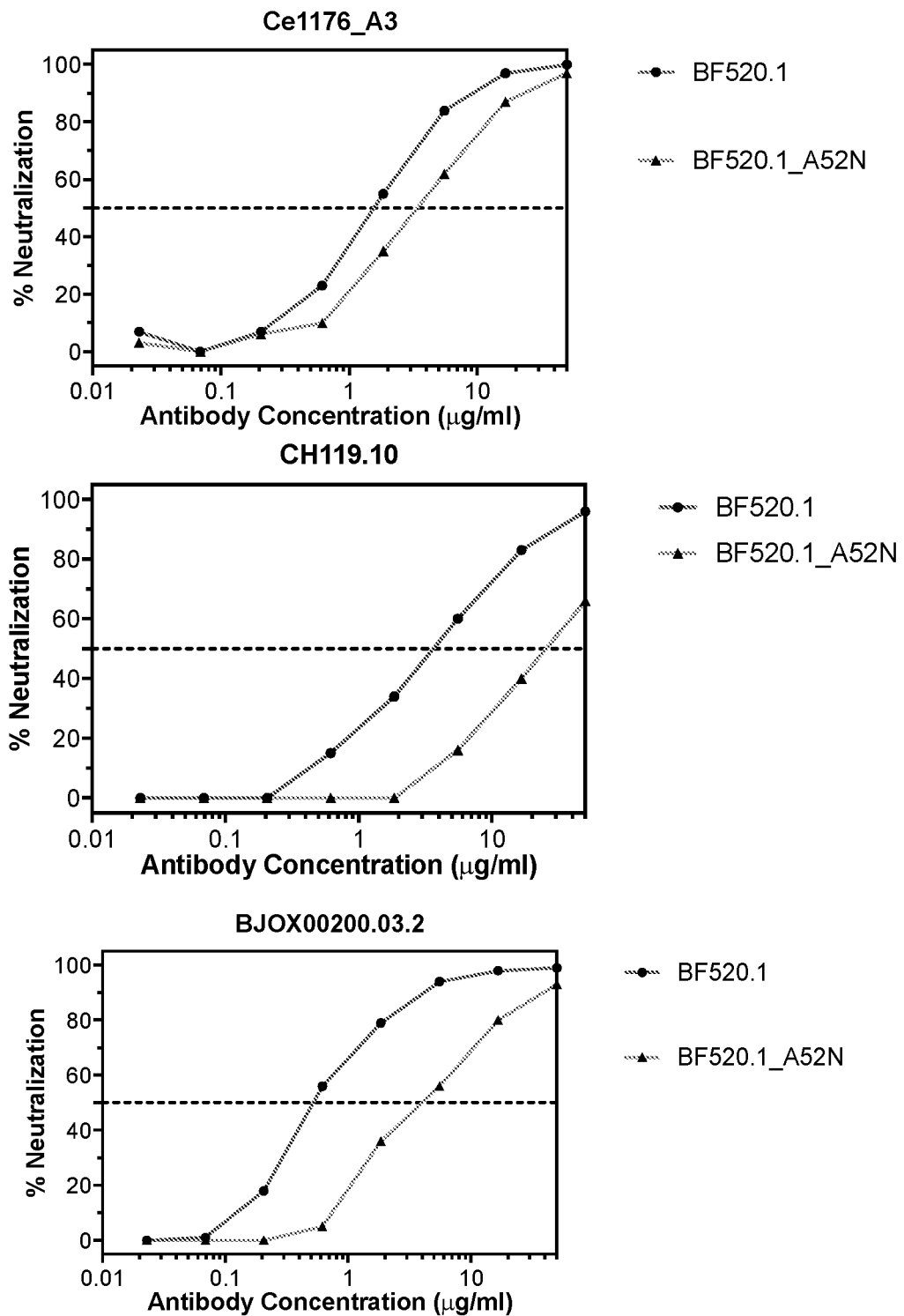
Figure 34C:
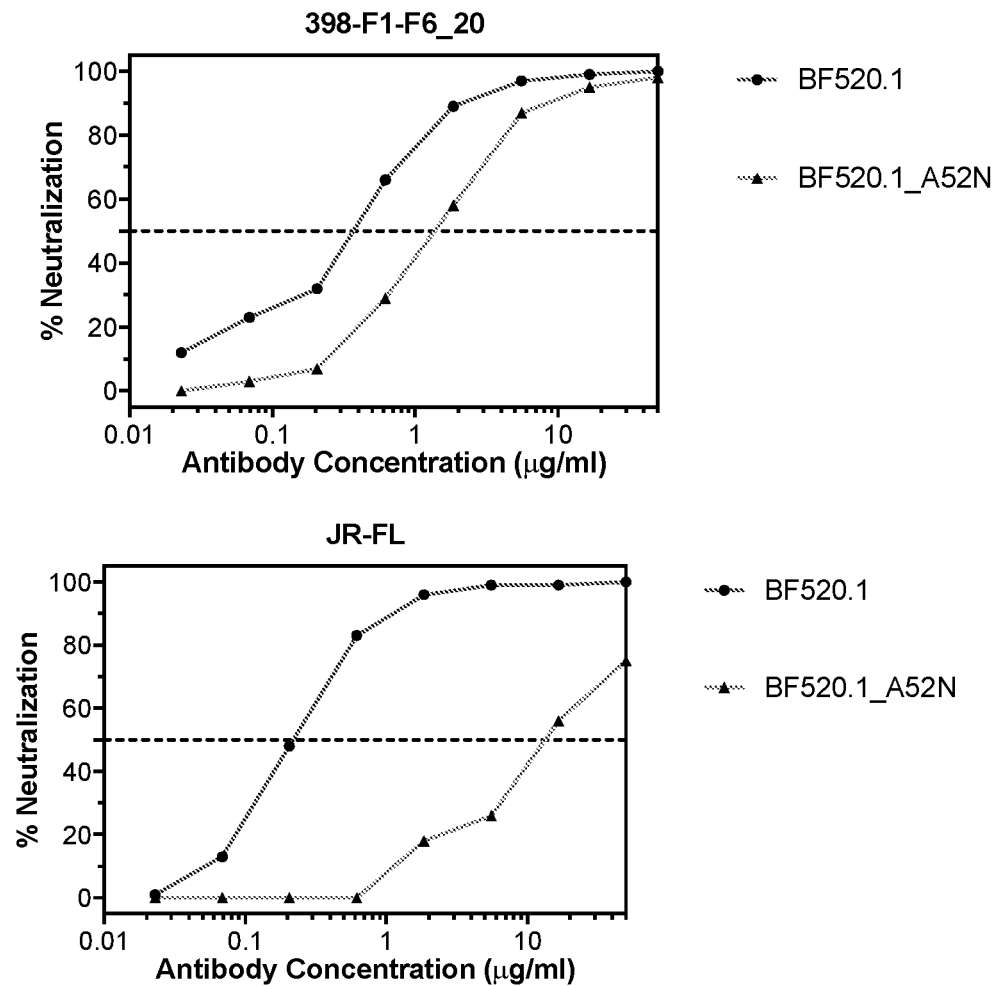

Babies are reported to develop bnAbs earlier after HIV-1 infection than adults (Goo et al., 2014; Muenchhoff et al., 2016). We analyzed the glycan-V3 epitope targeting BF520.1 bnAb, isolated from an HIV-1 infected infant with many fewer mutations (12 VH amino acid mutations) compared to VRC01 and CH235 (Simonich et al., 2016). We identified an improbable mutation, N52A, located in the CDR H2 of BF520.1, reverted it to germline, and expressed the resultant antibody mutant (A52N). Heterologous neutralization of the A52N reversion mutant against tier 2 JR-FL virus was markedly reduced relative to wildtype BF520.1 (FIG. 30C). The A52N reversion mutation antibody reduced neutralization potency for all tier 2 viruses that the BF520.1 bnAb could neutralize (FIG. 38 and FIG. 34C) demonstrating that the N52A mutation was critical to the neutralization potency of BF520.1 and suggested the early acquisition of this improbable mutation may have played a role in the relatively early elicitation (<15 months) of a bnAb with limited mutation frequency. Thus, the analysis of the three bnAbs studied here demonstrated that the ARMA-DiLLO program prospectively identified improbable mutations in bnAbs spanning multiple epitope specificities at distinct stages of bnAb development and functional antibody analysis demonstrated improbable mutations were critical for bnAb development of neutralization breadth and potency.

Improbable Antibody Mutations are Enriched in BnAbs

Figure 31B:
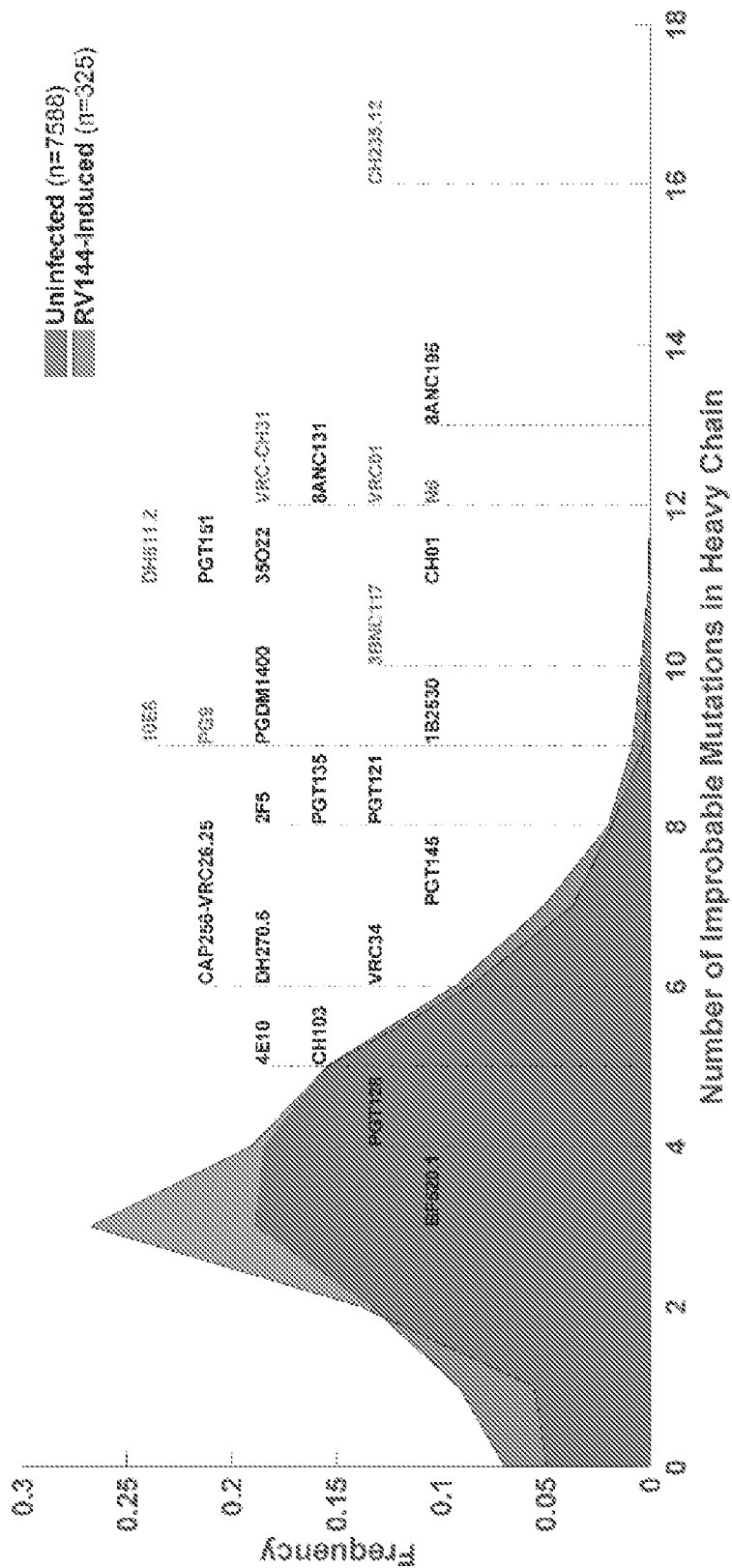
Figure 36B:
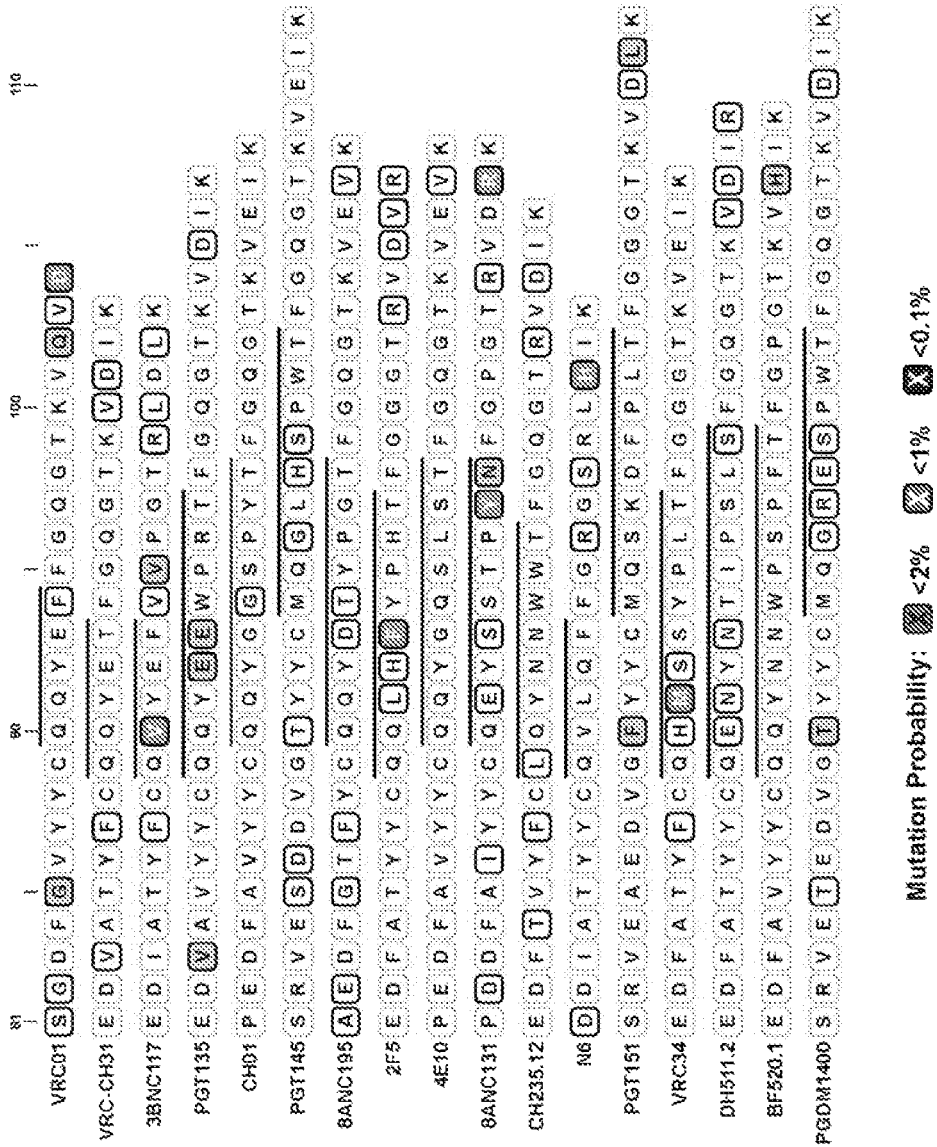
Figure 36C:
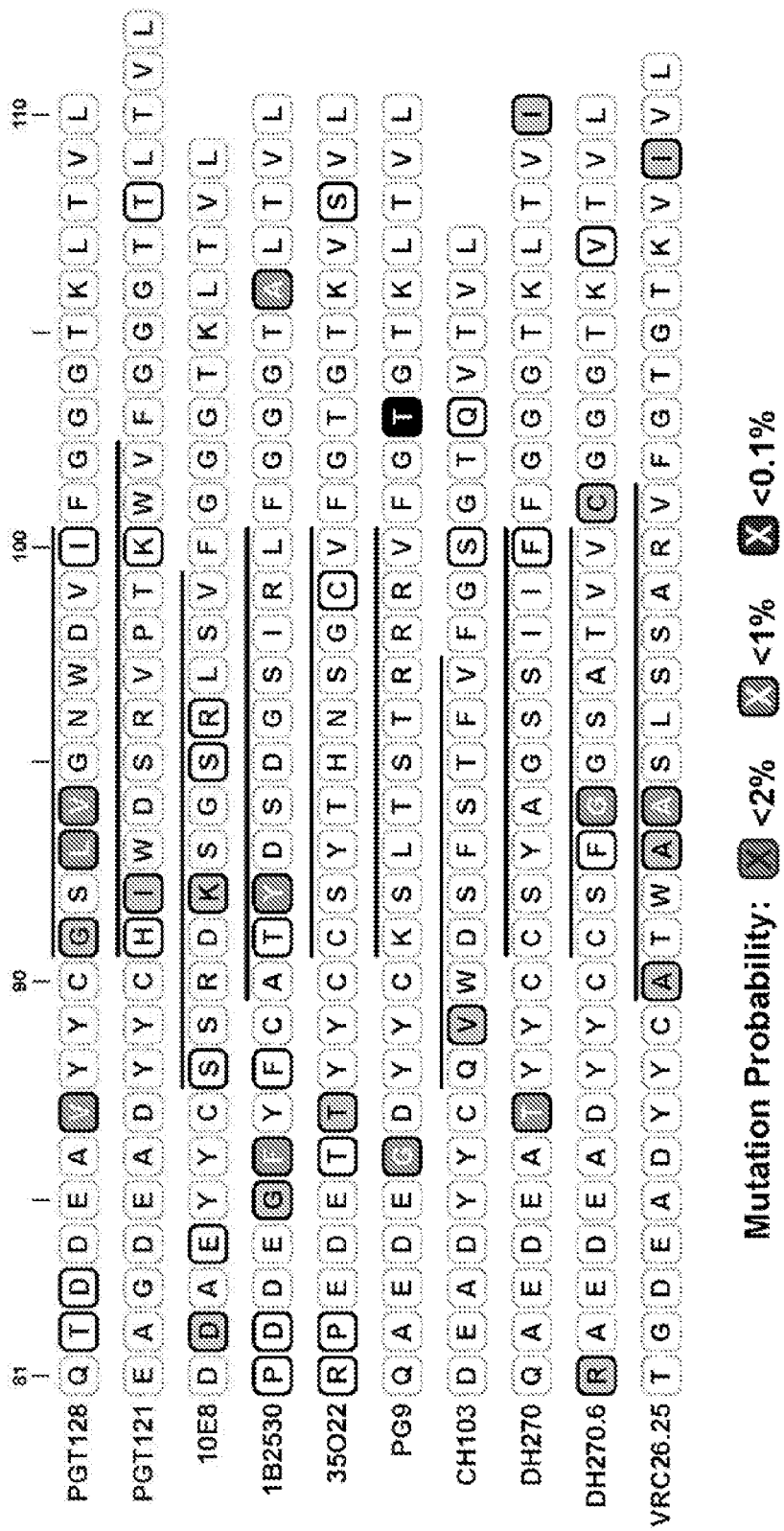
Figure 37A:
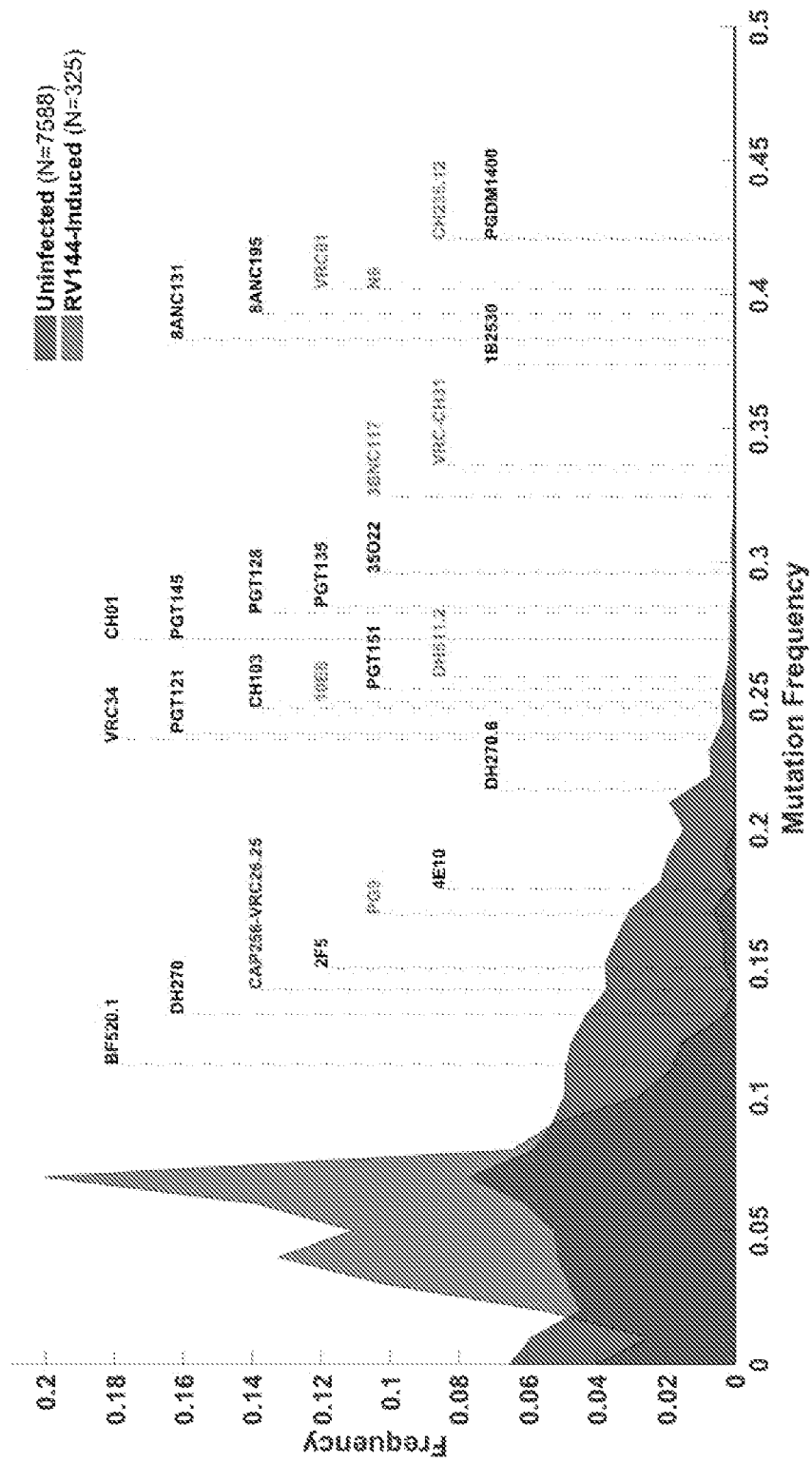
FIGS. 37A-C. BnAbs have high mutation frequencies and mutation frequency is correlated with improbable mutations. A) Histograms for the distributions of number of improbable mutations (A) and mutation frequency (B) from antibody heavy chain sequences from three groups: "RV144-induced" antibodies were isolated from RV144 vaccinated subjects by antigenically sorting with RV144 immunogens (red shaded area); "Uninfected" antibodies correspond to duplicated NGS reads from IgG antibodies isolated from PBMC samples from 8 HIV-uninfected individuals (blue shaded area; see methods for details on sampling); a representative set of published bnAb antibody sequences are shown labeled above dotted lines that correspond to their mutation frequency (defined as total number of amino acid mutations in non-CDRH3 VDJ sequence divided by non-CDRH3 VDJ sequence length). Scatterplots of B) number of improbable mutations versus amino acid mutation frequency for 7588 NGS reads from uninfected IgG antibodies from PBMC samples from 8 HIV-uninfected individuals and C) number of improbable mutations versus number of probable mutations (>2%). Number of improbable mutations was moderately correlated with number of probable mutations (Pearson's r=0.43). A stronger correlation was observed between improbable mutations and mutation frequency (Pearson's r=0.67) as expected because probable mutations are a subset of the total amino acid mutations used to calculate amino acid mutation frequency. Jitter added in order to alleviate over-plotting in panel C.
Figure 37B:
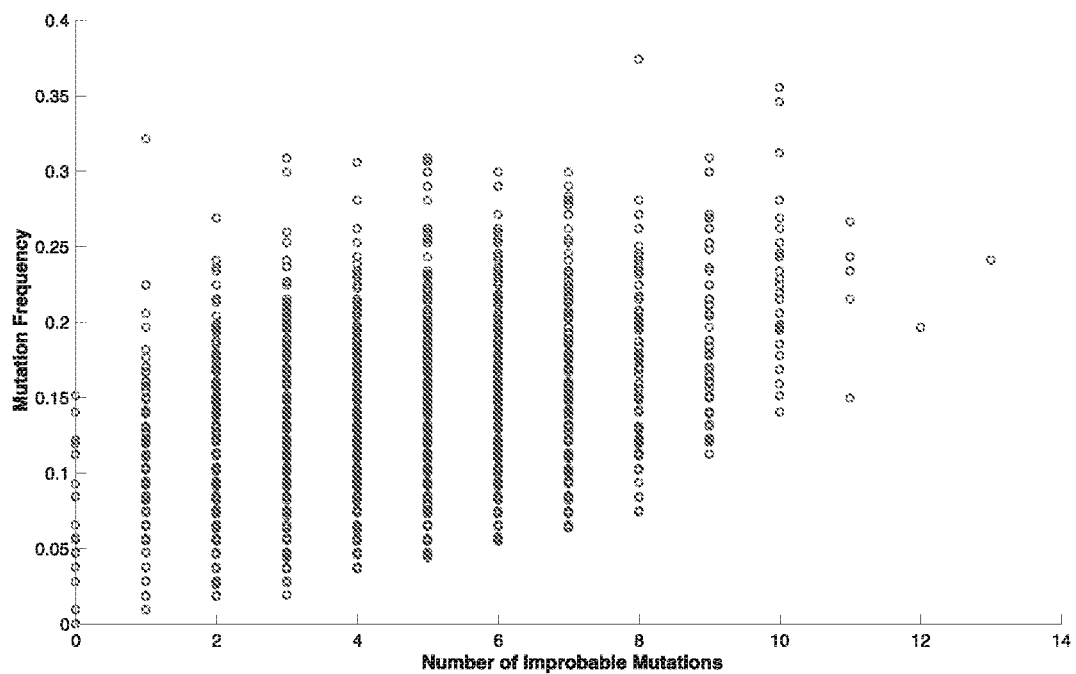
Figure 37C:
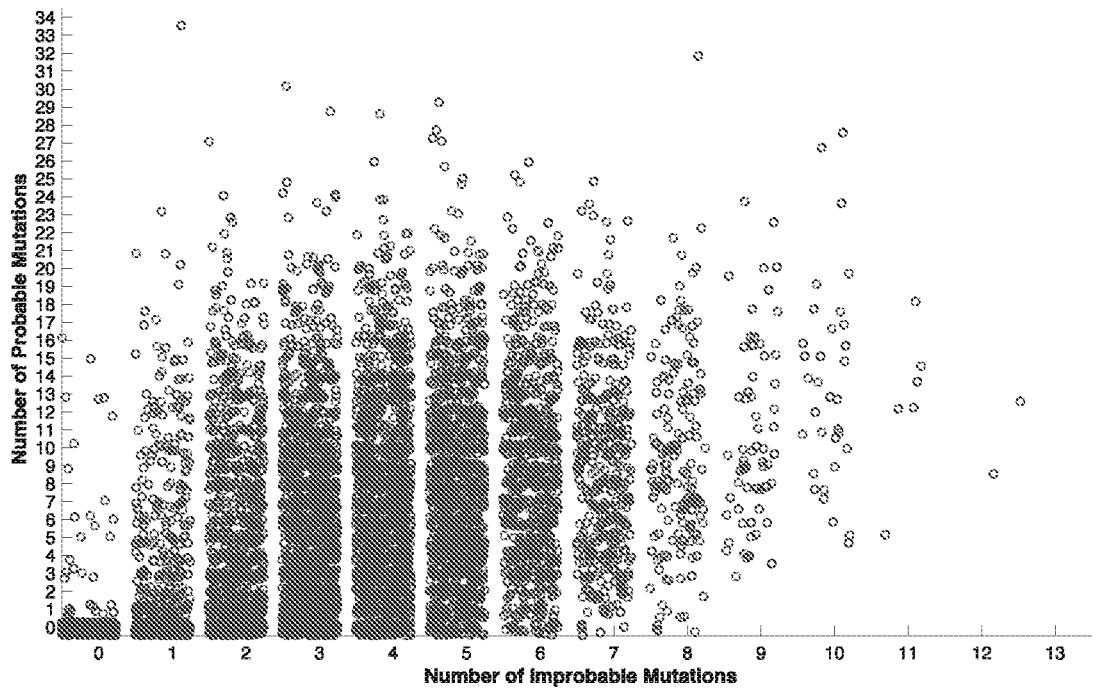

To provide a view of the scope of the problem for many bnAb B cell lineages, we estimated the number of improbable mutations for a representative set of known bnAb lineages spanning all known sites of vulnerability on the Env trimer (FIGS. 31A and 36, and FIG. 39). Study of a representative sample of bnAb lineages is plausible because of commonalities of Env recognition by bnAb germline precursors (Andrabi et al., 2015; Bonsignori et al., 2011; Gorman et al., 2016; Zhou et al., 2013). Compared to Env-reactive antibodies induced by an HIV-1 vaccine candidate (the RV144 vaccine) (Rerks-Ngarm et al., 2009) or antibodies isolated from non-HIV-1 infected individuals (Williams et al., 2015), the broadest and most potent HIV-1 bnAbs had the highest numbers of improbable mutations (FIG. 31B). This result may follow directly from the observations that bnAbs tend to be highly mutated (FIG. 37A) (Burton and Hangartner, 2016), and the number of improbable mutations an antibody possesses is correlated with its mutation frequency (FIG. 37B) (Sheng et al., 2017). However, it is not known why most bnAbs are highly mutated. Recent work has shown that not all mutations in bnAbs are essential for neutralization activity (Jardine et al., 2016). One hypothesis is that high mutation frequency is due to the extended number of rounds of somatic hypermutation required for a lineage to acquire a specific subset of mutations (Klein et al., 2013). If some of those specific mutations are also improbable, it is very likely that more probable mutations would be acquired prior to attaining key improbable ones. We found that for many bnAbs the number of improbable mutations exceeded what would be expected given their high mutation frequency alone. This observation, along with our experimental observations demonstrating that many improbable mutations are important for neutralization capacity, is consistent with the general rule that improbable mutations act as key bottlenecks in the development of bnAb neutralization breadth. Thus, during chronic HIV-1 infection with persistent high viral loads that are required for bnAbs with improbable mutations to develop (Gray et al., 2011), excess numbers of probable mutations also accumulate. Probable mutations arise easily from the intrinsic mutability of antibody genes and unlike improbable mutations may not require Env selection (Bonsignori et al., 2016; Hwang et al., 2017; Neuberger et al., 1998). Thus, if the selection of critical improbable mutations can be targeted with Env immunogens, it should be possible to accelerate bnAb maturation and result in the induction of bnAb lineages with fewer mutations than those that occur in the setting of chronic HIV-1 infection.

Implications for Vaccine Design

Figure 32:
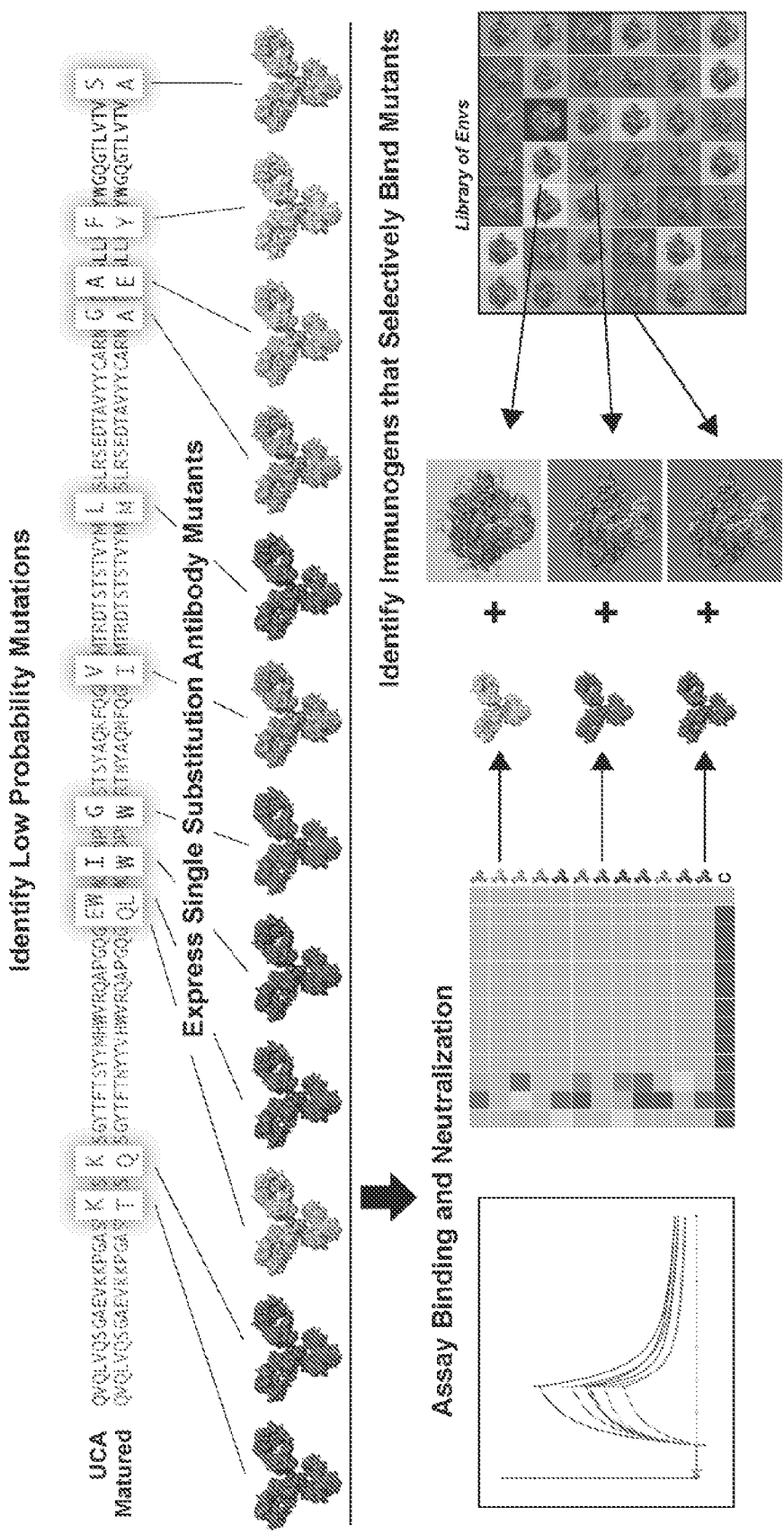
FIG. 32. Mutation Guided Lineage Design Vaccine Strategy. Improbable mutations can act as important bottlenecks in the development of bnAbs and we propose here a strategy to specifically target those mutations for selection through vaccination. First, for a specific bnAb lineage, low probability mutations are identified computationally and recombinant antibody mutants corresponding to these mutations are produced (top panel). Binding and neutralization assays are performed to validate which of the improbable mutations are functionally important for lineage development (middle panel, left) and Envs are chosen that can specifically bind the corresponding antibody mutants (middle panel, right). These Envs are then used in a sequential immunization regimen to select the most difficult-to-induce, critical mutations thus potentially alleviating key bottlenecks in bnAb elicitation.
Figure 32:
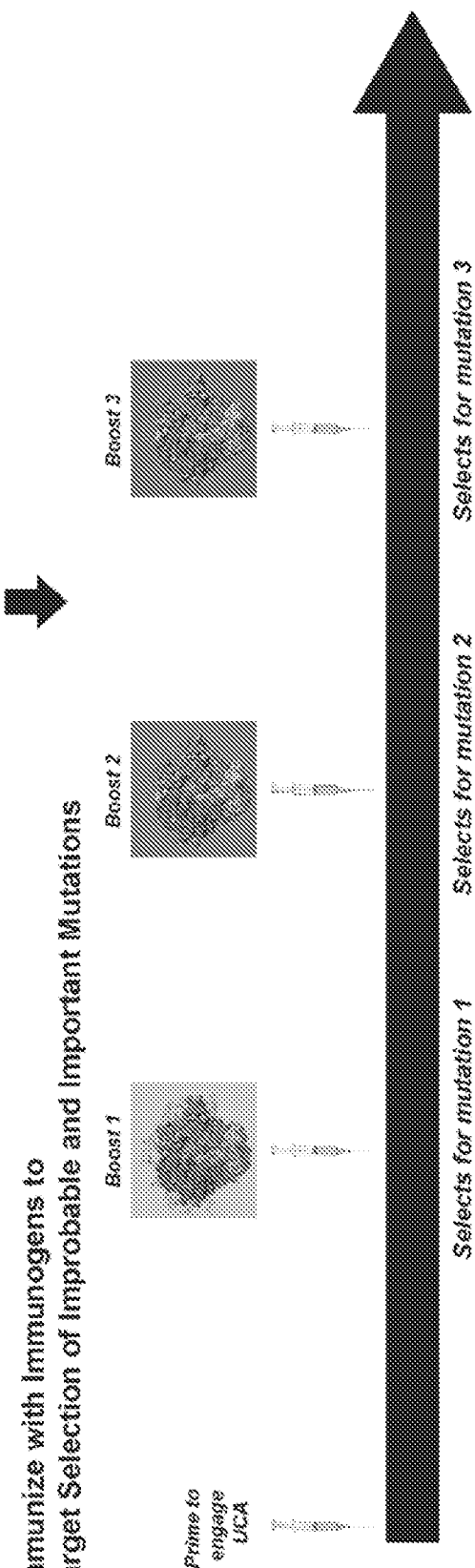

The ability to identify functional improbable bnAb mutations using the ARMADiLLO program and antibody mutation functional studies informs a mutation-guided vaccine design and immunization strategy (FIG. 32). The principal goal is to be able to choose the correct sequential Envs to precisely focus selection towards the most difficult to induce mutations, while allowing the easier, more probable mutations to occur due to antibody intrinsic mutability from immune activation-associated AID activity. In this strategy, improbable mutations are identified computationally using the ARMADiLLO program. Next, all improbable mutations identified are expressed as single amino acid substitution mutant antibodies and their functional importance validated by Env binding and neutralization assays. Envelopes that bind with high affinity are chosen as immunogens to select for these functional improbable mutations. Last, sequential immunization with the chosen immunogens are studied for optimization of regimens to select for B cells with BCRs with the required improbable mutations.

As expected, because improbable mutations arise as either neutral mutations or by selection by autologous virus, not all improbable mutations are required for mediation of heterologous neutralization (FIG. 38). Similarly, it is important to note that intrinsically mutable positions (Neuberger et al., 1998) can also be capable of conferring heterologous breadth. In this regard we identified one such functionally important probable intrinsic mutation in the CH235 lineage, S57R (FIG. 38). However, such highly probable mutations, by definition, should be easily inducible and are not likely to represent barriers in bnAb development.

Interestingly, bnAbs that demonstrated relatively low numbers of improbable single somatic mutations (FIG. 31A) possessed other unusual antibody characteristics that were due to additional improbable events such as insertion/deletions (indels) or extraordinary CDR H3 lengths. For example, the bnAbs with the two lowest number of improbable mutations were PGT128 and CAP256-VRC26.25. These bnAbs are notable for having the largest indels (PGT128; 11 aas) or the longest CDR H3 (CAP256-VRC26.25; 38 aas). In summary, our data presented here suggest Env trimers evolved to evade neutralizing B-cell responses by hiding within low probability regions of antibody sequence space. The ARMADiLLO program and mutation-guided vaccine design strategy presented here should be broadly applicable for vaccine design for other mutating pathogens.

Low probability mutation is the same as improbable or rare mutation. Functional or important mutations are improbable mutations which lead to loss of neutralization breadth when reverted back to a UCA amino acid.

Experimental Procedures

Analysis of the Probability of Antibody Mutations

The probability of an amino acid substitution at any given position in the antibody sequence of an antibody of interest was estimated using the ARMADiLLO program. The algorithm and the analysis performed using ARMADiLLO are described in Supplemental Experimental Procedures.

Antibody Site-directed Mutagenesis

BF520.1 mutant antibody genes were synthesized by Genscript and recombinantly produced. Mutations into antibody genes for CH235 and VRC01 mutants were introduced using the QuikChange II Lightning site-directed mutagenesis kit (Agilent Technologies) following the manufacturer's protocol. Single-colony sequencing was used to confirm the sequences of the mutant plasmid products. Primers used for introducing mutations are listed in the Supplemental Experimental Procedures.

Recombinant Antibody Production

Antibodies were recombinantly produced as previously described (Saunders et al., 2017).

HIV-1 Neutralization

Antibody neutralization was measured in TZM-bl cell-based neutralization assays as previously described (Li et al., 2005; Sarzotti-Kelsoe et al., 2014). CH235 and BF520.1 and selected mutants were assayed for neutralization using a global panel of 12 HIV-1 Env reference strains (deCamp et al., 2014). Neutralization values are reported as inhibitory concentrations of antibody in which 50% of virus was neutralized ($IC_{50}$) with units in µg/ml.

Antibody Binding Measurements

Binding of CH235.UCA and mutants to the monomeric CH505 transmitted/founder (T/F) delta7 gp120 and monomeric CH505 M5 (early autologous virus variant) delta8 gp120 (Bonsignori et al., 2016; Gao et al., 2014) was measured by surface plasmon resonance assays (SPR) on a Biacore S200 instrument and data analysis was performed with the S200 BIAevaluation software (Biacore/GE Healthcare) as previously described (Alam et al., 2013; Dennison et al., 2011).

Various other methods to determine and measure binding between an antibody and an antigen are known in the art and contemplated by the invention. Such methods are used to identify antigens which bind differentially to different antibodies such as a UCA, and an antibody variant having an improbable mutation(s).

REFERENCES FOR EXAMPLE 1

Alam, S. M., Liao, H. X., Tomaras, G. D., Bonsignori, M., Tsao, C. Y., Hwang, K. K., Chen, H., Lloyd, K. E., Bowman, C., Sutherland, L., et al. (2013). Antigenicity and immunogenicity of RV144 vaccine AIDSVAX Glade E envelope immunogen is enhanced by a gp120 N-terminal deletion. J Virol 87, 1554-1568.

Andrabi, R., Voss, J. E., Liang, C. H., Briney, B., McCoy, L. E., Wu, C. Y., Wong, C. H., Poignard, P., and Burton, D. R. (2015). Identification of Common Features in Prototype Broadly Neutralizing Antibodies to HIV Envelope V2 Apex to Facilitate Vaccine Design. Immunity 43, 959-973.

Behrens, A. J., Vasiljevic, S., Pritchard, L. K., Harvey, D. J., Andev, R. S., Krumm, S. A., Struwe, W. B., Cupo, A., Kumar, A., Zitzmann, N., et al. (2016). Composition and Antigenic Effects of Individual Glycan Sites of a Trimeric HIV-1 Envelope Glycoprotein. Cell Rep 14, 2695-2706.

Betz, A. G., Rada, C., Pannell, R., Milstein, C., and Neuberger, M. S. (1993). Passenger transgenes reveal intrinsic specificity of the antibody hypermutation mechanism: clustering, polarity, and specific hot spots. Proc Natl Acad Sci USA 90, 2385-2388.

Bonsignori, M., Hwang, K. K., Chen, X., Tsao, C. Y., Morris, L., Gray, E., Marshall, D. J., Crump, J. A., Kapiga, S. H., Sam, N. E., et al. (2011). Analysis of a clonal lineage of HIV-1 envelope V2/V3 conformational epitope-specific broadly neutralizing antibodies and their inferred unmutated common ancestors. J Virol 85, 9998-10009.

Bonsignori, M., Kreider, E. F., Fera, D., Meyerhoff, R. R., Bradley, T., Wiehe, K., Alam, S. M., Aussedat, B., Walkowicz, W. E., Hwang, K. K., et al. (2017). Staged induction of HIV-1 glycan-dependent broadly neutralizing antibodies. Sci Transl Med 9.

Bonsignori, M., Zhou, T., Sheng, Z., Chen, L., Gao, F., Joyce, M. G., Ozorowski, G., Chuang, G. Y., Schramm, C. A., Wiehe, K., et al. (2016). Maturation Pathway from Germline to Broad HIV-1 Neutralizer of a CD4-Mimic Antibody. Cell 165, 449-463.

Burton, D. R., and Hangartner, L. (2016). Broadly Neutralizing Antibodies to HIV and Their Role in Vaccine Design. Annu Rev Immunol 34, 635-659.

Cowell, L. G., and Kepler, T. B. (2000). The nucleotide-replacement spectrum under somatic hypermutation exhibits microsequence dependence that is strand-symmetric and distinct from that under germline mutation. J Immunol 164, 1971-1976.

deCamp, A., Hraber, P., Bailer, R. T., Seaman, M. S., Ochsenbauer, C., Kappes, J., Gottardo, R., Edlefsen, P., Self, S., Tang, H., et al. (2014). Global panel of HIV-1 Env reference strains for standardized assessments of vaccine-elicited neutralizing antibodies. J Virol 88, 2489-2507.

Dennison, S. M., Anasti, K., Scearce, R. M., Sutherland, L., Parks, R., Xia, S. M., Liao, H. X., Gorny, M. K., Zolla-Pazner, S., Haynes, B. F., and Alam, S. M. (2011). Nonneutralizing HIV-1 gp41 envelope cluster II human monoclonal antibodies show polyreactivity for binding to phospholipids and protein autoantigens. J Virol 85, 1340-1347.

Di Noia, J. M., and Neuberger, M. S. (2007). Molecular mechanisms of antibody somatic hypermutation. Annu Rev Biochem 76, 1-22.

Doria-Rose, N. A., Schramm, C. A., Gorman, J., Moore, P. L., Bhiman, J. N., DeKosky, B. J., Ernandes, M. J., Georgiev, I. S., Kim, H. J., Pancera, M., et al. (2014). Developmental pathway for potent V1V2-directed HIV-neutralizing antibodies. Nature 509, 55-62.

Gao, F., Bonsignori, M., Liao, H. X., Kumar, A., Xia, S. M., Lu, X., Cai, F., Hwang, K. K., Song, H., Zhou, T., et al. (2014). Cooperation of B cell lineages in induction of HIV-1-broadly neutralizing antibodies. Cell 158, 481-491.

Georgiev, I. S., Rudicell, R. S., Saunders, K. O., Shi, W., Kirys, T., McKee, K., O'Dell, S., Chuang, G. Y., Yang, Z. Y., Ofek, G., et al. (2014). Antibodies VRC01 and 10E8 neutralize HIV-1 with high breadth and potency even with Ig-framework regions substantially reverted to germline. J Immunol 192, 1100-1106.

Goo, L., Chohan, V., Nduati, R., and Overbaugh, J. (2014). Early development of broadly neutralizing antibodies in HIV-1-infected infants Nat Med 20, 655-658.

Gorman, J., Soto, C., Yang, M. M., Davenport, T. M., Guttman, M., Bailer, R. T., Chambers, M., Chuang, G. Y., DeKosky, B. J., Doria-Rose, N. A., et al. (2016). Structures of HIV-1 Env V1V2 with broadly neutralizing antibodies reveal commonalities that enable vaccine design. Nat Struct Mol Biol 23, 81-90.

Gray, E. S., Madiga, M. C., Hermanus, T., Moore, P. L., Wibmer, C. K., Tumba, N. L., Werner, L., Mlisana, K., Sibeko, S., Williamson, C., et al. (2011). The neutralization breadth of HIV-1 develops incrementally over four years and is associated with CD4+ T cell decline and high viral load during acute infection. J Virol 85, 4828-4840.

Haynes, B. F., and Burton, D. R. (2017). Developing an HIV vaccine. Science 355, 1129-1130.

Haynes, B. F., Kelsoe, G., Harrison, S. C., and Kepler, T. B. (2012). B-cell-lineage immunogen design in vaccine development with HIV-1 as a case study. Nat Biotechnol 30, 423-433.

Hraber, P., Seaman, M. S., Bailer, R. T., Mascola, J. R., Montefiori, D. C., and Korber, B. T. (2014). Prevalence of broadly neutralizing antibody responses during chronic HIV-1 infection. AIDS 28, 163-169.

Hwang, J. K., Wang, C., Du, Z., Meyers, R. M., Kepler, T. B., Neuberg, D., Kwong, P. D., Mascola, J. R., Joyce, M. G., Bonsignori, M., et al. (2017). Sequence Intrinsic Somatic Mutation Mechanisms Contribute to Affinity Maturation of VRC01-class HIV-1 Broadly Neutralizing Antibodies. Proc Natl Acad Sci USA In Press.

Jardine, J. G., Sok, D., Julien, J. P., Briney, B., Sarkar, A., Liang, C. H., Scherer, E. A., Henry Dunand, C. J., Adachi, Y., Diwanji, D., et al. (2016). Minimally Mutated HIV-1

Broadly Neutralizing Antibodies to Guide Reductionist Vaccine Design. PLoS Pathog 12, e1005815.

Kelsoe, G., and Haynes, B. F. (2017). Host controls of HIV broadly neutralizing antibody development. Immunol Rev 275, 79-88.

Kepler, T. B., Liao, H. X., Alam, S. M., Bhaskarabhatla, R., Zhang, R., Yandava, C., Stewart, S., Anasti, K., Kelsoe, G., Parks, R., et al. (2014). Immunoglobulin gene insertions and deletions in the affinity maturation of HIV-1 broadly reactive neutralizing antibodies. Cell Host Microbe 16, 304-313.

Klein, F., Diskin, R., Scheid, J. F., Gaebler, C., Mouquet, H., Georgiev, I. S., Pancera, M., Zhou, T., Incesu, R. B., Fu, B. Z., et al. (2013). Somatic mutations of the immunoglobulin framework are generally required for broad and potent HIV-1 neutralization. Cell 153, 126-138.

Li, M., Gao, F., Mascola, J. R., Stamatatos, L., Polonis, V. R., Koutsoukos, M., Voss, G., Goepfert, P., Gilbert, P., Greene, K. M., et al. (2005). Human immunodeficiency virus type 1 env clones from acute and early subtype B infections for standardized assessments of vaccine-elicited neutralizing antibodies. J Virol 79, 10108-10125.

Liao, H. X., Lynch, R., Zhou, T., Gao, F., Alam, S. M., Boyd, S. D., Fire, A. Z., Roskin, K. M., Schramm, C. A., Zhang, Z., et al. (2013). Co-evolution of a broadly neutralizing HIV-1 antibody and founder virus. Nature 496, 469-476.

Muenchhoff, M., Adland, E., Karimanzira, O., Crowther, C., Pace, M., Csala, A., Leitman, E., Moonsamy, A., McGregor, C., Hurst, J., et al. (2016). Nonprogressing HIV-infected children share fundamental immunological features of nonpathogenic SIV infection. Sci Transl Med 8, 358ra125.

Neuberger, M. S., Ehrenstein, M. R., Klix, N., Jolly, C. J., Yelamos, J., Rada, C., and Milstein, C. (1998). Monitoring and interpreting the intrinsic features of somatic hypermutation. Immunol Rev 162, 107-116.

Rerks-Ngarm, S., Pitisuttithum, P., Nitayaphan, S., Kaewkungwal, J., Chiu, J., Paris, R., Premsri, N., Namwat, C., de Souza, M., Adams, E., et al. (2009). Vaccination with ALVAC and AIDSVAX to prevent HIV-1 infection in Thailand. N Engl J Med 361, 2209-2220.

Sarzotti-Kelsoe, M., Bailer, R. T., Turk, E., Lin, C. L., Bilska, M., Greene, K. M., Gao, H., Todd, C. A., Ozaki, D. A., Seaman, M. S., et al. (2014). Optimization and validation of the TZM-bl assay for standardized assessments of neutralizing antibodies against HIV-1. J Immunol Methods 409, 131-146.

Saunders, K. O., Nicely, N. I., Wiehe, K., Bonsignori, M., Meyerhoff, R. R., Parks, R., Walkowicz, W. E., Aussedat, B., Wu, N. R., Cai, F., et al. (2017). Vaccine Elicitation of High Mannose-Dependent Neutralizing Antibodies against the V3-Glycan Broadly Neutralizing Epitope in Nonhuman Primates. Cell Rep 18, 2175-2188.

Scheid, J. F., Mouquet, H., Ueberheide, B., Diskin, R., Klein, F., Oliveira, T. Y., Pietzsch, J., Fenyo, D., Abadir, A., Velinzon, K., et al. (2011). Sequence and structural convergence of broad and potent HIV antibodies that mimic CD4 binding. Science 333, 1633-1637.

Seaman, M. S., Janes, H., Hawkins, N., Grandpre, L. E., Devoy, C., Giri, A., Coffey, R. T., Harris, L., Wood, B., Daniels, M. G., et al. (2010). Tiered categorization of a diverse panel of HIV-1 Env pseudoviruses for assessment of neutralizing antibodies. J Virol 84, 1439-1452.

Sheng, Z., Schramm, C. A., Kong, R., Program, N. C. S., Mullikin, J. C., Mascola, J. R., Kwong, P. D., and Shapiro, L. (2017). Gene-Specific Substitution Profiles Describe the Types and Frequencies of Amino Acid Changes during Antibody Somatic Hypermutation. Front Immunol 8, 537.

Simonich, C. A., Williams, K. L., Verkerke, H. P., Williams, J. A., Nduati, R., Lee, K. K., and Overbaugh, J. (2016). HIV-1 Neutralizing Antibodies with Limited Hypermutation from an Infant Cell 166, 77-87.

Stewart-Jones, G. B., Soto, C., Lemmin, T., Chuang, G. Y., Druz, A., Kong, R., Thomas, P. V., Wagh, K., Zhou, T., Behrens, A. J., et al. (2016). Trimeric HIV-1-Env Structures Define Glycan Shields from Clades A, B, and G. Cell 165, 813-826.

Teng, G., and Papavasiliou, F. N. (2007). Immunoglobulin somatic hypermutation. Annu Rev Genet 41, 107-120.

Williams, W. B., Liao, H. X., Moody, M. A., Kepler, T. B., Alam, S. M., Gao, F., Wiehe, K., Trama, A. M., Jones, K., Zhang, R., et al. (2015). HIV-1 VACCINES. Diversion of HIV-1 vaccine-induced immunity by gp41-microbiota cross-reactive antibodies. Science 349, aab1253.

Wu, X., Zhang, Z., Schramm, C. A., Joyce, M. G., Kwon, Y. D., Zhou, T., Sheng, Z., Zhang, B., O'Dell, S., McKee, K., et al. (2015). Maturation and Diversity of the VRC01-Antibody Lineage over 15 Years of Chronic HIV-1 Infection. Cell 161, 470-485.

Yaari, G., Vander Heiden, J. A., Uduman, M., Gadala-Maria, D., Gupta, N., Stern, J. N., O'Connor, K. C., Hafler, D. A., Laserson, U., Vigneault, F., and Kleinstein, S. H. (2013). Models of somatic hypermutation targeting and substitution based on synonymous mutations from high-throughput immunoglobulin sequencing data. Front Immunol 4, 358.

Yeap, L. S., Hwang, J. K., Du, Z., Meyers, R. M., Meng, F. L., Jakubauskaite, A., Liu, M., Mani, V., Neuberg, D., Kepler, T. B., et al. (2015). Sequence-Intrinsic Mechanisms that Target AID Mutational Outcomes on Antibody Genes. Cell 163, 1124-1137.

Yu, L., and Guan, Y. (2014). Immunologic Basis for Long HCDR3s in Broadly Neutralizing Antibodies Against HIV-1. Front Immunol 5, 250.

Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-817.

Zhou, T., Zhu, J., Wu, X., Moquin, S., Zhang, B., Acharya, P., Georgiev, I. S., Altae-Tran, H. R., Chuang, G. Y., Joyce, M. G., et al. (2013). Multidonor analysis reveals structural elements, genetic determinants, and maturation pathway for HIV-1 neutralization by VRC01-class antibodies. Immunity 39, 245-258.

Supplemental Experimental Procedures

Simulating the Somatic Hypermutation Process

Because AID targets hot spots according to their underlying sequence motifs, the probability of mutations is sequence context dependent, making an analytical computation of the probability of a mutation in the absence of selection is all but intractable. Instead, we take a numerical approach via simulation. In this approach, we estimate the probability of an amino acid substitution by simulating the somatic hypermutation (SHM) process and calculating the observed frequency of that substitution in the simulated sequences.

The simulation proceeds as follows. Given a matured antibody nucleotide sequence, we first infer its unmutated common ancestor (UCA) sequence by a computational tool called Clonalyst (Kepler, 2013; Kepler et al., 2014). The UCA determines the initial sequence and then the differences from the UCA in the mature sequence define which positions are mutations. In addition, the UCA sequence is used to initially define the mutability score at each nucleotide position using the S5F model. The mutability score is turned into a probability distribution that we randomly sample from to select a nucleotide position to mutate. A computational tool called Cloanalyst is used to infer UCAs, so if there is one sequence one can infer the UCA. If there are multiple clonally related sequences, typically referred to as lineage, one can infer a UCA using Cloanalyst and multiple sequences may help add confidence in UCA positions where there is less confidence when just using one sequence, for example one sequence of a bnAb.

In some embodiments, the availability of multiple clonally related sequences might be useful to inform the order of adding multiple functional mutations back to the UCA sequence to create intermediate antibodies used to identify antigens which would drive the selection of a functional mutation(s). Without the availability of clonally related sequences, the order of adding multiple functional mutations back to the UCA is determined experimentally. With reference to FIG. 32 (Mutation Guided Lineage Design Vaccine Strategy), a clonal lineage would be informative to determine the order of mutation 1, mutation 2, etc.

For the analysis in this example, one mature sequence was inputted to Cloanalyst to infer the UCA, in order to put all BNAbs on the same playing field. A skilled artisan appreciates that an inferred UCA is likely not truly correct, unless it has been observed. In all instances in this example, the UCAs are inferred. So there is uncertainty in the inference. The effect of the uncertainty on ARMADiLLO is that if the wrong base is called in the UCA, it would potentially affect the mutability score which affects the random targeting of positions for mutation Next, the matured antibody nucleotide sequence is aligned to the UCA nucleotide sequence and the number of sites mutated, t, is computed. Starting with the UCA sequence, first (1) the mutability score of all consecutive sequence pentamers is computed according to the S5F mutability model (Yaari et al., 2013).

Second (2) The mutability scores for each base position in the sequence are converted into the probability distribution, Q, by:

$$Q_i = \frac{C_i}{\sum_{i=1}^{L} C_i} \quad [1]$$

where $C_i$ is the mutability score at position i and L is the length of the sequence. 3) A base position, b, is drawn randomly according to Q. 4) The nucleotide n, at b, is substituted according to the S5F substitution model (Yaari et al., 2013), resulting in sequence $S_j$ where j is the number of mutations accrued during the simulation. The procedure then iterates over steps 1-4 until j=t. This results in a simulated sequence, $S_t$, that has acquired the same number of nucleotide mutations as observed in the matured antibody sequence of interest. If at any iteration during the simulation a mutation results in a stop codon, that sequence is discarded and the process restarts from the UCA sequence. This simulation procedure is then repeated to generate 100,000 simulated matured sequences. These nucleotide sequences are then translated to amino acid sequences.

Estimating the Probability of an Amino Acid Substitution

The estimate of the probability of any amino acid substitution U→Y at site i given the number of mutations t observed in the matured sequence of interest is then calculated as the amino acid frequency observed at site i in the simulated sequences according to:

$$\hat{P}(X_{i_{U \rightarrow Y}} | UCA, t) = \frac{1}{N} \sum_{j=0}^{N} 1(X_{ij} = Y) \quad [2]$$

where $X_i$ is the amino acid at site i which has the amino acid U in the UCA sequence mutating to amino acid Y in the matured sequence of interest, UCA is the UCA sequence, N is the number of simulated sequences, 1 is an indicator function for observing amino acid Y at site i in the jth simulated sequence. This estimate is for an amino acid substitution in the absence of selection and we use this probability as a gauge of how likely it is that a B cell would arise to have this mutation prior to antigenic selection. Amino acid substitutions that are the result of mutations that occur in AID hot spots will have high probabilities, occur frequently and a subset of the reservoir of B cell clonal members would likely have these mutations present prior to antigenic selection. Amino substitutions that are the result of cold spot mutations or require multiple base substitutions will be much less frequent and could represent significant hurdles to lineage development and these substitutions may require strong antigenic selection to be acquired during B cell maturation.

Improbable Mutations

The probability of a specific amino substitution at any given position is the product of two components. The first component is due to the bias of the AID enzyme in targeting that specific base position and the DNA repair mechanisms preference for substituting to an alternative base. Practically speaking, substitutions that require mutations at AID cold spots and/or result in disfavored base substitutions by DNA repair mechanisms are infrequent and thus improbable. The second component is the number and length of available paths through codon space to go from an amino acid encoded by the codon in the UCA to that of the codon for the substituted amino acid in the matured sequence. To illustrate this, we turn to a practical example: the TAT codon which encodes the amino acid, Tyr. From the TAT codon, 5 amino acids are achievable by a single nucleotide base substitution (C, D, F, H, N, S), 12 amino acids by two base substitutions (A, E, G, I, K, L, P, Q, R, T, V, W) and 1 amino acid (M) by three base substitutions. Without considering the bias of AID, the Y→M mutation starting from the TAT codon is inherently unlikely to occur because it requires three independent mutational events to occur within the same codon. By simulating the SHM process, ARMADiLLO captures the interplay of these two components and is able to estimate the probability of any amino acid substitution prior to selection by taking both components into account.

Without using ARMADiLLO one could use a reference set of NGS sequences from antibody repertoire sequencing and observe the frequency of an amino acid at a given position. So one could take 100 people, sequence their antibody repertoires, then see how many times in VH1-46 (CH235's V gene segment) does the K19 mutate to T. The distinction here is that frequency is after selection has occurred. Meaning there may be many times in which K19 mutated to T, but it was not beneficial to the antibody's maturation, and so would not be selected and then ultimately observed in the NGS data. What ARMADILLO does is simulate AID targeting and substitution in order to estimate the probability of a mutation BEFORE selection. The interest here is in what happens prior to selection, because the goal is designing immunogens that act to do that selection.

Calculating the Expected Number of Improbable Mutations

The number of improbable amino acid mutations, M, in an antibody sequence at a given probability cutoff can be estimated by applying [2] and enumerating over the entire amino acid sequence. For example, CH235.12 is estimated to have M=16 improbable mutations in its heavy chain when improbable mutations are defined as amino acid substitutions with <2% estimated probability. We estimate the probability of getting M improbable mutations or greater at a given amino acid mutation frequency, u, from the empirical distribution of the number of improbable mutations observed in sequences simulated to acquire T amino acid mutations, where T=u*L and L is the length of the sequence. To calculate the empirical distribution of improbable mutations for each antibody sequence of interest, we first randomly draw 1000 sequences from an antibody sequence dataset generated from NGS sequencing of 8 HIV-1 negative individuals and infer the UCA of each sequence (REF). From these randomly sampled UCAs, we then simulate the SHM process using the same simulation procedure as detailed above and stop the simulation when each sequence acquires T amino acid mutations. This results in a set of 1000 simulated sequences each with an amino acid mutation frequency of u. The probability of observing M or greater improbable mutations in the absence of selection is then:

$$P(X \geq M) = \frac{1}{N}\sum_{j=0}^{N} 1(X_j \geq M) \quad [3]$$

where N is the number of simulations (here N=1000), $X_j$ is the number of improbable mutations in the jth simulated sequence (calculated from [2] over all amino acid positions in the sequence) and 1 is an indicator function. Here we exclude the CDR3 sequence from our calculations of both M and u as the inference of the UCA has widely varying levels of uncertainty in the CDR3 region depending on the input matured sequence.

Standard methods for determining selection at an amino acid site typically rely on the measure co which is the ratio of non-synonymous mutations to synonymous mutations at that position in a multiple sequence alignment of related gene sequences. Here, we avoid this measure of selection for two reasons. In many instances in this study we have only two sequences to compare, the UCA and the matured sequence. This does not provide the number of observations needed for co to reliably indicate selection. In some case, where we do have multiple clonal member to align, the number of mutational events at a site is also not sufficiently large enough for co to be reliable. Secondly, co is calculated under the assumption that non-synonymous mutations are of neutral fitness advantage. Clearly, due to the sequence dependence of AID targeting this assumption is violated in B cell evolution. Instead, we employ the heuristic that amino acid mutations that are estimated to be improbable yet occur frequently within a clone are likely to have been selected for. While indicative of selection, this too can be misleading if mutations occur early in a lineage, are neutral and generate a cold spot or colder spot, thus making it less likely for the position to mutate again. Thus, it is apparent that much work remains on developing rigorous methods for measuring selection in B cell evolution. Our approach here is to treat improbable amino acid mutations as candidates for selection and to ultimately confirm the fitness advantage conferred by such mutations through experimentally testing their effect on virus neutralization and antigen binding Antibody Sequences from HIV-1 Negative Subjects We utilized a previously described next generation sequencing dataset generated from 8 HIV-1 negative individuals prior to vaccination (Williams et al., 2015). Briefly, to mitigate error introduced during the PCR amplification, we split the RNA sample into two samples, A and B, and performed PCR amplification on each, independently. Only VDJ sequences that duplicated identically in A and B were then retained. This approach allowed us to be highly confident that nucleotide variations from germline gene segments that occurred in the NGS reads were mutations and not error introduced during PCR. We refer to this dataset as "uninfected".

Antibody Sequences from RV144-Vaccinated Subjects

We utilized a previously described set of antibody sequences (Easterhoff et al., 2017) isolated from subjects enrolled in the RV144 HIV-1 vaccination trial (Rerks-Ngarm et al., 2009). Antibody sequences were isolated from peripheral blood mononuclear cells (PBMC) from 7 RV144-vaccinated subjects that were antigen-specific single-cell sorted with fluorophore-labeled AE.A244 gp120 dll (Liao et al., 2013). We refer to this dataset as "RV144-immunized".

Analysis of Improbable Mutations in BnAbs

Sequences of HIV-1 bnAbs were obtained either from NCBI GenBank or from the bNAber database (Eroshkin et al., 2014). For the comparison of improbable mutations for the representative set of bnAbs, improbable mutations were calculated using the ARMADiLLO program described above. UCAs were inferred using Cloanalyst (Kepler, 2013; Kepler et al., 2014). While many bnAbs had multiple clonal lineage member sequences available, some bnAbs had no other members isolated. Because of this, only the single sequence of the matured bnAb was used in the UCA inference in order to provide equal treatment of all sequences. Because uncertainty in the UCA inference is highest for the bases in the CDR3 region, precise determination of some mutations in this region is not feasible and we therefore ignored the CDR3 region in our analysis of the representative set of bnAbs. In the simulations, we prohibited any mutations from occurring in the CDR3 region by setting the probability of AID targeting to 0 for each base in the CDR3. Neutralization data for the bnAbs was obtained through the CATNAP database (Yoon et al., 2015) and corresponds to neutralization in the global panel of 12 HIV-1 Env reference strains (deCamp et al., 2014). For the calculation of geometric mean neutralization, undetectable neutralization was set to 100 μg/ml. Breadth was reported for all viruses that were tested and for several bnAbs (8ANC131, 1B2530, N6, CH103, BF520.1, PGT135, PGT145, VRC26.25, PGDM1400) neutralization data was not available for all 12 viruses in the global panel.

TABLE 1

Antibody Site-directed Mutagenesis Primers

| Primer | Chain | Sequence |
|---|---|---|
| CH235_L47W | Heavy | gatccatcccatccattgaagccctgtccag |
| CH235_W55G | Heavy | gtgcgacccccactagggtcgatccatccc |
| CH235_Q23K | Heavy | agtgacggtttcctgcaaggcatctggatacac |
| CH235_Q46E | Heavy | gatccatcccatcaactcaagccctgtccaggg |
| CH235_R57S | Heavy | cgaccctagttggggtagcacaaactacgca |
| CH235_T19K | Heavy | gcctggggcctcagtgaaggtttcctgc |
| CH235_T19R | Heavy | caggaaaccctcactgaggcccagg |
| CH235_T19N | Heavy | tgcctggcaggaaacattcactgaggcccag |
| VRC01_E28T | Heavy | gaatccaatttagcgtacaatcaataaacgtatatccagaagcccgacaagaaattctc |
| VRC01_P63K | Heavy | gccgtcaactacgcacgtaaacttcagggcagagt |
| VRC01_E16A | Heavy | caagaaattctcatcgacgcgccaggcttcttcatc |
| VRC01_Y28S | Kappa | accaggctaaggaaccactctgactggtccgacaag |
| VRC01_Y72F | Kappa | ctgatggtgagattgaagtctggcccccacc |
| VRC01_W68S | Kappa | tcagcggcagtcggtcggggccag |
| VRC01_N73T | Kappa | gtggggccagactacactctcaccatcagc |
| VRC01_I21L | Kappa | tggtccgacaagagaggatggctgtttcccc |

EXAMPLE 1 SUPPLEMENTAL REFERENCES deCamp, A., Hraber, P., Bailer, R. T., Seaman, M. S., Ochsenbauer, C., Kappes, J., Gottardo, R., Edlefsen, P., Self, S., Tang, H., et al. (2014). Global panel of HIV-1 Env reference strains for standardized assessments of vaccine-elicited neutralizing antibodies. J Virol 88, 2489-2507.

Easterhoff, D., Moody, M. A., Fera, D., Cheng, H., Ackerman, M., Wiehe, K., Saunders, K. O., Pollara, J., Vandergrift, N., Parks, R., et al. (2017). Boosting of HIV envelope CD4 binding site antibodies with long variable heavy third complementarity determining region in the randomized double blind RV305 HIV-1 vaccine trial. PLoS Pathog 13, e1006182.

Eroshkin, A. M., LeBlanc, A., Weekes, D., Post, K., Li, Z., Rajput, A., Butera, S. T., Burton, D. R., and Godzik, A. (2014). bNAber: database of broadly neutralizing HIV antibodies. Nucleic Acids Res 42, D1133-1139.

Kepler, T. B. (2013). Reconstructing a B-cell clonal lineage. I. Statistical inference of unobserved ancestors. F1000Res 2, 103.

Kepler, T. B., Munshaw, S., Wiehe, K., Zhang, R., Yu, J. S., Woods, C. W., Denny, T. N., Tomaras, G. D., Alam, S. M., Moody, M. A., et al. (2014). Reconstructing a B-Cell Clonal Lineage. II. Mutation, Selection, and Affinity Maturation. Front Immunol 5, 170.

Liao, H. X., Bonsignori, M., Alam, S. M., McLellan, J. S., Tomaras, G. D., Moody, M. A., Kozink, D. M., Hwang, K. K., Chen, X., Tsao, C. Y., et al. (2013). Vaccine induction of antibodies against a structurally heterogeneous site of immune pressure within HIV-1 envelope protein variable regions 1 and 2. Immunity 38, 176-186.

Rerks-Ngarm, S., Pitisuttithum, P., Nitayaphan, S., Kaewkungwal, J., Chiu, J., Paris, R., Premsri, N., Namwat, C., de Souza, M., Adams, E., et al. (2009). Vaccination with ALVAC and AIDSVAX to prevent HIV-1 infection in Thailand. N Engl J Med 361, 2209-2220.

Williams, W. B., Liao, H. X., Moody, M. A., Kepler, T. B., Alam, S. M., Gao, F., Wiehe, K., Trama, A. M., Jones, K., Zhang, R., et al. (2015). HIV-1 VACCINES. Diversion of HIV-1 vaccine-induced immunity by gp41-microbiota cross-reactive antibodies. Science 349, aab1253.

Yaari, G., Vander Heiden, J. A., Uduman, M., Gadala-Maria, D., Gupta, N., Stern, J. N., O'Connor, K. C., Hafler, D. A., Laserson, U., Vigneault, F., and Kleinstein, S. H. (2013). Models of somatic hypermutation targeting and substitution based on synonymous mutations from high-throughput immunoglobulin sequencing data. Front Immunol 4, 358.

Yoon, H., Macke, J., West, A. P., Jr., Foley, B., Bjorkman, P. J., Korber, B., and Yusim, K. (2015). CATNAP: a tool to compile, analyze and tally neutralizing antibody panels. Nucleic Acids Res 43, W213-219.

Example 2: Staged Induction of HIV-1 Glycan-Dependent Broadly Neutralizing Antibodies Stages of V3-glycan neutralizing antibody maturation are identified that explain the long duration required for their development.

Abstract

A preventive HIV-1 vaccine should induce HIV-1 specific broadly neutralizing antibodies (bnAbs). However, bnAbs generally require high levels of somatic hypermutation (SHM) to acquire breadth and current vaccine strategies have not been successful in inducing bnAbs. Since bnAbs directed against a glycosylated site adjacent to the third variable loop (V3) of the HIV-1 envelope protein require limited SHM, the V3 glycan epitope is a desirable vaccine target. By studying the cooperation among multiple V3-glycan B-cell lineages and their co-evolution with autologous virus throughout 5 years of infection, we identify here key events in the ontogeny of a V3-glycan bnAb. Two autologous neutralizing antibody lineages selected for virus escape mutations and consequently allowed initiation and affinity maturation of a V3-glycan bnAb lineage. The nucleotide substitution required to initiate the bnAb lineage occurred at a low probability site for activation-induced cytidine deaminase activity. Cooperation of B-cell lineages and an improbable mutation critical for bnAb activity define the necessary events leading to V3-glycan bnAb development, explain why initiation of V3-glycan bnAbs is rare, and suggest an immunization strategy for inducing V3-glycan bnAbs.

Introduction

A vaccine to prevent HIV-1 infection should include immunogens that can induce broadly neutralizing antibodies (bnAbs) (1, 2). Of the five major targets for bnAbs, the glycan-rich apex of the HIV-1 envelope (Env) trimer and the base of the third variable loop (V3) are distinguished by the potency of antibodies directed against them (3-8). Although these antibodies have less breadth than those directed against the CD4 binding site (CD4bs) or the gp41 membrane-proximal region (MPER), one current goal of vaccine development is to elicit them in combination with other bnAb specificities to achieve broad coverage of transmitted/founder (TF) viruses to prevent HIV-1 integration upon exposure (1, 2).

Mapping the co-evolution of virus and antibody lineages over time informs vaccine design by defining the succession of HIV-1 Env variants that evolve in vivo during the course of bnAb development (9-11). Antibody lineages with overlapping specificities can influence each other's affinity maturation by selecting for synergistic or antagonistic escape mutations: an example of such "cooperating" lineages is provided by two CD4bs-directed bnAbs that we characterized previously (11, 12). Thus, cooperating antibody lineages and their viral escape mutants allow identification of the specific Envs, among the diverse repertoire of mutated Envs that develop within the autologous quasi-species in the infected individual, that stimulate bnAb development and that we wish to mimic in a vaccine.

Here we describe the co-evolution of an HIV-1 Env quasispecies and a memory B-cell lineage of gp120 V3-glycan directed bnAbs in an acutely infected individual followed over time as neutralizing plasma activity developed. To follow virus evolution, we sequenced ~1,200 HIV-1 env genes sampled over a 5 year period; to follow the antibody response, we identified natural heavy- and light-chain pairs of six antibodies from a bnAb lineage, designated DH270, and augmented this lineage by next generation sequencing (NGS). Structural studies defined the position of the DH270 Fab on gp140 Env. We also found two B-cell lineages (DH272 and DH475) with neutralization patterns that likely selected for observed viral escape variants, which in turn stimulated the DH270 lineage to potent neutralization breadth. We found a mutation in the DH270 heavy chain that occurred early in affinity maturation at a disfavored activation-induced cytidine deaminase (AID) site and that was necessary for bnAb lineage initiation. This improbable mutation can explain the long period of antigenic stimulation needed for initial expansion of the bnAb B-cell lineage in this individual.

Results

Three N332 V3-Glycan Dependent Antibody Lineages

We studied an African male from Malawi (CH848) followed from the time of infection to 5 years post-transmission. He was infected with a Glade C virus, developed plasma neutralization breadth 3.5 years post-transmission and did not receive antiretroviral therapy during this time as per country treatment guidelines. Reduced plasma neutralization of N332A Env-mutated HIV-1 pseudoviruses and plasma neutralization fingerprinting demonstrated the presence of N332-sensitive broadly neutralizing antibodies (bnAbs) (see FIG. 29 of WO/2017/152146) (13). To identify these antibodies, we studied memory B cells from weeks 205, 232, and 234 post-infection using memory B cell cultures (14) and antigen-specific sorting (15, 16) and found three N332-sensitive lineages, designated DH270, DH272 and DH475. Their genealogy was augmented by NGS of memory B-cell cDNA from seven time points spanning week 11 to week 240 post-transmission.

Figure 1B:
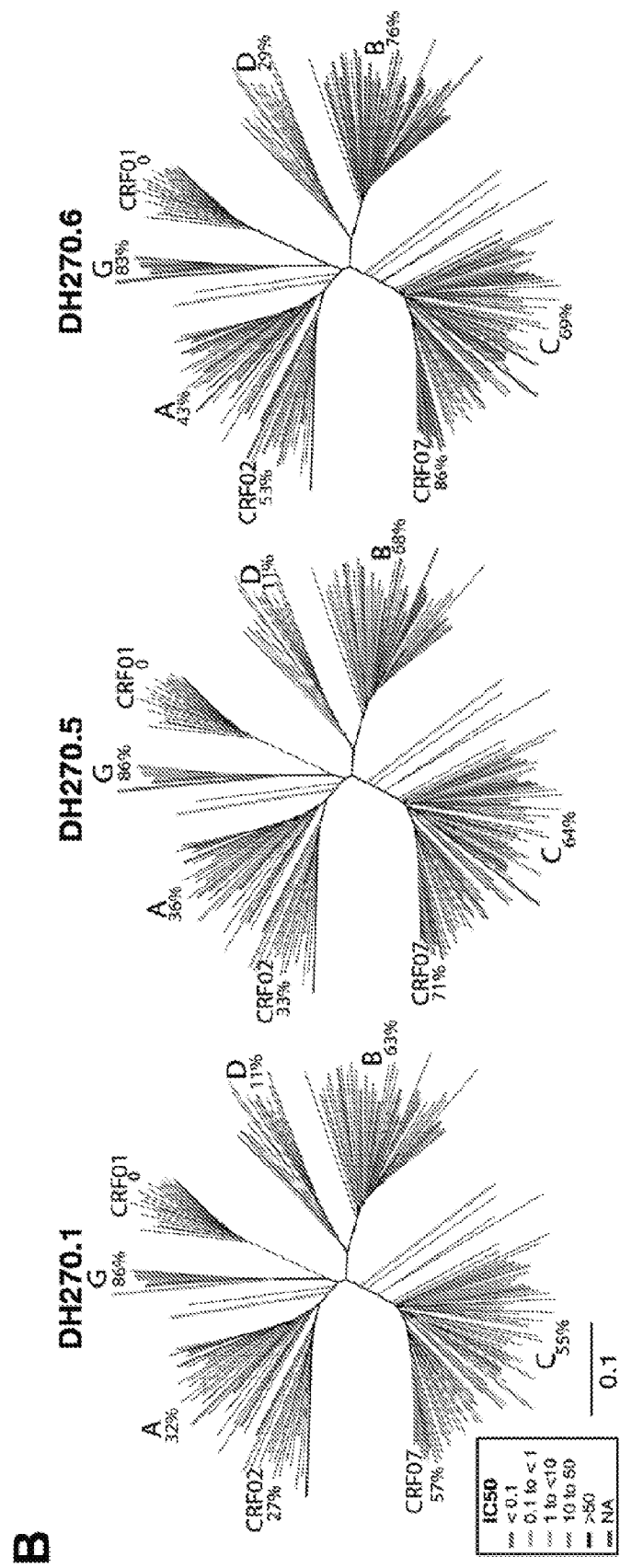
Figure 8B:
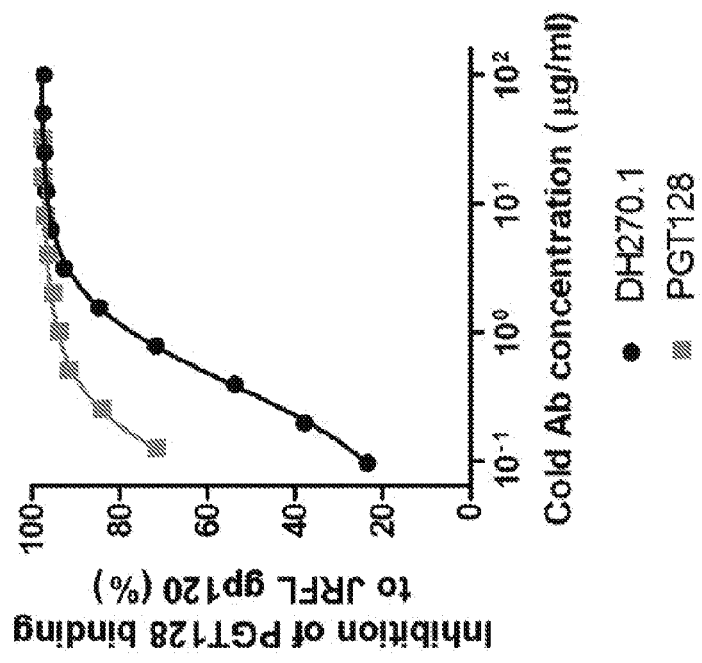
Figure 8C:
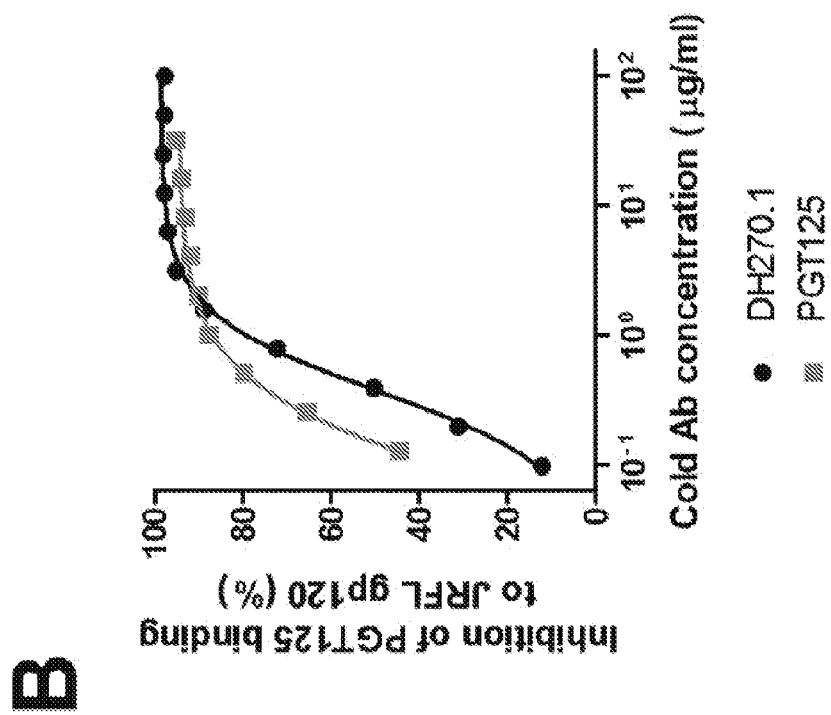

DH270 antibodies were recovered from memory B cells at all three sampling times (weeks 205, 232, and 234) and expansion of the clone did not occur until week 186 (FIG. 1A; see also FIGS. 30A-C of WO/2017/152146). Clonal expansion was concurrent with development of plasma neutralization breadth (see FIG. 31 of WO/2017/152146), and members of the DH270 lineage also displayed neutralization breadth (FIG. 1B; see also FIG. 33 of WO/2017/152146). The most potent DH270 lineage bnAb (DH270.6) was isolated using a fluorophore-labeled $Man_9$-V3 glycopeptide that is a mimic of the V3-glycan bnAb epitope (16) comprising a discontinuous 30 amino acid residue peptide segment within gp120 V3 and representative of the PGT128-bound minimal epitope described by Pejchal et al. (17). The synthetic $Man_9$-V3 glycopeptide includes high mannose glycan residues ($Man_9$) each at N301 and N332 and was synthesized using a chemical process similar to that described previously (18, 19). V3 glycan bnAb PGT128 affinity for the $Man_9$-V3 glycopeptide was similar to that of PGT128 for the BG505 SOSIP trimer and $Man_9$-V3 glycopeptide was therefore an effective affinity bait for isolating of V3 glycan bnAbs (16). The lineage derived from a $V_H1$-2*02 rearrangement that produced a CDRH3 of 20 amino acid residues paired with a light chain encoded by Vλ2-23 (FIGS. 7A-D). Neutralization assays and competition with V3-glycan bnAbs PGT125 and PGT128 confirmed lineage N332-dependence (FIGS. 8A-C).

Figure 9A:
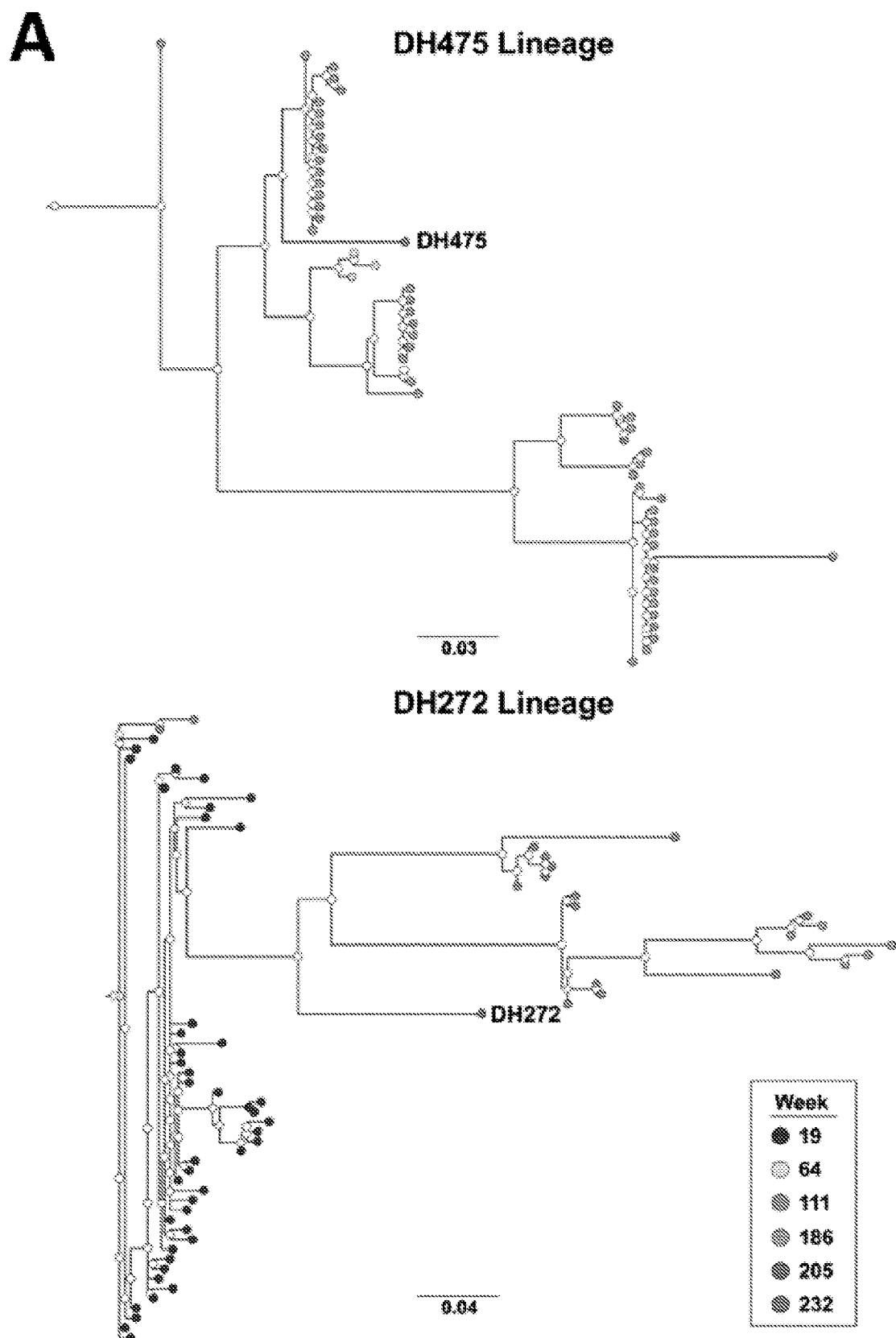

The DH475 mAb was recovered from memory B cells at week 232 post-transmission by antigen-specific sorting using the fluorophore-labeled Man9-V3 glycopeptide (1 6). The earliest DH475 lineage $V_HDJ_H$ rearrangements were identified with NGS at week 64 post-transmission (FIG. 9A; see also FIGS. 30A-C of WO/2017/152146). Its heavy chain came from VH3-23*01 ($V_H$ mutation frequency=10.1%) paired with a $V_□4$-69*02 light chain (FIG. 9B).

The DH272 mAb came from cultured memory B cells obtained at week 205 post-transmission. DH272 lineage $V_HDJ_H$ rearrangements were detected as early as 19 weeks post-transmission by NGS (FIG. 9A; see also FIGS. 30A-C of WO/2017/152146). The DH272 heavy chain used $V_H1$-2*02, as did DH270, but it paired with a $V_κ$ 2-30 light chain. Its CDRH3 was 17 amino acids long; VH mutation was 14.9%. DH272, an IgA isotype, had a 6-nt deletion in FRH3 (FIG. 9B).

Figures 9C, 9D:
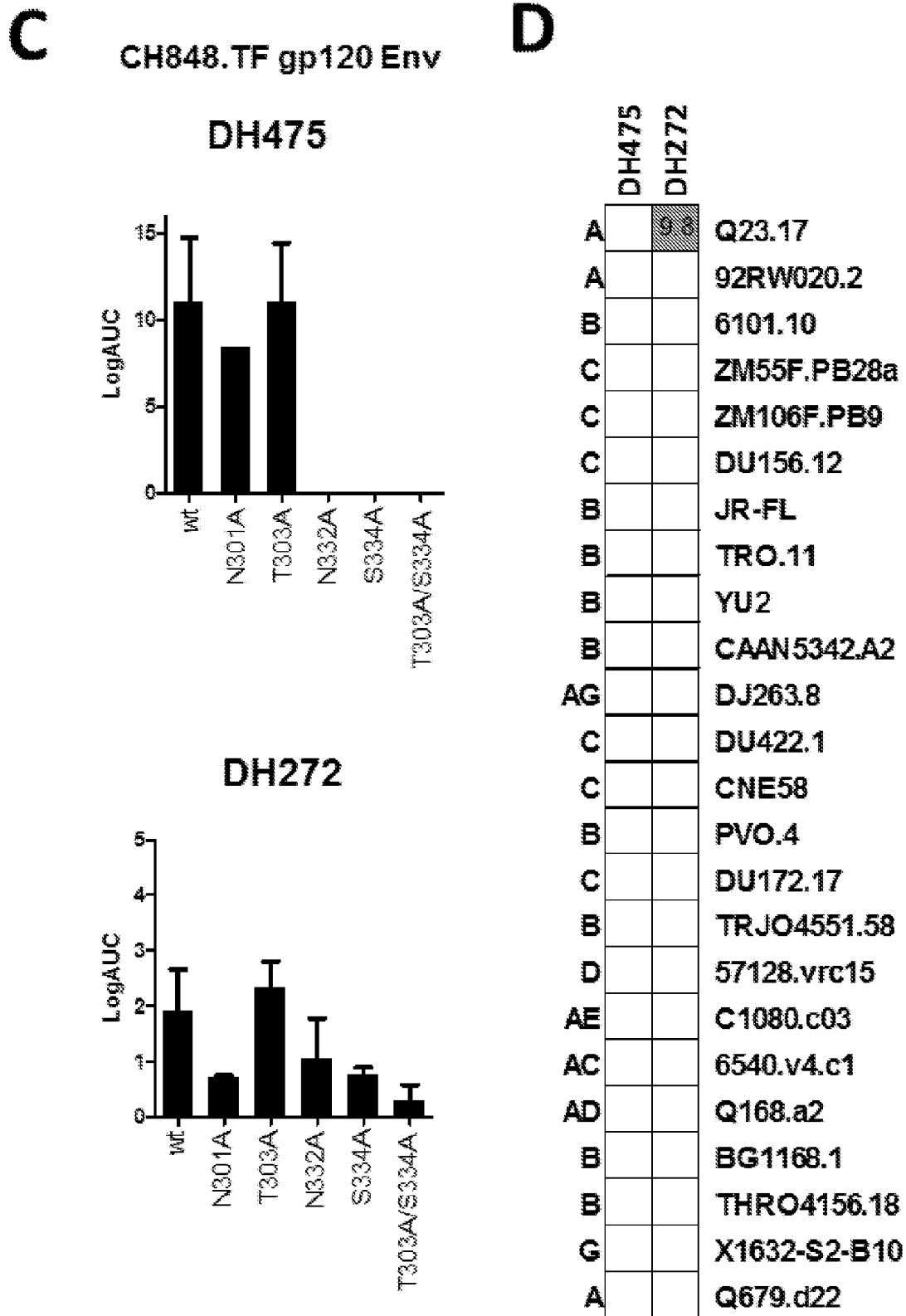

For both DH272 and DH475 lineages, binding to CH848 TF Env gp120 depended on the N332 potential N-linked glycosylation (PNG) site (FIG. 9C). DH272 binding also depended on the N301 PNG site (FIG. 9C). Neither lineage had neutralization breadth (FIG. 9D).

Evolution of the CH848 Virus Quasispecies

Figure 10:
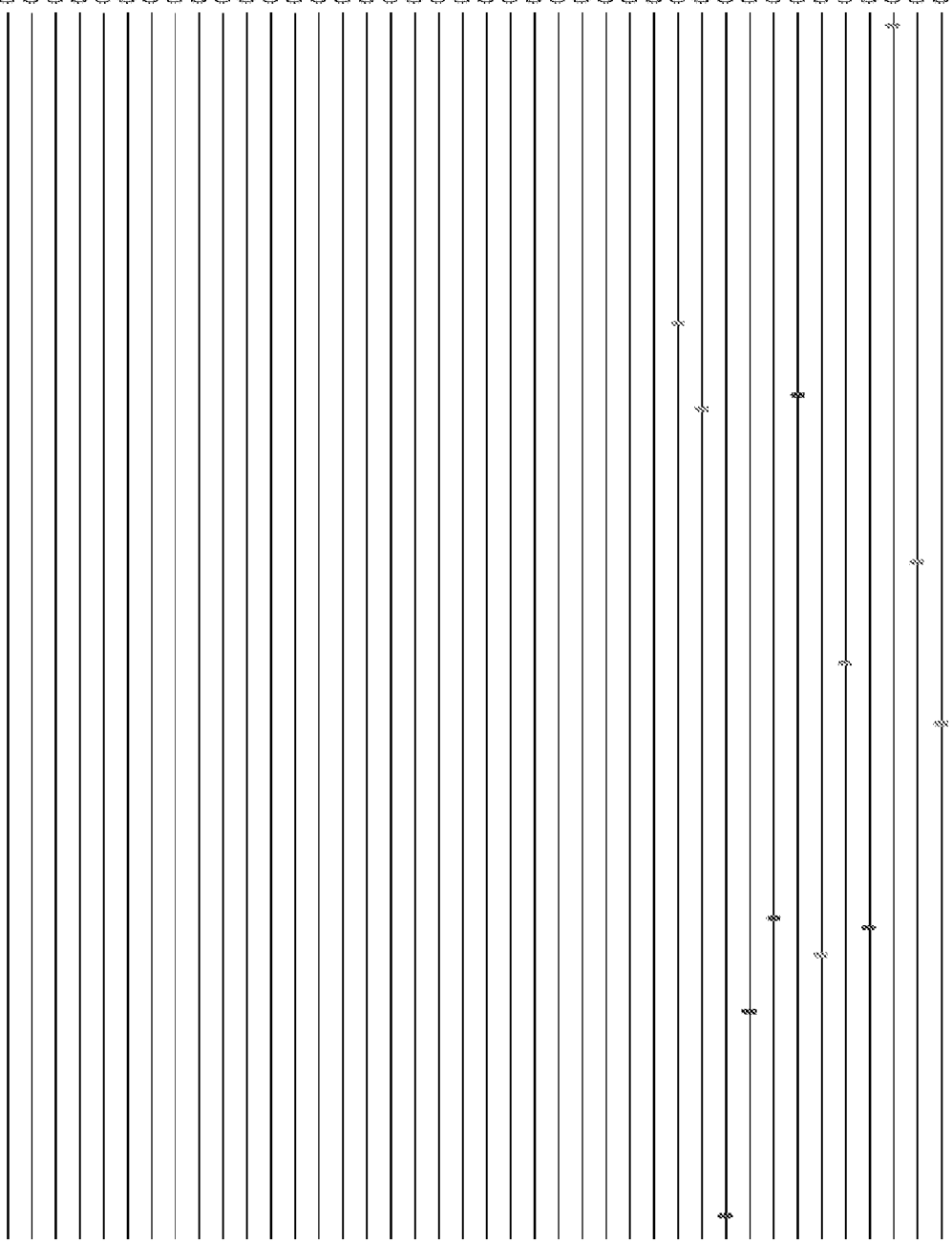
FIG. 10. CH848 was infected by a single transmitted founder virus. 79 HIV-1 3' half single genome sequences were generated from screening timepoint plasma. Depicted is a nucleotide Highlighter plot (http://www.hiv.lanl.gov/content/sequence/HIGHLIGHT/HIGHLIGHT_XYPLOT/highlighter.html). Horizontal lines represent single genome sequences and tic marks denote nucleotide changes relative to the inferred TF sequence (key at top, nucleotide position relative to HXB2).
Figure 10:
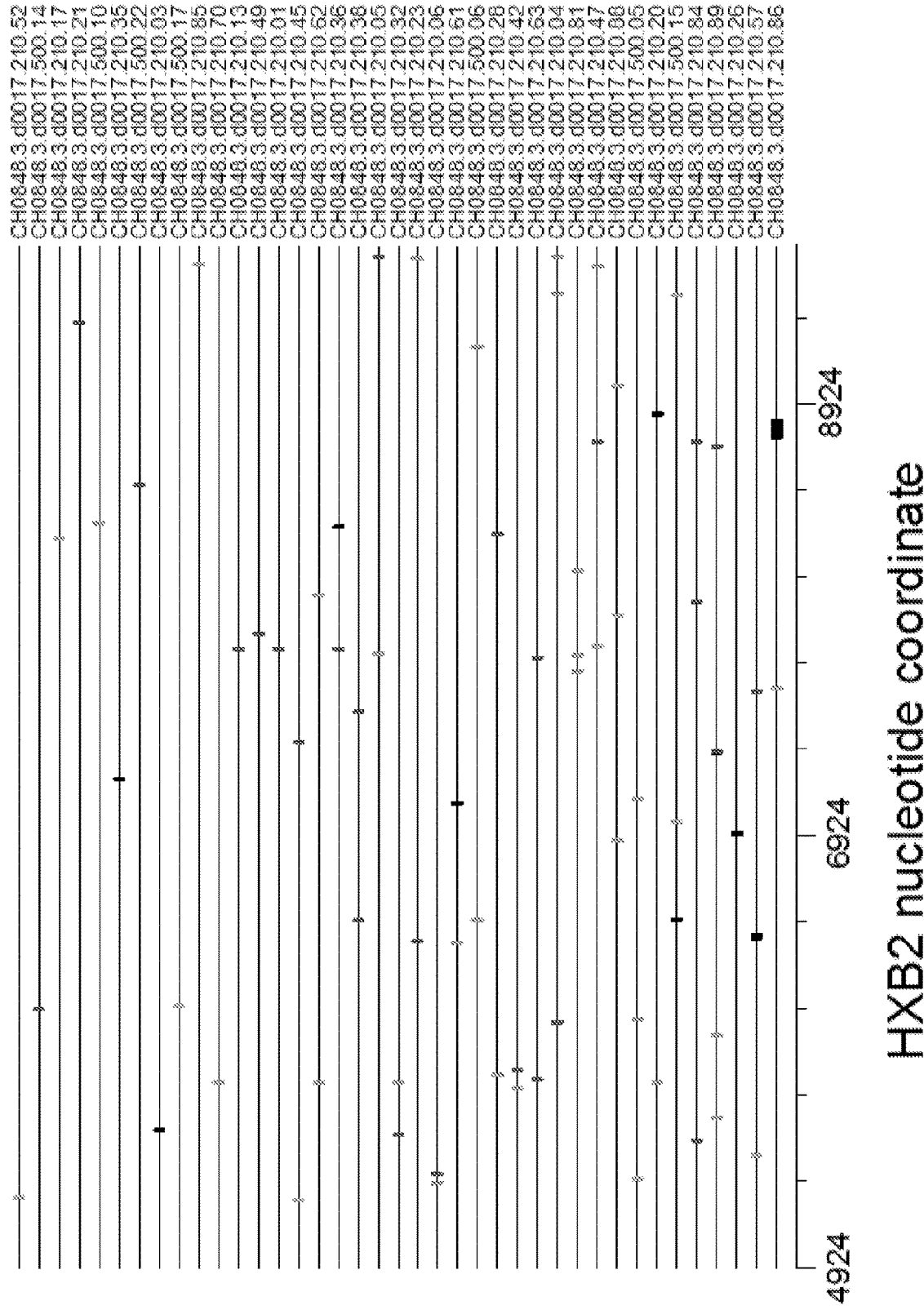
Figure 11A:
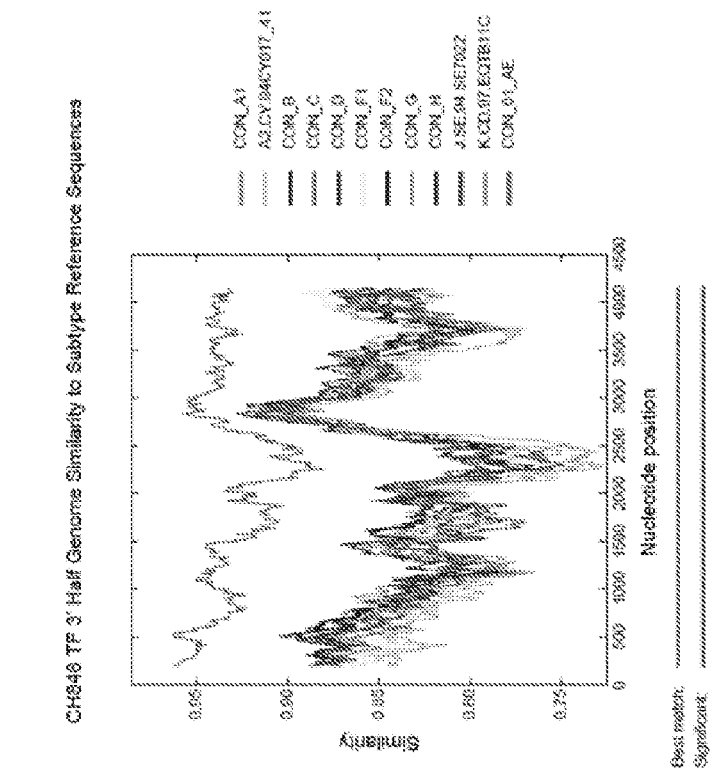
FIGS. 11A-B. CH848 was infected by a subtype C virus. (A) PhyML was used to construct a maximum likelihood phylogenetic tree comparing the CH848 transmitted founder virus to representative sequences from subtypes A1, A2, B, C, D, F1, F2, G, H, and K (substitution model: GTR+I+G, scale bar bottom right). The CH848 TF sequence in the subtype C virus cluster is shown in red. (B) Similarity to each subtype reference sequence is plotted on the y-axis and nucleotide position is plotted the x-axis (window size=400 nt, significance threshold=0.95, key to right). The two bars below the x-axis indicate which reference sequence is most similar to the CH848 TF sequence ("Best Match") and whether this similarity is statistically significant relative to the second best match ("Significant").
Figure 11B:
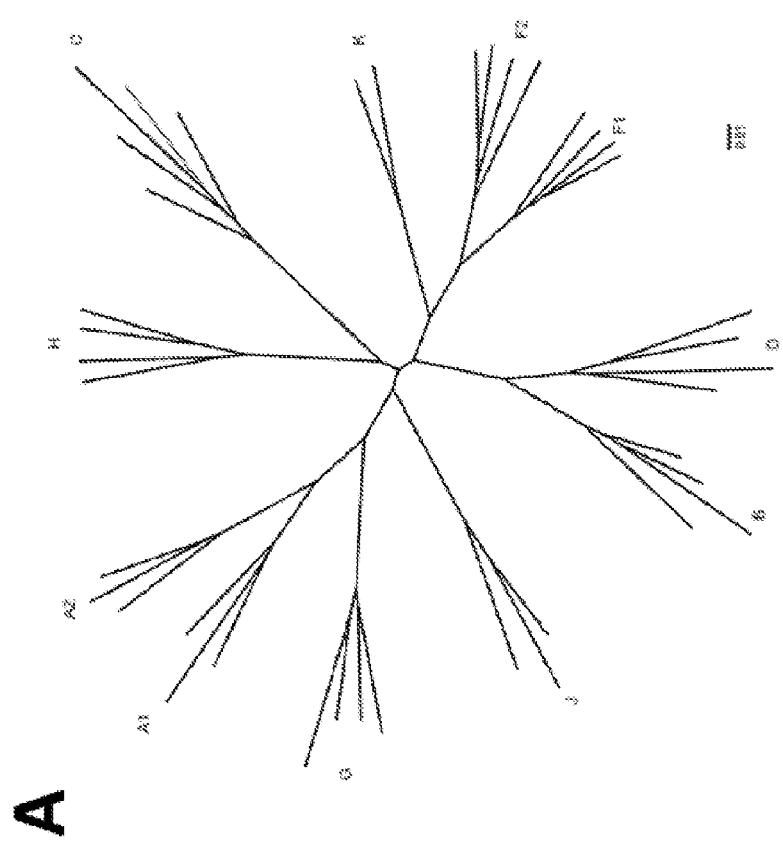
Figure 12:
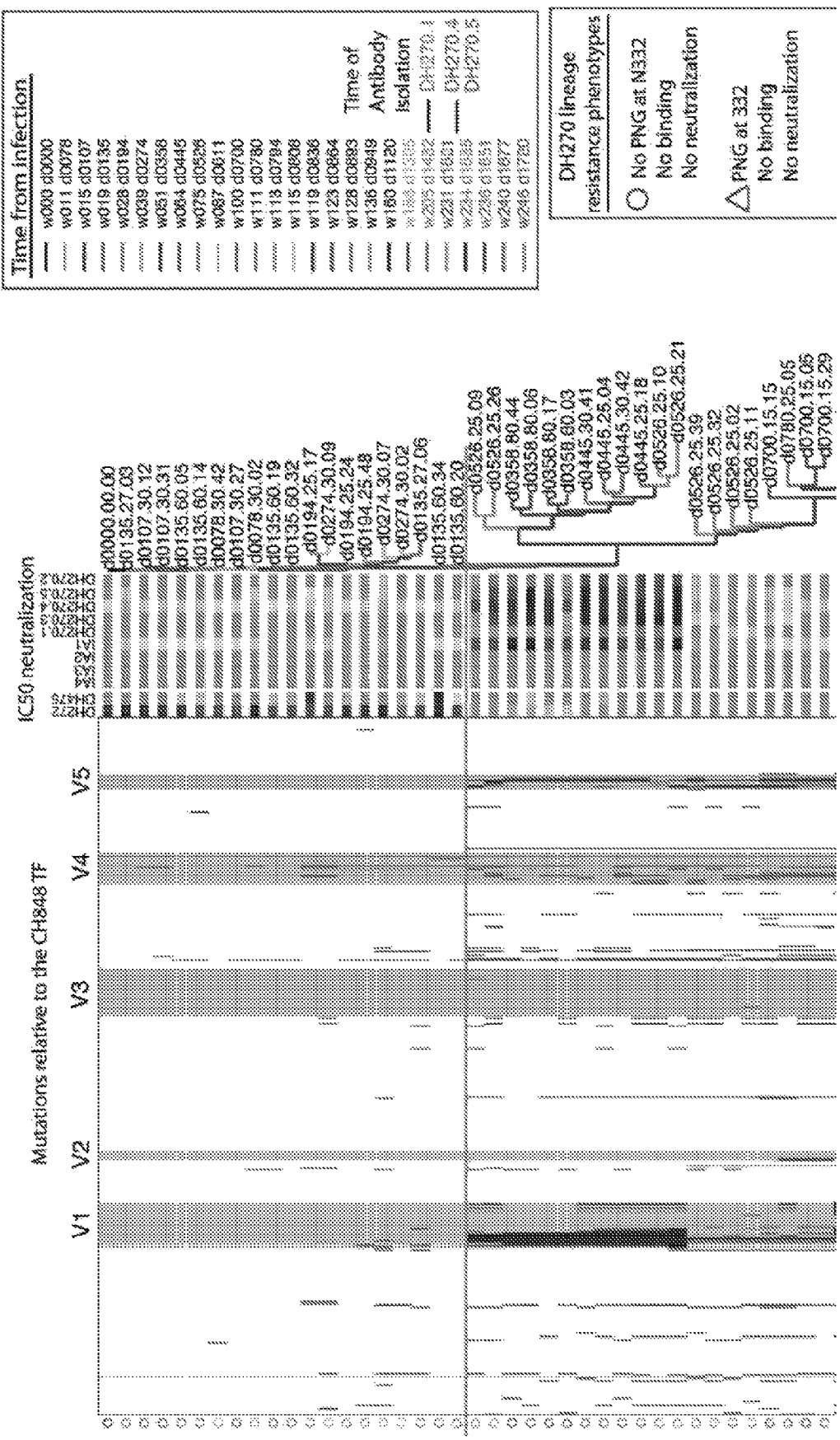
FIG. 12. Co-evolution of CH848 autologous virus and N332-dependent V3 glycan antibody lineages DH272, DH475 and DH270. Mutations relative to the CH848 TF virus in the alignment of CH848 sequences with accompanying neutralization data (Insertion/deletions=black. Substitutions: red=negative charge; blue=positive charge; cyan=PNG sites) (43). The green line indicates the transition between DH272/DH475 sensitive and DH270 lineage sensitive virus immunotypes at day 356 (week 51). Viruses isolated after week 186, time of first evidence of DH270 lineage presence, are highlighted in different colors according to week of isolation.
Figure 12:
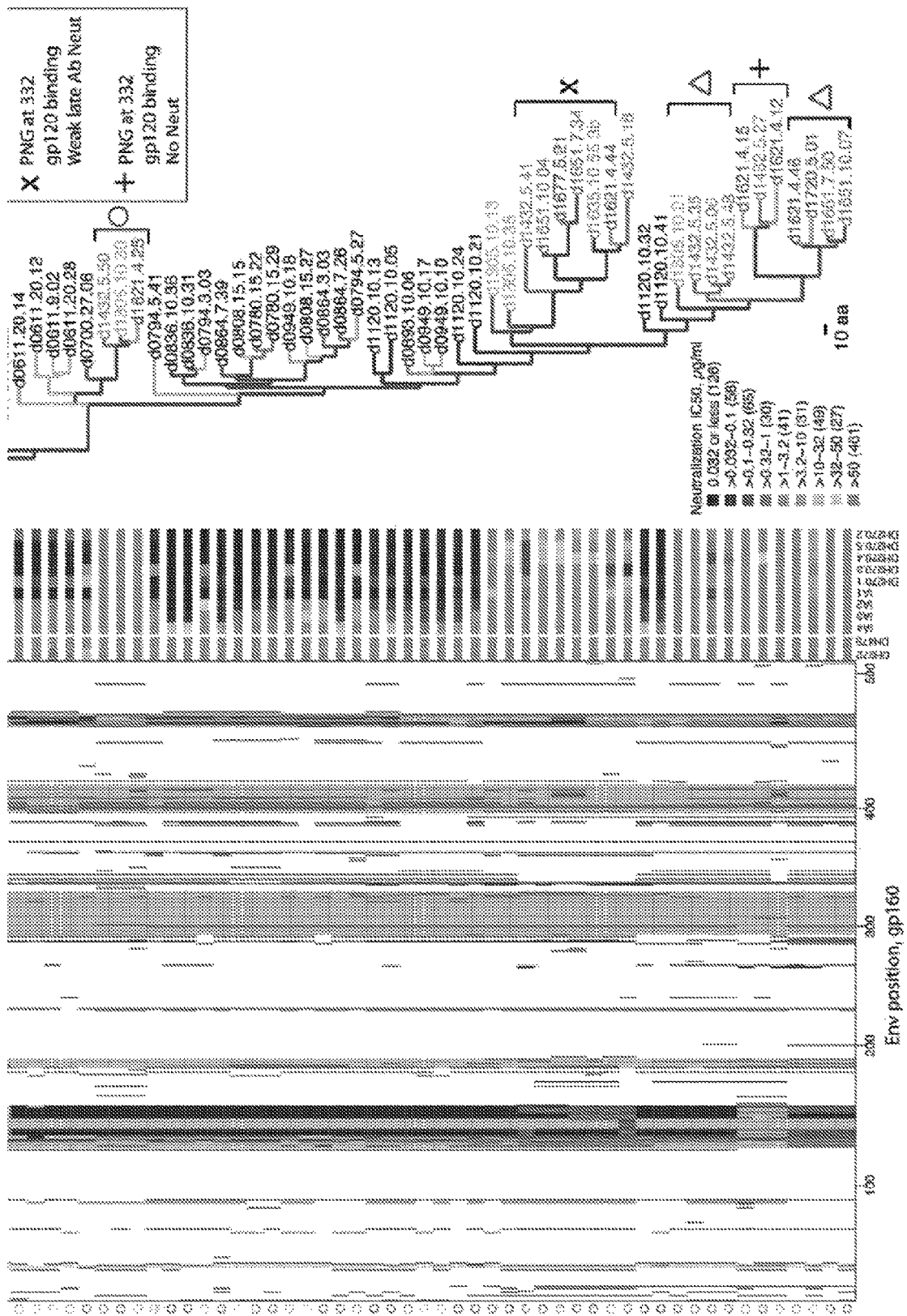
Figures 13A, 13B:
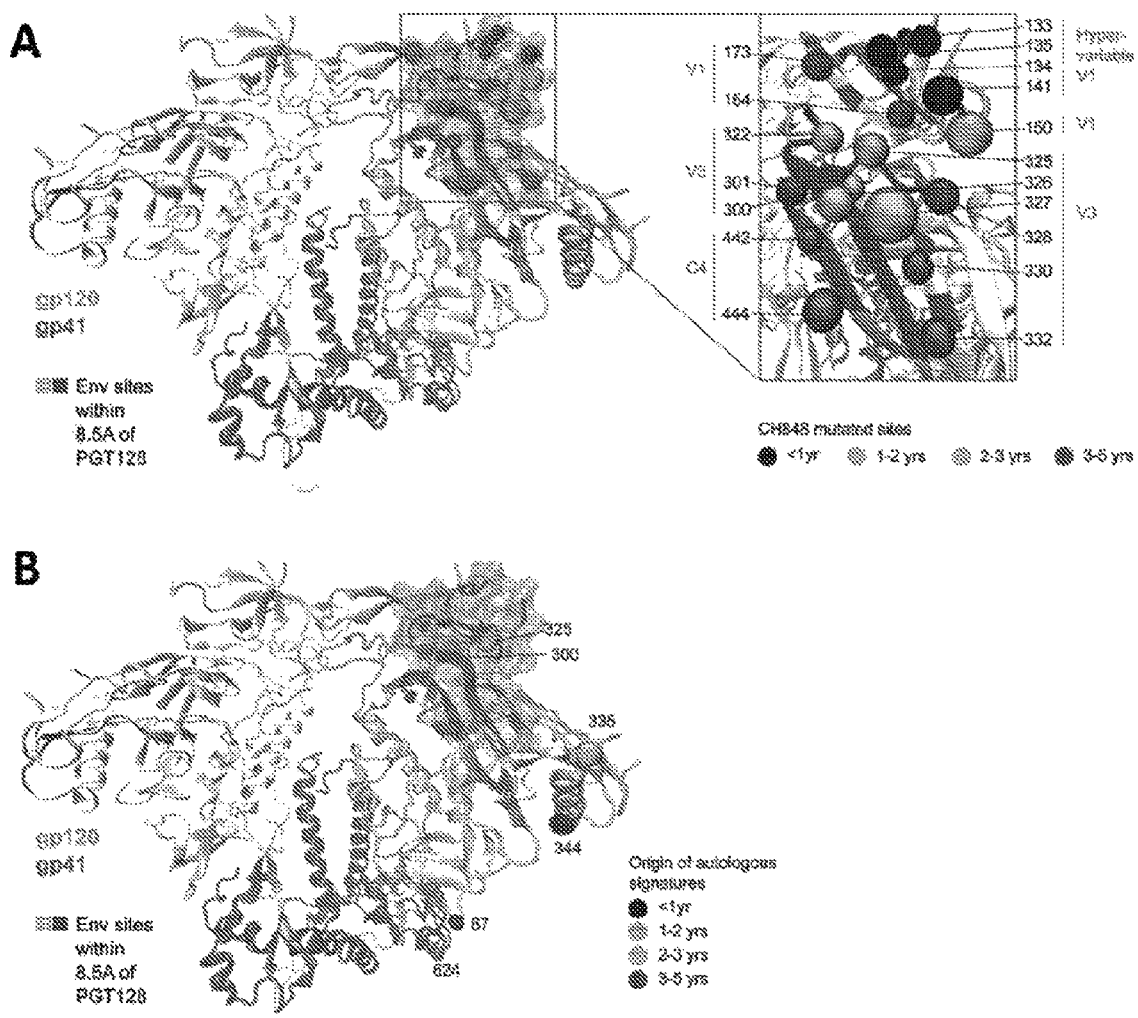
FIGS. 13A-B. Mutations in CH848 Env over time. (A) Variable positions that are close to the PGT128 epitope in a trimer structure (PDB ID: 4TVP) (13) are represented by spheres color-coded by the time post-infection when they first mutate away from the CH848 TF sequence. The PGT128 antibody structure (PDB ID: 5C7K) (29) was used as a surrogate for DH270, as a high resolution structure is not yet available for DH270. Env positions with either main chain, side chain or glycans within 8.5 Å of any PGT128 heavy atom are shown in yellow surface and brown ribbon representations. Time of appearance of mutations are color coded as indicated. (B) Same as (A) for mutating Env sites that were autologous antibody signatures of antibody sensitivity and resistance.
Figure 14:
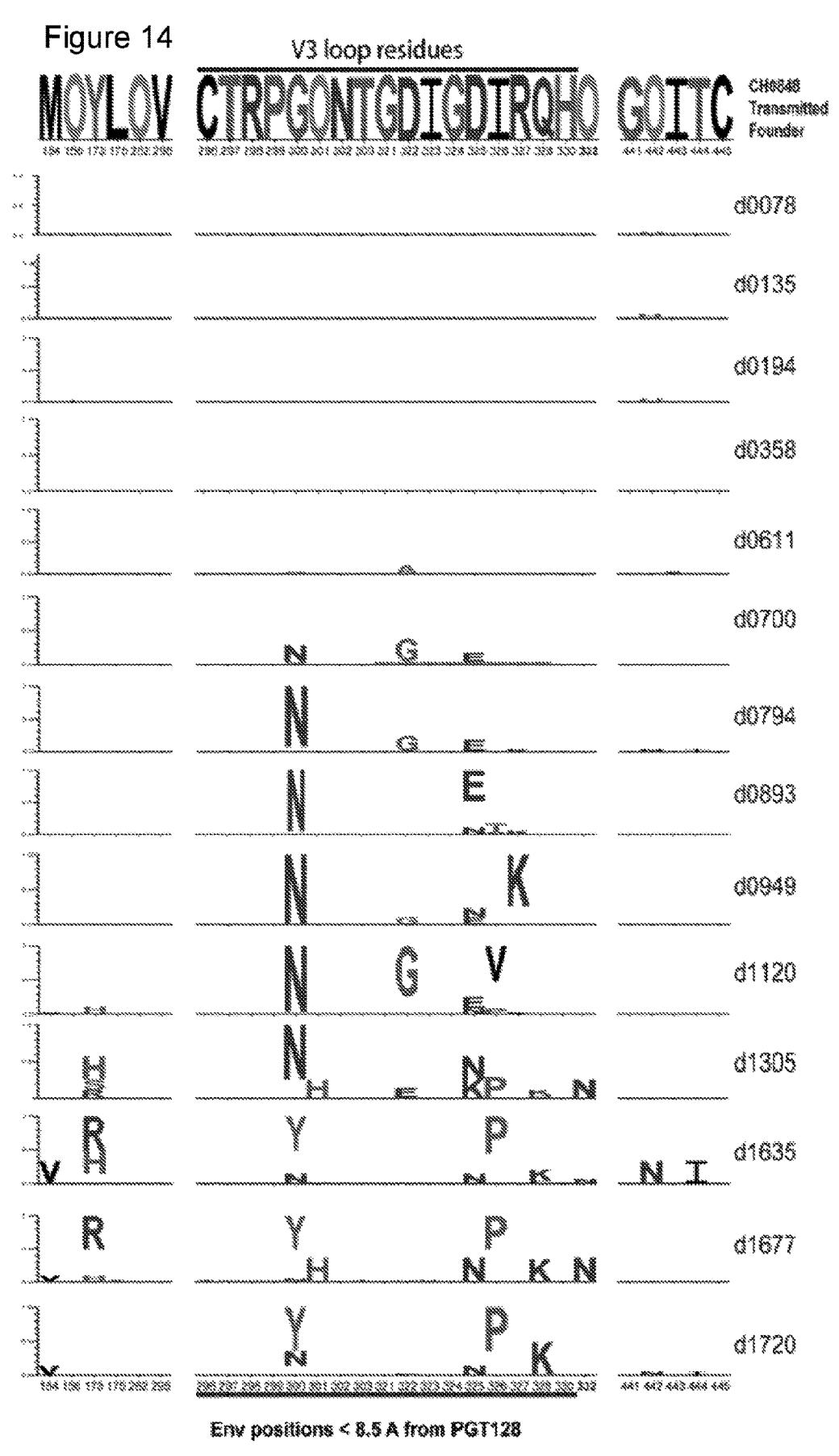
Figure 15:
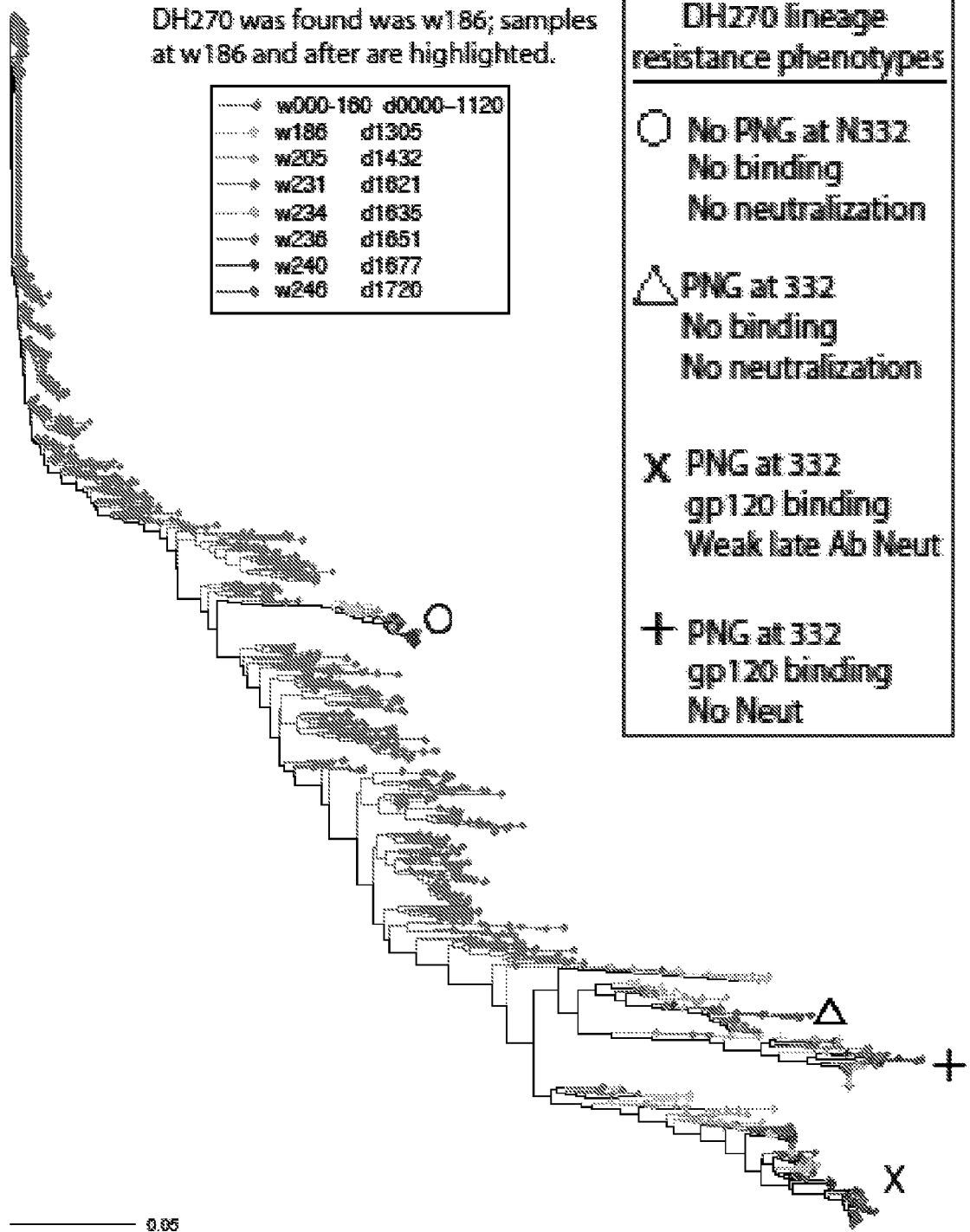
FIG. 15. CH848 virus lineage maximum likelihood phylogenetic tree rooted on the transmitted founder sequence. The phylogenetic tree shows 1,223 Env protein sequences translated from single genome sequences. Sequences sampled prior to the development of Tier 2 heterologous breadth (week 186) are shaded in grey and sequences from after week 186 are highlighted using the color scheme from FIG. 12. Four viral clades with distinct DH270 lineage phenotypes are indicated with a circle, triangle, cross and "X", respectively.

We sequenced 1,223 HIV-1 3'-half single-genomes from virus in plasma collected at 26 time points over 246 weeks. Analysis of sequences from the earliest plasma sample indicated that CH848 had been infected with a single, subtype Glade C founder virus, ~17 (CI 14-19) days prior to screening (FIGS. 10 and 11A-B). By week 51 post-infection, 91% of the sequences had acquired an identical, 10-residue deletion in variable loop 1, a region that includes the PGT128-proximal residues 133-135 and 141 (FIGS. 12 and 13A-B). Further changes accrued during the ensuing four years, including additional insertions and deletions (indels) in V1, mutations in the $^{324}$GDIR$^{327}$ motif within the V3 loop, deletion or shifting of N-linked glycosylation sites at positions 301 and 322, and mutations at PGT128-proximal positions in V1, V3, and C4, but none of these escape variants went to fixation during 4.5 years of follow-up (FIGS. 12-15).

Simultaneously with the first detection of DH270 lineage antibodies at week 186, four autologous virus clades emerged that defined distinct immunological resistance profiles of the CH848 autologous quasispecies (FIG. 12). The first Glade included viruses that shifted the potential N-glycosylation (PNG) site at N332 to 334 (FIG. 12, open circles) and despite this mutation was associated with complete resistance to the DH270 lineage bnAbs, this Glade was detected only transiently and at relatively low frequency (7-33% per sample), suggesting a balance where immune escape was countered by a cost in virological fitness. Conversely, viruses in the other three clades retained N332 and persisted throughout the 5 years of sampling. Viruses in the second Glade resisted DH270 lineage neutralization and comprised gp120 Envs that were not bound by the DH270 antibodies (FIG. 12, triangles; see also FIGS. 34-35 of WO/2017/152146). The third and fourth clades defined autologous viruses whose gp120 Env was bound by DH270 lineage antibodies but that were either only weakly neutralized by the most mature members of the DH270 lineage (FIG. 12, "X"; see also FIGS. 34-35 of WO/2017/152146) or were completely neutralization resistant (FIG. 12, "+"; see also FIGS. 34-35 of WO/2017/152146), respectively. Persistence of four divergent clades in the CH848 Env, each with distinctive immunological resistance phenotypes, suggests that multiple distinctive immune escape routes were explored and selected, allowing continuing Env escape mutations to accrue in distinct frameworks and exposing the antibody to Env diversity that may have been necessary to acquire neutralization breadth.

Ontogeny of DH270 Lineage and Acquisition of Neutralization Breadth

Figure 2A:
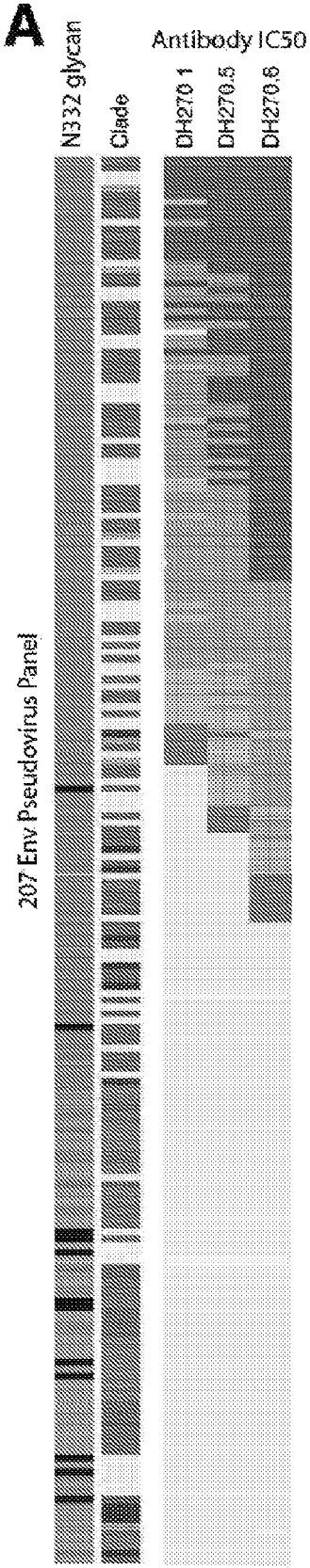

As with other V3-glycan bnAbs, viral neutralization Glade specificity and intra-clade breadth of DH270 depended primarily on the frequency of the N332 glycosylation site within the relevant Glade (FIG. 2A). Only one of 62 pseudoviruses tested that lacked the PNG site at N332, the B Glade virus 5768.04, was sensitive to DH270.5 and DH270.6 (see FIG. 33 of WO/2017/152146). Across the full M group HIV-1 virus isolate panel used in neutralization assays, the loss of the PNG N332 sites accounted for 70% of the observed neutralization resistance. The circulating recombinant form CRF01 very rarely has this glycosylation site (3% of sequences in the Los Alamos database and 4% (1/23) in our test panel) and DH270 lineage antibodies did not neutralize CRF01 strains (FIG. 2A). As a consequence of the N332 PNG site requirement of V3 glycan bnAbs to neutralize, in vitro estimation of neutralizing breadth was impacted simply by the fraction of CRF01 viruses included in the panel. Other V3-glycan bnAbs (10-1074, PGT121 and PGT128) shared this N332 glycan dependency but PGT121 and PGT128 were not as restrictive (see FIG. 33 of WO/2017/152146) (5, 6, 8). Antibody 10-1074 was similar to DH270.6 in that it more strictly required the N332 PNG site, and its neutralization potency correlated with that of DH270.6 (Pearson's $p=8.0e^{-13}$, $r=0.63$) (8).

Figure 2B:
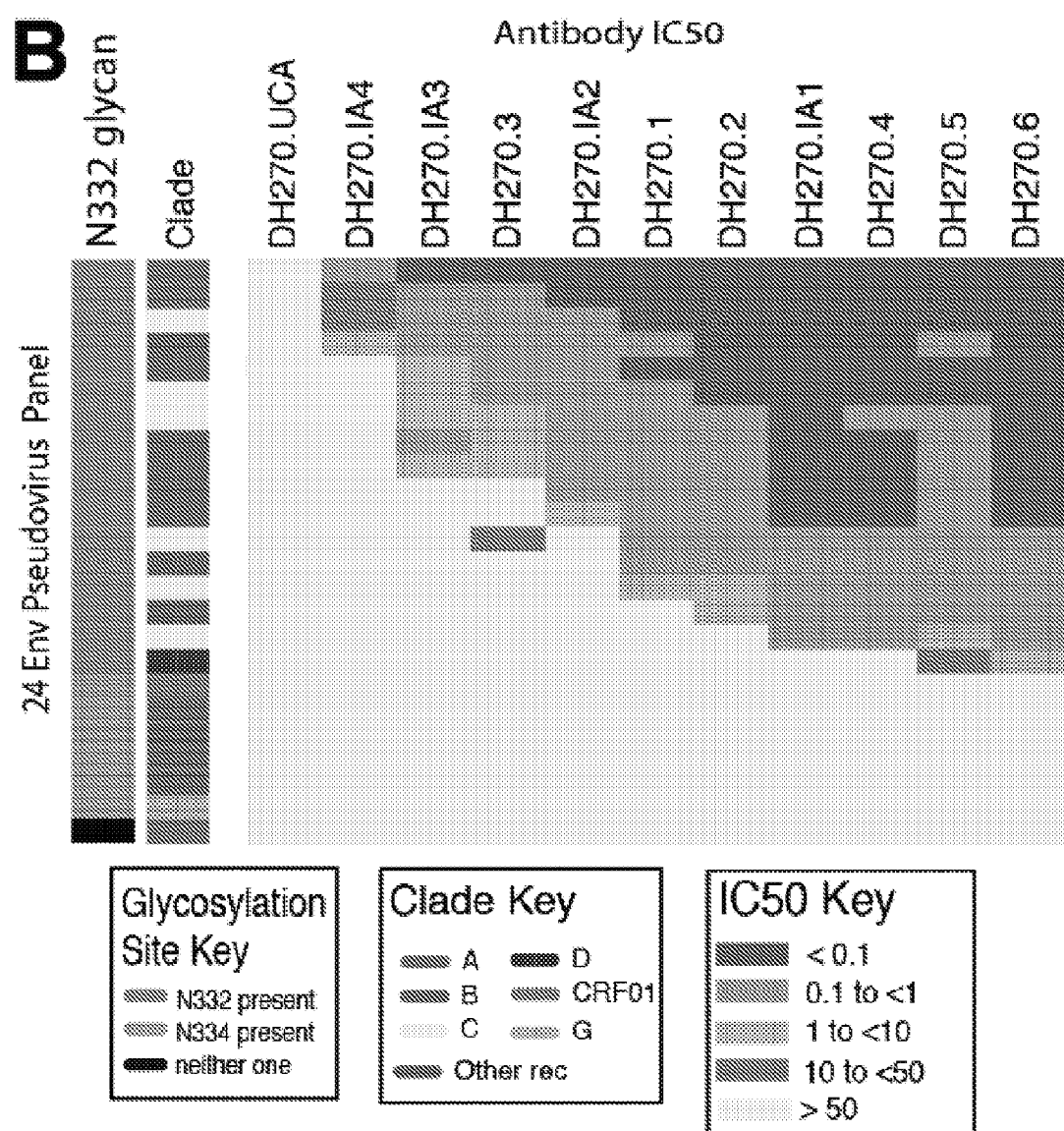
Figure 2C:
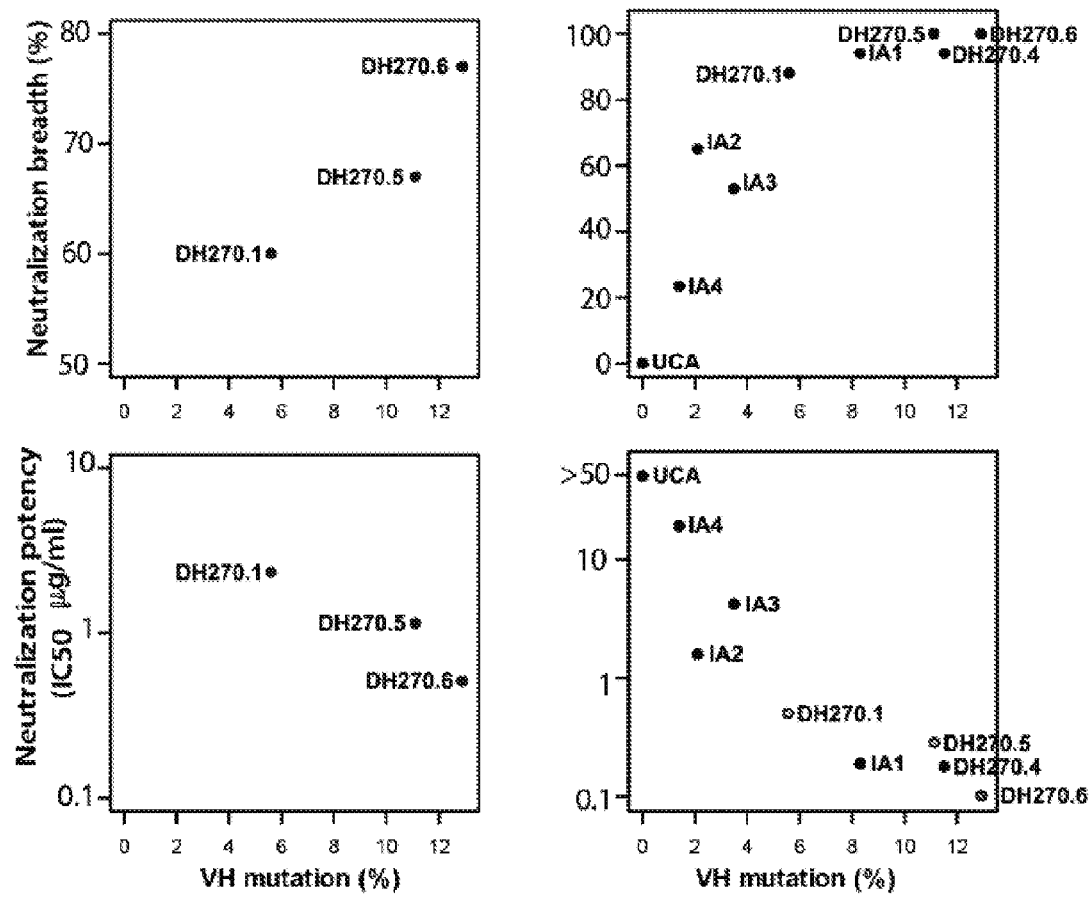

Heterologous breadth and potency of DH270 lineage antibodies increased with accumulation of $V_H$ mutations and although DH270.UCA did not neutralize heterologous HIV-1, five amino-acid substitutions in DH270.IA.4 (four in the heavy chain, one in the light chain) were sufficient to initiate the bnAb lineage and confer heterologous neutralization (FIGS. 2B, C; see also FIGS. 34-35 of WO/2017/152146).

Figures 16A, 16B, 16C, 16D, 16E, 16F:
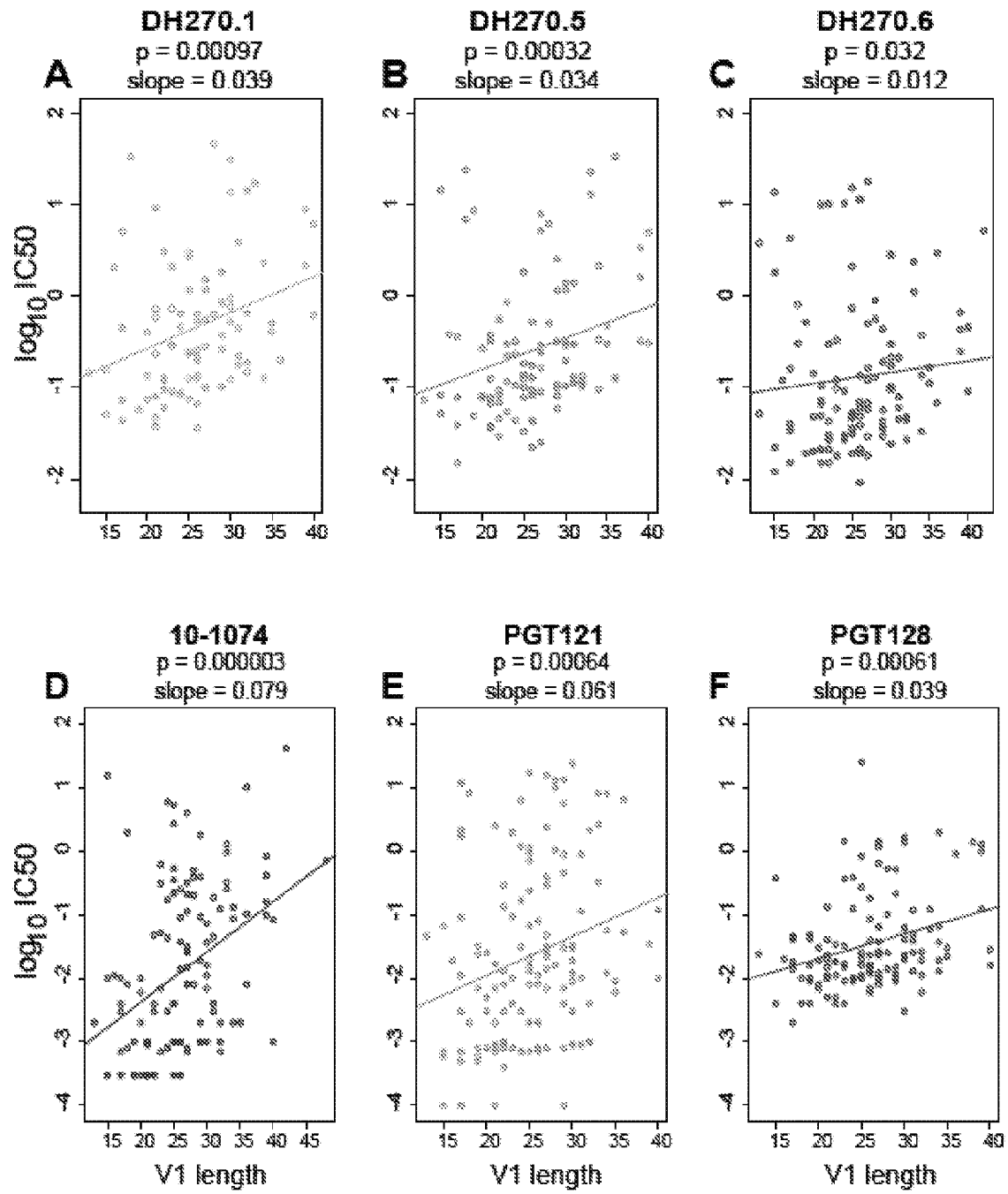
FIGS. 16A-F. Inverse-correlation between the potency of V3 glycan broadly neutralizing antibodies and V1 length shown for the full panel of 207 viruses. Correlation between neutralization potency (y-axis) and V1 length of the respective viruses (x-axis, n=207) of DH270 lineage bnAbs DH270.1 (A), DH270.5 (B), DH270.6 (C) and V3 glycan bnAbs 10-1074 (D), PGT121 (E) and PGT128 (F) isolated from other individuals. Correlation p-values are non-parametric two sided, Kendall's tau. Slopes show linear regression.

The capacity of the early DH270 lineage members to neutralize heterologous viruses correlated with the presence of short V1 loops (FIG. 2D). As the lineage evolved, it gained capacity to neutralize viruses with longer V1 loops, although with reduced potency (FIG. 2D and FIGS. 16A-C). Neutralization of the same virus panel by V3 glycan bnAbs 10-1074, PGT121 and PGT128 followed the same inverse correlation between potency and V1 length (FIGS. 16D-F).

Figure 17A:
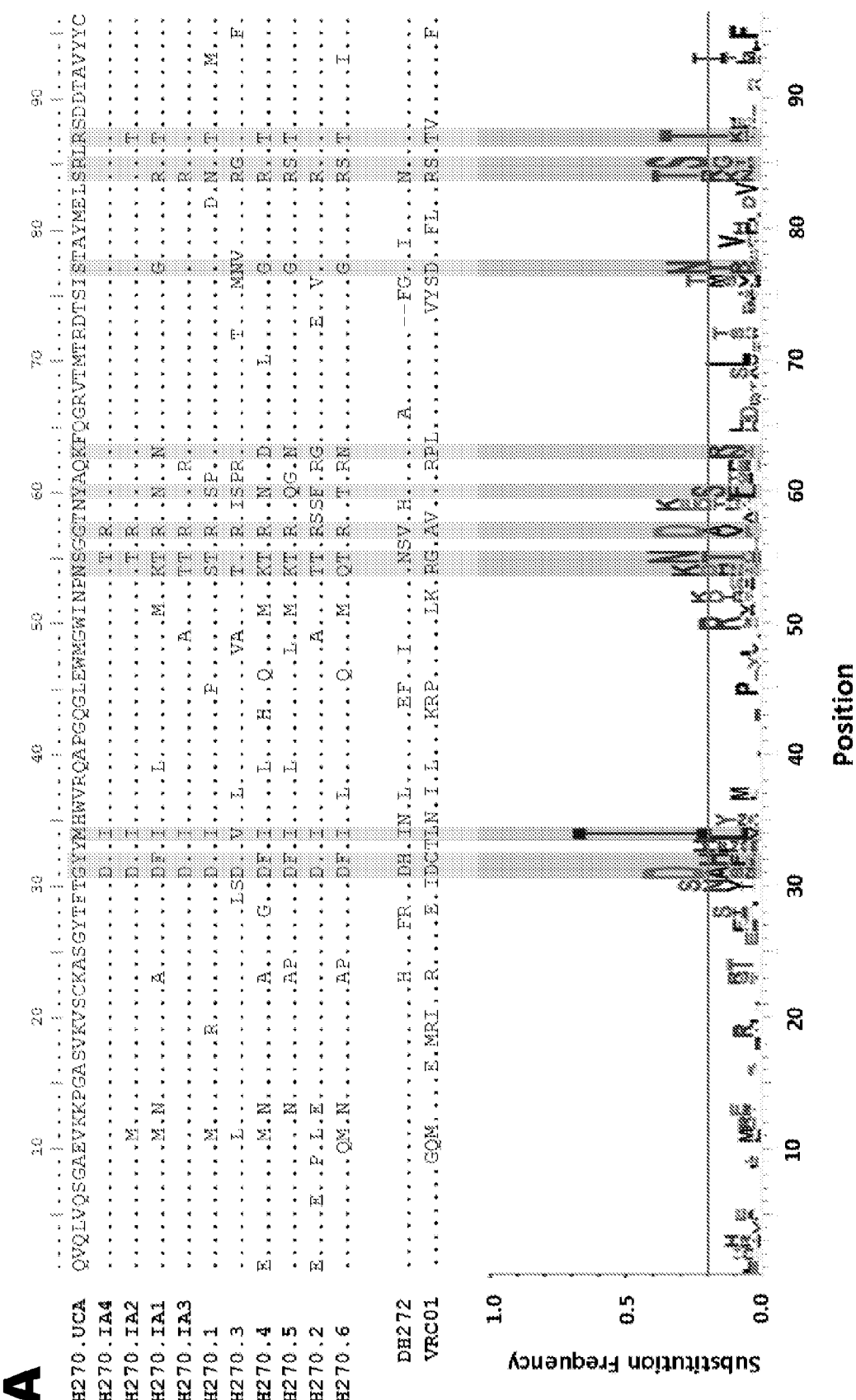
FIGS. 17A-B. Role of $V_H1$-2*02 intrinsic mutability in determining DH270 lineage antibody somatic hypermutation. (A) The sequence logo plot shows the frequency of VH1-2*02 amino acid (aa) mutations from germline at each position, calculated from an alignment of 10,995 VH1-2*02 reads obtained from 8 HIV-1 negative individuals by NGS that replicated across two independent Illumina experiments (35). The logo plot shows the frequency of mutated aa at each position. The red line indicates the threshold of mutation frequency (20%) used to define frequently mutated aa. The VH aa sequences of DH270 lineage antibodies, DH272 and VRC01 are aligned on the top. The 12 red vertical stripes indicate frequently mutated aa that were also frequently mutated (>25% of the VH sequences of isolated antibodies) in the DH270 lineage. (B) VH aa encoded by VH1-2 sequences from genomic DNA aligned to DH270 lineage antibodies aa sequences (see "Sequencing of germline variable region from genomic DNA" in Methods).

Mutations in the DH270 Antibody Lineage that Initiated Heterologous Neutralization The likelihood of AID-generated somatic mutation in immunoglobulin genes has strong nucleotide-sequence dependence (20)(21). Moreover, we have recently shown for CD4bs bnAbs that $V_H$ sites of high intrinsic mutability indeed determine many sites of somatic hypermutation (11). Like the VRC01-class CD4bs bnAbs, both DH270 and DH272 used $V_H1-2*02$ although unlike the CD4bs bnAbs, V3 glycan bnAbs in general can use quite disparate VH gene segments (3, 17, 22-25), and antibodies in both lineages have mutations at the same amino acid positions that correspond to sites of intrinsic mutability that we identified in the $V_H1-2*02$ CD4bs bnAbs (11) (FIG. 17A). In HIV-1 negative individuals, we identified 20 aa that frequently mutate from the $V_H1-2*02$ germline sequence (FIG. 17A). Twelve of these 20 aa were also frequently mutated in DH270 lineage antibodies and 11 of these 12 aa mutated to one of the two most frequent aa mutated in non-HIV-1 $V_H1-2*02$ sequences (identity conformity). G57R was the lone exception. DH272 mutated in 6 of these 12 positions and CD4bs bnAb VRC01 mutated in 11 out of 12 positions (FIG. 17A).

Figure 3A:
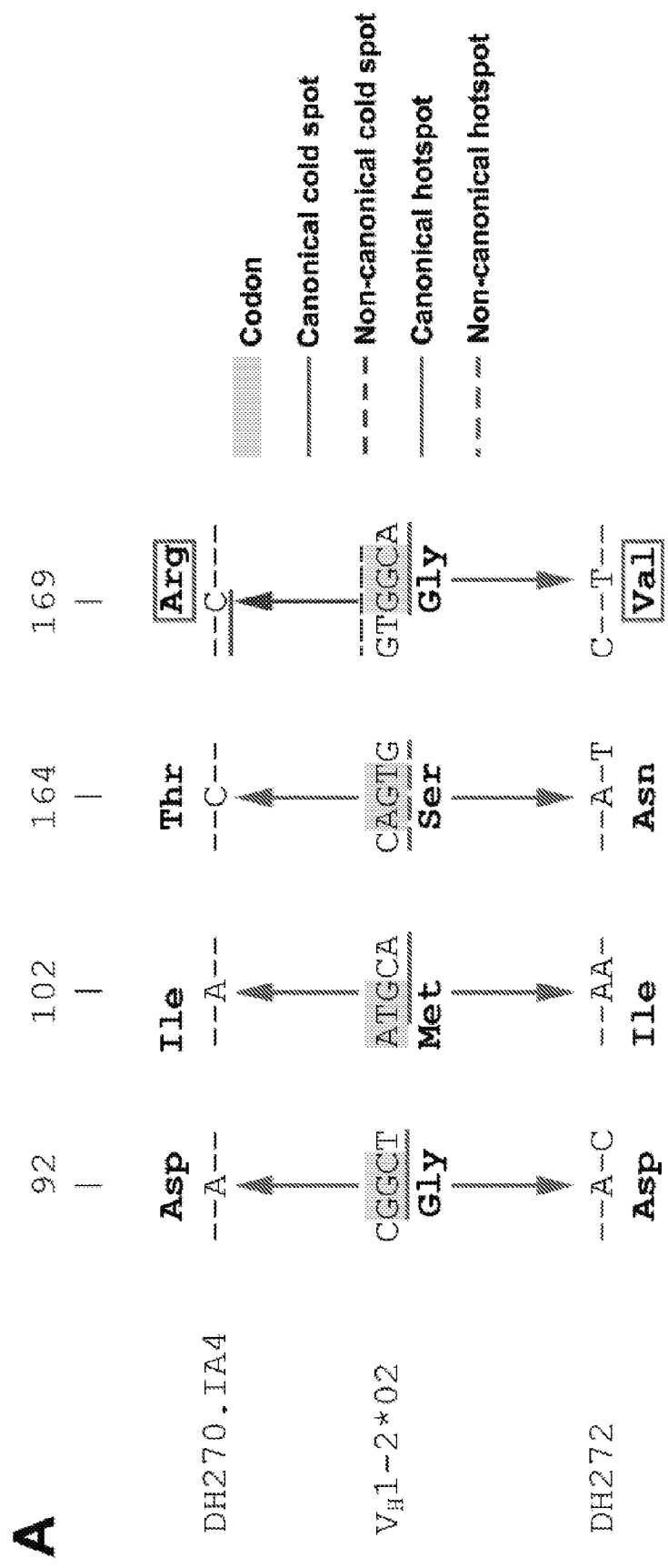
FIGS. 3A-E. A single disfavored mutation early during DH270 clonal development conferred neutralizing activity to the V3 glycan bnAb DH270 precursor antibodies. (A) Nucleotide (nt) alignment of DH270.IA4 and DH272 to $V_H 1$-2*02 sequence at the four $V_H$ positions that mutated from DH270.UCA to DH270.IA4. The mutated codons are highlighted in yellow. AID hotspots are indicated by red lines (solid: canonical; dashed: non-canonical); AID cold spots by blue lines (solid: canonical; dashed: non-canonical) (20). At position 169, DH270.IA4 retained positional conformity with DH272 but not identity conformity (red boxes). (B) Sequence logo plot of aa mutated from germline (top) in NGS reads of the DH270 (middle) and DH272 (bottom) lineages at weeks 186 and 111 post-transmission, respectively. Red asterisks indicate aa mutated in DH270.IA4. The black arrow indicates lack of identity conformity between the two lineages at aa position 57. (C) Sequence logo plot of nucleotide mutations (position 165-173) in the DH270 and DH272 lineages at weeks 186 and 111 post-transmission, respectively. The arrow indicates position 169. (D) Effect of reversion mutations on DH270.IA4 neutralization. Coloring is by $IC_{50}$. (E) Effect of G57R mutation on DH270.UCA autologous (top) and heterologous (bottom) neutralizing activity.
Figure 17B:
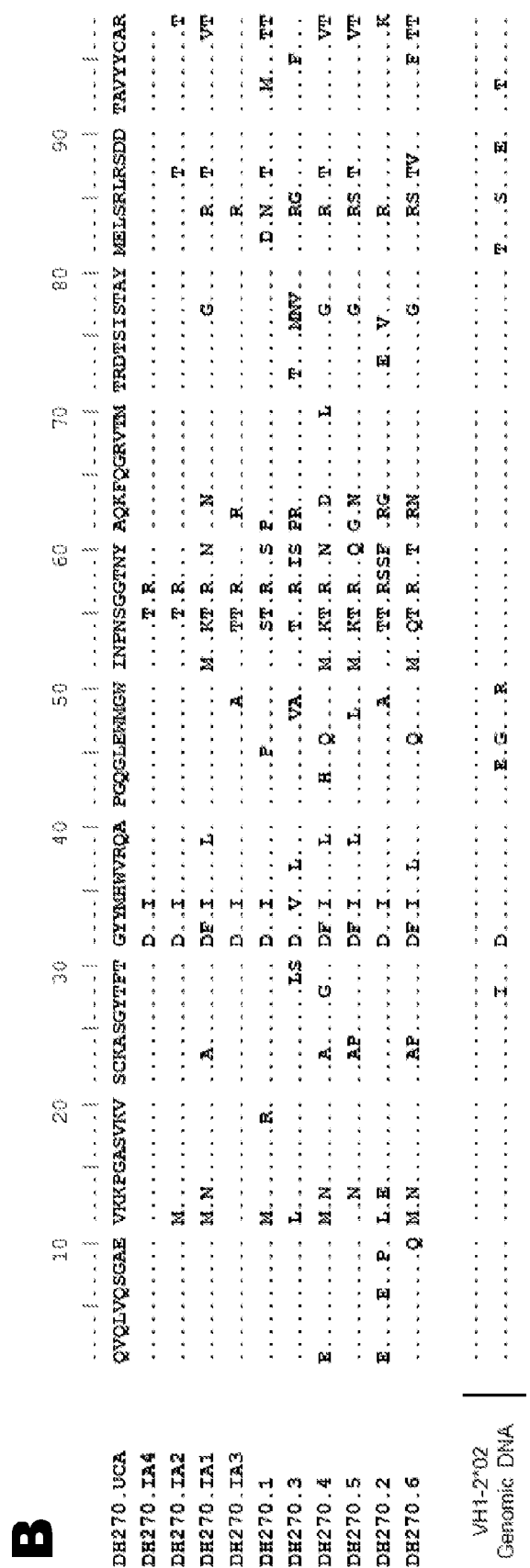

Presence of the canonical $V_H1-2*02$ allele in individual CH848 was confirmed by genomic DNA sequencing (FIG. 17B). Four nucleotide changes in the DH270 UCA conferred heterologous neutralization activity to the next intermediate antibody (IA4). The G92A and G102A nucleotide mutations in DH270.IA4 (and in DH272) occurred at "canonical" AID hotspots (DGYW) and encoded amino acid substitutions G31D and M34I, respectively (FIG. 3A). G164C (G164A for DH272) was in a "non-canonical" AID hotspot with a comparable level of mutability (20) and encoded the S55T (N for DH272) substitution (FIG. 3A). In contrast, the G169C mutation in DH270.IA4, which encoded the G57R amino acid mutation, occurred at a site with a very low predicted level of mutability (20), generated a canonical cold spot (GTC) and disrupted the overlapping AID hotspot at G170 within the same codon, which was instead used by DH272 and resulted in the G57V substitution (FIG. 3A). Thus, while both the DH270 bnAb and DH272 autologous neutralizing lineages had mutations at Gly57, the substitution in the DH270 lineage (G57R) was an improbable event whereas the substitution (G57V) in the DH272 lineage was much more probable.

Figures 3B, 3C:
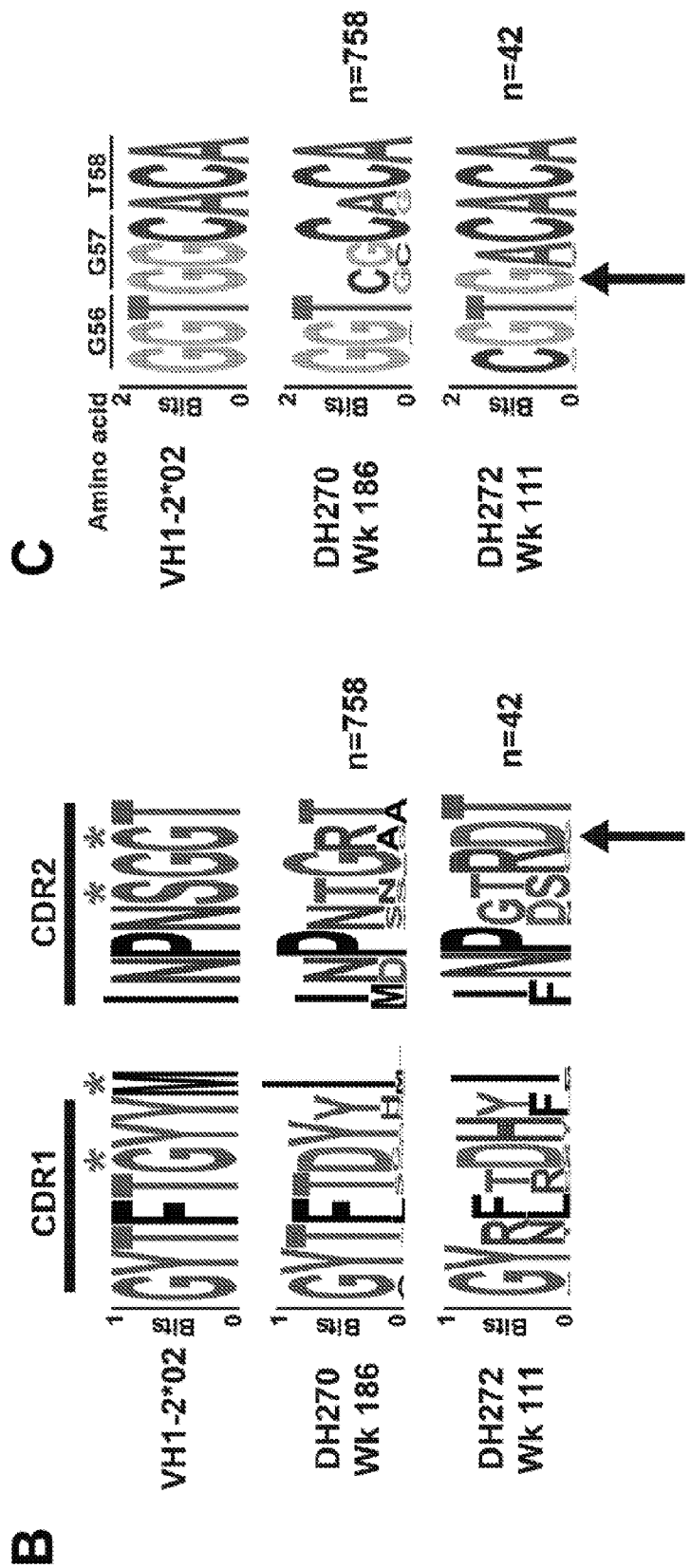

The G31D and M31I substitutions that occurred in AID hotspots became fixed in both lineages and S55T eventually became prevalent also in the DH272 lineage (FIG. 3B). By week 111 post-transmission, all DH272 lineage $V_HDJ_H$ transcripts sequenced by NGS harbored a mutation in the Gly57 codon, which resulted in the predominance of an encoded aspartic acid (FIG. 3B). In contrast, only 6/758 (0.8%) DH270 lineage transcripts isolated 186 weeks post-transmission had Val57 or Asp57; 48/758 (6.3%) retained Gly57, while over two-thirds, 514/758 (67.8%), had G57R (FIG. 3B).

Since the rare G169C nucleotide mutation in DH270.IA4 introduced a cold spot and simultaneously disrupted the overlapping AID hotspot, it had a high probability once it occurred of being maintained, and indeed it was present in 523/758 (68%) DH270 lineage VH sequences identified with NGS at week 186 post-transmission (FIG. 3C).

Figure 3D:
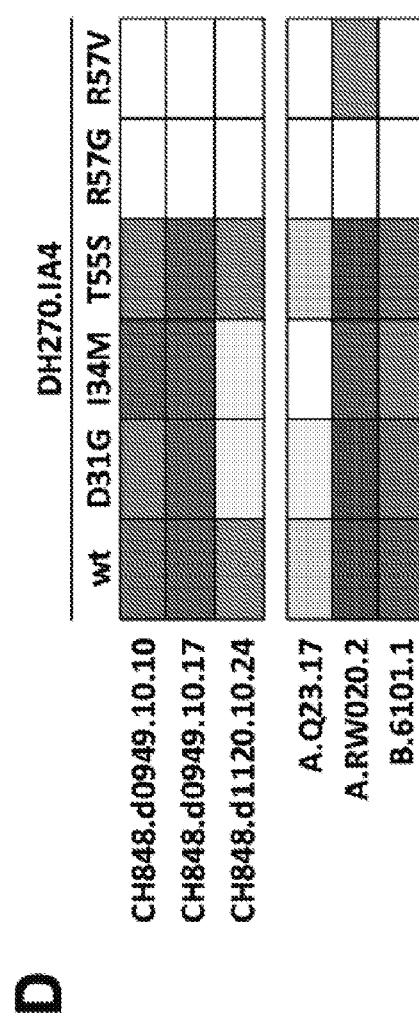
Figure 3E:
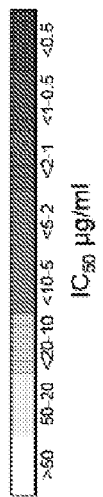

Reversion of Arg57 to Gly abrogated DH270.IA4 neutralization of autologous and heterologous HIV-1 isolates (FIG. 3D). A DH270.IA4 R57V mutant, with the base change that would have occurred had the overlapping AID hotspot been used, also greatly reduced DH270.IA4 neutralization, confirming that Arg57, rather than the absence of Gly57 was responsible for the acquired neutralizing activity (FIG. 3D). Finally, the DH270.UCA G57R mutant neutralized both autologous and heterologous viruses, confirming that G57R alone could confer neutralizing activity on the DH270 germline antibody (FIG. 3E). Thus, the improbable G169C mutation conferred reactivity against autologous virus and initiated acquisition of heterologous neutralization breadth in the DH270 lineage.

Figures 18A, 18B:
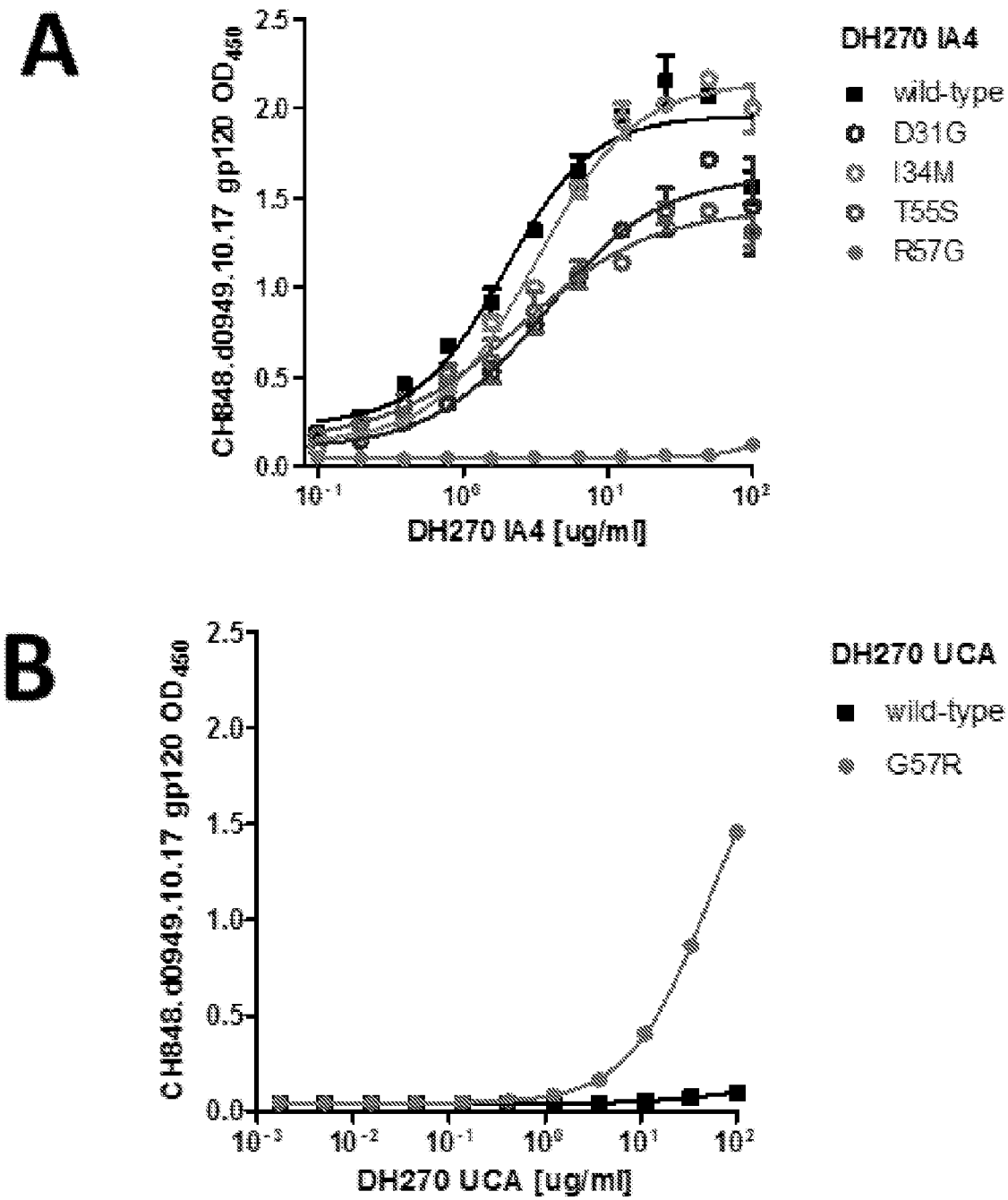
FIGS. 18A-B. Effect of the G57R mutation on DH270.IA4 and DH270.UCA binding to Env 10.17 gp120. (A) Binding to Env 10.17 gp120 by wild-type DH270.IA4 (black) and DH270.IA4 variants in which each mutated aa was reverted to germline (D31G, blue; I34M, orange; T55S, green, R57G, red). Mean and standard deviation from duplicate observations are indicated for each datapoint and curve fitting (non-linear, 4-parameters) is shown for each dataset. Binding is quantified as background subtracted OD450 values. (B) Binding to Env 10.17 by wild-type DH270.UCA (black) and the DH270.UCA with the G57R mutation (red).

A search for an Env that might select for the critical G57R mutation in DH270 UCA or IA4-like antibodies yielded Env 10.17 from week 135 of infection (FIGS. 18A, B), which derived from the only autologous virus Env that DH270.IA4 could bind. DH270.IA4 binding to Env 10.17 depended on presence of Arg57 and reversion of R57G was necessary and sufficient to abrogate binding (FIG. 18A). Also, binding to Env 10.17 was acquired by DH270.UCA upon introduction of the G57R mutation (FIG. 18B).

Autologous Neutralizing Antibody Lineages that Cooperated with DH270

Figure 4A:
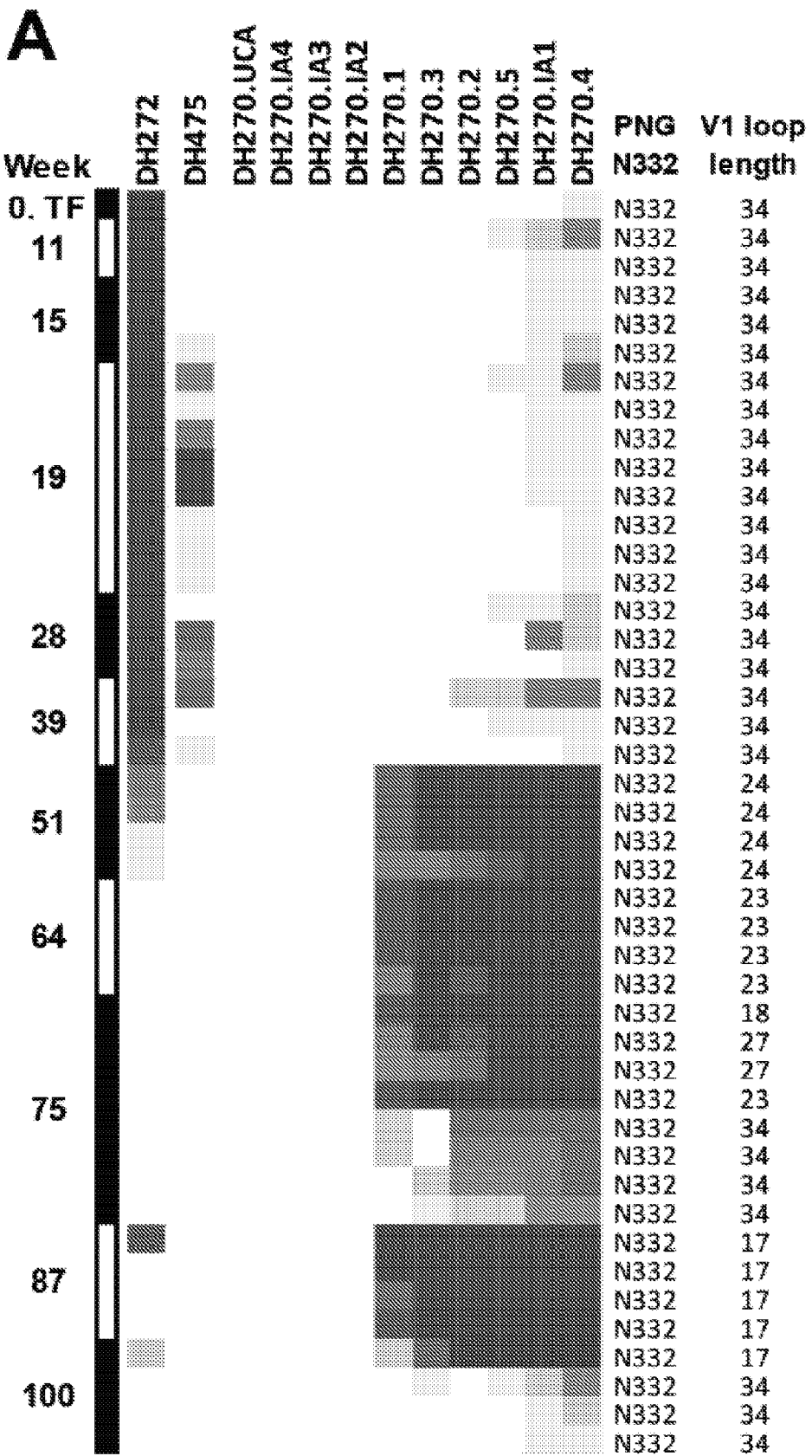
FIGS. 4A-C. Cooperation among DH270, DH272 and DH475 N332 dependent V3 glycan nAb lineages. (A) Neutralizing activity of DH272, DH475 and DH270 lineage antibodies (columns) against 90 autologous viruses isolated from CH848 over time (rows). Neutralization potency ($IC_{50}$) is shown as indicated in the bar. For each pseudovirus, presence of an N332 PNG site and V1 loop length are indicated on the right. See also FIGS. 34-35 of WO/2017/152146. (B, C) Susceptibility to DH270.1 and to (B) DH475 or (C) DH272 of autologous viruses bearing selected immunotype-specific mutations.
Figure 4A:
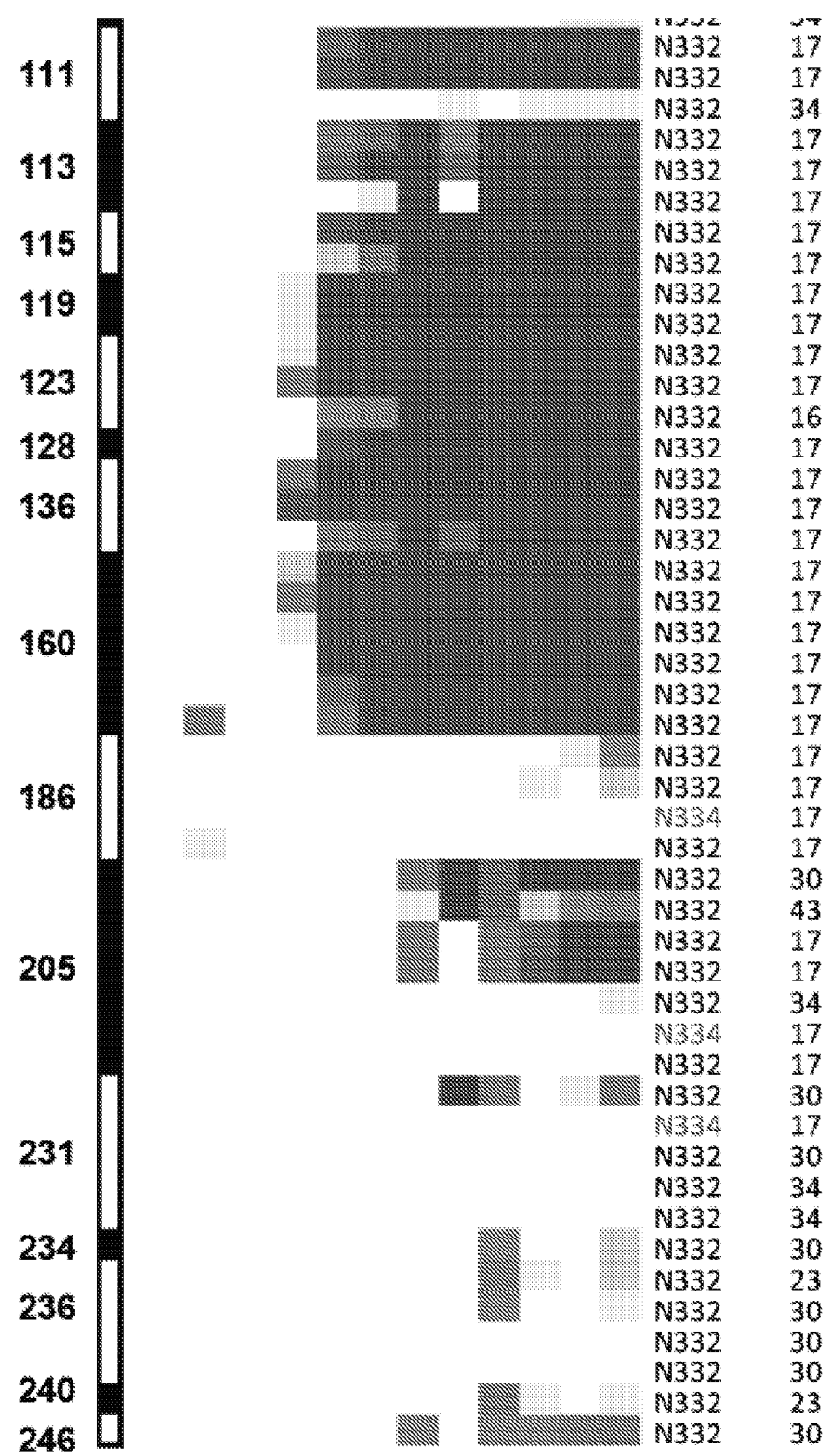

Evidence for functional interaction among the three N332-dependent lineages came from the respective neutralization profiles against a panel of 90 autologous viruses from transmitted/founder to week 240 post-transmission (FIG. 4A; see also FIGS. 34-35 of WO/2017/152146). Both DH475 and DH272 neutralized autologous viruses isolated during the first year of infection that were resistant to most DH270 lineage antibodies (only DH270.IA1 and DH270.4 neutralized weakly) (FIG. 4A). DH475 neutralized viruses from week 15 through week 39 and DH272 neutralized the CH848 transmitted/founder and all viruses isolated up to week 51, when viruses that resisted DH475 and DH272 became strongly sensitive to the more mature antibodies in the DH270 lineage ($V_H$ nt mutation frequency ≥5.6%) (FIG. 4A).

Figure 19:
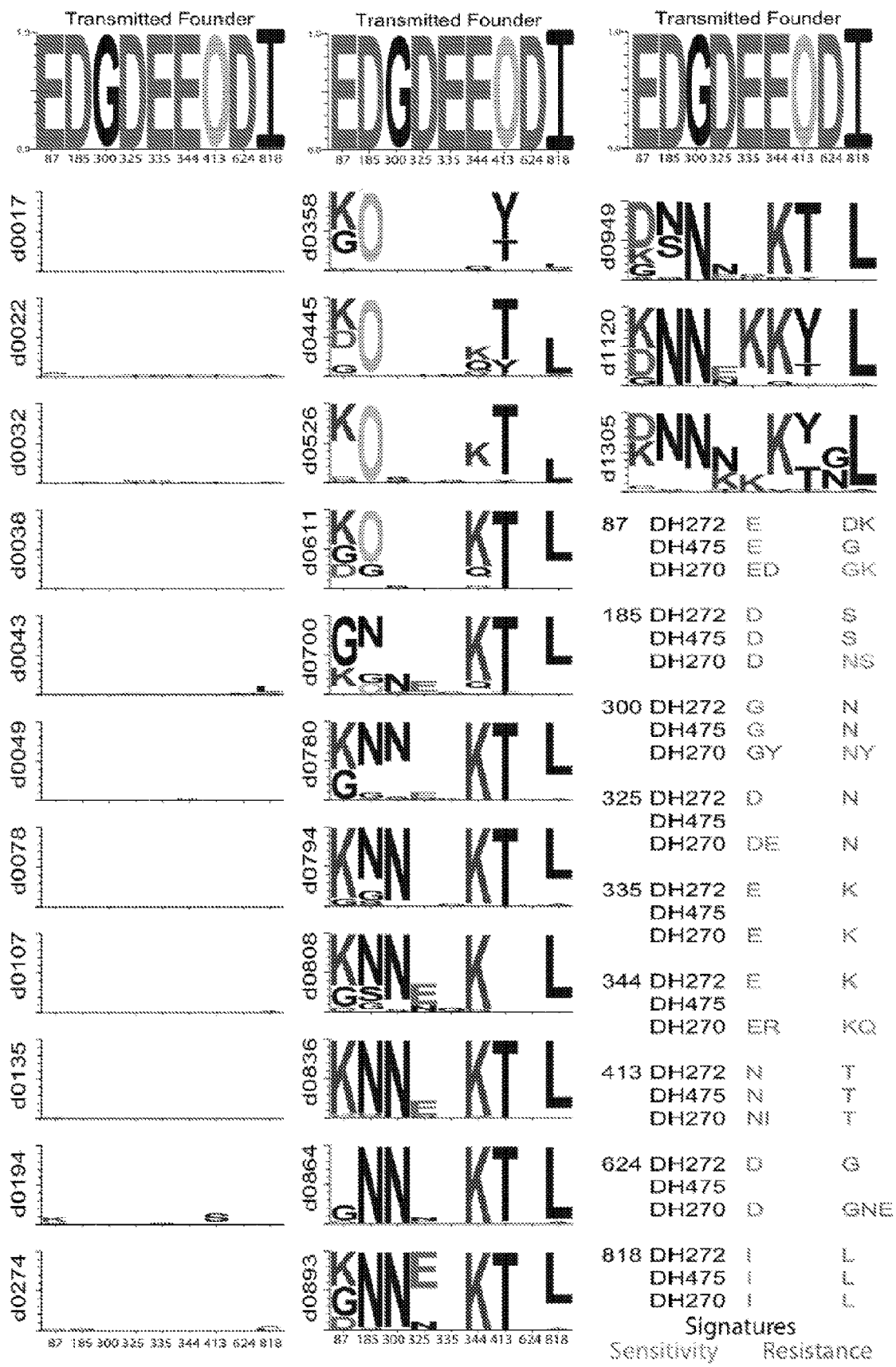
FIG. 19. Virus signature analysis. Logo plots represent the frequency of amino acids mutations in CH848 virus quasispecies from transmitted founder at indicated positions over time. Red indicates a negatively charged amino acid, blue positive, black neutral; the light blue O is a PNG site. The signatures outlined in detail in FIG. 36 of WO/2017/152146 are summarized in the bottom right column where a red amino acid is associated with resistance to the antibody on the right, a blue amino acid is associated with sensitivity.

The identification of specific mutations implicated in the switch of virus sensitivity was complicated by the high levels of mutations accumulated by virus Env over time (FIG. 19; see also FIG. 36 of WO/2017/152146). We identified virus signatures that defined the DH270.1 and DH272/DH475 immunotypes and introduced four of them, in various combinations, into the DH272/DH475-sensitive virus that was closest in sequence to the DH270.1-sensitive immunotype: a 10 amino-acid residue deletion in V1 (Δ134-143); a D185N mutation in V2, which introduced an N-linked glycosylation site; an N413Y mutation in V4, which disrupted an N-linked glycosylation site; and a 2 amino-acid residue deletion (Δ. 63-464) in V5.

Figures 4B, 4C:

The large V1 deletion was critical for DH270.1 neutralization, with smaller contributions from the other changes; the V1 deletion increased virus resistance to DH475 (3.5-fold increase). V1-loop-mediated resistance to DH475 neutralization increased further when combined with the Δ463-464 V5 deletion (5-fold increase) (FIG. 4B).

Figures 20A, 20B, 20C, 20D, 20E, 20F:
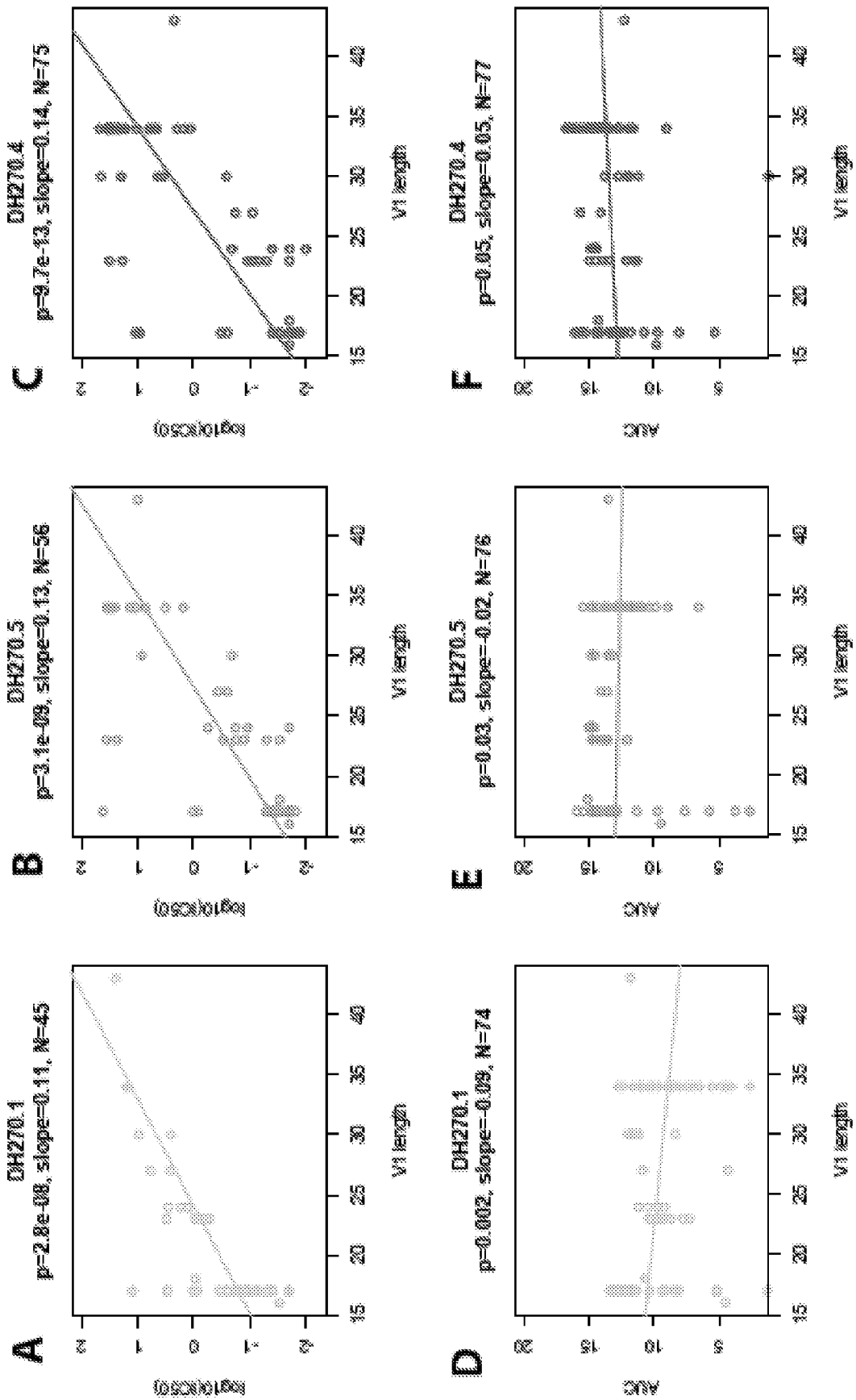
FIGS. 20A-F. Autologous Env V1 length associations with DH270 lineage neutralization and gp120 binding. Eighty-two virus Envs—the subset from FIGS. 34-35 of WO/2017/152146 that were assayed for both neutralization (A-C) and binding (D-F) to DH270.1, DH270.4 and DH270.5—were evaluated. The 3 Envs that had lost the PNG site at N332 were not included, as they were negative for all antibodies tested independently of V1 length. Only points from positive results are plotted: IC50<50 µg/ml for neutralization in panels A-C, and AUC>1 for binding in panels D-F. N is the number of positive sample.

The V1 loop of the transmitted/founder virus (34 residues) was longer than the average V1 length of 28 residues (range 11 to 64) of HIV-1 Env sequences found in the Los Alamos Sequence Database (26). As we found for heterologous neutralization, DH270 lineage antibodies acquired the ability to neutralize larger fractions of autologous viruses as maturation progressed by gaining activity for viruses with longer V1 loops, although at the expense of lower potency (FIGS. 20A-C). This correlation was less clear for gp120 binding (FIGS. 20D-F), however, suggesting that the V1 loop-length dependency of V3 glycan bnAb neutralization has a conformational component. Thus, DH475 cooperated with the DH270 bnAb lineage by selecting viral escape mutants sensitive to bnAb lineage members.

For DH272, the viral variants that we made did not implicate a specific cooperating escape mutation. The Δ134-143 (V1 deletion) mutated virus remained sensitive to DH272 neutralization; both combinations of the V1 deletion in our panel that were resistant to DH272 and sensitive to DH270.1 included D185N, which on its own also caused DH272 resistance but did not lead to DH270.1 sensitivity (FIG. 4C). Thus, we have suggestive, but not definitive, evidence that DH272 also participated in selecting escape mutants for the DH270 bnAb lineage.

Structure of DH270 Lineage Members

Figures 5A, 5B:
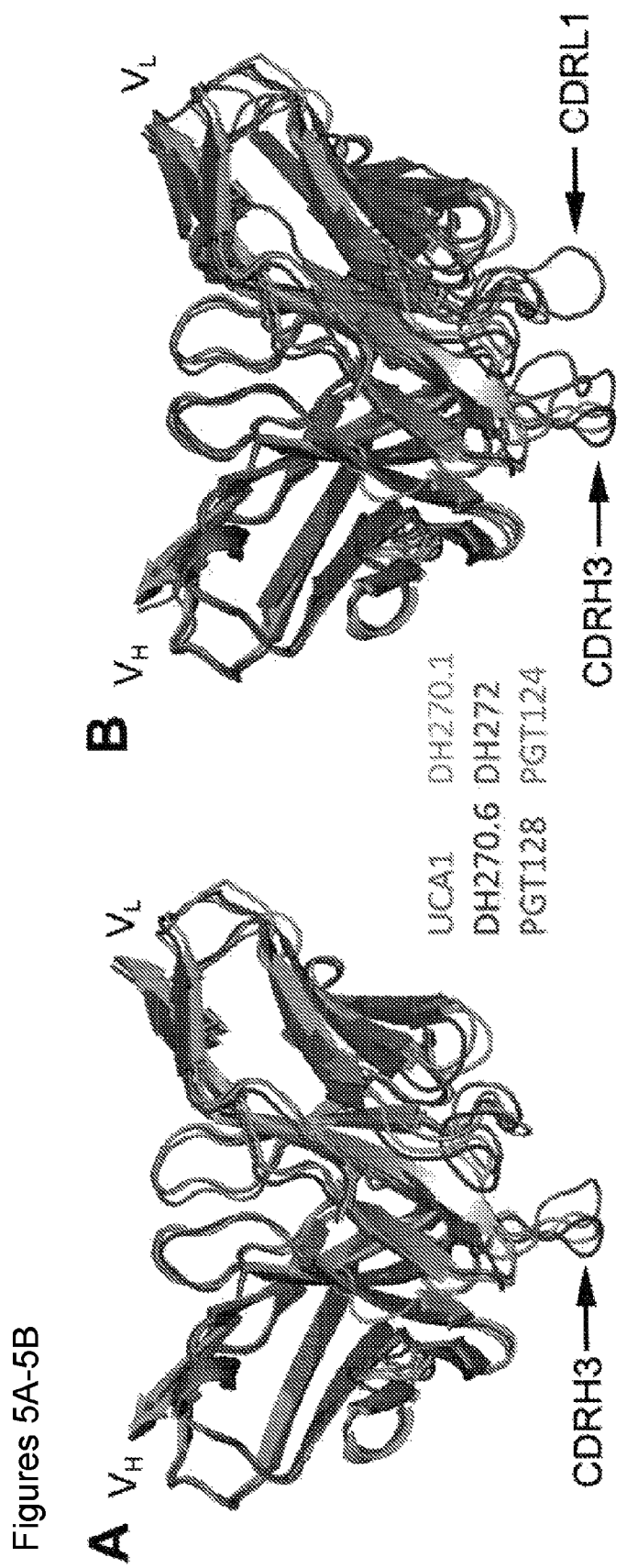
FIGS. 5A-H. Fab/scFv crystal structures and 3D-reconstruction of DH270.1 bound with the 92BR SOSIP.664 trimer. Superposition of backbone ribbon diagrams for DH270 lineage members: UCA1 (gray), DH270.1 (green), and DH270.6 (blue) (A) alone, (B) with the DH272 cooperating antibody (red), (C) with PGT128 (magenta), and (D) with PGT124 (orange). Arrows indicate major differences in CDR regions. (E) Top and (F) side views of a fit of the DH270.1 Fab (green) and the BG505 SOSIP trimer (gray) into a map obtained from negative-stain EM. (G) Top and (H) side views of the BG505 trimer (PDB ID: 5ACO) (28) (gray, with V1N2 and V3 loops highlighted in red and blue, respectively) bound with PGT124 (PDB ID: 4R2G) (27) (orange), PGT128 (PDB ID: 3TYG) (17) (magenta), PGT135 (PDB ID: 4JM2) (22) (cyan) and DH270.1 (green), superposed. The arrows indicate the direction of the principal axis of each of the bnAb Fabs; the color of each arrow matches that of the corresponding bnAb. See also FIG. 24.
Figure 21C:
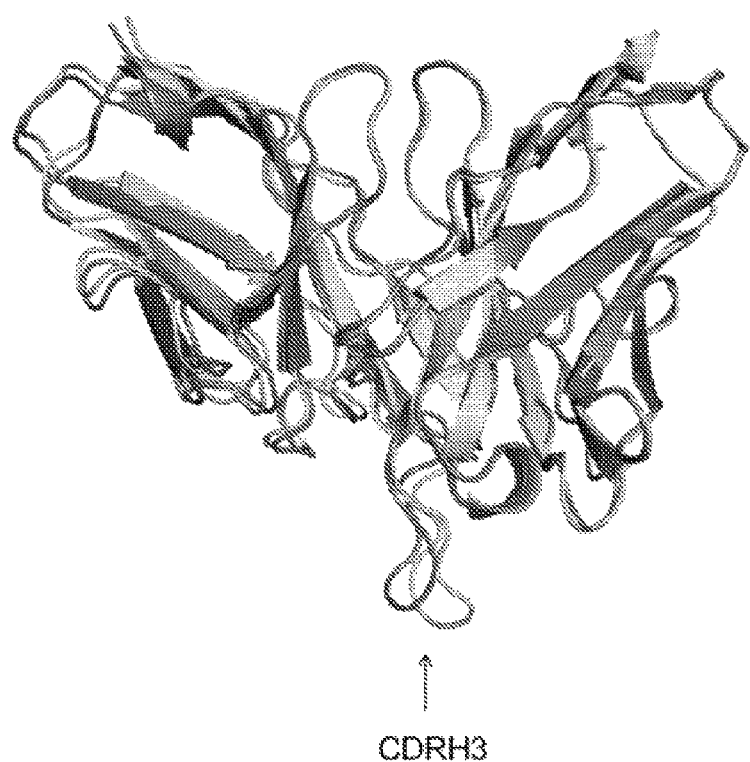
Figure 22:
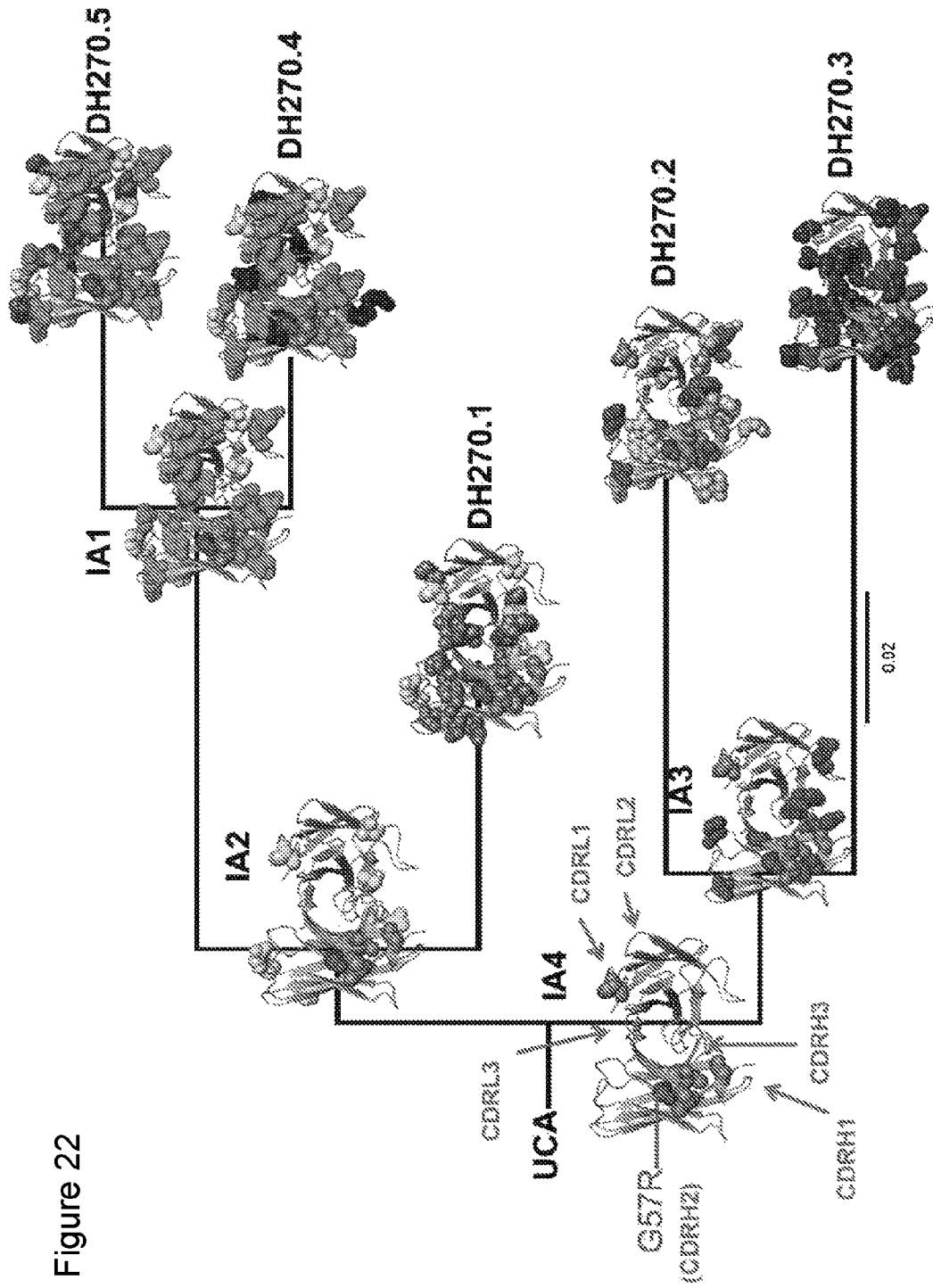
FIG. 22. Accumulation of mutation in DH270 lineage antibodies. Mutations are highlighted as spheres on the Fv region of each antibody, where the CDR regions, labeled on the backbone of the UCA, face outward. The G57R mutation is shown in red; the other mutations incurred between the UCA and IA4 are shown in orange. Mutations between intermediates are colored as follows: between IA2 and IA4, yellow; between IA1 and IA2, green; between IA3 and IA4, magenta. Mutations between the late intermediates and DH270.1, DH270.2, DH270.3, DH270.4, and DH270.5 are in brown, light purple, dark purple, blue, and dark blue, respectively.

We determined crystal structures for the single-chain variable fragment of DH270.1 and the Fabs of DH270.UCA3, DH270.3, DH270.5 and DH270.6, as well as for DH272 (see FIG. 32 of WO/2017/152146). Because of uncertainty in the inferred sequence of the germline precursor (FIGS. 21A, B), we also determined the structure of DH270.UCA1, which has a somewhat differently configured CDR H3 loop (FIG. 21C); reconfiguration of this loop during early affinity maturation could account for the observed increase with respect to the UCA in heterologous neutralization by several intermediates. The variable domains of the DH270 antibodies superposed well, indicating that affinity maturation modulated the antibody-antigen interface without substantially changing the antibody conformation (FIG. 5A). Mutations accumulated at different positions for DH270 lineage bnAbs in distinct branches (FIG. 22), possibly accounting for their distinct neutralization properties. DH272 had a CDRH3 configured differently from that of DH270 lineage members and a significantly longer CDRL1 (FIG. 5B), compatible with their distinct neutralization profiles.

Figures 5C, 5D:
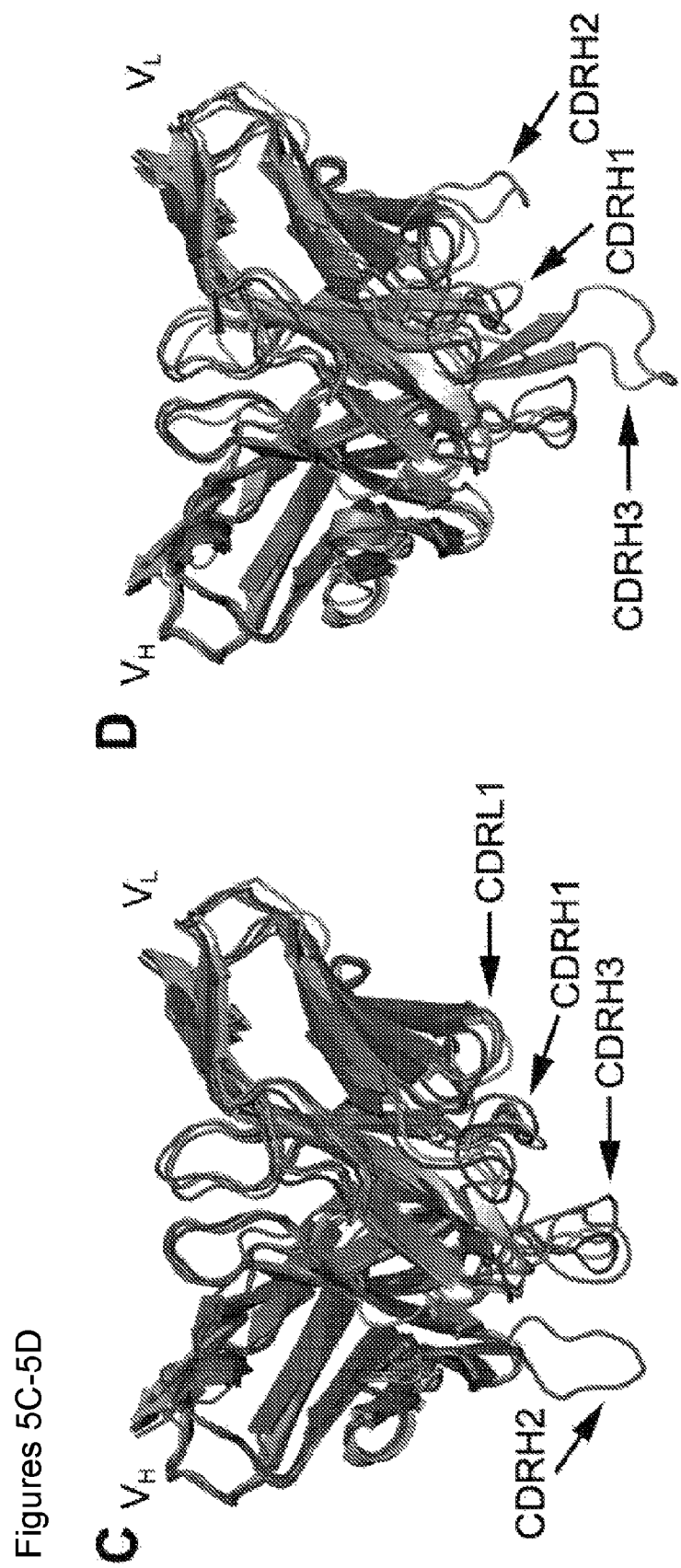

We also compared the structures of DH270 lineage members with those of other N332-dependent bnAbs. All appear to have one long CDR loop that can extend through the network of glycans on the surface of the gp120 subunit and contact the "shielded" protein surface. The lateral surfaces of the Fab variable module can then interact with the reconfigured or displaced glycans to either side. PGT128 has a long CDRH2 (FIG. 5C), in which a 6-residue insertion is critical for neutralization breadth and potency (5, 17).

PGT124 has a shorter and differently configured CDR H2 loop, but a long CDR H3 instead (FIG. 5D) (27).

Structure of the DH270—HIV Env Complex

Figures 5E, 5F:
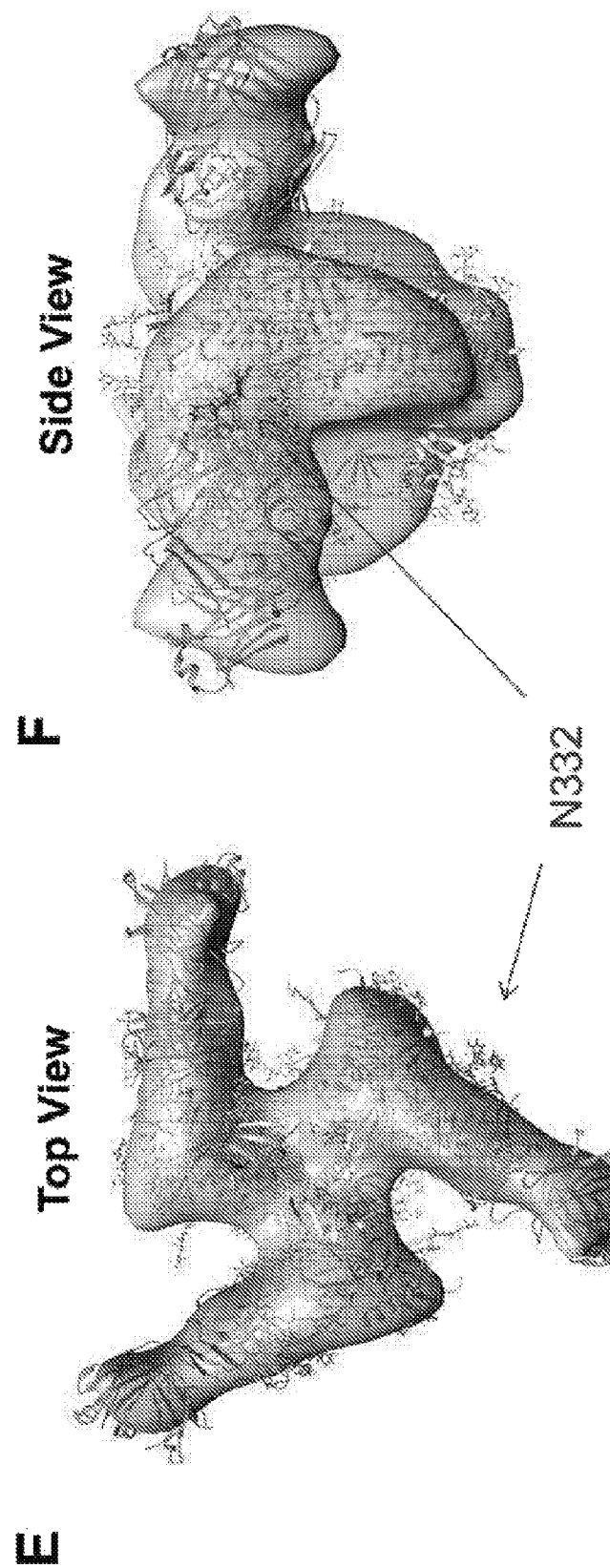
Figure 5G:
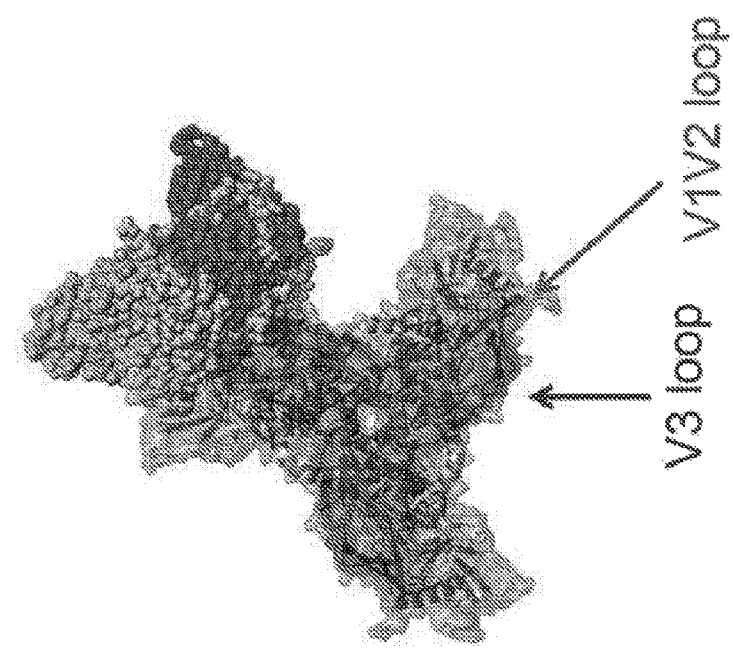
Figure 5H:
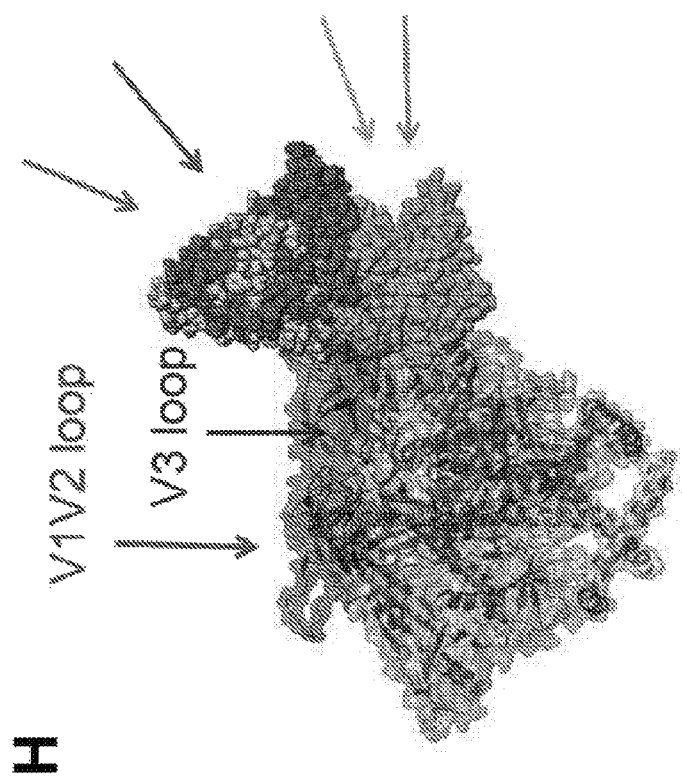
Figure 23A:
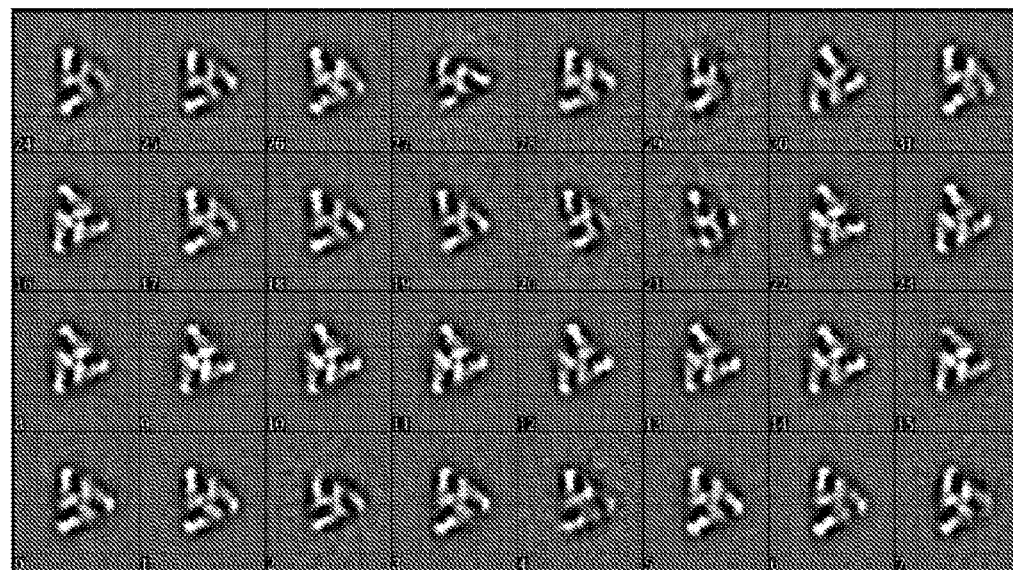
FIGS. 23A-B. Negative stain EM of DH270 Fab in complex with the 92BR SOSIP.664 trimer. (A) 2D class-averages of the complex. Fabs are indicated with a red arrow. (B) Fourier shell correlation curve for the complex along with the resolution determined using FSC=0.5.
Figure 23B:
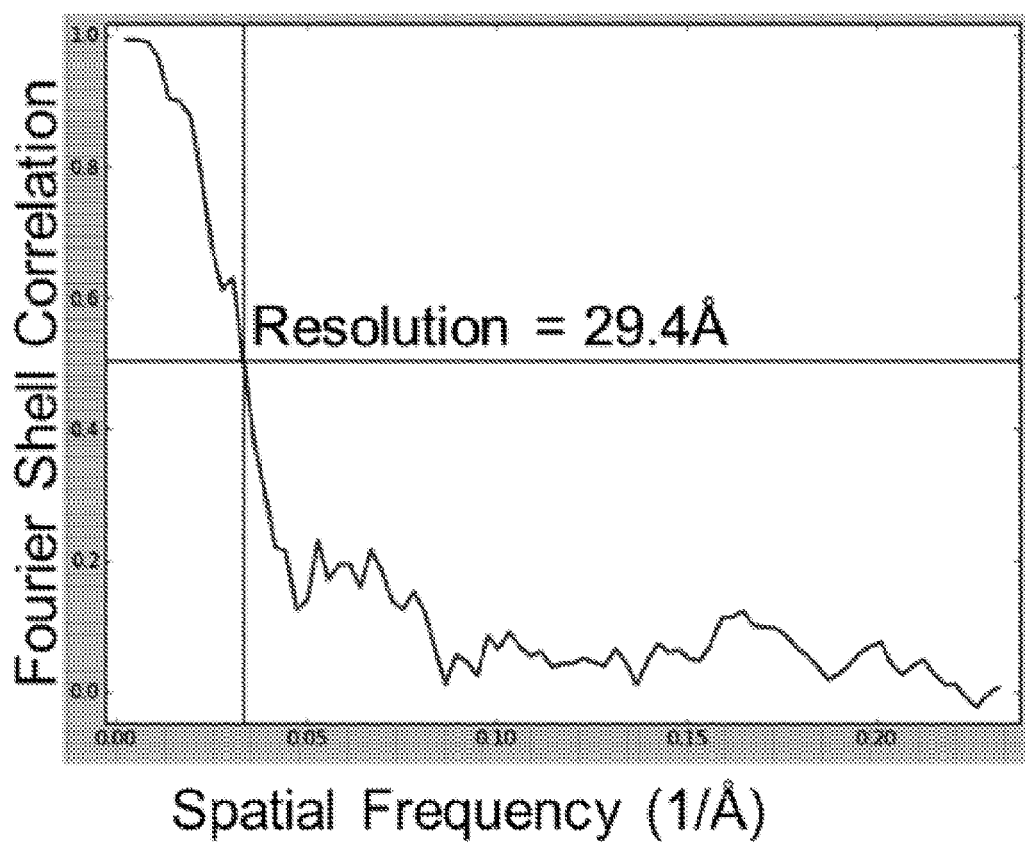
Figure 24:
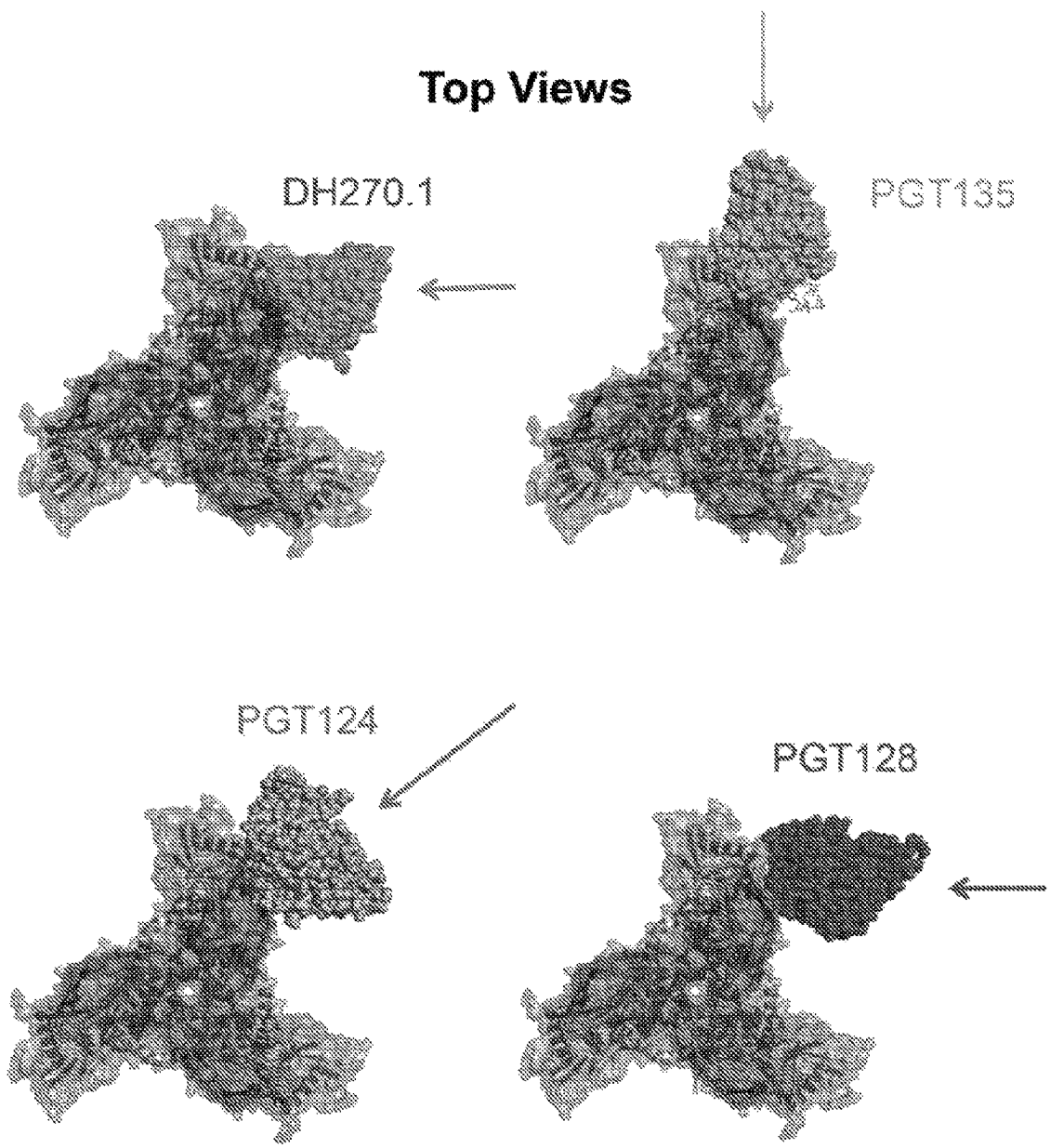
FIG. 24. DH270.1 and other N332 bnAbs bound to the 92BR SOSIP.664 trimer. Top and side views of the BG505 trimer (PDB ID: 5ACO) (28) (gray, with V1N2 and V3 loops highlighted in red and blue, respectively) bound with DH270.1 (green), PGT135 (PDB ID: 4JM2) (22) (cyan), PGT124 (PDB ID: 4R2G) (27) (orange) and PGT128 (PDB ID: 3TYG) (17) (magenta) illustrate the different positions of the several Fabs on gp140. The arrows indicate the direction of the principal axis of each of the bnAb Fabs; the color of each arrow matches that of the corresponding bnAb.
Figure 24:
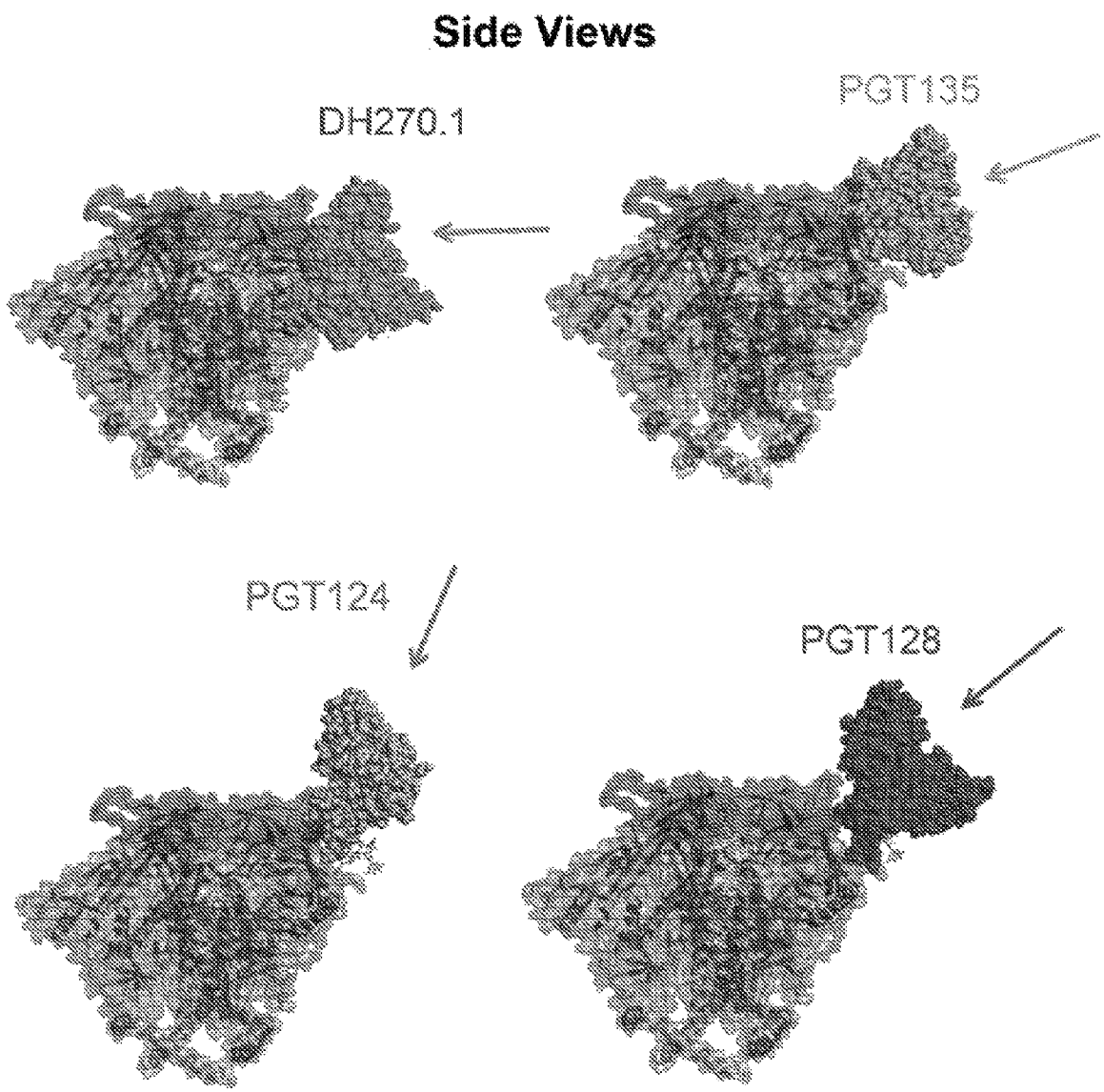
Figure 25A:
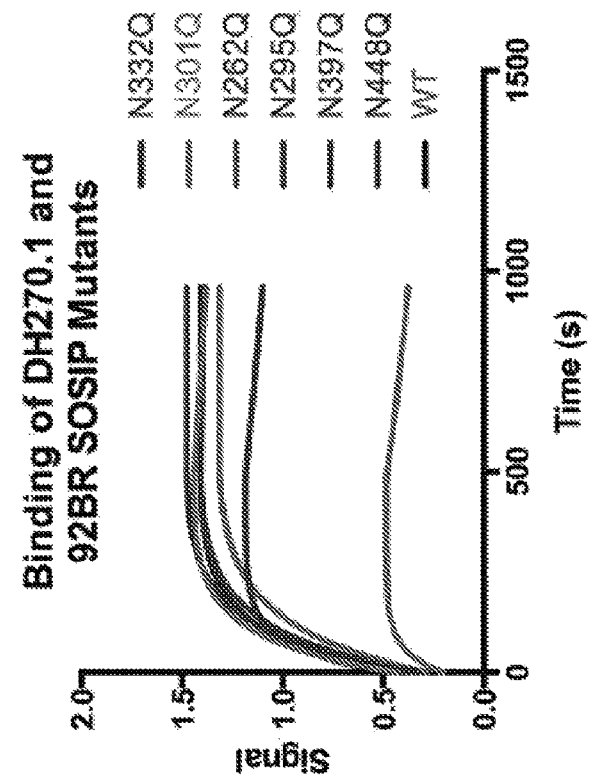
FIGS. 25A-B. DH270.1 binding kinetics to 92BR SOSIP.664 trimers with mutated PNG sites. (A) Glycans forming a "funnel" are shown on the surface of the trimer. V1-V2 and V3 loops are colored red and blue, respectively. (B) Association and dissociation curves, using biolayer interferometry, against different 92BR SOSIP.664 glycan mutants.
Figure 25B:
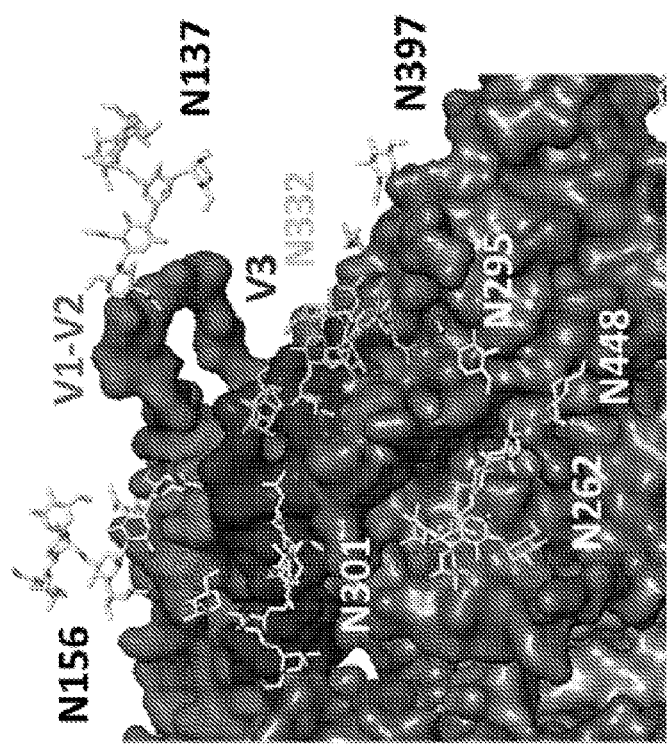
Figure 26A:
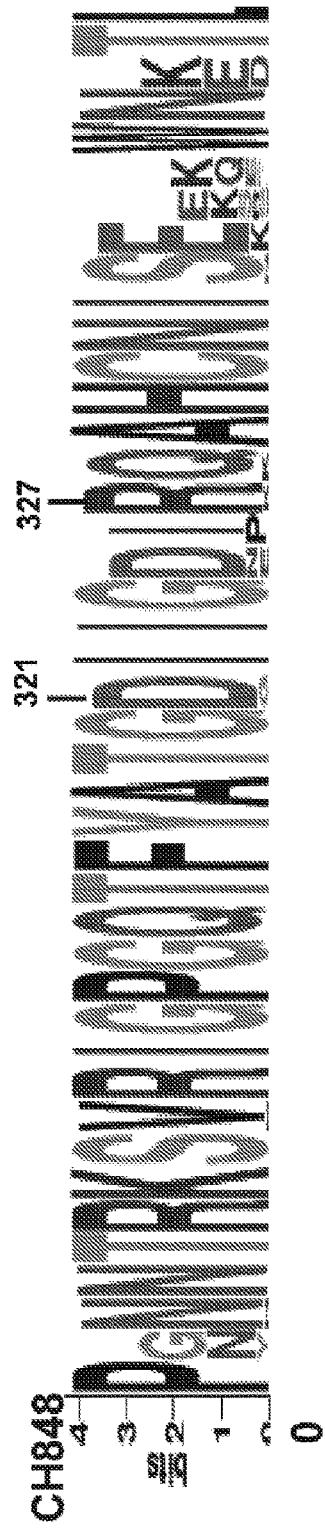
FIGS. 26A-C. DH270.1 binding kinetics to 92BR SOSIP.664 trimer with additional mutations. (A) Sequence Logo of the V3 region of CH848 autologous viruses are shown. (B) Binding kinetics, using biolayer interferometry, against different 92BR SOSIP.664 V3 loop region mutants. (C) DH270.1 heavy chain mutants and 92BR SOSIP.664. Biolayer interferometry association and dissociation curves for the indicated Fab mutants for binding to 92BR SOSIP.664 (600 nM curves are shown) Not shown are curves for DH270.1 heavy chain mutants K32A, R72A, D73A, S25D, S54D, S60D and double mutant S75/77A for which there was little or no reduction in affinity.
Figure 26B:
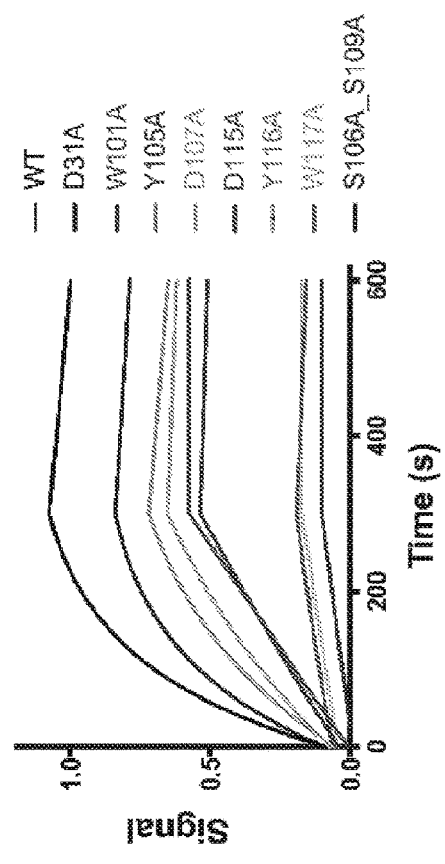
Figure 26C:
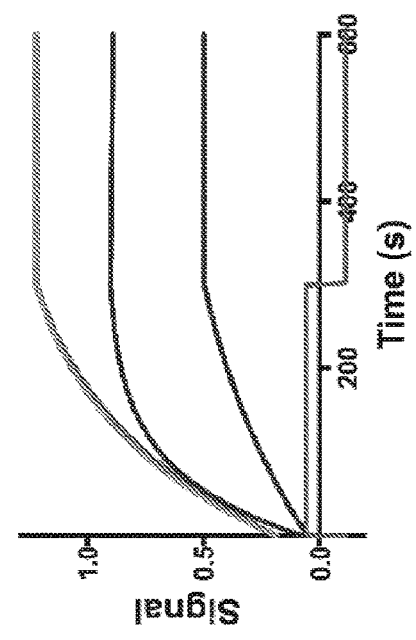

We determined a three-dimensional (3D) image reconstruction, from negative-stain electron microscopy (EM), of the DH270.1 Fab bound with a gp140 trimer (92Br SOSIP.664) (FIGS. 5E, F and FIGS. 23A-B). The three DH270.1 Fabs project laterally, with their axes nearly normal to the threefold of gp140, in a distinctly more "horizontal" orientation than seen for PGT124, PGT135 and PGT128 (FIGS. 5G, H and FIG. 24). This orientational difference is consistent with differences between DH270 and PGT124 or PGT128 in the lengths and configurations of their CDR loops, which required an alternative DH270 bnAb position when docked onto the surface of the Env trimer. We docked the BG505 SOSIP coordinates (28) and the Fab into the EM reconstruction, and further constrained the EM reconstruction image by the observed effects of BG505 SOSIP mutations in the gp140 surface image (FIGS. 23A-B and FIGS. 25A-B). Asp325 was essential for binding DH270.1 since it is a potential partner for Arg57 on the Fab. Mutating Asp321 led to a modest loss in affinity; R327A had no effect (FIG. 26A-C). These data further distinguish DH270 from PGT124 and PGT128. Mutating W101, Y105, D107, D115, Y116 or W117 in DH270.1 individually to alanine substantially reduced binding to the SOSIP trimer, as did pairwise mutation to alanines of S106 and S109. The effects of these mutations illustrate the critical role of the CDRH3 loop in binding with HIV-1 Env (FIGS. 26A-C).

DH270 UCA Binding

Figure 6A:
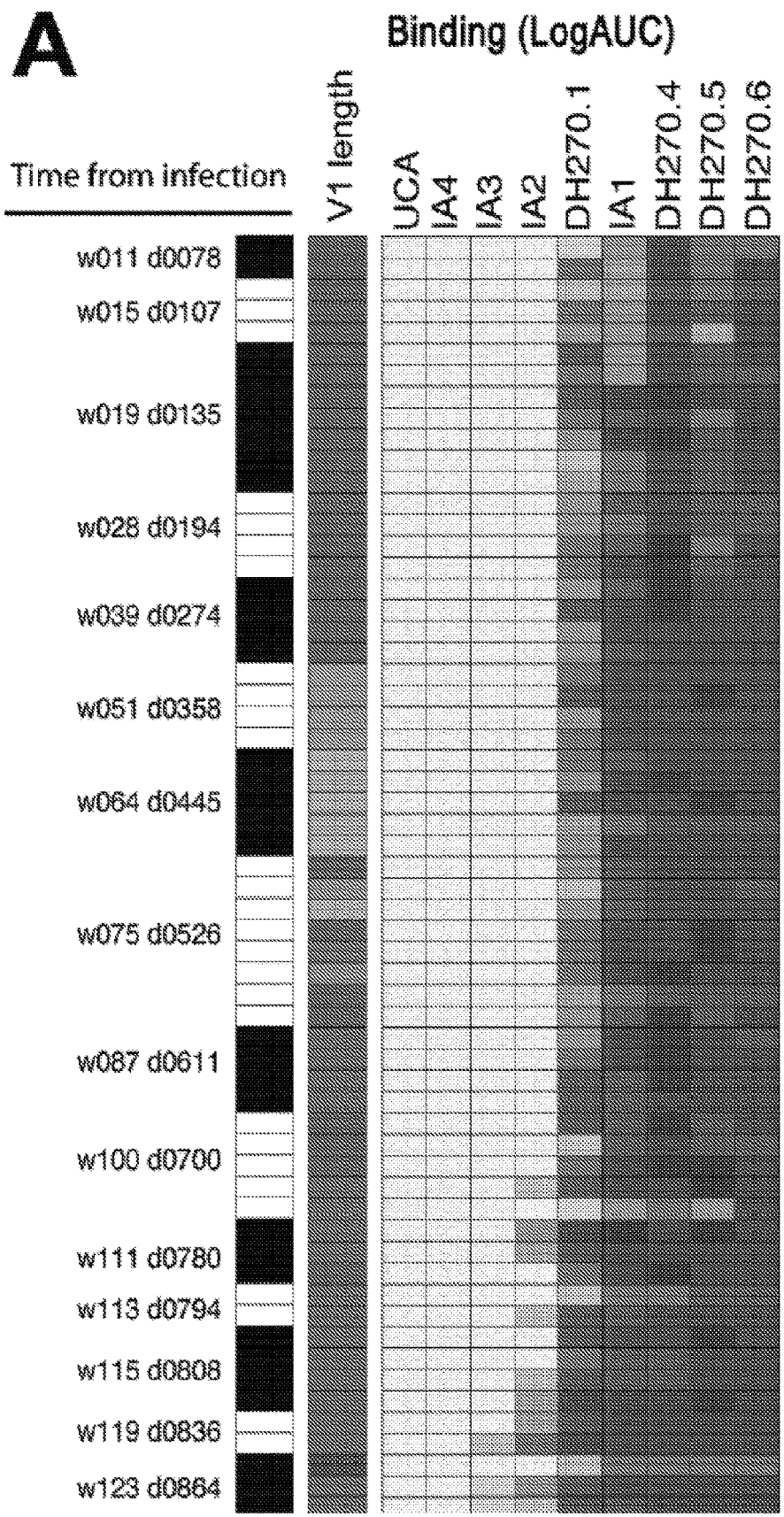
FIGS. 6A-B. DH270 lineage antibody binding to autologous CH848 Env components. (A) Binding of DH270 lineage antibodies (column) to 120 CH848 autologous gp120 Env glycoproteins (rows) grouped based on time of isolation (w: week; d: day; black and white blocks). The last three rows show the neutralization profile of the three autologous viruses that lost the PNG at position N332 (blue blocks). V1 aa length of each virus is color-coded as indicated. Antibody binding is measured in ELISA and expressed as log area under the curve (LogAUC) and color-coded based on the categories shown in the histogram. The histogram shows the distribution of the measured values in each category. The black arrow indicated Env 10.17. Viruses isolated at and after week 186, which is the time of first evidence of DH270 lineage presence, are highlighted in different colors according to week of isolation. (B) Left: Binding to CH848.TF mutants with disrupted N301 and/or N332 glycan sites. Results are expressed as LogAUC. $V_H$ mutation frequency is shown in parenthesis for each antibody (see also FIG. 7A). Middle: Binding to CH848 Env trimer expressed on the cell surface of CHO cells. Results are expressed as maximum percentage of binding and are representative of duplicate experiments. DH270 antibodies are shown in red. Palivizumab is the negative control (gray area). The curves indicate binding to the surface antigen on a 0 to 100 scale (y-axis), the highest peak between the test antibody and the negative control sets the value of 100. Right: Binding to free glycans measured on a microarray. Results are the average of background-subtracted triplicate measurements and are expressed in RU.
Figure 6B:
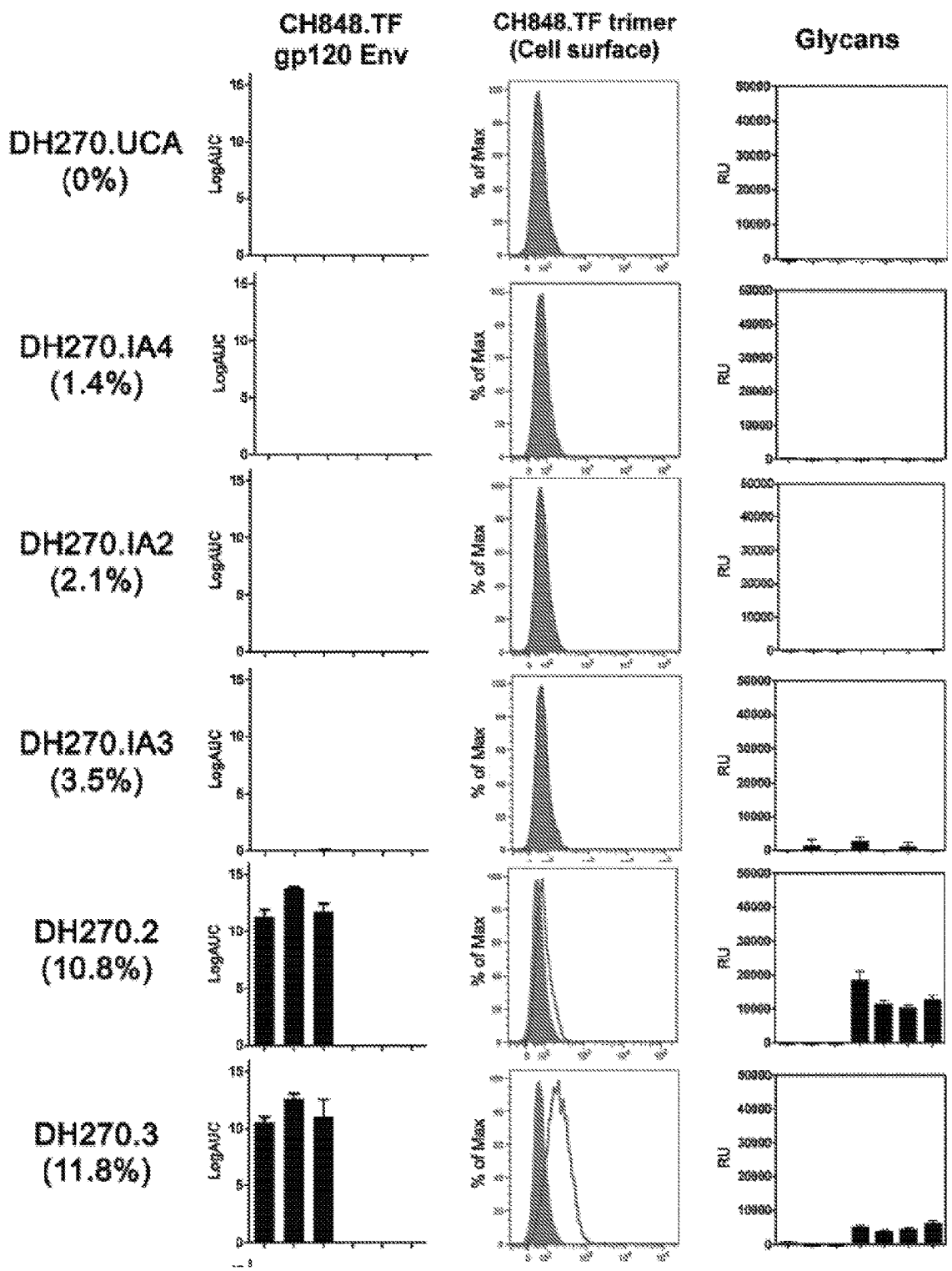
Figure 6B:
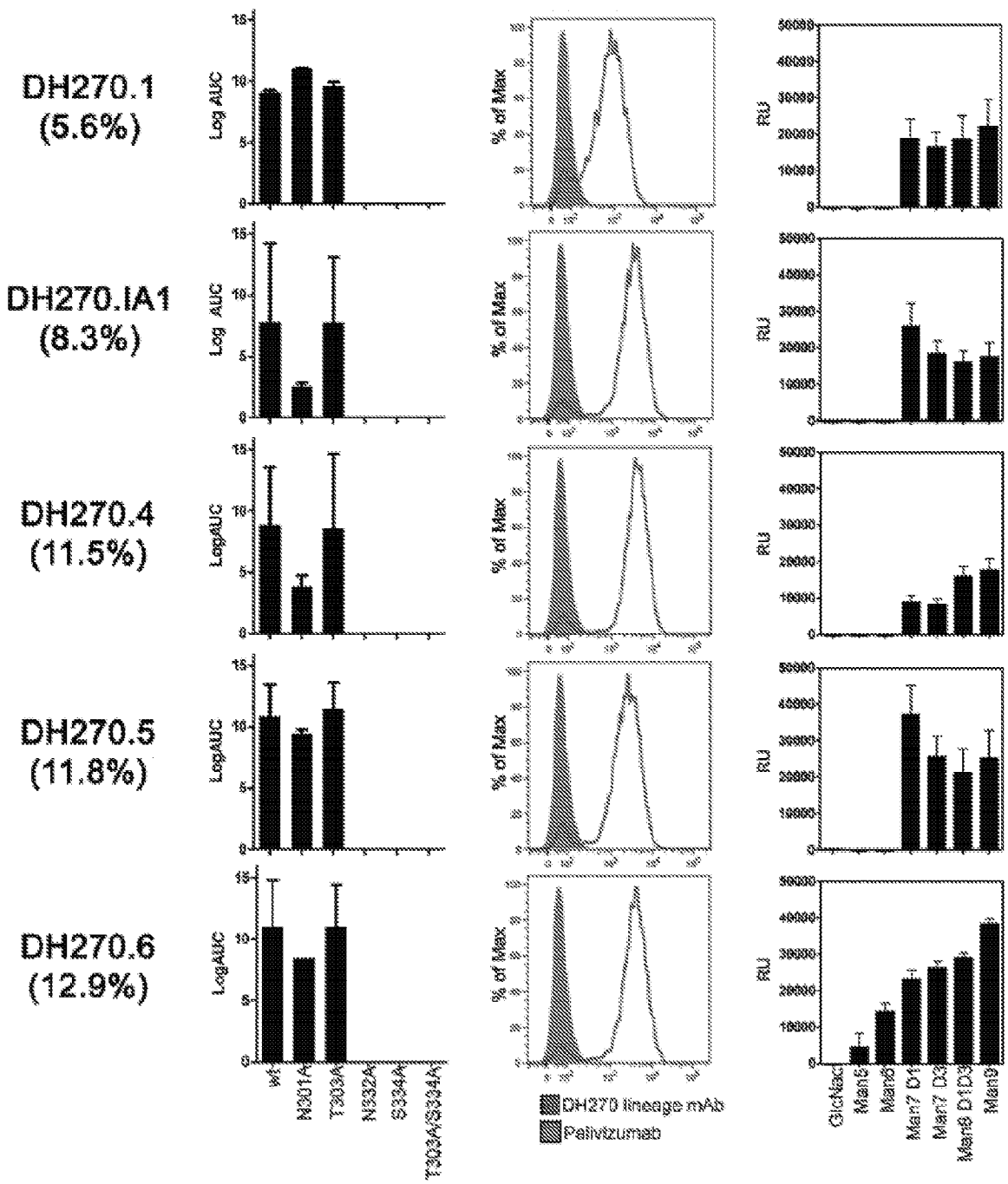
Figure 7B:
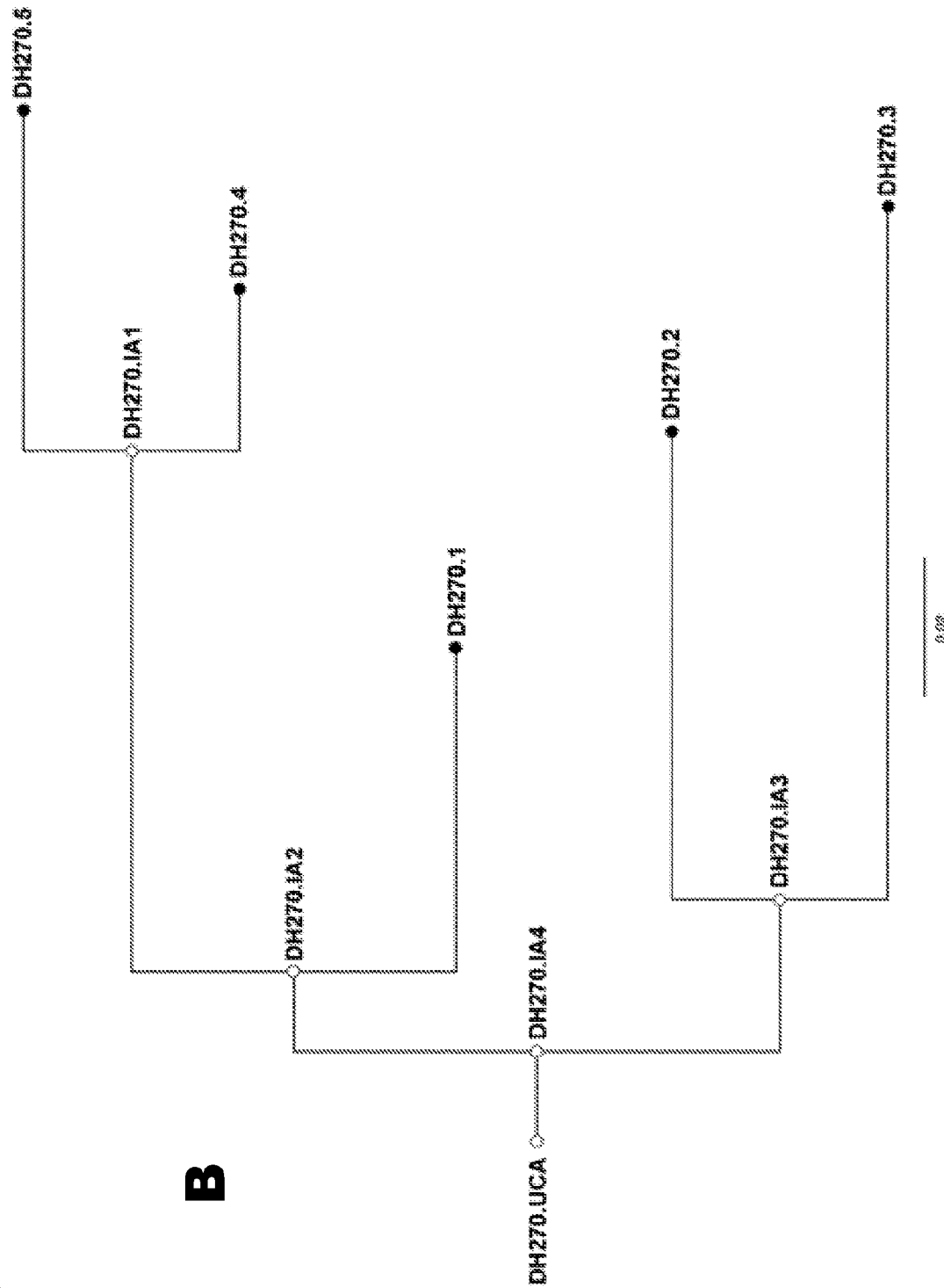
Figure 27A:
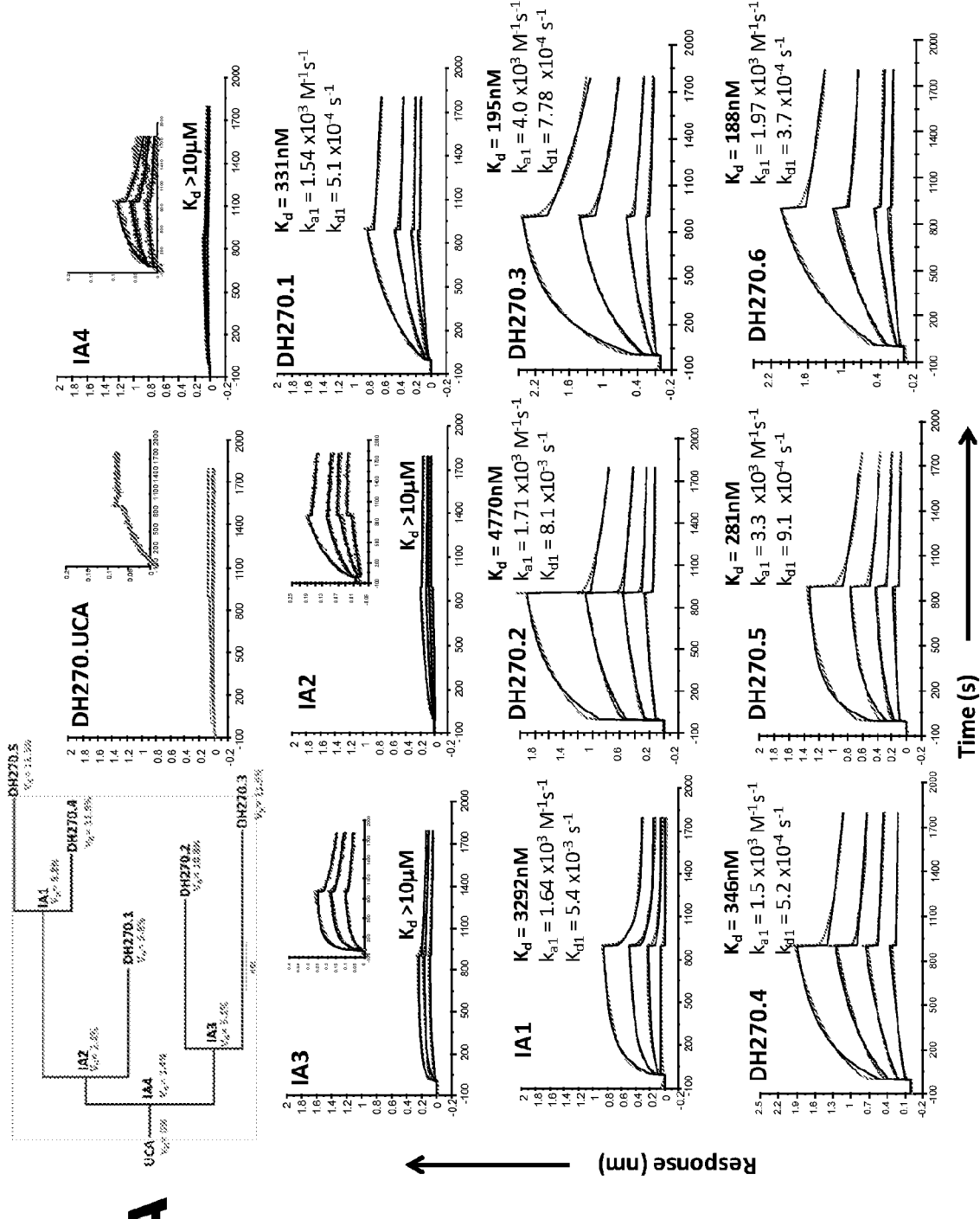
FIGS. 27A-B. Man$_9$-V3 glycopeptide binding of DH270 lineage antibodies. DH270 lineage tree (A, top left) is shown with VH mutations of intermediates and mature antibodies. DH270.6 mAb, which clusters close to DH270.4 and DH270.5, is not shown in the phylogenetic tree. Binding of Man9-V3 glycopeptide and its aglycone form to DH270 lineage antibodies was measured by BLI assay using either biotinylated Man9-V3 (A) or biotinylated aglycone V3 (B) as described in Methods. DH270 lineage antibodies were each used at concentrations of 5, 10, 25, 50, 100, 150 µg/mL. Insets in (A) for UCA (150 µg/mL), IA4 (100, 50, 25 µg/mL), IA3 and IA2 (100, 50, 25, 10 µg/mL) show rescaled binding curves following subtraction of non-specific signal on a control antibody (Palivizumab). Rate (ka, kd) and dissociation constants (Kd) were measured for intermediate IA1 and mature mAbs with glycan-dependent binding to Man9-V3. Kinetics analyses were performed by global curve fitting using bivalent avidity model and as described in methods ("Affinity measurements" section). Inset in (B) show overlay of binding of each mAbs to Man9-V3 (blue) and aglycone V3 (red) at the highest concentration used in each of the dose titrations.
Figure 27B:
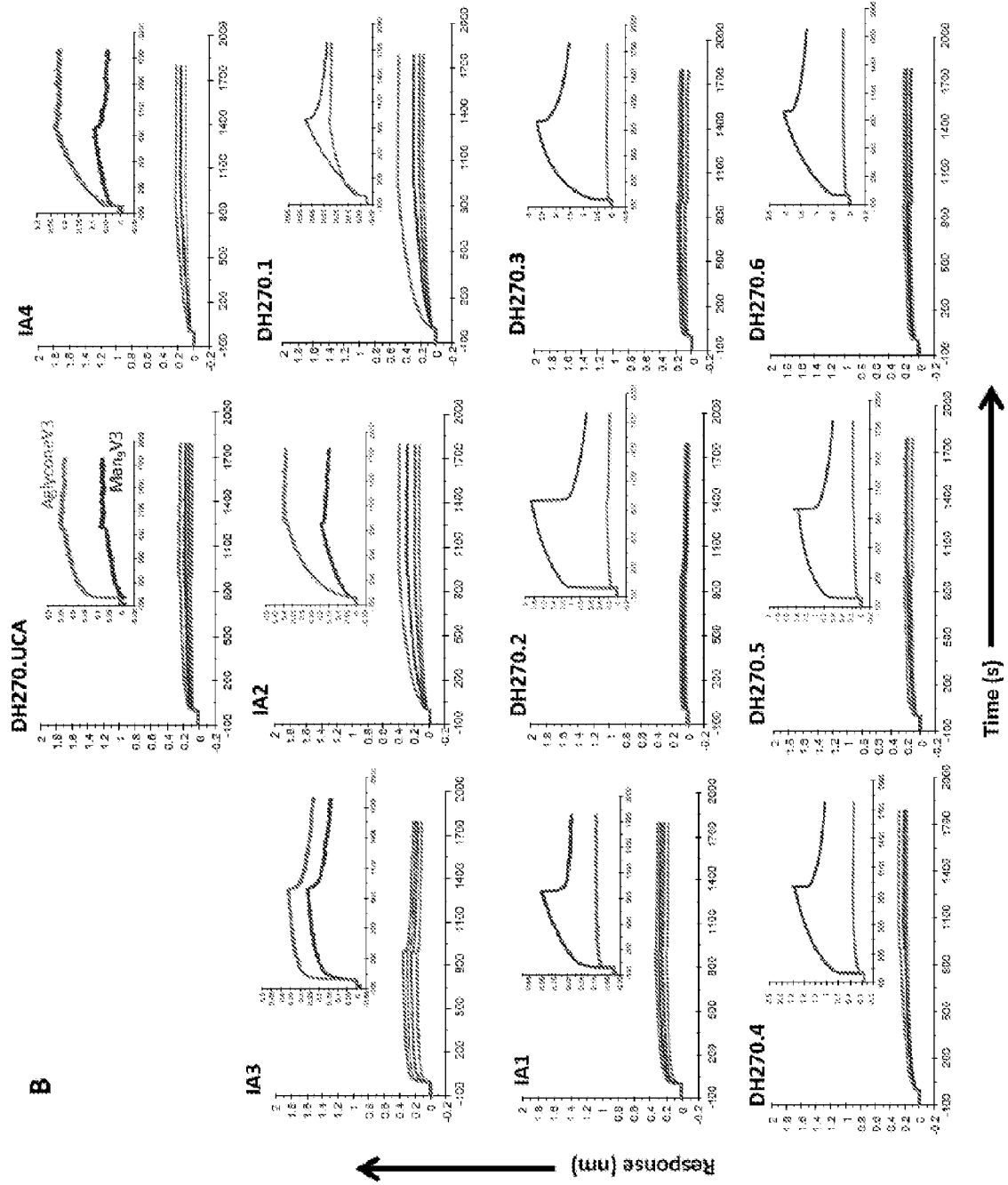

The DH270 UCA did not bind to any of the 120 CH848 autologous gp120 Env glycoproteins isolated from time of infection to 245 weeks post-infection, including the TF Env (FIG. 6A). DH270 UCA, as well as maturation intermediate antibodies, also did not recognize free glycans or cell surface membrane expressed gp160 trimers (FIG. 6B). Conversely, the DH270 UCA bound to the $Man_9$-V3 synthetic glycopeptide mimic of the V3-glycan bnAb gp120 epitope (FIG. 27A) and also bound to the aglycone form of the same peptide (FIG. 27B). Similarly, the early intermediate antibodies (IA4, IA3, IA2) each bound to both the $Man_9$-V3 glycopeptide and its aglycone form, and their binding was stronger to the aglycone V3 peptide than to the $Man_9$-V3 glycopeptide (FIG. 27B). Overall, DH270 UCA and early intermediate antibodies binding to the $Man_9$-V3 glycopeptide was low (>1004) (FIG. 27A). DH270.1 nt mutation frequency: 5.6%) bound the glycopeptide with higher affinity than did the aglycone ($K_{d,gycopeptide}$=331 nM) (FIGS. 27A, B) and, as mutations accumulated, binding of the $Man_9$-V3 glycopeptide also increased, culminating in a Ka of 188 nM in the most potent bnAb, DH270.6, which did not bind to the aglycone-V3 peptide (FIGS. 27A, B). Thus, both the $Man_9$-V3 glycopeptide and the aglycone-V3 peptide bound to the DH270 UCA, and antibody binding was independent of glycans until the DH270 lineage had acquired a nucleotide mutation frequency of ~6%.

Discussion

We can reconstruct from the data presented here a plausible series of events during the development of a V3-glycan bnAb in a natural infection. The DH272 and DH475 lineages neutralized the autologous TF and early viruses, and the resulting escape viruses were neutralized by the DH270 lineage. In particular, V1 deletions were necessary for neutralization of all but the most mature DH270 lineage antibodies. DH475 (and possibly DH272) escape variants stimulated DH270 affinity maturation, including both somatic mutations at sites of intrinsic mutability (11) and a crucial, improbable mutation at an AID coldspot within CDRH2 (G57R). The G57R mutation initiated expansion of the DH270 bnAb lineage. The low probability of this heterologous neutralization-conferring mutation and the complex lineage interactions that occurred is one explanation for why it took 4.5 years for the DH270 lineage to expand.

The CH848 viral population underwent a transition from a long V1 loop in the TF (34 residues) to short loops (16-17 residues) when escaping DH272/DH475 and facilitating expansion of DH270, to restoration of longer V1 loops later in infection as resistance to DH270 intermediates developed. Later DH270 antibodies adapted to viruses with longer V1 loops, allowing recognition of a broader spectrum of Envs and enhancing breadth. DH270.6 could neutralize heterologous viruses regardless of V1 loop length, but viruses with long loops tended to be less sensitive to it. Association of long V1 loops with reduced sensitivity was evident for three other V3 glycan bnAbs isolated from other individuals and may be a general feature of this class.

The V1 loop deletions in CH848 autologous virus removed the PNG site at position 137. While the hypervariable nature of the V1 loop (which evolves by insertion and deletion, resulting in extreme length heterogeneity, as well as extreme variation in number of PNG sites) complicates the interpretation of direct comparisons among unrelated HIV-1 strains, it is worth noting that a PNG in this region specified as N137 was shown to be important for regulating affinity maturation of the PGT121 V3 glycan bnAb family, with some members of the lineage evolving to bind (PGT121-123) and others (PGT124) to accommodate or avoid this glycan (29).

Since we cannot foresee the susceptibility to a particular bnAb lineage of each specific potential transmitted/founder virus to which vaccine recipients will be exposed, it will be important for a vaccine to induce bnAbs against multiple epitopes on the HIV-1 Env to minimize transmitted/founder virus escape (30, 31). In particular, induction of bnAb specificities beyond the HIV-1 V3 glycan epitope is critical for use in Asian populations where CRFO1 strains, which lack for the most part the N332 PNG required for efficient neutralization by V3 glycan bnAbs, is frequently observed.

Regarding what might have stimulated the UCA of the DH270 bnAb lineage, the absence of detectable binding to the CH848 TF Env raised at least two possibilities. One is that the lineage arose at the end of year 1, either from a primary response to viruses present at that time (e.g., with deletions in V1-V2) or from subversion of an antibody lineage initially elicited by some other antigen. The other is that some altered form of the CH848 TF envelope protein (e.g. shed gp120, or a fragment of it) exposed the V3 loop and the N301 and N332 glycans in a way that bound and stimulated the germline BCR, even though the native CH848 TF Env did not. Our findings suggest that a denatured, fragmented or otherwise modified form of Env may have initiated the DH270 lineage. We cannot exclude that the DH270 UCA could not bind to autologous Env as an IgG but could potentially be triggered as an IgM B cell receptor (BCR) on a cell surface.

It will be important to define how often an improbable mutation such as G57R determines the time it takes for a bnAb lineage in an HIV-1 infected individual to develop, and how many of the accompanying mutations are necessary for potency or breadth rather than being non-essential mutations at AID mutational hotspots (11, 32). Mutations of the latter type might condition the outcome or modulate the impact of a key, improbable mutation, without contributing directly to affinity. Should the occurrence of an unlikely mutation be rate-limiting for breadth or potency in many other cases, a program of rational immunogen design will need to focus on modified envelopes most likely to select very strongly for improbable yet critical antibody nucleotide changes The following proposal for a strategy to induce V3 glycan bnAbs recreates the events that led to bnAb induction in CH848: start by priming with a ligand that binds the bnAb UCA, such as the synthetic glycopeptide mimic of the V3-glycan bnAb gp120 epitope, then boost with an Env that can select G57R CDR H2 mutants, followed by Envs with progressive V1 lengths (FIG. 28). We hypothesize that more direct targeting of V3-glycan UCAs and intermediate antibodies can accelerate the time of V3-glycan bnAb development in the setting of vaccination.

A limitation of this approach is that the selection of immunogens was based on the analysis of a single lineage from a single individual and how frequently DH270-like lineages are present in the general population is unknown. Finally, our study describes a general strategy for the design of vaccine immunogens that can select specific antibody mutations thereby directing antibody lineage maturation pathways.

Material and Methods

Study Design. The CH848 donor, from which the DH270, DH272 and DH475 antibody lineages were isolated, is an African male enrolled in the CHAVI001 acute HIV-1 infection cohort (33) and followed for 5 years, after which he started antiretroviral therapy. During this time viral load ranged from 8,927 to 442,749 copies/ml (median=61,064 copies/10, and CD4 counts ranged from 288 to 624 cells/mm$^3$ (median=350 cells/mm$^3$). The time of infection was estimated by analyzing the sequence diversity in the first available sample using the Poisson Fitter tool as described in (10). Results were consistent with a single founder virus establishing the infection (34).

MAbs DH270.1 and DH270.3 were isolated from cultured memory B cells isolated 205 weeks post-transmission (14). DH270.6 and DH475 mAbs were isolated from Man9-V3 glycopeptide-specific memory B cells collected 232 and 234 weeks post-transmission, respectively, using direct sorting. DH270.2, DH270.4 and DH270.5 mAbs were isolated from memory B cells collected 232 weeks post-transmission that bound to Consensus C gp120 Env but not to Consensus C N332A gp120 Env using direct sorting Statistical Analyses. Statistical analysis was performed using R. The specific tests used to determine significance are reported for each instance in the text.

Flow Cytometry, Memory B Cell Cultures and mAb Isolation

A total of 30,700 memory B cells from individual CH848 were isolated from PBMC collected 205 weeks post-transmission using magnetic-activated cell sorting as described in (14). Memory B cells were cultured at limiting dilution at a calculated concentration of 2 cells/well for 2 weeks as described in (11) using irradiated CD40L L cells (7,500 cGy) as feeder cells at a concentration of 5,000 cells/well; culture medium was refreshed 7 days after plating. Cell culture supernatants were screened for neutralization of autologous CH848.TF virus using the tzm-bl neutralization assay (14) and for binding to CH848.TF gp120 Env, CH848.TF gp140 Env, Consensus C gp120 Env and consensus C N332A gp120 Env. Concurrently, cells from each culture were transferred in RNAlater (Qiagen) and stored at −80° C. until functional assays were completed.

MAbs DH270.1 and DH270.3 were isolated from cultures that bound to CH848.TF gp120 Env and Consensus C gp120 but did not bind to C N332A gp120 Env. DH272 was isolated from a culture that neutralized 99% CH848.TF virus infectivity. DH272 dependency to N332-linked glycans was first detected on the transiently transfected recombinant antibody tested at higher concentration and confirmed in the purified recombinant antibody. From the stored RNAlater samples, mRNA of cells from these cultures was extracted and retrotranscribed as previously described (14).

DH270.6 and DH475 mAbs were isolated from Man9-V3 glycopeptide-specific memory B cells collected 232 and 234 weeks post-transmission, respectively, using direct sorting (16). Briefly, biotinylated Man9-V3 peptides were tetramerized via streptavidin that was conjugated with either AlexaFluor 647 (AF647; ThermoScientific) or Brilliant Violet 421 (BV421) (Biolegend) dyes. Peptide tetramer quality following conjugation was assessed by flow cytometry to a panel of well-characterized HIV-1 V3 glycan antibodies (PGT128, and 2G12) and linear V3 antibodies (F39F) attached to polymer beads. PBMCs from donor CH848 were stained with LIVE/DEAD Fixable Aqua Stain (ThermoScientific), anti-human IgM (FITC), CD3 (PE-Cy5), CD235a (PE-Cy5), CD19 (APC-Cy7), and CD27 (PE-Cy7) (BD Biosciences); anti-human antibodies against IgD (PE); anti-human antibodies against CD10 (ECD), CD38 (APC-AF700), CD19 (APC-Cy7), CD16 (BV570), CD14 (BV605) (Biolegend); and Man9GlcNac2 V3 tetramer in both AF647 and BV421. PBMCs that were Aqua Stain−, CD14−, CD16−, CD3−, CD235a−, positive for CD19+, and negative for surface IgD were defined as memory B cells; these cells were then gated for Man9-V3+ positivity in both AF647 and BV421, and were single-cell sorted using a BD FACS Aria II into 96-well plates containing 20 µl of reverse transcriptase buffer (RT).

DH270.2, DH270.4 and DH270.5 mAbs were isolated from memory B cells collected 232 weeks post-transmission that bound to Consensus C gp120 Env but not to Consensus C N332A gp120 Env using direct sorting. Reagents were made using biotinylated Consensus C gp120 Env and Consensus C N332A gp120 Env by reaction with streptavidin that was conjugated with either AlexaFluor 647 (AF647; ThermoScientific) or Brilliant Violet 421 (BV421) (Biolegend) dyes, respectively. Env tetramer quality following conjugation was assessed by flow cytometry to a panel of well-characterized HIV-1 V3 glycan antibodies (PGT128, and 2G12) and linear V3 antibodies (F39F) attached to polymer beads. PBMCs were stained as outlined for DH475 and DH270.6, however these cells were then gated for Consensus C gp120 positivity and Consensus C N332A gp120 negativity in AF647 and BV421, respectively, and were single cell sorted and processed as outlined for DH475 and DH270.6.

For all antibodies, cDNA synthesis, PCR amplification, sequencing and V(D)J rearrangement analysis were conducted as previously described (11). Reported mutation frequency is calculated as frequency of nucleotide mutations in the V gene region of antibody sequence. CDRH3 lengths reported are defined as the number of residues after the invariant Cys in FR3 and before the invariant Trp in FR4.

Antibody Production

Immunoglobulin genes of mAbs DH270.1 through DH270.6, DH272 and DH475 were amplified from RNA from isolated cells, expression cassettes made, and mAbs expressed as described (12, 14). Inference of unmutated common ancestor (UCA) and intermediate antibodies DH270.IA1 through DH270.IA4 was conducted using methods previously described (36).

Heavy chain plasmids were co-transfected with appropriate light chain plasmids at an equal ratio in Expi 293 cells using ExpiFectamine 293 transfection reagents (Thermo Fisher Scientific) according to the manufacturer's protocols. We used the enhancer provided with the kit, transfected cultures were incubated at 37° C. 8% CO2 for 2-6 days, harvested, concentrated and incubated overnight with Protein A beads at 4° C. on a rotating shaker before loading the bead mixture in columns for purification; following PBS/NaCl wash, eluate was neutralized with trizma hydrochloride and antibody concentration was determined by Nanodrop. Purified antibodies were tested in SDS-Page Coomassie and western blots, and stored at 4° C.

Next-Generation Sequencing

PBMC-extracted RNA from weeks 11, 19, 64, 111, 160, 186, and 240 post-infection were used to generate cDNA amplicons for next-generation sequencing (Illumina Miseq) as described previously (35). Briefly, RNA isolated from PBMCs was separated into two equal aliquots before cDNA production; cDNA amplification and NGS were performed on both aliquots as independent samples (denoted A and B). Reverse transcription (RT) was carried out using human IgG, IgA, IgM, IgK and Ig), primers as previously described (12). After cDNA synthesis, IgG isotype IGHV1 and IGHV3 genes were amplified separately from weeks 11, 19, 64, 111, 160, and 186. IGHV1-IGHV6 genes were amplified at week 240. A second PCR step was performed to add Nextera index sequencing adapters (Illumina) and libraries were purified by gel extraction (Qiagen) and quantified by quantitative PCR using the KAPA SYBR FAST qPCR kit (KAPA Biosystems). Each replicate library was sequencing using the Illumina Miseq V3 2×300 bp kit.

NGS reads were computationally processed and analyzed as previously described (35). Briefly, forward and reverse reads were merged with FLASH with average read length and fragment read length parameters set to 450 and 300, respectively. Reads were quality filtered using FASTX (http://hannonlab.cshl.edu/fastx_toolkit/) for sequences with a minimum of 50 percent of bases with a Phred quality score of 20 or greater (corresponding to 99% base call accuracy). Primer sequences were discarded and only unique nucleotide sequences were retained. To mitigate errors introduced during PCR amplification, reads detected in sample A and B with identical nucleotide VHDJH rearrangement sequences were delineated as replicated sequences. The total number of unique reads per sample and total number of replicated sequences ("Overlap") across samples for each time point is listed (see FIG. 30 of WO/2017/152146). We used replicated sequences to define presence of antibody clonal lineages at any time-point.

We identified clonally-related sequences to DH270, DH272 and DH475 from the longitudinal NGS datasets by the following procedure. First, the CDR H3 of the probe-identified clonal parent sequence was BLASTed (E-value cutoff=0.01) against the pooled sample A and B sequence sets at each timepoint to get a candidate set of putative clonal members ("candidate set"). Next we identified replicated sequences across samples A and B in the candidate set. We then performed a clonal kinship test with the Cloanalyst software package (http://www.bu.edukomputationalimmunology/research/software/) as previously described (35) on replicated sequences. Clonally-related sequences within Sample A and B (including non-replicated sequences) were identified by performing the same clonal kinship test with Cloanalyst on the candidate set prior to identifying replicated sequences.

Clonal lineage reconstruction was performed on the NGS replicated sequences and probe-identified sequences of each clone using the Cloanalyst software package. A maximum of 100 sequences were used as input for inferring phylogenetic trees of clonal lineages. Clonal sequence sets were subsampled down to 100 sequences by collapsing to one sequence within a 2 or 9 base pair difference radius for the DH272 and DH270 clones, respectively.

The pre-vaccination NGS samples that were analyzed in FIG. 17A were obtained from HIV-1 uninfected participants of the HVTN082 and HVTN204 trials as previously described (35).

Sequence Analysis of Antibody Clonal Lineages

Unmutated common ancestors (UCA) and ancestral intermediate sequences were computationally inferred with the Cloanalyst software package. Cloanalyst uses Bayesian inference methods to infer the full unmutated V(D)J rearrangement thereby including a predicted unmutated CDR3 sequence. For lineage reconstructions when only cultured or sorted sequences were used as input, the heavy and light chain pairing relationship was retained during the inference of ancestral sequences. UCA inferences were performed each time a new member of the DH270 clonal lineage was experimentally isolated and thus several versions of the DH270 UCA were produced and tested. UCA1 and UCA3 were used for structural determination. UCA4 (referred to as DH270.UCA throughout the text), which was inferred using the most observed DH270 clonal members and had the lowest uncertainty of UCAs inferred (as quantified by the sum of the error probability over all base positions in the sequence), was used for binding and neutralization studies. Subsequently, the DH270 UCA was also re-inferred when NGS data became available. We applied a bootstrapping procedure to infer the UCA with the NGS data included, resampling clonal lineage trees 10 times with 100 input NGS sequences each. The UCA4 amino acid sequence was recapitulated by 7 out of 10 UCA inferences of the resampled NGS trees confirming support for UCA4.

Each inference of V(D)J calls is associated with a probability. The probability of the DH270 lineage to use the VH1-2 family gene was 99.99% and that of using allele 02 (VH1-2*02) was 98.26%. Therefore, there was a 0.01% probability that the family was incorrectly identified and a 1.74% probability that the allele was incorrectly identified. Therefore, we sequenced genomic DNA of individual CH848. As previously reported, positional conformity is defined as sharing a mutation at the same position in the V gene segment and identity conformity as sharing the same amino acid substitution at the same position (11).

We refer to the widely established AID hot and cold spots (respectively WRCY and SYC and their reverse-complements) as "canonical" and to other hot and cold spots defined by Yaari et al. as "non-canonical" (20, 37-39).

Sequencing of germline variable region from genomic DNA

Genomic DNA was isolated from donor CH848 from PBMCs 3 weeks after infection (QIAmp DNA Blood mini kit; Qiagen). IGVH1-2 and IGVL2-23 sequences were amplified using 2 independent primer sets by PCR. To ensure amplification of non-rearranged variable sequences, both primer sets reverse primers aligned to sequences present in the non-coding genomic DNA downstream the V-recombination site. The forward primer for set 1 resided in the IGVH1-2 and IGVL2-23 leader sequences and upstream of the leader in set 2. The PCR fragments were cloned into a pcDNA2.1 (TOPO-TA kit; Life technologies) and transformed into bacteria for sequencing of individual colonies. The following primers were used: VH1-2_1_S: tcctcttcttggtggcagcag; VH1-2_2_S: tacagatctgtcctgtgccct; VH1-2_1_tmAS: ttctcagccccagcacagctg; VH1-2_2_TmAS: gggtggcagagtgagactctgtcaca; VL2-23_2_S: agaggagcccaggatgctgat; VL2-23_1_S: actctcctcactcaggacaca; VL2-23_1_AS: tctcaaggccgcgctgcagca; VL2-23_2 AS: agctgtccctgtcctggatgg.

We identified two variants of VH1-2*02: the canonical sequence and a variant that encoded a VH that differed by 9 amino acids. Of these 9 amino acids, only 1 was shared among DH270 antibodies whereas 8 amino acids were not represented in DH270 lineage antibodies (FIG. 17B). The VH1-2*02 variant isolated from genomic DNA did not encode an arginine at position 57. We conclude that between the two variants of VH1-2*02 identified from genomic DNA from this individual, the DH270 lineage is likely derived from the canonical VH1-2*02 sequence.

Direct Binding ELISA

Direct-binding ELISAs were performed as described (11). Briefly, 384-well plates were blocked for 1 h at room temperature (RT) or overnight at 4° C. (both procedures were previously validated); primary purified antibodies were tested at a starting concentrations of 100 µg/ml, serially three-fold diluted and incubated for 1 h at RT; HRP-conjugated human IgG antibody was added at optimized concentration of 1:30,000 in assay diluent for 1 hour and developed using TMB substrate; plates were read at 450 nm in a SpectraMax 384 PLUS reader (Molecular Devices, Sunnyvale, Calif.); results are reported as logarithm area under the curve (LogAUC) unless otherwise noted.

For biotinylated avi-tagged antigens, plates were coated with streptavidin (2 µg/ml); blocked plates were stored at −20° C. until used and biotinylated avi-tagged antigens were added at 2 µg/ml for 30 minutes at RT.

Competition ELISAs were performed using 10 µl of primary purified monoclonal antibody, starting at 100 µg/ml and diluted in a two-fold concentration, incubated for 1 h at RT. Ten µl of biotinylated target Mab was added at the EC50 determined by a direct binding of biotinylated-Mab for one hour at RT. After background subtractions, percent inhibition was calculated as follows: 100-(test Ab triplicate mean/ no inhibition control mean)*100.

Assessment of Virus Neutralization

Antibody and plasma neutralization was measured in TZM-bl cell-based assays. Neutralization breadth of DH270.1, DH270.5 and DH270.6 was assessed using the 384-well plate declination of the assay using an updated panel of 207 geographically and genetically diverse Env-pseudoviruses representing the major circulating genetic subtypes and recombinant forms as described (40). The data were calculated as a reduction in luminescence units compared with control wells, and reported as IC50 in µg/ml.

Single Genome Sequencing and Pseudovirus Production

3' half genome single genome sequencing of HIV-1 from longitudinally collected plasma was performed as previously described (41, 42). Sequence alignment was performed using ClustalW (version 2.11) and was adjusted manually using Geneious 8 (version 8.1.6). Env amino acid sequences were then aligned and evaluated for sites under selection using code derived from the Longitudinal Antigenic Sequences and Sites from Intra-host Evolution (LASSIE) tool (43). Using both LASSIE-based analysis and visual inspection, 100 representative env genes were selected for pseudovirus production. CMV promoter-ligated env genes were prepared and used to generate pseudotyped viruses as previously described (44).

Generation of Cell Surface-Expressed CH848 Env Trimer CHO Cell Line

The membrane-anchored CH848 TF Env trimer was expressed in CHO-S cells. Briefly, the CH848 env sequence was codon-optimized and cloned into an HIV-1-based lentiviral vector. A heterologous signal sequence from CD5 was inserted replacing that of the HIV-1 Env. The proteolytic cleavage site between gp120 and gp41 was altered, substituting serine residues for Arg508 and Arg511, the tyrosine at residues 712 was changed to alanine (Y712A), and the cytoplasmic tail was truncated by replacing the Lys808 codon with a sequence encoding (Gly)3 (His)6 followed immediately by a TAA stop codon. This env-containing sequences was inserted into the vector immediately downstream of the tetracycline (tet)-responsive element (TRE), and upstream of an internal ribosome entry site (IRES) and a contiguous puromycin (puro)-T2A-EGFP open reading frame (generating K4831), as described previously for the JRFL and CH505 Envs (45).

CHO-S cells (Invitrogen) modified to constitutively express the reverse tet transactivator (rtTA) were transduced with packaged vesicular stomatitis virus (VSV) G glycoprotein-pseudotyped CH848 Env expression vector. Transduced cells were incubated in culture medium containing 1 µg/ml of doxycycline (dox) and selected for 7 days in medium supplemented with 25 µg/ml of puromycin, generating the Env expressor-population cell line termed D831. From D831, a stable, high-expressor clonal cell line was derived, termed D835. The integrity of the recombinant env sequence in the clonal cell lines was confirmed by direct (without cloning) sequence analysis of PCR amplicons.

Cell Surface-Expressed Trimeric CH848 Env Binding

D831 Selected TRE2.CH848.JF-8.IRS6A Chinese Hamster Ovary Cells were cultured in DMEM/F-12 supplemented with HEPES and L-glutamine (Thermo Fischer, Cat #11330057) 10% heat inactivated fetal bovine serum [FBS] (Thermo Fischer, Cat #10082147) and 1% Penicillin-Streptomycin (Thermo Fischer, Cat #15140163) and harvested when 70-80% confluent by trypsinization. A total 75,000 viable cells/well were transferred in 24-well tissue culture plates. After a 24-to-30-hour incubation at 37° C./5% CO2 in humidified atmosphere, CH848 Envs expression was induced with 1 µg/mL doxycycline (Sigma-Aldrich, Cat #D9891) treatment for 16-20 hours. Cells were then washed in Stain buffer [PBS/2% FBS] and incubated at 4° C. for 30 minutes. Stain buffer was removed from cells and 0.2 ml/well of DH270 lineage antibodies, palivizumab (negative control) or PGT128 (positive control) were added at optimal concentration of 5 µg/mL for 30 minutes at 4° C. After a 2× wash, cells were stained with 40 ul of APC-conjugated mouse anti-Human IgG (BD Pharmigen, Cat #562025) per well (final volume 0.2 ml/well) for 30 minutes at 4° C. Unstained cells were used as further negative control. Cells were washed 3× and gently dissociated with 0.3 ml/well PBS/5 mM EDTA for 30 minutes at 4° C., transferred into 5 mL Polystyrene Round-Bottom Tubes (Falcon, Cat #352054), fixed with 0.1 mL of BD Cytofix/Cytoperm Fixation solution (BD Biosciences, Cat #554722) and kept on ice until analyzed using a BD LSRFortessa Cell Analyzer. Live cells were gated through Forward/Side Scatter exclusion, and then gated upon GFP+ and APC.

Oligomannose Arrays

Oligomannose arrays were printed with glycans at 100, 33, and 10 µM (Z Biotech). Arrays were blocked for 1 h in Hydrazide glycan blocking buffer. Monoclonal antibodies were diluted to 50 µg/mL in Hydrazide Glycan Assay Buffer, incubated on an individual subarray for 1 h, and then washed 5 times with PBS supplemented with 0.05% tween-20 (PBS-T). Subarrays that received biotinylated Concanavalin A were incubated with streptavidin-Cy3 (Sigma), whereas all other wells were incubated with anti-IgG-Cy3 (Sigma) for 1 h while rotating at 40 rpm covered from light. The arrays were washed 5 times with 70 µL of PBS-T and then washed once with 0.01×PBS. The washed arrays were spun dry and scanned with a GenePix 4000B (Molecular Devices) scanner at wavelength 532 nm using GenePix Pro7 software. The fluorescence within each feature was background subtracted using the local method in GenePix Pro7 software (Molecular Devices). To determine glycan specific binding, the local background corrected fluorescence of the print buffer alone was subtracted from each feature containing a glycan.

Synthesis of Man9-V3 Glycopeptide

A 30-amino acid V3 glycopeptide with oligomannose glycans (Man9-V3), based on the Glade B JRFL mini-V3 construct (16), was chemically synthesized as described earlier (18). Briefly, after the synthesis of the oligomannose glycans in solution phase (18), two partially protected peptide fragments were obtained by Fmoc-based solid phase peptide synthesis, each featuring a single unprotected aspartate residue. The Man9G1cNAc2 anomeric amine was conjugated to each fragment (D301 or D332) using our one-flask aspartylation/deprotection protocol yielding the desired N-linked glycopeptide. These two peptide fragments were then joined by native chemical ligation immediately followed by cyclization via disulfide formation to afford Man9-V3-biotin. The control peptide, aglycone V3-biotin, had identical amino acid sequence as its glycosylated counterpart.

Affinity Measurements

Antibody binding kinetic rate constants (ka, kd) of the Man9-V3 glycopeptide and its aglycone form (16) were measured by Bio-layer Interferometry (BLI, ForteBio Octet Red96) measurements. The BLI assay was performed using streptavidin coated sensors (ForteBio) to capture either biotin-tagged Man9-V3 glycopeptide or Aglycone-V3 peptide. The V3 peptide immobilized sensors were dipped into varying concentrations of antibodies following blocking of sensors in BSA (0.1%). Antibody concentrations ranged from 0.5 to 150 µg/mL and non-specific binding interactions were subtracted using the control anti-RSV Palivizumab (Synagis) mAb. Rate constants were calculated by global curve fitting analyses to the Bivalent Avidity model of binding responses with a 10 min association and 15 min dissociation interaction time. The dissociation constant (Kd) values without avidity contribution were derived using the initial components of the association and dissociation rates (kal and kdl) respectively. Steady-state binding Kd values for binding to Man9-V3 glycopeptide with avidity contribution were derived using near steady-state binding responses at varying antibody concentrations (0.5-80 µg/mL) and using a non-linear 4-paramater curve fitting analysis.

HIV-1 Env Site-Directed Mutagenesis

Deletion Mutant of CH0848.d0274.30.07 env gene was constructed using In Fusion HD EcoDry Cloning kit (Clontech) as per manufacturer instructions. Quick Change II Site-Directed Mutagenesis kit (Agilent Technologies) was used to introduce point mutations. All final env mutants were confirmed by sequencing.

Antibody Site-Directed Mutagenesis

Site-directed mutagenesis of antibody genes was performed using the Quikchange II lightening multi-site-directed mutagenesis kit following manufacturer's protocol (Agilent). Mutant plasmid products were confirmed by single-colony sequencing. Primers used for introducing mutations were: DH270_IA4_D31G: cccagtgtatatagtagccggtgaaggtgtatcca; DH270.IA4 I34M: tcgcacccagtgcatatagtagtcggtgaaggtgt; DH270.IA4 T55S: gatggatcaaccctaactctggtcgcacaaactat; DH270.IA4 R57G: tgtgcatagtttgtgccaccagtgttagggttgat; DH270.IA4 R57V: cttctgtgcatagtttgtgacaccagtgttagggttgatc; DH270.UCA G57R: atcaaccctaacagtggtcgcacaaactatgcaca.

Env Glycoprotein Expression

The codon-optimized CH848-derived env genes were generated by de novo synthesis (GeneScript, Piscataway, N.J.) or site-directed mutagenesis in mammalian expression plasmid pcDNA3.1/hygromycin (Invitrogen) as described (10), and stored at −80° C. until use.

Expression and purification of DH270 lineage members for crystallization studies The heavy- and light-chain variable and constant domains of the DH270 lineage Fabs were cloned into the pVRC-8400 expression vector using Not1 and Nhe1 restriction sites and the tissue plasminogen activator signal sequence. The DH270.1 single chain variable fragment (scFv) was cloned into the same expression vector. The C terminus of the heavy-chain constructs and scFv contained a noncleavable 6× histidine tag. Site-directed mutagenesis was carried out, using manufacturer's protocols (Stratagene), to introduce mutations into the CDR regions of DH270.1. Fabs were expressed and purified as described previously (46). The DH270.1 scFv was purified the same way as the Fabs.

Crystallization, Structure Determination, and Refinement

All His-tagged Fabs and scFv were crystallized at 20-25 mg/mL. Crystals were grown in 96-well format using hanging drop vapor diffusion and appeared after 24-48 h at 20° C. Crystals were obtained in the following conditions: 2.5M ammonium sulfate and 100 mM sodium acetate, pH 5.0 for DH272; 1.5M ammonium sulfate and 100 mM sodium acetate pH 4.0 for UCA1; 20% PEG 4K, 100 mM sodium acetate, pH 5 and 100 mM magnesium sulfate for UCA3; 100 mM sodium acetate, pH 4.5, 200 mM lithium sulfate, and 2.5M NaCl for DH270.1; 1.4M lithium sulfate and 100 mM sodium acetate, pH 4.5 for DH270.3; 40% PEG 400 and 100 mM sodium citrate, pH 4.0 for DH270.5; and 30% PEG 4K, 100 mM PIPES pH 6, 1M NaCl for DH270.6. All crystals were harvested and cryoprotected by the addition of 20-25% glycerol to the reservoir solution and then flash-cooled in liquid nitrogen.

Diffraction data were obtained at 100 K from beam lines 24-ID-C and 24-ID-E at the Advanced Photon Source using a single wavelength. Datasets from individual crystals (multiple crystals for UCA1, DH270.1 and DH270.5) were processed with HKL2000. Molecular replacement calculations for the free Fabs were carried out with PHASER, using 13.2 from the CH103 lineage [Protein Data Bank (PDB) ID 4QHL] (46) or VRC01 from the VRC01/gp120 complex [Protein Data Bank (PDB) ID 4LST] (47) as the starting models. Subsequent structure determinations were performed using DH270 lineage members as search models. The Fab models were separated into their variable and constant domains for molecular replacement.

Refinement was carried out with PHENIX, and all model modifications were carried out with Coot. During refinement, maps were generated from combinations of positional, group B-factor, and TLS (translation/libration/screw) refinement algorithms. Secondary-structure restraints were included at all stages for all Fabs; noncrystallographic symmetry restraints were applied to the DH270.1 scFv and UCA3 Fab throughout refinement. The resulting electron density map for DH270.1 was further improved by solvent flattening, histogram matching, and non-crystallographic symmetry averaging using the program PARROT. Phase combination was disabled in these calculations. After density modification, restrained refinement was performed using Refmac in Coot. Structure validations were performed periodically during refinement using the MolProbity server. For the final refinement statistics see FIG. 32 of WO/2017/152146.

Design of the 92BR SOSIP.664 Construct

To generate the Glade B HIV-1 92BR SOSIP.664 expression construct we followed established SOSIP design parameters (48). Briefly, the 92BR SOSIP.664 trimer was engineered with a disulfide linkage between gp120 and gp41 by introducing A501C and T605C mutations (HxB2 numbering system) to covalently link the two subunits of the heterodimer (48). The I559P mutation was included in the heptad repeat region 1 (HR1) of gp41 for trimer stabilization, and part of the hydrophobic membrane proximal external region (MPER), in this case residues 664-681 of the Env ectodomain, was deleted (48). The furin cleavage site between gp120 and gp41 (508REKR511) was altered to 506RRRRRR511 to enhance cleavage (48). The resulting, codon-optimized 92BR SOSIP.664 env gene was obtained from GenScript (Piscataway, N.J.) and cloned into pVRC-8400 as described above for Fabs using Nhe 1 and NotI.

Purification of Envs for Analysis by Biolayer Interferometry and Negative Stain EM SOSIP.664 constructs were transfected along with a plasmid encoding the cellular protease furin at a 4:1 Env:furin ratio in HEK 293F cells. Site-directed mutagenesis was performed using manufacturer's protocols (Stratagene) for mutations in the V3 region and glycosylation sites. The cells were allowed to express soluble SOSIP.664 trimers for 5-7 days. Culture supernatants were collected and cells were removed by centrifugation at 3,800×g for 20 min, and filtered with a 0.2 µm pore size filter. SOSIP.664 proteins were purified by flowing the supernatant over a lectin (*Galanthus nivalis*) affinity chromatography column overnight at 4° C. The lectin column was washed with 1×PBS and proteins were eluted with 0.5M methyl-a-D-mannopyranoside and 0.5M NaCl. The eluate was concentrated and loaded onto a Superdex 200 10/300 GL column (GE Life Sciences) prequilibrated in a buffer of 10 mM Hepes, pH 8.0, 150 mM NaCl and 0.02% sodium azide for EM, or in 2.5 mM Tris, pH 7.5, 350 mM NaCl, 0.02% sodium azide for binding analysis, to separate the trimer-size oligomers from aggregates and gp140 monomers.

Electron Microscopy

Purified 92BR SOSIP.664 trimer was incubated with a five molar excess of DH270.1 Fab at 4° C. for 1 hour. A 3ł aliquot containing ~0.01 mg/ml of the Fab—92BR SOSIP.664 complex was applied for 15 s onto a carbon coated 400 Cu mesh grid that had been glow discharged at 20 mA for 30s, followed by negative staining with 2% uranyl formate for 30 s. Samples were imaged using a FEI Tecnai T12 microscope operating at 120 kV, at a magnification of 52,000× that resulted in a pixel size of 2.13 Å at the specimen plane. Images were acquired with a Gatan 2K CCD camera using a nominal defocus of 1,500 nm at 10° tilt increments, up to 50°. The tilts provided additional particle orientations to improve the image reconstructions.

Negative Stain Image Processing and 3D Reconstruction

Particles were picked semi-automatically using EMAN2 and put into a particle stack. Initial, reference-free, two-dimensional (2D) class averages were calculated and particles corresponding to complexes (with three Fabs bound) were selected into a substack for determination of an initial model. The initial model was calculated in EMAN2 using 3-fold symmetry and EMAN2 was used for subsequent refinement using 3-fold symmetry. In total, 5,419 particles were included in the final reconstruction for the 3D average of 92BR SOSIP.664 trimer complex with DH270.1. The resolution of the final model was determined using a Fourier Shell Correlation (FSC) cut-off of 0.5.

Model Fitting into the EM Reconstructions

The cryo-EM structure of PGT128-liganded BG505 SOSIP.664 (PDB ID: SACO) (28) and crystal structure of DH270.1 were manually fitted into the EM density and refined by using the UCSF Chimera 'Fit in map' function.

Biolayer Interferometry

Kinetic measurements of Fab binding to Envs were carried out using the Octet QKe system (ForteBio); 0.2 mg/mL of each His-tagged Fab was immobilized onto an anti-Human Fab-CH1 biosensor until it reached saturation. The SOSIP.664 trimers were tested at concentrations of 200 nM and 600 nM in duplicate. A reference sample of buffer alone was used to account for any signal drift that was observed during the experiment. Association and dissociation were each monitored for 5 min. All experiments were conducted in the Octet instrument at 30° C. in a buffer of 2.5 mM Tris, pH 7.5, 350 mM NaCl and 0.02% sodium azide with agitation at 1,000 rpm. Analyses were performed using nonlinear regression curve fitting using the Graphpad Prism software, version 6.

Protein Structure Analysis and Graphical Representations

The Fabs and their complexes analyzed in this study were superposed by least squares fitting in Coot. All graphical representations with protein crystal structures were made using PyMol.

Definition of Immunological Virus Phenotypes and Virus Signature Analysis

The maximum likelihood trees depicting the heterologous virus panel and the full set of Env sequences for the subject CH848 were created using the Los Alamos HIV database PhyML interface. HIV substitution models (49) were used and the proportion of invariable sites and the gamma parameters were estimated from the data. Illustrations were made using the Rainbow Tree interface that utilizes Ape. The analysis that coupled neutralization data with the within-subject phylogeny based on Envs that were evaluated for neutralization sensitivity was performed using LASSIE (43). Signature analysis was performed using the methods fully described in (50, 51).

Heat Maps and Logo Plots

Heat maps and logo plots were generated using the Los Alamos HIV database web interfaces (www.hiv.lanl.gov, version December 2015, HEATMAP and Analyze Align).

Selection of CH848 Env signatures for antibody lineage cooperation studies.

We previously studied cooperation between lineages that occurred soon after infection, at a time when diversity in the autologous quasispecies was limited (12). In contrast, in CH848 the earliest autologous quasispecies transition in sensitivity to DH272/DH475 neutralization to DH270 lineage members occurred between week 39 and week 51, when multiple virus variants were circulating. Viral diversity made it impractical to test all the possible permutations or mutations from the transmitted founder virus. To select a smaller pool of candidate mutations, we sought the two most similar CH848 Env sequences at the amino acid level with opposite sensitivity to DH272/DH475 and DH270.1 neutralization around week 51 and identified clones CH0848.3.d0274.30.07 and CH0848.3.d0358.80.06 being the most similar (sim: 0.98713). Among the differences in amino acid sequences between these two clones, the four that we selected (Δ134-143 in V1); D185N in V2; N413Y in V4; 4463-464 in V5) were the only ones consistently different among all clones with differential sensitivity to DH272 and DH270.1. We elected to use DH270.1 for these cooperating studies as the least mutated representative of DH270 antibodies that gained autologous neutralization at week 51. The D185N and N413Y mutations were also identified by the signature analysis shown in FIG. 19 (see also FIG. 36).

EXAMPLE 2 REFERENCES AND NOTES

1. D. R. Burton, J. R. Mascola, Antibody responses to envelope glycoproteins in HIV-1 infection. *Nature immunology* 16, 571-576 (2015).
2. J. R. Mascola, B. F. Haynes, HIV-1 neutralizing antibodies: understanding nature's pathways. *Immunological Reviews* 254, 225-244 (2013).
3. L. M. Walker, M. Huber, K. J. Doores, E. Falkowska, R. Pejchal, J. P. Julien, S. K. Wang, A. Ramos, P. Y. Chan-Hui, M. Moyle, J. L. Mitcham, P. W. Hammond, 0. A. Olsen, P. Phung, S. Fling, C. H. Wong, S. Phogat, T. Wrin, M. D. Simek, W. C. Koff, I. A. Wilson, D. R. Burton, P. Poignard, Broad neutralization coverage of HIV by multiple highly potent antibodies. *Nature* 477, 466-470 (2011).
4. L. M. Walker, S. K. Phogat, P. Y. Chan-Hui, D. Wagner, P. Phung, J. L. Goss, T. Wrin, M. D. Simek, S. Fling, J. L. Mitcham, J. K. Lehrman, F. H. Priddy, O. A. Olsen, S. M. Frey, P. W. Hammond, S. Kaminsky, T. Zamb, M. Moyle, W. C. Koff, P. Poignard, D. R. Burton, Broad and potent neutralizing antibodies from an African donor reveal a new HIV-1 vaccine target. *Science* 326, 285-289 (2009).
5. K. J. Doores, L. Kong, S. A. Krumm, K. M. Le, D. Sok, U. Laserson, F. Garces, P. Poignard, I. A. Wilson, D. R. Burton, Two classes of broadly neutralizing antibodies within a single lineage directed to the high-mannose patch of HIV envelope. *Journal of virology* 89, 1105-1118 (2015).
6. D. Sok, K. J. Doores, B. Briney, K. M. Le, K. L. Saye-Francisco, A. Ramos, D. W. Kulp, J. P. Julien, S. Menis, L. Wickramasinghe, M. S. Seaman, W. R. Schief, I. A. Wilson, P. Poignard, D. R. Burton, Promiscuous glycan site recognition by antibodies to the high-mannose patch of gp120 broadens neutralization of HIV. *Science translational medicine* 6, 236ra263 (2014).
7. D. Sok, U. Laserson, J. Laserson, Y. Liu, F. Vigneault, J. P. Julien, B. Briney, A. Ramos, K. F. Saye, K. Le, A. Mahan, S. Wang, M. Kardar, G. Yaari, L. M. Walker, B. B. Simen, E. P. St John, P. Y. Chan-Hui, K. Swiderek, S. H. Kleinstein, G. Alter, M. S. Seaman, A. K. Chakraborty, D. Koller, I. A. Wilson, G. M. Church, D. R. Burton, P. Poignard, The effects of somatic hypermutation on neutralization and binding in the PGT121 family of broadly neutralizing HIV antibodies. *PLoS pathogens* 9, e1003754 (2013).
8. H. Mouquet, L. Scharf, Z. Euler, Y. Liu, C. Eden, J. F. Scheid, A. Halper-Stromberg, P. N. Gnanapragasam, D. I. Spencer, M. S. Seaman, H. Schuitemaker, T. Feizi, M. C. Nussenzweig, P. J. Bjorkman, Complex-type N-glycan recognition by potent broadly neutralizing HIV antibodies. *Proceedings of the National Academy of Sciences of the United States of America* 109, E3268-3277 (2012).
9. B. F. Haynes, G. Kelsoe, S. C. Harrison, T. B. Kepler, B-cell-lineage immunogen design in vaccine development with HIV-1 as a case study. *Nature Biotechnology* 30, 423-433 (2012).
10. H. X. Liao, R. Lynch, T. Zhou, F. Gao, S. M. Alam, S. D. Boyd, A. Z. Fire, K. M. Roskin, C. A. Schramm, Z. Zhang, J. Zhu, L. Shapiro, J. C. Mullikin, S. Gnanakaran, P. Hraber, K. Wiehe, G. Kelsoe, G. Yang, S. M. Xia, D. C. Montefiori, R. Parks, K. E. Lloyd, R. M. Scearce, K. A. Soderberg, M. Cohen, G. Kamanga, M. K. Louder, L. M. Tran, Y. Chen, F. Cai, S. Chen, S. Moquin, X. Du, M. G. Joyce, S. Srivatsan, B. Zhang, A. Zheng, G. M. Shaw, B. H. Hahn, T. B. Kepler, B. T. Korber, P. D. Kwong, J. R. Mascola, B. F. Haynes, Co-evolution of a broadly neutralizing HIV-1 antibody and founder virus. *Nature* 496, 469-476 (2013).
11. M. Bonsignori, T. Zhou, Z. Sheng, L. Chen, F. Gao, M. G. Joyce, G. Ozorowski, G. Y. Chuang, C. A. Schramm, K. Wiehe, S. M. Alam, T. Bradley, M. A. Gladden, K. K. Hwang, S. Iyengar, A. Kumar, X. Lu, K. Luo, M. C. Mangiapani, R. J. Parks, H. Song, P. Acharya, R. T. Bailer, A. Cao, A. Druz, I. S. Georgiev, Y. D. Kwon, M. K. Louder, B. Zhang, A. Zheng, B. J. Hill, R. Kong, C. Soto, J. C. Mullikin, D. C. Douek, D. C. Montefiori, M. A. Moody, G. M. Shaw, B. H. Hahn, G. Kelsoe, P. T. Hraber, B. T. Korber, S. D. Boyd, A. Z. Fire, T. B. Kepler, L. Shapiro, A. B. Ward, J. R. Mascola, H. X. Liao, P. D. Kwong, B. F. Haynes, Maturation Pathway from Germline to Broad HIV-1 Neutralizer of a CD4-Mimic Antibody. *Cell* 165, 449-463 (2016).
12. F. Gao, M. Bonsignori, H. X. Liao, A. Kumar, S. M. Xia, X. Lu, F. Cai, K. K. Hwang, H. Song, T. Zhou, R. M. Lynch, S. M. Alam, M. A. Moody, G. Ferrari, M. Berrong, G. Kelsoe, G. M. Shaw, B. H. Hahn, D. C. Montefiori, G. Kamanga, M. S. Cohen, P. Hraber, P. D. Kwong, B. T. Korber, J. R. Mascola, T. B. Kepler, B. F. Haynes, Cooperation of B cell lineages in induction of HIV-1-broadly neutralizing antibodies. *Cell* 158, 481-491 (2014).
13. M. Pancera, T. Zhou, A. Druz, I. S. Georgiev, C. Soto, J. Gorman, J. Huang, P. Acharya, G. Y. Chuang, G. Ofek, G. B. Stewart-Jones, J. Stuckey, R. T. Bailer, M. G. Joyce, M. K. Louder, N. Tumba, Y. Yang, B. Zhang, M. S. Cohen, B. F. Haynes, J. R. Mascola, L. Morris, J. B. Munro, S. C. Blanchard, W. Mothes, M. Connors, P. D. Kwong, Structure and immune recognition of trimeric pre-fusion HIV-1 Env. *Nature* 514, 455-461 (2014).
14. M. Bonsignori, K. K. Hwang, X. Chen, C. Y. Tsao, L. Morris, E. Gray, D. J. Marshall, J. A. Crump, S. H. Kapiga, N. E. Sam, F. Sinangil, M. Pancera, Y. Yongping, B. Zhang, J. Zhu, P. D. Kwong, S. O'Dell, J. R. Mascola, L. Wu, G. J. Nabel, S. Phogat, M. S. Seaman, J. F. Whitesides, M. A. Moody, G. Kelsoe, X. Yang, J. Sodroski, G. M. Shaw, D. C. Montefiori, T. B. Kepler, G. D. Tomaras, S. M. Alam, H. X. Liao, B. F. Haynes, Analysis of a clonal lineage of HIV-1 envelope V2/V3 conformational epitope-specific broadly neutralizing antibodies and their inferred unmutated common ancestors. *Journal of virology* 85, 9998-10009 (2011).
15. E. S. Gray, M. A. Moody, C. K. Wibmer, X. Chen, D. Marshall, J. Amos, P. L. Moore, A. Foulger, J. S. Yu, B. Lambson, S. Abdool Karim, J. Whitesides, G. D. Tomaras, B. F. Haynes, L. Morris, H. X. Liao, Isolation of a monoclonal antibody that targets the alpha-2 helix of gp120 and represents the initial autologous neutralizing-antibody response in an HIV-1 subtype C-infected individual. *Journal of virology* 85, 7719-7729 (2011).

16. S. M. Alam, B. Aussedat, Y. Vohra, R. R. Meyerhoff, E. M. Cale, W. E. Walkowicz, N. A. Radakovich, L. Armand, R. Parks, L. Sutherland, R. Scearce, M. G. Joyce, M. Pancera, A. Druz, I. Georgiev, T. Von Holle, A. Eaton, C. Fox, S. G. Reed, M. K. Louder, R. T. Bailer, L. Morris, S. Abdool Karim, M. Cohen, H. X. Liao, D. Montefiori, P. K. Park, A. Fernandez-Tejada, K. Wiehe, S. Santra, T. B. Kepler, K. O. Saunders, J. Sodroski, P. D. Kwong, J. R. Mascola, M. Bonsignori, M. A. Moody, S. J. Danishefsky, B. F. Haynes, Mimicry of an HIV broadly neutralizing antibody epitope with a synthetic glycopeptide. under review.

17. R. Pejchal, K. J. Doores, L. M. Walker, R. Khayat, P. S. Huang, S. K. Wang, R. L. Stanfield, J. P. Julien, A. Ramos, M. Crispin, R. Depetris, U. Katpally, A. Marozsan, A. Cupo, S. Maloveste, Y. Liu, R. McBride, Y. Ito, R. W. Sanders, C. Ogohara, J. C. Paulson, T. Feizi, C. N. Scanlan, C H. Wong, J. P. Moore, W. C. Olson, A. B. Ward, P. Poignard, W. R. Schief, D. R. Burton, I. A. Wilson, A potent and broad neutralizing antibody recognizes and penetrates the HIV glycan shield. *Science* 334, 1097-1103 (2011).

18. B. Aussedat, Y. Vohra, P. K. Park, A. Fernandez-Tejada, S. M. Alam, S. M. Dennison, F. H. Jaeger, K. Anasti, S. Stewart, J. H. Blinn, H. X. Liao, J. G. Sodroski, B. F. Haynes, S. J. Danishefsky, Chemical synthesis of highly congested gp120 V1V2 N-glycopeptide antigens for potential HIV-1-directed vaccines. *Journal of the American Chemical Society* 135, 13113-13120 (2013).

19. S. M. Alam, S. M. Dennison, B. Aussedat, Y. Vohra, P. K. Park, A. Fernandez-Tejada, S. Stewart, F. H. Jaeger, K. Anasti, J. H. Blinn, T. B. Kepler, M. Bonsignori, H. X. Liao, J. G. Sodroski, S. J. Danishefsky, B. F. Haynes, Recognition of synthetic glycopeptides by HIV-1 broadly neutralizing antibodies and their unmutated ancestors. *Proc Natl Acad Sci USA* 110, 18214-18219 (2013).

20. G. Yaari, J. A. Vander Heiden, M. Uduman, D. Gadala-Maria, N. Gupta, J. N. Stern, K. C. O'Connor, D. A. Hafler, U. Laserson, F. Vigneault, S. H. Kleinstein, Models of somatic hypermutation targeting and substitution based on synonymous mutations from high-throughput immunoglobulin sequencing data. *Frontiers in immunology* 4, 358 (2013).

21. We accessed the SF5 mutability model dataset at http://clip.med.yale.edu/shm/download.php.

22. L. Kong, J. H. Lee, K. J. Doores, C. D. Murin, J. P. Julien, R. McBride, Y. Liu, A. Marozsan, A. Cupo, P. J. Klasse, S. Hoffenberg, M. Caulfield, C. R. King, Y. Hua, K. M. Le, R. Khayat, M. C. Deller, T. Clayton, H. Tien, T. Feizi, R. W. Sanders, J. C. Paulson, J. P. Moore, R. L. Stanfield, D. R. Burton, A. B. Ward, I. A. Wilson, Supersite of immune vulnerability on the glycosylated face of HIV-1 envelope glycoprotein gp120. *Nature structural & molecular biology* 20, 796-803 (2013).

23. J. P. Julien, D. Sok, R. Khayat, J. H. Lee, K. J. Doores, L. M. Walker, A. Ramos, D. C. Diwanji, R. Pejchal, A. Cupo, U. Katpally, R. S. Depetris, R. L. Stanfield, R. McBride, A. J. Marozsan, J. C. Paulson, R. W. Sanders, J. P. Moore, D. R. Burton, P. Poignard, A. B. Ward, I. A. Wilson, Broadly neutralizing antibody PGT121 allosterically modulates CD4 binding via recognition of the HIV-1 gp120 V3 base and multiple surrounding glycans. *PLoS pathogens* 9, e1003342 (2013).

24. M. Pancera, Y. Yang, M. K. Louder, J. Gorman, G. Lu, J. S. McLellan, J. Stuckey, J. Zhu, D. R. Burton, W. C. Koff, J. R. Mascola, P. D. Kwong, N332-Directed broadly neutralizing antibodies use diverse modes of HIV-1 recognition: inferences from heavy-light chain complementation of function. *PloS one* 8, e55701 (2013).

25. P. L. Moore, E. S. Gray, C. K. Wibmer, J. N. Bhiman, M. Nonyane, D. J. Sheward, T. Hermanus, S. Bajimaya, N. L. Tumba, M. R. Abrahams, B. E. Lambson, N. Ranchobe, L. Ping, N. Ngandu, Q. Abdool Karim, S. S. Abdool Karim, R. I. Swanstrom, M. S. Seaman, C. Williamson, L. Morris, Evolution of an HIV glycan-dependent broadly neutralizing antibody epitope through immune escape. *Nature medicine* 18, 1688-1692 (2012).

26. LANL HIV Sequence Database (http://www.hiv.lanl.gov/content/sequence/HIV/mainpage.html)

27. F. Garces, D. Sok, L. Kong, R. McBride, H. J. Kim, K. F. Saye-Francisco, J. P. Julien, Y. Hua, A. Cupo, J. P. Moore, J. C. Paulson, A. B. Ward, D. R. Burton, I. A. Wilson, Structural evolution of glycan recognition by a family of potent HIV antibodies. *Cell* 159, 69-79 (2014).

28. J. H. Lee, N. de Val, D. Lyumkis, A. B. Ward, Model Building and Refinement of a Natively Glycosylated HIV-1 Env Protein by High-Resolution Cryoelectron Microscopy. *Structure* 23, 1943-1951 (2015).

29. F. Garces, J. H. Lee, N. de Val, A. T. de la Pena, L. Kong, C. Puchades, Y. Hua, R. L. Stanfield, D. R. Burton, J. P. Moore, R. W. Sanders, A. B. Ward, I. A. Wilson, Affinity Maturation of a Potent Family of HIV Antibodies Is Primarily Focused on Accommodating or Avoiding Glycans. *Immunity* 43, 1053-1063 (2015).

30. M. Bonsignori, D. C. Montefiori, X. Wu, X. Chen, K. K. Hwang, C. Y. Tsao, D. M. Kozink, R. J. Parks, G. D. Tomaras, J. A. Crump, S. H. Kapiga, N. E. Sam, P. D. Kwong, T. B. Kepler, H. X. Liao, J. R. Mascola, B. F. Haynes, Two distinct broadly neutralizing antibody specificities of different clonal lineages in a single HIV-1-infected donor: implications for vaccine design. *Journal of virology* 86, 4688-4692 (2012).

31. K. Wagh, T. Bhattacharya, C. Williamson, A. Robles, M. Bayne, J. Garrity, M. Rist, C. Rademeyer, H. Yoon, A. Lapedes, H. Gao, K. Greene, M. K. Louder, R. Kong, S. A. Karim, D. R. Burton, D. H. Barouch, M. C. Nussenzweig, J. R. Mascola, L. Morris, D. C. Montefiori, B. Korber, M. S. Seaman, Optimal Combinations of Broadly Neutralizing Antibodies for Prevention and Treatment of HIV-1 Clade C Infection. *PLoS pathogens* 12, e1005520 (2016).

32. L. S. Yeap, J. K. Hwang, Z. Du, R. M. Meyers, F. L. Meng, A. Jakubauskaite, M. Liu, V. Mani, D. Neuberg, T. B. Kepler, J. H. Wang, F. W. Alt, Sequence-Intrinsic Mechanisms that Target AID Mutational Outcomes on Antibody Genes. *Cell* 163, 1124-1137 (2015).

33. G. D. Tomaras, N. L. Yates, P. Liu, L. Qin, G. G. Fouda, L. L. Chavez, A. C. Decamp, R. J. Parks, V. C. Ashley, J. T. Lucas, M. Cohen, J. Eron, C. B. Hicks, H. X. Liao, S. G. Self, G. Landucci, D. N. Forthal, K. J. Weinhold, B. F. Keele, B. H. Hahn, M. L. Greenberg, L. Morris, S. S. Karim, W. A. Blattner, D. C. Montefiori, G. M. Shaw, A. S. Perelson, B. F. Haynes, Initial B-cell responses to transmitted human immunodeficiency virus type 1: virion-binding immunoglobulin M (IgM) and IgG antibodies followed by plasma anti-gp41 antibodies with ineffective control of initial viremia. *Journal of virology* 82, 12449-12463 (2008).

34. G. M. Shaw, E. Hunter, HIV transmission. *Cold Spring Harbor perspectives in medicine* 2, (2012).

35. W. B. Williams, H. X. Liao, M. A. Moody, T. B. Kepler, S. M. Alam, F. Gao, K. Wiehe, A. M. Trama, K. Jones, R.

Zhang, H. Song, D. J. Marshall, J. F. Whitesides, K. Sawatzki, A. Hua, P. Liu, M. Z. Tay, K. E. Seaton, X. Shen, A. Foulger, K. E. Lloyd, R. Parks, J. Pollara, G. Ferrari, J. S. Yu, N. Vandergrift, D. C. Montefiori, M. E. Sobieszczyk, S. Hammer, S. Karuna, P. Gilbert, D. Grove, N. Grunenberg, M. J. McElrath, J. R. Mascola, R. A. Koup, L. Corey, G. J. Nabel, C. Morgan, G. Churchyard, J. Maenza, M. Keefer, B. S. Graham, L. R. Baden, G. D. Tomaras, B. F. Haynes, HIV-1 VACCINES. Diversion of HIV-1 vaccine-induced immunity by gp41-microbiota cross-reactive antibodies. *Science* 349, aab1253 (2015).
36. T. B. Kepler, Reconstructing a B-cell clonal lineage. I. Statistical inference of unobserved ancestors. *F1000Res* 2, 103 (2013).
37. L. G. Cowell, T. B. Kepler, The nucleotide-replacement spectrum under somatic hypermutation exhibits microsequence dependence that is strand-symmetric and distinct from that under germline mutation. *Journal of Immunology* 164, 1971-1976 (2000).
38. A. G. Betz, C. Rada, R. Pannell, C. Milstein, M. S. Neuberger, Passenger transgenes reveal intrinsic specificity of the antibody hypermutation mechanism: clustering, polarity, and specific hot spots. *Proceedings of the National Academy of Sciences of the United States of America* 90, 2385-2388 (1993).
39. R. Bransteitter, P. Pham, P. Calabrese, M. F. Goodman, Biochemical analysis of hypermutational targeting by wild type and mutant activation-induced cytidine deaminase. *The Journal of biological chemistry* 279, 51612-51621 (2004).
40. M. S. Seaman, H. Janes, N. Hawkins, L. E. Grandpre, C. Devoy, A. Gifi, R. T. Coffey, L. Harris, B. Wood, M. G. Daniels, T. Bhattacharya, A. Lapedes, V. R. Polonis, F. E. McCutchan, P. B. Gilbert, S. G. Self, B. T. Korber, D. C. Montefiori, J. R. Mascola, Tiered categorization of a diverse panel of HIV-1 Env pseudoviruses for assessment of neutralizing antibodies. *Journal of virology* 84, 1439-1452 (2010).
41. J. F. Salazar-Gonzalez, M. G. Salazar, B. F. Keele, G. H. Learn, E. E. Giorgi, H. Li, J. M. Decker, S. Wang, J. Baalwa, M. F. Kraus, N. F. Parrish, K. S. Shaw, M. B. Guffey, K. J. Bar, K. L. Davis, C. Ochsenbauer-Jambor, J. C. Kappes, M. S. Saag, M. S. Cohen, J. Mulenga, C. A. Derdeyn, S. Allen, E. Hunter, M. Markowitz, P. Hraber, A. S. Perelson, T. Bhattacharya, B. F. Haynes, B. T. Korber, B. H. Hahn, G. M. Shaw, Genetic identity, biological phenotype, and evolutionary pathways of transmitted/founder viruses in acute and early HIV-1 infection. *The Journal of experimental medicine* 206, 1273-1289 (2009).
42. B. F. Keele, E. E. Giorgi, J. F. Salazar-Gonzalez, J. M. Decker, K. T. Pham, M. G. Salazar, C. Sun, T. Grayson, S. Wang, H. Li, X. Wei, C. Jiang, J. L. Kirchherr, F. Gao, J. A. Anderson, L. H. Ping, R. Swanstrom, G. D. Tomaras, W. A. Blattner, P. A. Goepfert, J. M. Kilby, M. S. Saag, E. L. Delwart, M. P. Busch, M. S. Cohen, D. C. Montefiori, B. F. Haynes, B. Gaschen, G. S. Athreya, H. Y. Lee, N. Wood, C. Seoighe, A. S. Perelson, T. Bhattacharya, B. T. Korber, B. H. Hahn, G. M. Shaw, Identification and characterization of transmitted and early founder virus envelopes in primary HIV-1 infection. *Proceedings of the National Academy of Sciences of the United States of America* 105, 7552-7557 (2008).
43. P. Hraber, B. Korber, K. Wagh, E. E. Giorgi, T. Bhattacharya, S. Gnanakaran, A. S. Lapedes, G. H. Learn, E. F. Kreider, Y. Li, G. M. Shaw, B. H. Hahn, D. C. Montefiori, S. M. Alam, M. Bonsignori, M. A. Moody, H. X. Liao, F. Gao, B. F. Haynes, Longitudinal Antigenic Sequences and Sites from Intra-Host Evolution (LASSIE) Identifies Immune-Selected HIV Variants. *Viruses* 7, 5443-5475 (2015).
44. J. L. Kirchherr, X. Lu, W. Kasongo, V. Chalwe, L. Mwananyanda, R. M. Musonda, S. M. Xia, R. M. Scearce, H. X. Liao, D. C. Montefiori, B. F. Haynes, F. Gao, High throughput functional analysis of HIV-1 env genes without cloning. *Journal of virological methods* 143, 104-111 (2007).
45. E. P. Go, A. Herschhorn, C. Gu, L. Castillo-Menendez, S. Zhang, Y. Mao, H. Chen, H. Ding, J. K. Wakefield, D. Hua, H. X. Liao, J. C. Kappes, J. Sodroski, H. Desaire, Comparative Analysis of the Glycosylation Profiles of Membrane-Anchored HIV-1 Envelope Glycoprotein Trimers and Soluble gp140. *Journal of virology* 89, 8245-8257 (2015).
46. D. Fera, A. G. Schmidt, B. F. Haynes, F. Gao, H. X. Liao, T. B. Kepler, S. C. Harrison, Affinity maturation in an HIV broadly neutralizing B-cell lineage through reorientation of variable domains. *Proceedings of the National Academy of Sciences of the United States of America* 111, 10275-10280 (2014).
47. T. Zhou, J. Zhu, X. Wu, S. Moquin, B. Zhang, P. Acharya, I. S. Georgiev, H. R. Altae-Tran, G. Y. Chuang, M. G. Joyce, Y. D. Kwon, N. S. Longo, M. K. Louder, T. Luongo, K. McKee, C. A. Schramm, J. Skinner, Y. Yang, Z. Yang, Z. Zhang, A. Zheng, M. Bonsignori, B. F. Haynes, J. F. Scheid, M. C. Nussenzweig, M. Simek, D. R. Burton, W. C. Koff, J. C. Mullikin, M. Connors, L. Shapiro, G. J. Nabel, J. R. Mascola, P. D. Kwong, Multidonor analysis reveals structural elements, genetic determinants, and maturation pathway for HIV-1 neutralization by VRC01-class antibodies. *Immunity* 39, 245-258 (2013).
48. R. W. Sanders, R. Derking, A. Cupo, J. P. Julien, A. Yasmeen, N. de Val, H. J. Kim, C. Blattner, A. T. de la Pena, J. Korzun, M. Golabek, K. de Los Reyes, T. J. Ketas, M. J. van Gils, C. R. King, I. A. Wilson, A. B. Ward, P. J. Klasse, J. P. Moore, A next-generation cleaved, soluble HIV-1 Env trimer, BG505 SOSIP.664 gp140, expresses multiple epitopes for broadly neutralizing but not non-neutralizing antibodies. *PLoS pathogens* 9, e1003618 (2013).
49. D. C. Nickle, L. Heath, M. A. Jensen, P. B. Gilbert, J. I. Mullins, S. L. Kosakovsky Pond, HIV-specific probabilistic models of protein evolution. *PloS one* 2, e503 (2007).
50. S. Gnanakaran, M. G. Daniels, T. Bhattacharya, A. S. Lapedes, A. Sethi, M. Li, H. Tang, K. Greene, H. Gao, B. F. Haynes, M. S. Cohen, G. M. Shaw, M. S. Seaman, A. Kumar, F. Gao, D. C. Montefiori, B. Korber, Genetic signatures in the envelope glycoproteins of HIV-1 that associate with broadly neutralizing antibodies. *PLoS computational biology* 6, e 1000955 (2010).
51. T. Bhattacharya, M. Daniels, D. Heckerman, B. Foley, N. Frahm, C. Kadie, J. Carlson, K. Yusim, B. McMahon, B. Gaschen, S. Mallal, J. I. Mullins, D. C. Nickle, J. Herbeck, C. Rousseau, G. H. Learn, T. Miura, C. Brander, B. Walker, B. Korber, Founder effects in the assessment of HIV polymorphisms and HLA allele associations. *Science* 315, 1583-1586 (2007).
52. L. Kong, A. Torrents de la Pena, M. C. Deller, F. Garces, K. Sliepen, Y. Hua, R. L. Stanfield, R. W. Sanders, I. A. Wilson, Complete epitopes for vaccine design derived from a crystal structure of the broadly neutralizing antibodies PGT128 and 8ANC195 in complex with an HIV-1

Env trimer. *Acta crystallographica. Section D, Biological crystallography* 71, 2099-2108 (2015).

Data and Materials Availability.

The V(D)J rearrangement sequences of DH272, DH475 and the DH270 lineage antibodies (DH270.UCA, DH270.IA1 through IA4, and DH270.1 through 6) have been deposited in GenBank with accession numbers KY354938 through KY354963. NGS sequence data for clones DH270, DH272 and DH475 have been deposited in GenBank with accession numbers KY347498 through KY347701. Coordinates and structure factors for UCA1, UCA3, DH270.1, DH270.3, DH270.5, DH270.6, and DH272 have been deposited in the Protein Data Bank with accession code 5UOR, 5U15, 5UOU, 5TPL, 5TPP, 5TQA, and 5TRP, respectively. The EM map of the 92BR SOSIP.664 trimer in complex with DH270.1 has been deposited in the EM Data Bank with accession code EMD-8507.

Example 3: Mouse Models

Once a functional mutation is identified, various antigens are tested for their ability to bind differentially to an antibody comprising this functional mutation compared to a UCA antibody. In Example 1, one such mutation was identified-_G57R. An HIV-1 envelope antigen SOSIP CH84810.17 N301A was found to bind best to the UCA antibody DH270.UCA4. An intermediate antibody DH270.I4 carrying this mutation was found to bind to an HIV-1 envelope antigen SOSIP CH848 10.17.

MU378 is a DH270.UCA4 knock-in mouse study. This is a mouse model with the VH and VL chain of DH270UCA.4, so the mouse can make endogenous mouse antibodies as well as DH270.UCA4. It is primed with 10.17 SOSIP that has an N301A mutation that bound to the DH270.UCA4 antibody best. After two immunizations of that prime, the mouse is boosted with 10.17 SOSIP without the N301A (adding the glycan back). The immunogens are delivered in with a suitable adjuvant, e.g. but not limited to GLA-SE, polyIC. The control group gets adjuvant only. In MU378 the mice are so-called constitutive heavy and light chain mice. In this model, the DH270.UCA4 is sensitive to tolerance mechanisms and only a small % of the UCA4 gets out to the periphery in these mice because of problems with the UCA4 light chain.

MU379 is another mouse study. For MU379, the mice are constitutive HC/conditional LC. This is a mouse system, where the UCA uses one light chain to start, gets past the deletional checkpoints and then switches to the bonafide UCA4 light chain. The result is that much more UCA4 effectively gets to the periphery. The immunization regimen is the same in MU378 and MU379, so the only variable changed is the constitutive to conditional UCA4 light chain. The hope is that the 10.17 N301A binds well to the UCA4 activating that lineage. Then the boost with 10.17 preferentially binds intermediates with G57R and does not bind as well to the UCA4. So the expectation is that there will be selection for UCA4+G57R with this regimen. The readout will be a comparison of the frequency of sequences with G57R in the treatment group vs. the control (adjuvant only) group. If there is a significant difference in G57R frequency, it suggests the immunogen is selecting for G57R and would demonstrate that an antigen could be used to select an antibody with a single amino acid substitution.

Example 4: Calcium Flux with Ramos Cells

We have developed BNAb UCA Ramos cells, including cell lines for CH103 antibodies, DH270, CH235, DH511 UCAs and a control, CH65. Additional cell lines will be made for CH01 and VRC01 UCAs, and the DH270 intermediate, IA4. These cell lines, and others, comprising without limitation any desired improbable mutation and/or improbable functional mutation, will be used for testing calcium flux to test and select immunogens with the mutation guided design strategy.

What is claimed is:

1. A method for identifying improbable mutations in the heavy or light chains of broadly neutralizing anti-HIV-1 antibodies comprising:
   (a) identifying at least one improbable somatic mutation in the heavy or light chain variable domain of a broadly neutralizing anti-HIV-1 antibody compared to the sequence of the corresponding unmutated common ancestor (UCA) antibody, wherein the somatic mutation is an improbable somatic mutation if in the absence of antigenic selection the somatic mutation occurs in the broad-neutralizing anti-HIV antibody with a probability of less than 2%;
   (b) reverting the at least one improbable somatic mutation identified in step (a) to its UCA-encoded amino acid(s) to thereby provide a recombinant antibody;
   (c) expressing the recombinant antibody of step (b) and testing the expressed recombinant antibody for neutralizing activity against an HIV-1 virus or for binding ability against the envelope of an HIV-1 virus, and
   (d) determining whether the improbable mutation identified in step (a) is functionally significant by testing whether the expressed recombinant antibody of step (c) exhibits a reduction of neutralizing activity or reduction of envelope binding as compared to an antibody with the same amino acid sequence but for the reverted amino acid sequence.

2. The method of claim 1, further comprising step (e):
   (e) testing whether the anti-HIV-1 antibody with the improbable mutation determined to be functionally significant in step (d) binds to an HIV-1 antigen with high affinity, wherein if the anti-HIV-1 antibody binds with high affinity to the HIV-1 antigen, then the antigen is identified as an HIV-1 vaccine antigen.

3. The method of claim 2, wherein the HIV-1 vaccine antigen identified in step (e) is administered to a subject in an amount sufficient to induce the production of broadly neutralizing anti-HIV-1 antibodies in the subject.

4. The method of claim 1, in step (a), wherein the somatic mutation is an improbable mutation if in the absence of antigenic selection the somatic mutation occurs in the broadly neutralizing anti-HIV-1 antibody with a probability of less than 1%.

5. The method of claim 1, wherein step (a) comprises antibody sequence analysis with the ARMADiLLO program.

6. The method of claim 1, in step (a), wherein the broadly neutralizing anti-HIV-1 antibody binds with high affinity to an HIV-1 envelope antigen.

7. The method of claim 1, in step (a), wherein the broadly neutralizing anti-HIV-1 antibody binds with a $K_D$ of at least $10^{-8}$ or $10^{-9}$ to an HIV-1 envelope antigen.

8. The method of claim 1, in step (c), wherein the testing the expressed recombinant antibody for neutralizing activity is conducted against a heterologous, difficult-to-neutralize HIV-1 virus.

9. The method of claim 1, in step (d), wherein the somatic mutation identified in step (a) is a functionally significant improbable mutation if the expressed recombinant antibody of step (c) exhibits at least a 25% reduction of neutralizing activity as compared to an antibody with the same amino acid sequence but for the reverted amino acid sequence.

10. The method of claim 1, in step (d), wherein the somatic mutation identified in step (a) is a functionally significant improbable mutation if the expressed recombinant antibody of step (c) exhibits substantially no neutralizing activity as compared to an antibody with the same amino acid sequence but for the reverted amino acid sequence.

11. The method of claim 1, in step (d), wherein the somatic mutation identified in step (a) is a functionally significant improbable mutation if the expressed recombinant antibody of step (c) exhibits a reduction of envelope binding of least one order of magnitude of $K_D$ as compared to an antibody with the same amino acid sequence but for the reverted amino acid sequence.

12. The method of claim 2, in step (e), wherein high affinity is a $K_D$ of at least $10^{-8}$ or $10^{-9}$.

13. The method of claim 1, wherein the broadly neutralizing anti-HIV-1 antibody is isolated from a biological sample and wherein the amino acid and/or nucleic acid sequence of the heavy or light chain variable domain thereof is determined.

14. The method of claim 1, further comprising isolating from a biological sample and determining the amino acid and/or nucleic acid sequence of the heavy or light chain variable domain of at least one additional antibody clonally related to the broadly neutralizing anti-HIV-1 antibody.

15. The method of claim 1, wherein the broadly neutralizing anti-HIV-1 antibody comprises:
   a heavy chain variable domain polypeptide of an anti-HIV-1 antibody with at least one improbable mutation selected from DH270.6 (SEQ ID NO: 138), CH235.12 (SEQ ID NO: 128), DH511.2 (SEQ ID NO: 137), VRC01 (SEQ ID NO:114), VRCCH31 (SEQ ID NO: 115), PGT121 (SEQ ID NO:116), PGT145 (SEQ ID NO:117), 3BNC117 (SEQ ID NO:118) 10E8 (SEQ ID NO:119), CH01 (SEQ ID NO:120), PGDM1400 (SEQ ID NO:121), PGT128 (SEQ ID NO:122), PGT135 (SEQ ID NO:123), 1B2530 (SEQ ID NO:124), 2F5 (SEQ ID NO:125), 35O22 (SEQ ID NO:126), 4E10 (SEQ ID NO:127), N6 (SEQ ID NO:129), PGT151 (SEQ ID NO:130), VRC34 (SEQ ID NO:131), CH103 (SEQ ID NO:132), DH270 (SEQ ID NO:133), 8ANC131 (SEQ ID NO:134), PG9 (SEQ ID NO:135), 8ANC195 (SEQ ID NO:136), BF520.1 (SEQ ID NO:139), or VRC26.25 (SEQ ID NO:140), and a corresponding light chain variable domain polypeptide of an anti-HIV-1 antibody with at least one improbable mutation selected from DH270.6 (SEQ ID NO: 166), CH235.12 (SEQ ID NO: 151), DH511.2 (SEQ ID NO: 155), VRC01 (SEQ ID NO:141), VRC-CH31 (SEQ ID NO: 142), PGT121 (SEQ ID NO:159), PGT145 (SEQ ID NO:146), 3BNC117 (SEQ ID NO:143) 10E8 (SEQ ID NO:160), CH01 (SEQ ID NO:145), PGDM1400 (SEQ ID NO:157), PGT128 (SEQ ID NO:158), PGT135 (SEQ ID NO:144), 1B2530 (SEQ ID NO:161), 2F5 (SEQ ID NO:148), 35O22 (SEQ ID NO:162), 4E10 (SEQ ID NO:149), N6 (SEQ ID NO:152), PGT151 (SEQ ID NO:153), VRC34 (SEQ ID NO:154), CH103 (SEQ ID NO:164), DH270 (SEQ ID NO:165), 8ANC131 (SEQ ID NO:150), PG9 (SEQ ID NO:163), 8ANC195 (SEQ ID NO:147), BF520.1 (SEQ ID NO:156), or VRC26.25 (SEQ ID NO:167).

16. The method of claim 2, in step (a), wherein the somatic mutation is an improbable mutation if in the absence of antigenic selection the somatic mutation occurs in the broadly neutralizing anti-HIV-1 antibody with a probability of less than 1%.

17. The method of claim 2, wherein step (a) comprises antibody sequence analysis with the ARMADiLLO program.

18. The method of claim 2, in step (a), wherein the broadly neutralizing anti-HIV-1 antibody binds with high affinity to an HIV-1 envelope antigen.

19. The method of claim 2, in step (a), wherein the broadly neutralizing anti-HIV-1 antibody binds with a $K_D$ of least $10^{-8}$ or $10^{-9}$ to an HIV-1 envelope antigen.

20. The method of claim 2, in step (c), wherein the testing the expressed recombinant antibody for neutralizing activity is conducted against a heterologous, difficult-to-neutralize HIV-1 virus.

21. The method of claim 2, in step (d), wherein the somatic mutation identified in step (a) is a functionally significant improbable mutation if the expressed recombinant antibody of step (c) exhibits at least a 25% reduction of neutralizing activity as compared to an antibody with the same amino acid sequence but for the reverted amino acid sequence.

22. The method of claim 2, in step (d), wherein the somatic mutation identified in step (a) is a functionally significant improbable mutation if the expressed recombinant antibody of step (c) exhibits substantially no neutralizing activity as compared to an antibody with the same amino acid sequence but for the reverted amino acid sequence.

23. The method of claim 2, in step (d), wherein the somatic mutation identified in step (a) is a functionally significant improbable mutation if the expressed recombinant antibody of step (c) exhibits a reduction of envelope binding of least one order of magnitude of $K_D$ as compared to an antibody with the same amino acid sequence but for the reverted amino acid sequence.

24. The method of claim 2, broadly neutralizing anti-HIV-1 antibody is isolated from a biological sample and wherein the amino acid and/or nucleic acid sequence of the heavy or light chain variable domain thereof is determined.

25. The method of claim 2, further comprising isolating from a biological sample and determining the amino acid and/or nucleic acid sequence of the heavy or light chain variable domain of at least one additional antibody clonally related to the broadly neutralizing anti-HIV-1 antibody.

26. The method of claim 18, further comprising step (e):
(e) testing whether the anti-HIV-1 antibody with the improbable mutation determined to be functionally significant in step (d) binds to an HIV-1 antigen with high affinity, wherein if the anti-HIV-1 antibody binds with high affinity to the HIV-1 antigen, then the antigen is identified as an HIV-1 vaccine antigen.

* * * * *

SEQUENCE LISTING

```
<160> NUMBER OF SEQ ID NOS: 168

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatccatccc atccattgaa gccctgtcc ag                                    32

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtgcgacccc cactagggtc gatccatccc                                      30

<210> SEQ ID NO 3
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 3
agtgacggtt tcctgcaagg catctggata cac                                    33

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatccatccc atcaactcaa gcccctgtcc aggg                                   34

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgaccctagt tggggtagca caaactacgc a                                      31

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctggggcc tcagtgaagg tttcctgc                                          28

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caggaaaccc tcactgaggc cccagg                                            26

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgcctggcag gaaacattca ctgaggcccc ag                                     32

<210> SEQ ID NO 9
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
gaatccaatt tagcgtacaa tcaataaacg tatatccaga agcccgacaa gaaattctc        59

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccgtcaact acgcacgtaa acttcagggc agagt                                 35

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagaaattc tcatcgacgc gccaggcttc ttcatc                                36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
accaggctaa ggaaccactc tgactggtcc gacaag                                36

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgatggtga gattgaagtc tggcccccac c                                     31

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcagcggcag tcggtcgggg ccag                                             24

<210> SEQ ID NO 15
<211> LENGTH: 31
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 15
gtgggggcca gactacactc tcaccatcag c                               31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggtccgaca agagaggatg gctgtttccc c                               31

<210> SEQ ID NO 17
<211> LENGTH: 4
<212> TYPE: PRT
<213> ORGANISM: Human immunodeficiency virus 1

<400> SEQUENCE: 17

Gly Asp Ile Arg
1

<210> SEQ ID NO 18
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Ser Leu Gln Pro Leu Ala Thr Leu Tyr Leu Leu Gly Met Leu
1               5                   10                  15

Val Ala Ser Val Leu Ala Ala Glu Asn Leu Trp Val Thr Val Tyr Tyr
            20                  25                  30

Gly Val Pro Val Trp Lys Glu Ala Lys Thr Thr Leu Phe Cys Ala Ser
        35                  40                  45

Asp Ala Arg Ala Tyr Glu Lys Glu Val His Asn Val Trp Ala Thr His
    50                  55                  60

Ala Cys Val Pro Thr Asp Pro Ser Pro Gln Glu Leu Val Leu Gly Asn
65                  70                  75                  80

Val Thr Glu Asn Phe Asn Met Trp Lys Asn Asp Met Val Asp Gln Met
                85                  90                  95

His Glu Asp Ile Ile Ser Leu Trp Asp Gln Ser Leu Lys Pro Cys Val
            100                 105                 110

Lys Leu Thr Pro Leu Cys Val Thr Leu Ile Cys Ser Asn Ala Thr Val
        115                 120                 125

Lys Asn Gly Thr Val Glu Glu Met Lys Asn Cys Ser Phe Asn Thr Thr
    130                 135                 140

Thr Glu Ile Arg Asp Lys Glu Lys Lys Glu Tyr Ala Leu Phe Tyr Lys
145                 150                 155                 160

Pro Asp Ile Val Pro Leu Ser Glu Thr Asn Asn Thr Ser Glu Tyr Arg
                165                 170                 175

Leu Ile Asn Cys Asn Thr Ser Ala Cys Thr Gln Ala Cys Pro Lys Val
            180                 185                 190

Thr Phe Glu Pro Ile Pro Ile His Tyr Cys Ala Pro Ala Gly Tyr Ala

```
                195                 200                 205
Ile Leu Lys Cys Asn Asp Glu Thr Phe Asn Gly Thr Gly Pro Cys Ser
210                 215                 220

Asn Val Ser Thr Val Gln Cys Thr His Gly Ile Arg Pro Val Val Ser
225                 230                 235                 240

Thr Gln Leu Leu Leu Asn Gly Ser Leu Ala Glu Lys Glu Ile Val Ile
                245                 250                 255

Arg Ser Glu Asn Leu Thr Asn Asn Ala Lys Ile Ile Ile Val His Leu
            260                 265                 270

His Thr Pro Val Glu Ile Val Cys Thr Arg Pro Asn Asn Asn Thr Arg
        275                 280                 285

Lys Ser Val Arg Ile Gly Pro Gly Gln Thr Phe Tyr Ala Thr Gly Asp
    290                 295                 300

Ile Ile Gly Asp Ile Lys Gln Ala His Cys Asn Ile Ser Glu Glu Lys
305                 310                 315                 320

Trp Asn Asp Thr Leu Gln Lys Val Gly Ile Glu Leu Gln Lys His Phe
                325                 330                 335

Pro Asn Lys Thr Ile Lys Tyr Asn Gln Ser Ala Gly Gly Asp Met Glu
            340                 345                 350

Ile Thr Thr His Ser Phe Asn Cys Gly Gly Glu Phe Phe Tyr Cys Asn
        355                 360                 365

Thr Ser Asn Leu Phe Asn Gly Thr Tyr Asn Gly Thr Tyr Ile Ser Thr
    370                 375                 380

Asn Ser Ser Ala Asn Ser Thr Ser Thr Ile Thr Leu Gln Cys Arg Ile
385                 390                 395                 400

Lys Gln Ile Ile Asn Met Trp Gln Gly Val Gly Arg Cys Met Tyr Ala
                405                 410                 415

Pro Pro Ile Ala Gly Asn Ile Thr Cys Arg Ser Asn Ile Thr Gly Leu
            420                 425                 430

Leu Leu Thr Arg Asp Gly Gly Thr Asn Ser Asn Glu Thr Glu Thr Phe
        435                 440                 445

Arg Pro Ala Gly Gly Asp Met Arg Asp Asn Trp Arg Ser Glu Leu Tyr
    450                 455                 460

Lys Tyr Lys Val Val Lys Ile Glu Pro Leu Gly Val Ala Pro Thr Arg
465                 470                 475                 480

Cys Lys Arg Arg Val Val Gly Arg Arg Arg Arg Arg Ala Val Gly
                485                 490                 495

Ile Gly Ala Val Phe Leu Gly Phe Leu Gly Ala Ala Gly Ser Thr Met
            500                 505                 510

Gly Ala Ala Ser Met Thr Leu Thr Val Gln Ala Arg Asn Leu Leu Ser
        515                 520                 525

Gly Ile Val Gln Gln Gln Ser Asn Leu Leu Arg Ala Pro Glu Ala Gln
    530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Arg Asp Gln Leu Leu Gly
                565                 570                 575

Ile Trp Gly Cys Ser Gly Lys Leu Ile Cys Cys Thr Asn Val Pro Trp
            580                 585                 590

Asn Ser Ser Trp Ser Asn Arg Asn Leu Ser Glu Ile Trp Asp Asn Met
        595                 600                 605

Thr Trp Leu Gln Trp Asp Lys Glu Ile Ser Asn Tyr Thr Gln Ile Ile
    610                 615                 620
```

-continued

Tyr Gly Leu Leu Glu Glu Ser Gln Asn Gln Gln Glu Lys Asn Glu Gln
625                 630                 635                 640

Asp Leu Leu Ala Leu Asp
            645

<210> SEQ ID NO 19
<211> LENGTH: 646
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Leu Gln Pro Leu Ala Thr Leu Tyr Leu Leu Gly Met Leu
1               5                   10                  15

Val Ala Ser Val Leu Ala Ala Glu Asn Leu Trp Val Thr Val Tyr Tyr
            20                  25                  30

Gly Val Pro Val Trp Lys Glu Ala Lys Thr Thr Leu Phe Cys Ala Ser
        35                  40                  45

Asp Ala Arg Ala Tyr Glu Lys Glu Val His Asn Val Trp Ala Thr His
    50                  55                  60

Ala Cys Val Pro Thr Asp Pro Ser Pro Gln Glu Leu Val Leu Gly Asn
65                  70                  75                  80

Val Thr Glu Asn Phe Asn Met Trp Lys Asn Asp Met Val Asp Gln Met
                85                  90                  95

His Glu Asp Ile Ile Ser Leu Trp Asp Gln Ser Leu Lys Pro Cys Val
            100                 105                 110

Lys Leu Thr Pro Leu Cys Val Thr Leu Ile Cys Ser Asn Ala Thr Val
        115                 120                 125

Lys Asn Gly Thr Val Glu Glu Met Lys Asn Cys Ser Phe Asn Thr Thr
130                 135                 140

Thr Glu Ile Arg Asp Lys Glu Lys Lys Glu Tyr Ala Leu Phe Tyr Lys
145                 150                 155                 160

Pro Asp Ile Val Pro Leu Ser Glu Thr Asn Asn Thr Ser Glu Tyr Arg
                165                 170                 175

Leu Ile Asn Cys Asn Thr Ser Ala Cys Thr Gln Ala Cys Pro Lys Val
            180                 185                 190

Thr Phe Glu Pro Ile Pro Ile His Tyr Cys Ala Pro Ala Gly Tyr Ala
        195                 200                 205

Ile Leu Lys Cys Asn Asp Glu Thr Phe Asn Gly Thr Gly Pro Cys Ser
210                 215                 220

Asn Val Ser Thr Val Gln Cys Thr His Gly Ile Arg Pro Val Val Ser
225                 230                 235                 240

Thr Gln Leu Leu Leu Asn Gly Ser Leu Ala Glu Lys Glu Ile Val Ile
                245                 250                 255

Arg Ser Glu Asn Leu Thr Asn Asn Ala Lys Ile Ile Val His Leu
            260                 265                 270

His Thr Pro Val Glu Ile Val Cys Thr Arg Pro Asn Ala Asn Thr Arg
        275                 280                 285

Lys Ser Val Arg Ile Gly Pro Gly Gln Thr Phe Tyr Ala Thr Gly Asp
    290                 295                 300

Ile Ile Gly Asp Ile Lys Gln Ala His Cys Asn Ile Ser Glu Glu Lys
305                 310                 315                 320

Trp Asn Asp Thr Leu Gln Lys Val Gly Ile Glu Leu Gln Lys His Phe

```
                    325                 330                 335
Pro Asn Lys Thr Ile Lys Tyr Asn Gln Ser Ala Gly Gly Asp Met Glu
                340                 345                 350
Ile Thr Thr His Ser Phe Asn Cys Gly Gly Glu Phe Phe Tyr Cys Asn
            355                 360                 365
Thr Ser Asn Leu Phe Asn Gly Thr Tyr Asn Gly Thr Tyr Ile Ser Thr
        370                 375                 380
Asn Ser Ser Ala Asn Ser Thr Ser Thr Ile Thr Leu Gln Cys Arg Ile
385                 390                 395                 400
Lys Gln Ile Ile Asn Met Trp Gln Gly Val Gly Arg Cys Met Tyr Ala
                405                 410                 415
Pro Pro Ile Ala Gly Asn Ile Thr Cys Arg Ser Asn Ile Thr Gly Leu
                420                 425                 430
Leu Leu Thr Arg Asp Gly Gly Thr Asn Ser Asn Glu Thr Glu Thr Phe
            435                 440                 445
Arg Pro Ala Gly Gly Asp Met Arg Asp Asn Trp Arg Ser Glu Leu Tyr
        450                 455                 460
Lys Tyr Lys Val Val Lys Ile Glu Pro Leu Gly Val Ala Pro Thr Arg
465                 470                 475                 480
Cys Lys Arg Arg Val Val Gly Arg Arg Arg Arg Arg Ala Val Gly
                485                 490                 495
Ile Gly Ala Val Phe Leu Gly Phe Leu Gly Ala Ala Gly Ser Thr Met
                500                 505                 510
Gly Ala Ala Ser Met Thr Leu Thr Val Gln Ala Arg Asn Leu Leu Ser
            515                 520                 525
Gly Ile Val Gln Gln Gln Ser Asn Leu Leu Arg Ala Pro Glu Ala Gln
        530                 535                 540
Gln His Leu Leu Lys Leu Thr Val Trp Gly Ile Lys Gln Leu Gln Ala
545                 550                 555                 560
Arg Val Leu Ala Val Glu Arg Tyr Leu Arg Asp Gln Gln Leu Leu Gly
                565                 570                 575
Ile Trp Gly Cys Ser Gly Lys Leu Ile Cys Cys Thr Asn Val Pro Trp
            580                 585                 590
Asn Ser Ser Trp Ser Asn Arg Asn Leu Ser Glu Ile Trp Asp Asn Met
        595                 600                 605
Thr Trp Leu Gln Trp Asp Lys Glu Ile Ser Asn Tyr Thr Gln Ile Ile
        610                 615                 620
Tyr Gly Leu Leu Glu Glu Ser Gln Asn Gln Gln Glu Lys Asn Glu Gln
625                 630                 635                 640
Asp Leu Leu Ala Leu Asp
            645

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcctcttctt ggtggcagca g                                              21

<210> SEQ ID NO 21
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
tacagatctg tcctgtgccc t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttctcagccc cagcacagct g                                              21

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggtggcaga gtgagactct gtcaca                                         26

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agaggagccc aggatgctga t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actctcctca ctcaggacac a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tctcaaggcc gcgctgcagc a                                              21

<210> SEQ ID NO 27
<211> LENGTH: 21
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 27
agctgtccct gtcctggatg g                                     21

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 28

His His His His His His
1               5

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cccagtgtat atagtagccg gtgaaggtgt atcca                      35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
tcgcacccag tgcatatagt agtcggtgaa ggtgt                      35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gatggatcaa ccctaactct ggtcgcacaa actat                      35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tgtgcatagt ttgtgccacc agtgttaggg ttgat                      35

<210> SEQ ID NO 33
<211> LENGTH: 40
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 33
cttctgtgca tagtttgtga caccagtgtt agggttgatc                            40

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atcaaccctA acagtggtcg cacaaactat gcaca                                 35

<210> SEQ ID NO 35
<211> LENGTH: 4
<212> TYPE: PRT
<213> ORGANISM: Human immunodeficiency virus 1

<400> SEQUENCE: 35

Arg Glu Lys Arg
1

<210> SEQ ID NO 36
<211> LENGTH: 6
<212> TYPE: PRT
<213> ORGANISM: Human immunodeficiency virus 1

<400> SEQUENCE: 36

Arg Arg Arg Arg Arg Arg
1               5

<210> SEQ ID NO 37
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Ile Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Gly Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125
```

```
<210> SEQ ID NO 38
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Arg Thr Asn Tyr Ala Gln Lys Phe
    50                  55                  60

Gln Gly Arg Val Ile Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Gly Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125

<210> SEQ ID NO 39
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Thr Gly Arg Thr Asn Tyr Ala Arg Lys Phe
    50                  55                  60

Gln Gly Arg Val Ile Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Gly Gly Trp Ile Gly Leu Tyr Val Asp Tyr Ser Gly Tyr Pro
            100                 105                 110

Asn Phe Asp Ser Trp Gly Gln Gly Thr Leu Val Thr Val Ser Ser
        115                 120                 125

<210> SEQ ID NO 40
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40
```

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Ala Trp Ile Asn Pro Thr Thr Gly Arg Ser Ser Phe Ala Arg Gly Phe
        50                  55                  60

Gln Gly Arg Val Ile Met Thr Arg Glu Thr Ser Val Ser Thr Ala Tyr
65              70                  75                  80

Met Glu Leu Arg Arg Leu Arg Ser Asp Asp Thr Ala Val Tyr Tyr Cys
                85                  90                  95

Ala Lys Ala Gly Tyr Ile Ala Leu Tyr Val Asp Tyr Ser Gly Tyr Pro
                100                 105                 110

Asn Phe Asn Ser Trp Gly Gln Gly Thr Leu Val Thr Val Ser Ser
            115                 120                 125

<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
                20                  25                  30

Tyr Val His Trp Leu Arg Gln Ala Pro Gly Gln Gly Leu Glu Trp Val
            35                  40                  45

Ala Trp Ile Asn Pro Thr Ser Gly Arg Thr Ile Ser Pro Arg Lys Phe
        50                  55                  60

Gln Gly Arg Val Ile Met Thr Thr Asp Thr Ser Met Asn Val Ala Tyr
65              70                  75                  80

Met Glu Leu Arg Gly Leu Arg Ser Asp Asp Thr Ala Val Tyr Phe Cys
                85                  90                  95

Ala Arg Gly Gly Trp Ile Ser Leu Tyr Val Asp Tyr Ser Tyr Tyr Pro
                100                 105                 110

Asn Phe Asp Ser Trp Gly Gln Gly Thr Leu Val Ser Val Ser Ser
            115                 120                 125

<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

```
Gly Trp Ile Asn Pro Asn Thr Gly Arg Thr Asn Tyr Ala Gln Lys Phe
        50                  55                  60

Gln Gly Arg Val Ile Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Thr Gly Gly Trp Ile Gly Leu Tyr Tyr Asp Ser Ser Gly Tyr Pro
            100                 105                 110

Asn Phe Asp Tyr Trp Gly Gln Gly Thr Leu Val Thr Val Ser Ser
            115                 120                 125

<210> SEQ ID NO 43
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Met Lys Lys Pro Gly Ala
1               5                   10                  15

Ser Val Arg Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Met
            35                  40                  45

Gly Trp Ile Asn Pro Ser Thr Gly Arg Thr Asn Ser Pro Gln Lys Phe
        50                  55                  60

Gln Gly Arg Val Ile Met Thr Arg Asp Thr Ser Ile Ser Thr Ala Tyr
65                  70                  75                  80

Met Asp Leu Asn Arg Leu Thr Ser Asp Thr Ala Met Tyr Tyr Cys
                85                  90                  95

Thr Thr Gly Gly Trp Ile Gly Leu Tyr Ser Asp Thr Ser Gly Tyr Pro
            100                 105                 110

Asn Phe Asp Tyr Trp Gly Gln Gly Thr Leu Val Thr Val Ser Ser
            115                 120                 125

<210> SEQ ID NO 44
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Met Lys Asn Pro Gly Ala
1               5                   10                  15

Ser Val Lys Val Ser Cys Ala Ala Ser Gly Tyr Thr Phe Thr Asp Phe
                20                  25                  30

Tyr Ile His Trp Val Arg Leu Ala Pro Gly Gln Gly Leu Glu Trp Met
            35                  40                  45

Gly Trp Met Asn Pro Lys Thr Gly Arg Thr Asn Asn Ala Gln Asn Phe
        50                  55                  60

Gln Gly Arg Val Ile Met Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95
```

```
Val Thr Gly Gly Trp Ile Ser Pro Tyr Tyr Asp Ser Ser Tyr Tyr Pro
                100                 105                 110

Asn Phe Asp His Trp Gly Gln Gly Thr Leu Val Thr Val Ser Ser
            115                 120                 125

<210> SEQ ID NO 45
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
            20                  25                  30

Tyr Ile His Trp Val Arg Leu Ala Pro Gly His Gly Leu Gln Trp Met
        35                  40                  45

Gly Trp Met Asn Pro Lys Thr Gly Arg Thr Asn Asn Ala Gln Asp Phe
    50                  55                  60

Gln Gly Arg Val Ile Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr Gly Gly Trp Ile Ser Pro Tyr Tyr Asp Ser Ser Tyr Tyr Pro
                100                 105                 110

Asn Phe Asp His Trp Gly Gln Gly Thr Leu Ile Thr Val Ser Ser
            115                 120                 125

<210> SEQ ID NO 46
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Val Arg Leu Ala Pro Gly Gln Gly Leu Glu Trp Leu
        35                  40                  45

Gly Trp Met Asn Pro Lys Thr Gly Arg Thr Asn Gln Gly Gln Asn Phe
    50                  55                  60

Gln Gly Arg Val Ile Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95

Val Thr Gly Ala Trp Ile Ser Asp Tyr Tyr Asp Ser Ser Tyr Tyr Pro
                100                 105                 110

Asn Phe Asp His Trp Gly Gln Gly Thr Leu Val Thr Val Ser Ser
            115                 120                 125

<210> SEQ ID NO 47
```

<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Ile Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
            100                 105                 110

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ser Ala Leu Thr Gln Pro Ala Ser Val Ser Gly Ser Pro Gly Gln
1               5                   10                  15

```
Ser Ile Thr Ile Ser Cys Thr Gly Thr Ser Tyr Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
                100                 105                 110
```

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Trp Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
                100                 105                 110
```

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
                20                  25                  30

Asn Leu Val Ser Trp Tyr Gln Gln His Pro Gly Lys Ala Pro Lys Leu
            35                  40                  45

Ile Ile Tyr Glu Val Ser Gln Trp Pro Ser Gly Val Ser Lys Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala His Tyr Tyr Cys Cys Ser Tyr Ala Gly Ser
                85                  90                  95
```

```
Ser Thr Val Ile Phe Gly Gly Gly Thr Ser Leu Thr Val Leu
            100                 105                 110
```

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gln Pro Val Leu Thr Gln Pro Ala Ser Val Ser Gly Ser Pro Gly Gln
1               5                   10                  15

Ser Ile Thr Ile Ser Cys Thr Gly Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Asn Lys Trp Ala Ser Gly Val Ser Asp Arg Phe
    50                  55                  60

Ala Gly Ser Lys Ser Gly Asn Thr Ala Ser Leu Thr Ile Ser Arg Leu
65                  70                  75                  80

Gln Ala Glu Asp Glu Ala Asn Tyr Phe Cys Ser Ser Thr Asn Ser
                85                  90                  95

Ala Thr Val Ile Phe Gly Gly Gly Thr Lys Leu Thr Val Leu
            100                 105                 110
```

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Ser Tyr
            20                  25                  30

Asn Leu Val Ser Trp Tyr Gln Gln His Pro Gly Lys Ala Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
            100                 105                 110
```

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Ser Ala Leu Thr Gln Pro Ala Ser Val Ser Gly Ser Pro Gly Gln

```
1               5                   10                  15
Ser Ile Thr Ile Ser Cys Thr Gly Thr Asn Tyr Asp Val Gly Ser Tyr
            20                  25                  30

Asn Leu Val Ser Trp Tyr Gln Gln His Pro Gly Lys Val Pro Lys Tyr
        35                  40                  45

Ile Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
            85                  90                  95

Ser Ile Ile Phe Phe Gly Gly Gly Thr Lys Leu Thr Val Ile
            100                 105                 110

<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Gly Lys Phe
            20                  25                  30

Asp Leu Val Ser Trp Tyr Gln Gln His Pro Gly Lys Ala Pro Lys Tyr
        35                  40                  45

Met Ile Tyr Glu Val Asn Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
            85                  90                  95

Ala Thr Val Val Cys Gly Gly Gly Thr Lys Val Thr Val Leu
            100                 105                 110

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Tyr Asp Val Ala Lys Phe
            20                  25                  30

Asp Leu Val Ser Trp Phe Gln Gln His Pro Gly Lys Ala Pro Lys Tyr
        35                  40                  45

Met Ile Tyr Glu Val Asn Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Gly Gly Ser
```

```
Ala Thr Val Val Cys Gly Gly Gly Thr Lys Val Thr Val Leu
            100                 105                 110
```

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Leu Pro Val Leu Thr Gln Pro Ala Ser Val Ser Gly Ser Pro Gly Gln
1               5                   10                  15

Ser Ile Thr Ile Ser Cys Thr Gly Thr Ile Tyr Asp Val Gly Lys Phe
            20                  25                  30

Asp Leu Val Ser Trp Tyr Gln His His Pro Gly Lys Ala Pro Lys Tyr
        35                  40                  45

Leu Ile Tyr Glu Val Lys Lys Trp Pro Ser Gly Val Ser His Arg Phe
    50                  55                  60

Ser Gly Ser Lys Ser Gly Asn Thr Ala Ser Leu Thr Ile Ser Gly Leu
65                  70                  75                  80

Gln Val Glu Asp Glu Ala Asp Tyr Tyr Cys Cys Ser Phe Gly Gly Ser
                85                  90                  95

Ala Ala Val Val Cys Gly Gly Gly Thr Lys Val Thr Val Leu
            100                 105                 110
```

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Thr Ser Leu Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
            20                  25                  30

Asp Leu Val Ser Trp Tyr Gln Gln Tyr Pro Gly Lys Val Pro Lys Tyr
        35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
            100                 105                 110
```

<210> SEQ ID NO 59
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

<210> SEQ ID NO 60
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Thr Gly Arg Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

<210> SEQ ID NO 61
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Thr Gly Arg Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

<210> SEQ ID NO 62

```
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Ala Glu Met Lys Asn Pro Gly Ala
1               5                   10                  15

Ser Val Lys Val Ser Cys Ala Ala Ser Gly Tyr Thr Phe Thr Asp Phe
            20                  25                  30

Tyr Ile His Trp Val Arg Leu Ala Pro Gly Gln Gly Leu Glu Trp Met
        35                  40                  45

Gly Trp Met Asn Pro Lys Thr Gly Arg Thr Asn Asn Ala Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

<210> SEQ ID NO 63
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Ala Trp Ile Asn Pro Thr Thr Gly Arg Thr Asn Tyr Ala Arg Lys Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

<210> SEQ ID NO 64
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Gln Ser Gly Ala Glu Met Lys Lys Pro Gly Ala
1               5                   10                  15

Ser Val Arg Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Ser Thr Gly Arg Thr Asn Ser Pro Gln Lys Phe
    50                  55                  60
```

```
Gln Gly Arg Val Thr Met Thr Arg Asp Thr Ser Ile Ser Thr Ala Tyr
65                  70                  75                  80

Met Asp Leu Asn Arg Leu Thr Ser Asp Asp Thr Ala Met Tyr Tyr Cys
                85                  90                  95

<210> SEQ ID NO 65
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
                20                  25                  30

Tyr Val His Trp Leu Arg Gln Ala Pro Gly Gln Gly Leu Glu Trp Val
            35                  40                  45

Ala Trp Ile Asn Pro Thr Ser Gly Arg Thr Ile Ser Pro Arg Lys Phe
        50                  55                  60

Gln Gly Arg Val Thr Met Thr Thr Asp Thr Ser Met Asn Val Ala Tyr
65                  70                  75                  80

Met Glu Leu Arg Gly Leu Arg Ser Asp Asp Thr Ala Val Tyr Phe Cys
                85                  90                  95

<210> SEQ ID NO 66
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
                20                  25                  30

Tyr Ile His Trp Val Arg Leu Ala Pro Gly His Gly Leu Gln Trp Met
            35                  40                  45

Gly Trp Met Asn Pro Lys Thr Gly Arg Thr Asn Asn Ala Gln Asp Phe
        50                  55                  60

Gln Gly Arg Val Thr Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

<210> SEQ ID NO 67
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
```

```
                20                  25                  30

Tyr Ile His Trp Val Arg Leu Ala Pro Gly Gln Gly Leu Glu Trp Leu
            35                  40                  45

Gly Trp Met Asn Pro Lys Thr Gly Arg Thr Asn Gln Gly Gln Asn Phe
        50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95
```

<210> SEQ ID NO 68
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Ala Trp Ile Asn Pro Thr Thr Gly Arg Ser Ser Phe Ala Arg Gly Phe
        50                  55                  60

Gln Gly Arg Val Thr Met Thr Arg Glu Thr Ser Val Ser Thr Ala Tyr
65                  70                  75                  80

Met Glu Leu Arg Arg Leu Arg Ser Asp Asp Thr Ala Val Tyr Tyr Cys
                85                  90                  95
```

<210> SEQ ID NO 69
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
                20                  25                  30

Tyr Ile His Trp Leu Arg Gln Ala Pro Gly Gln Gly Leu Gln Trp Met
            35                  40                  45

Gly Trp Met Asn Pro Gln Thr Gly Arg Thr Asn Thr Ala Arg Asn Phe
        50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Ile Tyr Tyr Cys
                85                  90                  95
```

<210> SEQ ID NO 70
<211> LENGTH: 94
<212> TYPE: PRT
<213> ORGANISM: Homo sapiens

<400> SEQUENCE: 70

Gln Val Gln Leu Val Gln Ser Gly Ala Glu Val Lys Pro Gly Ala
1               5                   10                  15

Ser Val Lys Val Ser Cys His Ala Ser Gly Phe Arg Phe Thr Asp His
                20                  25                  30

Tyr Ile Asn Trp Leu Arg Gln Ala Pro Gly Gln Glu Phe Glu Trp Ile
            35                  40                  45

Gly Trp Ile Asn Pro Asn Asn Ser Val Thr His Tyr Ala Gln Lys Phe
50                      55                  60

Gln Ala Arg Val Thr Met Thr Arg Phe Gly Ser Thr Ile Tyr Met Glu
65                  70                  75                  80

Leu Asn Arg Leu Arg Ser Asp Asp Thr Ala Val Tyr Tyr Cys
                85                  90

<210> SEQ ID NO 71
<211> LENGTH: 96
<212> TYPE: PRT
<213> ORGANISM: Homo sapiens

<400> SEQUENCE: 71

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Phe Leu
50                      55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

<210> SEQ ID NO 72
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
50                      55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 73
<211> LENGTH: 98

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 74
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Thr Gly Arg Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Thr

<210> SEQ ID NO 75
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Met Lys Asn Pro Gly Ala
1               5                   10                  15

Ser Val Lys Val Ser Cys Ala Ala Ser Gly Tyr Thr Phe Thr Asp Phe
            20                  25                  30

Tyr Ile His Trp Val Arg Leu Ala Pro Gly Gln Gly Leu Glu Trp Met
        35                  40                  45

```
Gly Trp Met Asn Pro Lys Thr Gly Arg Thr Asn Asn Ala Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr

<210> SEQ ID NO 76
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Ala Trp Ile Asn Pro Thr Thr Gly Arg Thr Asn Tyr Ala Arg Lys Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg

<210> SEQ ID NO 77
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Ala Glu Met Lys Lys Pro Gly Ala
1               5                   10                  15

Ser Val Arg Val Ser Cys Lys Ala Ser Gly Tyr Thr Phe Thr Asp Tyr
                20                  25                  30

Tyr Ile His Trp Val Arg Gln Ala Pro Gly Gln Gly Pro Glu Trp Met
            35                  40                  45

Gly Trp Ile Asn Pro Ser Thr Gly Arg Thr Asn Ser Pro Gln Lys Phe
    50                  55                  60

Gln Gly Arg Val Thr Met Thr Arg Asp Thr Ser Ile Ser Thr Ala Tyr
65                  70                  75                  80

Met Asp Leu Asn Arg Leu Thr Ser Asp Asp Thr Ala Met Tyr Tyr Cys
                85                  90                  95

Thr Thr

<210> SEQ ID NO 78
<211> LENGTH: 98
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 78

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Leu Ser Asp Tyr
            20                  25                  30

Tyr Val His Trp Leu Arg Gln Ala Pro Gly Gln Gly Leu Glu Trp Val
        35                  40                  45

Ala Trp Ile Asn Pro Thr Ser Gly Arg Thr Ile Ser Pro Arg Lys Phe
    50                  55                  60

Gln Gly Arg Val Thr Met Thr Thr Asp Thr Ser Met Asn Val Ala Tyr
65                  70                  75                  80

Met Glu Leu Arg Gly Leu Arg Ser Asp Asp Thr Ala Val Tyr Phe Cys
                85                  90                  95

Ala Arg

<210> SEQ ID NO 79
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Gln Ser Gly Ala Glu Met Lys Asn Pro Gly Ala
1               5                   10                  15

Ser Val Lys Val Ser Cys Ala Ala Ser Gly Tyr Gly Phe Thr Asp Phe
            20                  25                  30

Tyr Ile His Trp Val Arg Leu Ala Pro Gly His Gly Leu Gln Trp Met
        35                  40                  45

Gly Trp Met Asn Pro Lys Thr Gly Arg Thr Asn Asn Ala Gln Asp Phe
    50                  55                  60

Gln Gly Arg Val Thr Leu Thr Arg Asp Thr Ser Ile Gly Thr Ala Tyr
65                  70                  75                  80

Met Glu Leu Arg Arg Leu Thr Ser Asp Asp Thr Ala Val Tyr Tyr Cys
                85                  90                  95

Val Thr

<210> SEQ ID NO 80
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Gln Ser Gly Ala Glu Val Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Val Arg Leu Ala Pro Gly Gln Gly Leu Glu Trp Leu
        35                  40                  45

Gly Trp Met Asn Pro Lys Thr Gly Arg Thr Asn Gln Gly Gln Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Asp Thr Ala Val Tyr Tyr Cys
                85                  90                  95

Val Thr

<210> SEQ ID NO 81
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Pro Glu Leu Lys Glu Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Ala Trp Ile Asn Pro Thr Thr Gly Arg Ser Ser Phe Ala Arg Gly Phe
    50                  55                  60

Gln Gly Arg Val Thr Met Thr Arg Glu Thr Ser Val Ser Thr Ala Tyr
65                  70                  75                  80

Met Glu Leu Arg Arg Leu Arg Ser Asp Asp Thr Ala Val Tyr Tyr Cys
                85                  90                  95

Ala Lys

<210> SEQ ID NO 82
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
                20                  25                  30

Tyr Ile His Trp Leu Arg Gln Ala Pro Gly Gln Gly Leu Gln Trp Met
            35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Val Asp Asp Thr Ala Val Tyr Phe Cys
                85                  90                  95

Thr Thr

<210> SEQ ID NO 83
<211> LENGTH: 98
<212> TYPE: PRT
<213> ORGANISM: Homo sapiens

<400> SEQUENCE: 83

Gln Val Gln Leu Val Gln Ser Gly Ala Glu Val Lys Lys Pro Gly Ala

```
               1               5                  10                  15
            Ser Val Lys Val Ser Cys Lys Ala Ser Gly Tyr Thr Phe Thr Gly Tyr
                            20                  25                  30

Tyr Met His Trp Val Arg Gln Ala Pro Gly Gln Gly Leu Glu Trp Met
                            35                  40              45

Gly Trp Ile Asn Pro Asn Ser Gly Gly Thr Asn Tyr Ala Gln Lys Phe
                        50                  55                  60

Gln Gly Arg Val Thr Met Thr Arg Asp Thr Ser Ile Ser Thr Ala Tyr
            65                      70                  75                  80

Met Glu Leu Ser Arg Leu Arg Ser Asp Asp Thr Ala Val Tyr Tyr Cys
                                85                  90                  95

Ala Arg

<210> SEQ ID NO 84
<211> LENGTH: 98
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Ile Phe Thr Asp Tyr
                            20                  25                  30

Tyr Met His Trp Val Arg Gln Ala Pro Gly Gln Glu Leu Gly Trp Met
                            35                  40                  45

Gly Arg Ile Asn Pro Asn Ser Gly Gly Thr Asn Tyr Ala Gln Lys Phe
                        50                  55                  60

Gln Gly Arg Val Thr Met Thr Arg Asp Thr Ser Ile Ser Thr Ala Tyr
            65                      70                  75                  80

Thr Glu Leu Ser Ser Leu Arg Ser Glu Asp Thr Ala Thr Tyr Tyr Cys
                                85                  90                  95

Ala Arg

<210> SEQ ID NO 85
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Gly Tyr
                            20                  25                  30

Tyr Met His Trp Val Arg Gln Ala Pro Gly Gln Gly Leu Glu Trp Met
                            35                  40                  45

Gly Trp Ile Asn Pro Asn Ser Gly Gly Thr Asn Tyr Ala Gln Lys Phe
                        50                  55                  60

Gln Gly Arg Val Thr Met Thr Arg Asp Thr Ser Ile Ser Thr Ala Tyr
            65                      70                  75                  80

Met Glu Leu Ser Arg Leu Arg Ser Asp Asp Thr Ala Val Tyr Tyr Cys
                                85                  90                  95

Ala Thr Gly Gly Trp Ile Gly Leu Tyr Tyr Asp Ser Ser Gly Tyr Pro
                            100                 105                 110
```

```
Asn Phe Asp Tyr Trp Gly Gln Gly Thr Leu Val Thr Val Ser
            115                 120                 125

<210> SEQ ID NO 86
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Ser Leu Tyr Tyr Asp Ser Ser Gly Tyr Pro
            100                 105                 110

Asn Phe Asp Tyr Trp Gly Gln Gly Thr Leu Val Thr Val Ser
            115                 120                 125

<210> SEQ ID NO 87
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Ile Gly Leu Tyr Tyr Asp Ser Ser Gly Tyr Pro
            100                 105                 110

Asn Phe Asp Tyr Trp Gly Gln Gly Thr Leu Val Thr Val Ser
            115                 120                 125

<210> SEQ ID NO 88
<211> LENGTH: 110
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 88

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Val Ile Phe Gly Gly Gly Thr Lys Leu Thr Val Leu
            100                 105                 110

<210> SEQ ID NO 89
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Ile Ile Leu Phe Gly Gly Gly Thr Lys Leu Thr Val Leu
            100                 105                 110

<210> SEQ ID NO 90
<211> LENGTH: 100
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 90
caggtgcagc tggtgcagtc tggggctgag gtgaagaagc ctggggcctc agtgaaggtt      60
tcctgcaagg catctggata caccttcacc agctactata                           100

<210> SEQ ID NO 91
<211> LENGTH: 100
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 91
cagctgcagc tggtgcagtc tggggctgag gtgaagaagc ctggggcctc agtgaaggtt      60
tcctgcaagg catctggata caccttcacc agctactata                           100

<210> SEQ ID NO 92
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
cagctgcagc tggtgcagtc tgggtctgag gtgaagaagc ctggggcctc agtgaaggtt      60
tcctgcaagg catctggata caccttcacc agctactata                           100

<210> SEQ ID NO 93
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
cagctgcagc tggtgcagtc tgggtctgag gtgaagaagc ctggggcctc agtgaaggtt      60
tcctgcaagg catctggata caccttcacc agctattata                           100

<210> SEQ ID NO 94
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
cagctgcagc tggtgcagtc tgggtctgag gtgatgaagc ctggggcctc agtgaaggtt      60
tcctgcaagg catctggata caccttcacc agctattata                           100

<210> SEQ ID NO 95
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cagctgcagc tggtgcagtc tgggtctgag gtgatgaagc ctggggcctc agtgacggtt      60
tcctgcaagg catctggata caccttcacc agctattata                           100

<210> SEQ ID NO 96
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg atgggatgg atcaaccta acagtggtgg cacaaactat   180
gcacagaagt tcagggcag gtcaccatg accaggaca cgtccatcag cacagcctac   240
atggagctga gcaggctgag atctgacgac acggccgtgt attactgtgc gaccggggg   300 tggatcggtc tttactatga tagtagtggt taccctaact ttgactactg gggccaggga   360
accctggtca ccgtctcctc a                                            381
```

<210> SEQ ID NO 97
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Gly Gly Trp Ile Gly Leu Tyr Tyr Asp Ser Ser Gly Tyr Pro
            100                 105                 110

Asn Phe Asp Tyr Trp Gly Gln Gly Thr Leu Val Thr Val Ser Ser
        115                 120                 125
```

<210> SEQ ID NO 98
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
caggtgcagc tggtgcagtc tggggctgag atgaagaagc ctggggcctc agtgagggtc    60
tcctgcaagg cttctggata caccttcacc gactactata tacactgggt gcgacaggcc   120
cctggacaag gcctgagtg atgggatgg atcaaccta gcactggtcg cacaaactct   180
ccacagaagt tcagggcag gtcaccatg accaggaca cgtccatcag cacagcctac   240
atggacctga acagactgac gtctgacgac acggccatgt attactgtac gaccggggg   300 tggatcggtc tttactctga tactagtggt taccctaact ttgactactg gggccaggga   360
accctggtca ccgtctcctc a                                            381
```

<210> SEQ ID NO 99
<211> LENGTH: 127
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 99

```
Gln Val Gln Leu Val Gln Ser Gly Ala Glu Met Lys Lys Pro Gly Ala
1               5                   10                  15
Ser Val Arg Val Ser Cys Lys Ala Ser Gly Tyr Thr Phe Thr Asp Tyr
            20                  25                  30
Tyr Ile His Trp Val Arg Gln Ala Pro Gly Gln Gly Pro Glu Trp Met
        35                  40                  45
Gly Trp Ile Asn Pro Ser Thr Gly Arg Thr Asn Ser Pro Gln Lys Phe
    50                  55                  60
Gln Gly Arg Val Thr Met Thr Arg Asp Thr Ser Ile Ser Thr Ala Tyr
65                  70                  75                  80
Met Asp Leu Asn Arg Leu Thr Ser Asp Thr Ala Met Tyr Tyr Cys
                85                  90                  95
Thr Thr Gly Gly Trp Ile Gly Leu Tyr Ser Asp Thr Ser Gly Tyr Pro
            100                 105                 110
Asn Phe Asp Tyr Trp Gly Gln Gly Thr Leu Val Thr Val Ser Ser
        115                 120                 125
```

<210> SEQ ID NO 100
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg atgggaata  atcaaccta  gtggtggtag cacaagctac   180
gcacagaagt tccagggcag agtcaccatg accaggaca  cgtccacgag cacagtctac   240
atggagctga gcagcctgag atctgaggac acggccgtgt attactgtgc gagaaacgtg   300
ggaacggctg ggagcttact ccactttgac tactggggcc agggaaccct ggtcaccgtc   360
```

<210> SEQ ID NO 101
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
caggtgcagc tggtgcagtc tggggctgag gtgaagaagc ctggggcctc agtgacggtt    60
tcctgccagg catctggata caccttcacc aactactatg tacactgggt gcgacaggcc   120
cctggacagg gcttcaatt gatgggatgg atcgaccta  gttggggtcg cacaaactac   180
gcacagaatt tccagggcag aatcaccatg accaggaca  cgtccacgag cacagtctac   240
atggagatga  gaagcctgag atctgaggac acggccgttt attattgtgc gagaaatgtg   300
gcaacggagg ggagcttact ccactatgac tactggggcc agggaaccct ggtcaccgtc   360
```

<210> SEQ ID NO 102

<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Val Gly Thr Ala Gly Ser Leu Leu His Phe Asp Tyr Trp
            100                 105                 110

Gly Gln Gly Thr Leu Val Thr Val Ser Ser
        115                 120

<210> SEQ ID NO 103
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Pro Gly Ala
1               5                   10                  15

Ser Val Thr Val Ser Cys Gln Ala Ser Gly Tyr Thr Phe Thr Asn Tyr
            20                  25                  30

Tyr Val His Trp Val Arg Gln Ala Pro Gly Gln Gly Leu Gln Leu Met
        35                  40                  45

Gly Trp Ile Asp Pro Ser Trp Gly Arg Thr Asn Tyr Ala Gln Asn Phe
    50                  55                  60

Gln Gly Arg Ile Thr Met Thr Arg Asp Thr Ser Thr Ser Thr Val Tyr
65                  70                  75                  80

Met Glu Met Arg Ser Leu Arg Ser Glu Asp Thr Ala Val Tyr Tyr Cys
                85                  90                  95

Ala Arg Asn Val Ala Thr Glu Gly Ser Leu Leu His Tyr Asp Tyr Trp
            100                 105                 110

Gly Gln Gly Thr Leu Val Thr Val Ser Ala
        115                 120

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Val Gln Leu Val Gln Ser Gly Ala Ala Val Lys Arg Pro Gly Ala
1               5                   10                  15

Ser Val Thr Ile Ser Cys Arg Ala Ser Gly Tyr Thr Phe Thr Thr Tyr
            20                  25                  30

Tyr Ile His Trp Val Arg Gln Ala Pro Gly Gln Arg Leu Glu Leu Met
        35                  40                  45

Gly Met Ile Asp Pro Ser Arg Gly Arg Thr Asp Tyr Ala Gln Lys Phe
    50                  55                  60

Gln Gly Arg Val Thr Met Ser Arg Asp Thr Ser Thr Ser Thr Leu Tyr
65                  70                  75                  80

Met Glu Leu Arg Ser Leu Arg Pro Asp Asp Thr Ala Leu Tyr Tyr Cys
                85                  90                  95

Val Arg Asn Val Gly Thr Glu Gly Ser Leu Leu His Tyr Asp Tyr Trp
                100                 105                 110

Gly Gln Gly Thr Leu Val Thr Val Ser Ser
            115                 120
```

<210> SEQ ID NO 105
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Val Gln Ser Gly Ala Glu Val Arg Lys Pro Gly Ala
1               5                   10                  15

Ser Val Thr Val Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45

Gly Trp Ile Asp Pro Ser Val Gly Arg Ile Asn Tyr Ala Gln Lys Phe
    50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Ile Tyr Tyr Cys
                85                  90                  95

Val Arg Asp Val Gly Thr Glu Gly Ser Leu Leu His Phe Asp His Trp
                100                 105                 110

Gly Gln Gly Thr Leu Val Ile Val Ser Ala
            115                 120
```

<210> SEQ ID NO 106
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Gln Val Gln Leu Val Gln Ser Gly Thr Glu Val Arg Lys Pro Gly Ala
1               5                   10                  15

Ser Val Thr Ile Ser Cys Lys Ala Ser Gly Tyr Thr Phe Asn Asn Phe
            20                  25                  30

Tyr Val His Trp Val Arg Gln Ala Pro Gly Gln Gly Leu Glu Cys Met
        35                  40                  45
```

Gly Trp Ile Asp Pro Ser Val Gly Arg Ile Ser Tyr Gly Gln Lys Phe
            50                  55                  60

Gln Gly Arg Val Thr Met Thr Arg Asp Arg Ser Thr Ser Thr Val Tyr
65                  70                  75                  80

Met Gly Leu Ser Ser Leu Arg Ser Glu Asp Thr Ala Met Tyr Tyr Cys
                85                  90                  95

Val Arg Asp Val Gly Thr Glu Gly Ser Leu Leu His Phe Asp His Trp
                100                 105                 110

Gly Gln Gly Thr Leu Val Ile Val Ser Ala
            115                 120

<210> SEQ ID NO 107
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Ala Val Lys Lys Pro Gly Ala
1               5                   10                  15

Ser Val Arg Val Ser Cys Lys Ala Ser Gly Tyr Thr Phe Thr Ser Ser
                20                  25                  30

His Ile His Trp Val Arg Gln Ala Pro Gly Gln Gly Pro Glu Trp Met
            35                  40                  45

Gly Met Ile Asp Pro Ser Val Gly Arg Pro Thr Thr Ala Gly Lys Phe
        50                  55                  60

Gln Gly Arg Val Thr Met Thr Arg Asp Arg Tyr Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Ser Val Glu Thr Thr Gly Ser Leu Leu Tyr Phe Asp Tyr Trp
                100                 105                 110

Gly Gln Gly Thr Leu Ile Thr Val Ser Ser
            115                 120

<210> SEQ ID NO 108
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Gly Gly Val Lys Arg Pro Gly Ser
1               5                   10                  15

Thr Thr Thr Ile Ser Cys Val Ala Ser Gly Tyr Ser Phe Asn Asp Tyr
                20                  25                  30

Tyr Ile His Trp Val Arg Gln Ala Pro Gly Gln Gly Leu Glu Val Leu
            35                  40                  45

Gly Phe Ile Asp Pro Ser Asn Gly Arg Thr Asn Tyr Ala Gly Ala Phe
        50                  55                  60

Gly Asp Arg Phe Ser Met Tyr Arg Asp Lys Ser Met Glu Thr Leu Tyr
65                  70                  75                  80

Met Asp Leu Arg Asn Leu Arg Ser Asp Asp Thr Ala Met Tyr Tyr Cys
                85                  90                  95

Val Arg Asn Val Gly Thr Ala Gly Ser Leu Leu His Tyr Asp His Trp
            100                 105                 110

Gly Thr Gly Ser Lys Ile Ile Val Ser Ser
        115                 120

<210> SEQ ID NO 109
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
            20                  25                  30

Tyr Ile His Trp Val Arg Gln Ala Pro Gly Gln Gly Phe Glu Leu Leu
        35                  40                  45

Gly Tyr Ile Asp Pro Ala Asn Gly Arg Pro Asp Tyr Ala Gly Ala Leu
    50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Thr Ala Met Tyr Tyr Cys
                85                  90                  95

Val Arg Asn Val Gly Thr Ala Gly Ser Leu Leu His Tyr Asp His Trp
            100                 105                 110

Gly Ser Gly Ser Pro Val Ile Val Ser Ser
        115                 120

<210> SEQ ID NO 110
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Gly Thr Val Lys Ser Pro Gly Thr
1               5                   10                  15

Ser Val Thr Leu Ser Cys Lys Thr Ser Gly Tyr Asn Phe Ile Asp Tyr
            20                  25                  30

Tyr Ile His Trp Val Arg Arg Ala Pro Gly Gln Arg Pro Glu Leu Met
        35                  40                  45

Gly Tyr Ile Asp Pro Ser His Gly Arg Pro Asp Tyr Glu Gly Lys Phe
    50                  55                  60

Arg Asp Arg Ile Ser Leu Tyr Arg Asp Thr Ser Thr Ser Val Val Tyr
65                  70                  75                  80

Met Asp Val Arg Gly Leu Arg Leu Asp Asp Thr Ala Leu Tyr Tyr Cys
                85                  90                  95

Val Arg Gly Gly Gly Val Glu Val Ser Ser Asn His Tyr Asp His Trp
            100                 105                 110

Gly Pro Gly Thr Met Val Phe Val Ser Pro
        115                 120

<210> SEQ ID NO 111
<211> LENGTH: 122

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Gln Ser Gly Ala Thr Val Lys Lys Pro Arg Ala
1               5                   10                  15

Ser Val Thr Leu Ser Cys Arg Thr Ser Gly Tyr Asn Phe Ile Asp Tyr
            20                  25                  30

Phe Ile His Trp Val Arg Arg Ala Pro Gly Gln Arg Leu Glu Val Met
        35                  40                  45

Gly Tyr Ile Asp Pro Ser Arg Gly Arg Pro Tyr Ala Pro Asn Phe
    50                  55                  60

Arg Asp Arg Val Ser Leu Tyr Arg Asp Thr Ser Met Ser Ile Val Tyr
65                  70                  75                  80

Leu Asp Leu Arg Asp Leu Thr Pro Asp Thr Ala Ile Tyr Tyr Cys
                85                  90                  95

Val Arg Ser Glu Gly Thr Glu Gly Thr Val Leu His Tyr Asp His Trp
                100                 105                 110

Gly Pro Gly Thr Arg Val Thr Val Ser Pro
            115                 120

<210> SEQ ID NO 112
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Gly Gln Leu Val Gln Ser Gly Gly Gly Leu Lys Lys Pro Gly Thr
1               5                   10                  15

Ser Val Thr Ile Ser Cys Leu Ala Ser Glu Tyr Thr Phe Asn Glu Phe
            20                  25                  30

Val Ile His Trp Ile Arg Gln Ala Pro Gly Gln Gly Pro Leu Trp Leu
        35                  40                  45

Gly Leu Ile Lys Arg Ser Gly Arg Leu Met Thr Ala Tyr Asn Phe Gln
    50                  55                  60

Asp Arg Leu Ser Leu Arg Arg Asp Arg Ser Thr Gly Thr Val Phe Met
65                  70                  75                  80

Glu Leu Arg Gly Leu Arg Pro Asp Asp Thr Ala Val Tyr Tyr Cys Ala
                85                  90                  95

Arg Asp Gly Leu Gly Glu Val Ala Pro Asp Tyr Arg Tyr Gly Ile Asp
                100                 105                 110

Val Trp Gly Gln Gly Ser Thr Val Ile Val Thr Ser Ala Ser Thr Lys
            115                 120                 125

Gly Pro Ser Val Phe
        130

<210> SEQ ID NO 113
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 113

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
    50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
                85                  90                  95

Ala Arg Ala Glu Ala Ala Ser Asp Ser His Ser Arg Pro Ile Met Phe
            100                 105                 110

Asp His Trp Gly Gln Gly Ser Leu Val Thr Val Ser Ser Ala Ser Thr
        115                 120                 125

Lys Gly Pro Ser Val Phe
    130

<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 115
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Gln Ser Gly Ala Ala Val Arg Lys Pro Gly Ala
1               5                   10                  15

Ser Val Thr Val Ser Cys Lys Phe Ala Glu Asp Asp Asp Tyr Ser Pro

```
            20                  25                  30

Tyr Trp Val Asn Pro Ala Pro Glu His Phe Ile His Phe Leu Arg Gln
        35                  40                  45

Ala Pro Gly Gln Gln Leu Glu Trp Leu Ala Trp Met Asn Pro Thr Asn
    50                  55                  60

Gly Ala Val Asn Tyr Ala Trp Tyr Leu Asn Gly Arg Val Thr Ala Thr
65                  70                  75                  80

Arg Asp Arg Ser Met Thr Thr Ala Phe Leu Glu Val Lys Ser Leu Arg
                85                  90                  95

Ser Asp Asp Thr Ala Val Tyr Tyr Cys Ala Arg Ala Gln Lys Arg Gly
            100                 105                 110

Arg Ser Glu Trp Ala Tyr Ala His Trp Gly Gln Gly Thr Pro Val Val
        115                 120                 125

Val Ser Ser
    130

<210> SEQ ID NO 116
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 117
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Asn Ser Phe Ser Asn His
            20                  25                  30

Asp Val His Trp Val Arg Gln Ala Thr Gly Gln Gly Leu Glu Trp Met
```

```
                    35                  40                  45
Gly Trp Met Ser His Glu Gly Asp Lys Thr Gly Leu Ala Gln Lys Phe
         50                  55                  60

Gln Gly Arg Val Thr Ile Thr Arg Asp Ser Gly Ala Ser Thr Val Tyr
 65                  70                  75                  80

Met Glu Leu Arg Gly Leu Thr Ala Asp Thr Ala Ile Tyr Tyr Cys
                 85                  90                  95

Leu Thr Gly Ser Lys His Arg Leu Arg Asp Tyr Phe Leu Tyr Asn Glu
                100                 105                 110

Tyr Gly Pro Asn Tyr Glu Glu Trp Gly Asp Tyr Leu Ala Thr Leu Asp
            115                 120                 125

Val Trp Gly His Gly Thr Ala Val Thr Val Ser Ser
        130                 135                 140

<210> SEQ ID NO 118
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Leu Gln Ser Gly Ala Ala Val Thr Lys Pro Gly Ala
 1               5                  10                  15

Ser Val Arg Val Ser Cys Glu Ala Ser Gly Tyr Asn Ile Arg Asp Tyr
                 20                  25                  30

Phe Ile His Trp Trp Arg Gln Ala Pro Gly Gln Gly Leu Gln Trp Val
             35                  40                  45

Gly Trp Ile Asn Pro Lys Thr Gly Gln Pro Asn Asn Pro Arg Gln Phe
         50                  55                  60

Gln Gly Arg Val Ser Leu Thr Arg His Ala Ser Trp Asp Phe Asp Thr
 65                  70                  75                  80

Phe Ser Phe Tyr Met Asp Leu Lys Ala Leu Arg Ser Asp Asp Thr Ala
                 85                  90                  95

Val Tyr Phe Cys Ala Arg Gln Arg Ser Asp Tyr Trp Asp Phe Asp Val
                100                 105                 110

Trp Gly Ser Gly Thr Gln Val Thr Val Ser Ser
            115                 120

<210> SEQ ID NO 119
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Lys Pro Gly Gly
 1               5                  10                  15

Ser Leu Arg Leu Ser Cys Ser Ala Ser Gly Phe Asp Phe Asp Asn Ala
                 20                  25                  30

Trp Met Thr Trp Val Arg Gln Pro Pro Gly Lys Gly Leu Glu Trp Val
             35                  40                  45

Gly Arg Ile Thr Gly Pro Gly Glu Gly Trp Ser Val Asp Tyr Ala Ala
         50                  55                  60

Pro Val Glu Gly Arg Phe Thr Ile Ser Arg Leu Asn Ser Ile Asn Phe
```

```
                65                  70                  75                  80
Leu Tyr Leu Glu Met Asn Asn Leu Arg Met Glu Asp Ser Gly Leu Tyr
                85                  90                  95

Phe Cys Ala Arg Thr Gly Lys Tyr Tyr Asp Phe Trp Ser Gly Tyr Pro
                100                 105                 110

Pro Gly Glu Glu Tyr Phe Gln Asp Trp Gly Arg Gly Thr Leu Val Thr
                115                 120                 125

Val Ser Ser
    130

<210> SEQ ID NO 120
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Ala Asn Val Val Arg Pro Gly Gly
1               5                   10                  15

Ser Leu Arg Leu Ser Cys Lys Ala Ser Gly Phe Ile Phe Glu Asn Phe
                20                  25                  30

Gly Phe Ser Trp Val Arg Gln Ala Pro Gly Lys Gly Leu Gln Trp Val
            35                  40                  45

Ala Gly Leu Asn Trp Asn Gly Gly Asp Thr Arg Tyr Ala Asp Ser Val
        50                  55                  60

Lys Gly Arg Phe Arg Met Ser Arg Asp Asn Arg Asn Phe Val Tyr
65                  70                  75                  80

Leu Asp Met Asp Lys Val Gly Val Asp Thr Ala Phe Tyr Tyr Cys
                85                  90                  95

Ala Arg Gly Thr Asp Tyr Thr Ile Asp Ala Gly Ile His Tyr Gln
                100                 105                 110

Gly Ser Gly Thr Phe Trp Tyr Phe Asp Leu Trp Gly Arg Gly Thr Leu
            115                 120                 125

Val Ser Val Ser Ser
    130

<210> SEQ ID NO 121
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val His Leu Thr Gln Ser Gly Pro Glu Val Arg Lys Pro Gly Thr
1               5                   10                  15

Ser Val Lys Val Ser Cys Lys Ala Pro Gly Asn Thr Leu Lys Thr Tyr
                20                  25                  30

Asp Leu His Trp Val Arg Ser Val Pro Gly Gln Gly Leu Gln Trp Met
            35                  40                  45

Gly Trp Ile Ser His Glu Gly Asp Lys Lys Val Ile Val Glu Arg Phe
        50                  55                  60

Lys Ala Lys Val Thr Ile Asp Trp Asp Arg Ser Thr Asn Thr Ala Tyr
65                  70                  75                  80

Leu Gln Leu Ser Gly Leu Thr Ser Gly Asp Thr Ala Val Tyr Tyr Cys
```

```
                85                  90                  95
Ala Lys Gly Ser Lys His Arg Leu Arg Asp Tyr Ala Leu Tyr Asp Asp
                100                 105                 110

Asp Gly Ala Leu Asn Trp Ala Val Asp Val Asp Tyr Leu Ser Asn Leu
            115                 120                 125

Glu Phe Trp Gly Gln Gly Thr Ala Val Thr Val Ser Ser
    130                 135                 140
```

<210> SEQ ID NO 122
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

```
Gln Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
        35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
                85                  90                  95

Asp Thr Ala Thr Tyr Tyr Cys Ala Arg Phe Gly Gly Glu Val Leu Arg
                100                 105                 110

Tyr Thr Asp Trp Pro Lys Pro Ala Trp Val Asp Leu Trp Gly Arg Gly
            115                 120                 125

Thr Leu Val Thr Val Ser Ser
        130                 135
```

<210> SEQ ID NO 123
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Gln Leu Gln Met Gln Glu Ser Gly Pro Gly Leu Val Lys Pro Ser Glu
1               5                   10                  15

Thr Leu Ser Leu Ser Cys Thr Val Ser Gly Asp Ser Ile Arg Gly Gly
            20                  25                  30

Glu Trp Gly Asp Lys Asp Tyr His Trp Gly Trp Val Arg His Ser Ala
        35                  40                  45

Gly Lys Gly Leu Glu Trp Ile Gly Ser Ile His Trp Arg Gly Thr Thr
    50                  55                  60

His Tyr Lys Glu Ser Leu Arg Arg Arg Val Ser Met Ser Ile Asp Thr
65                  70                  75                  80

Ser Arg Asn Trp Phe Ser Leu Arg Leu Ala Ser Val Thr Ala Ala Asp
                85                  90                  95

Thr Ala Val Tyr Phe Cys Ala Arg His Arg His His Asp Val Phe Met
```

```
                    100                 105                 110
Leu Val Pro Ile Ala Gly Trp Phe Asp Val Trp Gly Pro Gly Val Gln
            115                 120                 125

Val Thr Val Ser Ser
        130

<210> SEQ ID NO 124
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Glu Gln Ser Gly Thr Ala Val Arg Lys Pro Gly Ala
1               5                   10                  15

Ser Val Thr Leu Ser Cys Gln Ala Ser Gly Tyr Asn Phe Val Lys Tyr
            20                  25                  30

Ile Ile His Trp Val Arg Gln Lys Pro Gly Leu Gly Phe Glu Trp Val
        35                  40                  45

Gly Met Ile Asp Pro Tyr Arg Gly Arg Pro Trp Ser Ala His Lys Phe
50                  55                  60

Gln Gly Arg Leu Ser Leu Ser Arg Asp Thr Ser Met Glu Ile Leu Tyr
65                  70                  75                  80

Met Thr Leu Thr Ser Leu Lys Ser Asp Asp Thr Ala Thr Tyr Phe Cys
            85                  90                  95

Ala Arg Ala Glu Ala Ala Ser Asp Ser His Ser Arg Pro Ile Met Phe
            100                 105                 110

Asp His Trp Gly Gln Gly Ser Leu Val Thr Val Ser Ser
        115                 120                 125

<210> SEQ ID NO 125
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Arg Ile Thr Leu Lys Glu Ser Gly Pro Pro Leu Val Lys Pro Thr Gln
1               5                   10                  15

Thr Leu Thr Leu Thr Cys Ser Phe Ser Gly Phe Ser Leu Ser Asp Phe
            20                  25                  30

Gly Val Gly Val Gly Trp Ile Arg Gln Pro Pro Gly Lys Ala Leu Glu
        35                  40                  45

Trp Leu Ala Ile Ile Tyr Ser Asp Asp Lys Arg Tyr Ser Pro Ser
50                  55                  60

Leu Asn Thr Arg Leu Thr Ile Thr Lys Asp Thr Ser Lys Asn Gln Val
65                  70                  75                  80

Val Leu Val Met Thr Arg Val Ser Pro Val Asp Thr Ala Thr Tyr Phe
            85                  90                  95

Cys Ala His Arg Arg Gly Pro Thr Thr Leu Phe Gly Val Pro Ile Ala
            100                 105                 110

Arg Gly Pro Val Asn Ala Met Asp Val Trp Gly Gln Gly Ile Thr Val
        115                 120                 125

Thr Ile Ser Ser
```

-continued

130

<210> SEQ ID NO 126
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Gly Gln Leu Val Gln Ser Gly Ala Glu Leu Lys Pro Gly Ala
1               5                   10                  15

Ser Val Lys Ile Ser Cys Lys Thr Ser Gly Tyr Arg Phe Asn Phe Tyr
                20                  25                  30

His Ile Asn Trp Ile Arg Gln Thr Ala Gly Arg Gly Pro Glu Trp Met
            35                  40                  45

Gly Trp Ile Ser Pro Tyr Ser Gly Asp Lys Asn Leu Ala Pro Ala Phe
        50                  55                  60

Gln Asp Arg Val Ile Met Thr Thr Asp Thr Glu Val Pro Val Thr Ser
65                  70                  75                  80

Phe Thr Ser Thr Gly Ala Ala Tyr Met Glu Ile Arg Asn Leu Lys Phe
                85                  90                  95

Asp Asp Thr Gly Thr Tyr Phe Cys Ala Lys Gly Leu Leu Arg Asp Gly
                100                 105                 110

Ser Ser Thr Trp Leu Pro Tyr Leu Trp Gly Gln Gly Thr Leu Leu Thr
            115                 120                 125

Val Ser Ser
    130

<210> SEQ ID NO 127
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Arg Pro Gly Ser
1               5                   10                  15

Ser Val Thr Val Ser Cys Lys Ala Ser Gly Gly Ser Phe Ser Thr Tyr
                20                  25                  30

Ala Leu Ser Trp Val Arg Gln Ala Pro Gly Arg Gly Leu Glu Trp Met
            35                  40                  45

Gly Gly Val Ile Pro Leu Leu Thr Ile Thr Asn Tyr Ala Pro Arg Phe
        50                  55                  60

Gln Gly Arg Ile Thr Ile Thr Ala Asp Arg Ser Thr Ser Thr Ala Tyr
65                  70                  75                  80

Leu Glu Leu Asn Ser Leu Arg Pro Glu Asp Thr Ala Val Tyr Tyr Cys
                85                  90                  95

Ala Arg Glu Gly Thr Thr Gly Trp Gly Trp Leu Gly Lys Pro Ile Gly
                100                 105                 110

Ala Phe Ala His Trp Gly Gln Gly Thr Leu Val Thr Val Ser Ser
            115                 120                 125

<210> SEQ ID NO 128
<211> LENGTH: 122
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Ala Gln Tyr Gly Gly Gly Val Lys Arg Leu Gly Ala
1               5                   10                  15

Thr Met Thr Leu Ser Cys Val Ala Ser Gly Tyr Thr Phe Asn Asp Tyr
                20                  25                  30

Tyr Ile His Trp Val Arg Gln Ala Pro Gly Gln Gly Phe Glu Leu Leu
            35                  40                  45

Gly Tyr Ile Asp Pro Ala Asn Gly Arg Pro Tyr Ala Gly Ala Leu
        50                  55                  60

Arg Glu Arg Leu Ser Phe Tyr Arg Asp Lys Ser Met Glu Thr Leu Tyr
65                  70                  75                  80

Met Asp Leu Arg Ser Leu Arg Tyr Asp Thr Ala Met Tyr Tyr Cys
                85                  90                  95

Val Arg Asn Val Gly Thr Ala Gly Ser Leu Leu His Tyr Asp His Trp
                100                 105                 110

Gly Ser Gly Ser Pro Val Ile Val Ser Ser
            115                 120

<210> SEQ ID NO 129
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
                20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
        50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Thr Ala Val Tyr Tyr Cys
                85                  90                  95

Ala Arg Asp Arg Ser Tyr Gly Asp Ser Ser Trp Ala Leu Asp Ala Trp
                100                 105                 110

Gly Gln Gly Thr Thr Val Val Val Ser Ala
            115                 120

<210> SEQ ID NO 130
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Arg Val Gln Leu Val Glu Ser Gly Gly Gly Val Val Gln Pro Gly Lys
1               5                   10                  15

```
Ser Val Arg Leu Ser Cys Val Val Ser Asp Phe Pro Phe Ser Lys Tyr
            20                  25                  30

Pro Met Tyr Trp Val Arg Gln Ala Pro Gly Lys Gly Leu Glu Trp Val
            35                  40                  45

Ala Ala Ile Ser Gly Asp Ala Trp His Val Val Tyr Ser Asn Ser Val
        50                  55                  60

Gln Gly Arg Phe Leu Val Ser Arg Asp Asn Val Lys Asn Thr Leu Tyr
65                  70                  75                  80

Leu Glu Met Asn Ser Leu Lys Ile Glu Asp Thr Ala Val Tyr Arg Cys
                85                  90                  95

Ala Arg Met Phe Gln Glu Ser Gly Pro Pro Arg Leu Asp Arg Trp Ser
            100                 105                 110

Gly Arg Asn Tyr Tyr Tyr Tyr Ser Gly Met Asp Val Trp Gly Gln Gly
                115                 120                 125

Thr Thr Val Thr Val Ser Ser
            130                 135

<210> SEQ ID NO 131
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Glu Val Leu Val Gln Ser Gly Ala Glu Val Lys Lys Pro Gly Ala
1               5                   10                  15

Ser Val Lys Val Ser Cys Arg Ala Phe Gly Tyr Thr Phe Thr Gly Asn
            20                  25                  30

Ala Leu His Trp Val Arg Gln Ala Pro Gly Gln Gly Leu Glu Trp Leu
            35                  40                  45

Gly Trp Ile Asn Pro His Ser Gly Asp Thr Thr Thr Ser Gln Lys Phe
        50                  55                  60

Gln Gly Arg Val Tyr Met Thr Arg Asp Lys Ser Ile Asn Thr Ala Phe
65                  70                  75                  80

Leu Asp Val Thr Arg Leu Thr Ser Asp Thr Gly Ile Tyr Tyr Cys
                85                  90                  95

Ala Arg Asp Lys Tyr Tyr Gly Asn Glu Ala Val Gly Met Asp Val Trp
            100                 105                 110

Gly Gln Gly Thr Ser Val Thr Val Ser Ser
                115                 120

<210> SEQ ID NO 132
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Gln Glu Ser Gly Pro Gly Val Val Lys Ser Ser Glu
1               5                   10                  15

Thr Leu Ser Leu Thr Cys Thr Val Ser Gly Gly Ser Met Gly Gly Thr
            20                  25                  30

Tyr Trp Ser Trp Leu Arg Leu Ser Pro Gly Lys Gly Leu Glu Trp Ile
            35                  40                  45
```

Gly Tyr Ile Phe His Thr Gly Glu Thr Asn Tyr Ser Pro Ser Leu Lys
            50                  55                  60

Gly Arg Val Ser Ile Ser Val Asp Thr Ser Glu Asp Gln Phe Ser Leu
 65                  70                  75                  80

Arg Leu Arg Ser Val Thr Ala Ala Asp Thr Ala Val Tyr Phe Cys Ala
                85                  90                  95

Ser Leu Pro Arg Gly Gln Leu Val Asn Ala Tyr Phe Arg Asn Trp Gly
            100                 105                 110

Arg Gly Ser Leu Val Ser Val Thr Ala
            115                 120

<210> SEQ ID NO 133
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Met Lys Lys Pro Gly Ala
 1               5                  10                  15

Ser Val Arg Val Ser Cys Lys Ala Ser Gly Tyr Thr Phe Thr Asp Tyr
            20                  25                  30

Tyr Ile His Trp Val Arg Gln Ala Pro Gly Gln Gly Pro Glu Trp Met
        35                  40                  45

Gly Trp Ile Asn Pro Ser Thr Gly Arg Thr Asn Ser Pro Gln Lys Phe
    50                  55                  60

Gln Gly Arg Val Thr Met Thr Arg Asp Thr Ser Ile Ser Thr Ala Tyr
 65                  70                  75                  80

Met Asp Leu Asn Arg Leu Thr Ser Asp Thr Ala Met Tyr Tyr Cys
                85                  90                  95

Thr Thr Gly Gly Trp Ile Gly Leu Tyr Ser Asp Thr Ser Gly Tyr Pro
            100                 105                 110

Asn Phe Asp Tyr Trp Gly Gln Gly Thr Leu Val Thr Val Ser Ser
        115                 120                 125

<210> SEQ ID NO 134
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Gly Gln Leu Val Gln Ser Gly Gly Gly Leu Lys Lys Pro Gly Thr
 1               5                  10                  15

Ser Val Thr Ile Ser Cys Leu Ala Ser Glu Tyr Thr Phe Asn Glu Phe
            20                  25                  30

Val Ile His Trp Ile Arg Gln Ala Pro Gly Gln Gly Pro Leu Trp Leu
        35                  40                  45

Gly Leu Ile Lys Arg Ser Gly Arg Leu Met Thr Ala Tyr Asn Phe Gln
    50                  55                  60

Asp Arg Leu Ser Leu Arg Asp Arg Ser Thr Gly Thr Val Phe Met
 65                  70                  75                  80

Glu Leu Arg Gly Leu Arg Pro Asp Asp Thr Ala Val Tyr Tyr Cys Ala
                85                  90                  95

```
Arg Asp Gly Leu Gly Glu Val Ala Pro Asp Tyr Arg Tyr Gly Ile Asp
            100                 105                 110

Val Trp Gly Gln Gly Ser Thr Val Ile Val Thr Ser
        115                 120

<210> SEQ ID NO 135
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Gln Arg Leu Val Glu Ser Gly Gly Gly Val Val Gln Pro Gly Ser
1               5                   10                  15

Ser Leu Arg Leu Ser Cys Ala Ala Ser Gly Phe Asp Phe Ser Arg Gln
                20                  25                  30

Gly Met His Trp Val Arg Gln Ala Pro Gly Gln Gly Leu Glu Trp Val
            35                  40                  45

Ala Phe Ile Lys Tyr Asp Gly Ser Glu Lys Tyr His Ala Asp Ser Val
50                  55                  60

Trp Gly Arg Leu Ser Ile Ser Arg Asp Asn Ser Lys Asp Thr Leu Tyr
65                  70                  75                  80

Leu Gln Met Asn Ser Leu Arg Val Glu Asp Thr Ala Thr Tyr Phe Cys
                85                  90                  95

Val Arg Glu Ala Gly Gly Pro Asp Tyr Arg Asn Gly Tyr Asn Tyr Tyr
            100                 105                 110

Asp Phe Tyr Asp Gly Tyr Tyr Asn Tyr His Tyr Met Asp Val Trp Gly
        115                 120                 125

Lys Gly Thr Thr Val Thr Val Ser Ser
        130                 135

<210> SEQ ID NO 136
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Ile His Leu Val Gln Ser Gly Thr Glu Val Lys Lys Pro Gly Ser
1               5                   10                  15

Ser Val Thr Val Ser Cys Lys Ala Tyr Gly Val Asn Thr Phe Gly Leu
                20                  25                  30

Tyr Ala Val Asn Trp Val Arg Gln Ala Pro Gly Gln Ser Leu Glu Tyr
            35                  40                  45

Ile Gly Gln Ile Trp Arg Trp Lys Ser Ser Ala Ser His His Phe Arg
50                  55                  60

Gly Arg Val Leu Ile Ser Ala Val Asp Leu Thr Gly Ser Ser Pro Pro
65                  70                  75                  80

Ile Ser Ser Leu Glu Ile Lys Asn Leu Thr Ser Asp Asp Thr Ala Val
                85                  90                  95

Tyr Phe Cys Thr Thr Thr Ser Thr Tyr Asp Lys Trp Ser Gly Leu His
            100                 105                 110

His Asp Gly Val Met Ala Phe Ser Ser Trp Gly Gln Gly Thr Leu Ile
        115                 120                 125
```

Ser Val Ser Ala
     130

<210> SEQ ID NO 137
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Gln Ser Gly Gly Gly Leu Val Lys Pro Gly Gly
1               5                   10                  15

Ser Leu Thr Leu Ser Cys Ser Ala Ser Gly Phe Phe Phe Asp Asn Ser
            20                  25                  30

Trp Met Gly Trp Val Arg Gln Ala Pro Gly Lys Gly Leu Glu Trp Val
        35                  40                  45

Gly Arg Ile Arg Arg Leu Lys Asp Gly Ala Thr Gly Glu Tyr Gly Ala
    50                  55                  60

Ala Val Lys Asp Arg Phe Thr Ile Ser Arg Asp Asp Ser Arg Asn Met
65                  70                  75                  80

Leu Tyr Leu His Met Arg Thr Leu Lys Thr Glu Asp Ser Gly Thr Tyr
                85                  90                  95

Tyr Cys Thr Met Asp Glu Gly Thr Pro Val Thr Arg Phe Leu Glu Trp
            100                 105                 110

Gly Tyr Phe Tyr Tyr Tyr Met Ala Val Trp Gly Arg Gly Thr Thr Val
        115                 120                 125

Ile Val Ser Ser
    130

<210> SEQ ID NO 138
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Gln Ser Gly Ala Gln Met Lys Asn Pro Gly Ala
1               5                   10                  15

Ser Val Lys Val Ser Cys Ala Pro Ser Gly Tyr Thr Phe Thr Asp Phe
            20                  25                  30

Tyr Ile His Trp Leu Arg Gln Ala Pro Gly Gln Gly Leu Gln Trp Met
        35                  40                  45

Gly Trp Met Asn Pro Gln Thr Gly Arg Thr Asn Thr Ala Arg Asn Phe
    50                  55                  60

Gln Gly Arg Val Thr Met Thr Arg Asp Thr Ser Ile Gly Thr Ala Tyr
65                  70                  75                  80

Met Glu Leu Arg Ser Leu Thr Ser Asp Thr Ala Ile Tyr Tyr Cys
                85                  90                  95

Thr Thr Gly Gly Trp Ile Ser Leu Tyr Tyr Asp Ser Ser Tyr Tyr Pro
            100                 105                 110

Asn Phe Asp His Trp Gly Gln Gly Thr Leu Leu Thr Val Ser Ser
        115                 120                 125

<210> SEQ ID NO 139

```
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Gln Ser Gly Ala Glu Met Lys Met Pro Gly Ala
1               5                   10                  15

Ser Val Lys Val Ser Cys Lys Ala Ser Gly Tyr Thr Phe Thr Gly Asn
            20                  25                  30

Tyr Ile His Trp Val Arg Gln Ala Pro Gly Gln Gly Leu Glu Trp Met
        35                  40                  45

Gly Trp Ile Ala Pro His Ser Gly Asp Thr Ser Tyr Ala Gln Arg Phe
    50                  55                  60

Gln Gly Arg Val Thr Met Thr Gly Asp Thr Ser Leu Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Phe Pro Asn Tyr Tyr Gly Pro Gly Ser Tyr Trp Gly
            100                 105                 110

Gly Leu Asp Phe Trp Gly Gln Gly Thr Leu Val Ser Val Ser Ser
        115                 120                 125

<210> SEQ ID NO 140
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Val Glu Ser Gly Gly Gly Val Val Gln Pro Gly Thr
1               5                   10                  15

Ser Leu Arg Leu Ser Cys Ala Ala Ser Gln Phe Arg Phe Asp Gly Tyr
            20                  25                  30

Gly Met His Trp Val Arg Gln Ala Pro Gly Lys Gly Leu Glu Trp Val
        35                  40                  45

Ala Ser Ile Ser His Asp Gly Ile Lys Lys Tyr His Ala Glu Lys Val
    50                  55                  60

Trp Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Ala Lys Asp Leu Arg Glu Asp Glu Cys Glu Glu Trp Trp Ser Asp Tyr
            100                 105                 110

Tyr Asp Phe Gly Lys Gln Leu Pro Cys Ala Lys Ser Arg Gly Gly Leu
        115                 120                 125

Val Gly Ile Ala Asp Asn Trp Gly Gln Gly Thr Met Val Thr Val Ser
    130                 135                 140

Ser
145

<210> SEQ ID NO 141
<211> LENGTH: 101
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 141

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp
            100

<210> SEQ ID NO 142
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Ser Leu Ser Ala Ser Leu Gly
1               5                   10                  15

Asp Arg Val Thr Ile Thr Cys Gln Ala Ser Arg Gly Ile Gly Lys Asp
            20                  25                  30

Leu Asn Trp Tyr Gln Gln Lys Ala Gly Lys Ala Pro Lys Leu Leu Val
        35                  40                  45

Ser Asp Ala Ser Thr Leu Glu Gly Gly Val Pro Ser Arg Phe Ser Gly
    50                  55                  60

Ser Gly Phe His Gln Asn Phe Ser Leu Thr Ile Ser Ser Leu Gln Ala
65                  70                  75                  80

Glu Asp Val Ala Thr Tyr Phe Cys Gln Gln Tyr Glu Thr Phe Gly Gln
                85                  90                  95

Gly Thr Lys Val Asp Ile Lys
            100

<210> SEQ ID NO 143
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Met Thr Gln Ser Pro Ser Ser Leu Ser Ala Ser Val Gly
1               5                   10                  15

Asp Thr Val Thr Ile Thr Cys Gln Ala Asn Gly Tyr Leu Asn Trp Tyr
            20                  25                  30

Gln Gln Arg Arg Gly Lys Ala Pro Lys Leu Leu Ile Tyr Asp Gly Ser
        35                  40                  45
```

```
Lys Leu Glu Arg Gly Val Pro Ser Arg Phe Ser Gly Arg Arg Trp Gly
 50                  55                  60

Gln Glu Tyr Asn Leu Thr Ile Asn Asn Leu Gln Pro Glu Asp Ile Ala
 65                  70                  75                  80

Thr Tyr Phe Cys Gln Val Tyr Glu Phe Val Val Pro Gly Thr Arg Leu
                 85                  90                  95

Asp Leu Lys

<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Met Thr Gln Ser Pro Asp Thr Leu Ser Val Ser Pro Gly
 1               5                  10                  15

Glu Thr Val Thr Leu Ser Cys Arg Ala Ser Gln Asn Ile Asn Lys Asn
                 20                  25                  30

Leu Ala Trp Tyr Gln Tyr Lys Pro Gly Gln Ser Pro Arg Leu Val Ile
             35                  40                  45

Phe Glu Thr Tyr Ser Lys Ile Ala Ala Phe Pro Ala Arg Phe Val Ala
 50                  55                  60

Ser Gly Ser Gly Thr Glu Phe Thr Leu Thr Ile Asn Asn Met Gln Ser
 65                  70                  75                  80

Glu Asp Val Ala Val Tyr Tyr Cys Gln Gln Tyr Glu Glu Trp Pro Arg
                 85                  90                  95

Thr Phe Gly Gln Gly Thr Lys Val Asp Ile Lys
            100                 105

<210> SEQ ID NO 145
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Leu Ala Gln Ser Pro Gly Thr Leu Ser Leu Ser Pro Gly
 1               5                  10                  15

Glu Arg Ala Thr Leu Ser Cys Arg Ala Ser His Asn Val His Pro Lys
                 20                  25                  30

Tyr Phe Ala Trp Tyr Gln Gln Lys Pro Gly Gln Ser Pro Arg Leu Leu
             35                  40                  45

Ile Tyr Gly Gly Ser Thr Arg Ala Ala Gly Ile Pro Gly Lys Phe Ser
 50                  55                  60

Gly Ser Gly Ser Gly Thr Asp Phe Thr Leu Thr Ile Ser Arg Val Asp
 65                  70                  75                  80

Pro Glu Asp Phe Ala Val Tyr Tyr Cys Gln Gln Tyr Gly Gly Ser Pro
                 85                  90                  95

Tyr Thr Phe Gly Gln Gly Thr Lys Val Glu Ile Lys
            100                 105

<210> SEQ ID NO 146
<211> LENGTH: 112
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 146

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
            20                  25                  30

Thr Gly Ala Asn Tyr Leu Ala Trp Tyr Leu Gln Arg Pro Gly Gln Thr
        35                  40                  45

Pro Arg Leu Leu Ile His Leu Ala Thr His Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Asp Asp Val Gly Thr Tyr Tyr Cys Met Gln Gly
                85                  90                  95

Leu His Ser Pro Trp Thr Phe Gly Gln Gly Thr Lys Val Glu Ile Lys
            100                 105                 110

<210> SEQ ID NO 147
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Thr Leu Ser Ala Ser Ile Gly
1               5                   10                  15

Asp Thr Val Arg Ile Ser Cys Arg Ala Ser Gln Ser Ile Thr Gly Asn
            20                  25                  30

Trp Val Ala Trp Tyr Gln Gln Arg Pro Gly Lys Ala Pro Arg Leu Leu
        35                  40                  45

Ile Tyr Arg Gly Ala Ala Leu Leu Gly Gly Val Pro Ser Arg Phe Ser
    50                  55                  60

Gly Ser Ala Ala Gly Thr Asp Phe Thr Leu Thr Ile Gly Asn Leu Gln
65                  70                  75                  80

Ala Glu Asp Phe Gly Thr Phe Tyr Cys Gln Gln Tyr Asp Thr Tyr Pro
                85                  90                  95

Gly Thr Phe Gly Gln Gly Thr Lys Val Glu Val Lys
            100                 105

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ala Leu Gln Leu Thr Gln Ser Pro Ser Ser Leu Ser Ala Ser Val Gly
1               5                   10                  15

Asp Arg Ile Thr Ile Thr Cys Arg Ala Ser Gln Gly Val Thr Ser Ala
            20                  25                  30

Leu Ala Trp Tyr Arg Gln Lys Pro Gly Ser Pro Gln Leu Leu Ile
        35                  40                  45

Tyr Asp Ala Ser Ser Leu Glu Ser Gly Val Pro Ser Arg Phe Ser Gly
            50                  55                  60

Ser Gly Ser Gly Thr Glu Phe Thr Leu Thr Ile Ser Thr Leu Arg Pro
65                  70                  75                  80

Glu Asp Phe Ala Thr Tyr Tyr Cys Gln Gln Leu His Phe Tyr Pro His
                85                  90                  95

Thr Phe Gly Gly Gly Thr Arg Val Asp Val Arg
            100                 105

<210> SEQ ID NO 149
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Ile Val Leu Thr Gln Ser Pro Gly Thr Gln Ser Leu Ser Pro Gly
1               5                   10                  15

Glu Arg Ala Thr Leu Ser Cys Arg Ala Ser Gln Ser Val Gly Asn Asn
            20                  25                  30

Lys Leu Ala Trp Tyr Gln Gln Arg Pro Gly Gln Ala Pro Arg Leu Leu
        35                  40                  45

Ile Tyr Gly Ala Ser Ser Arg Pro Ser Gly Val Ala Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gln Ser Leu
                85                  90                  95

Ser Thr Phe Gly Gln Gly Thr Lys Val Glu Val Lys
            100                 105

<210> SEQ ID NO 150
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Leu Asn Phe Val
            20                  25                  30

Val Trp Tyr Gln Gln Lys Arg Gly Gln Ala Pro Arg Leu Leu Ile His
        35                  40                  45

Ala Pro Ser Gly Arg Ala Pro Gly Val Pro Asp Arg Phe Ser Ala Arg
    50                  55                  60

Gly Ser Gly Thr Glu Phe Ser Leu Val Ile Ser Ser Val Glu Pro Asp
65                  70                  75                  80

Asp Phe Ala Ile Tyr Tyr Cys Gln Glu Tyr Ser Ser Thr Pro Tyr Asn
                85                  90                  95

Phe Gly Pro Gly Thr Arg Val Asp Arg Lys
            100                 105

<210> SEQ ID NO 151

```
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Leu Thr Gln Ser Pro Ala Thr Leu Ser Ala Ser Pro Gly
1               5                   10                  15

Glu Arg Val Thr Leu Thr Cys Arg Ala Ser Arg Ser Val Arg Asn Asn
            20                  25                  30

Val Ala Trp Tyr Gln His Lys Gly Gly Gln Ser Pro Arg Leu Leu Ile
        35                  40                  45

Tyr Asp Ala Ser Thr Arg Ala Ala Gly Val Pro Ala Arg Phe Ser Gly
    50                  55                  60

Ser Ala Ser Gly Thr Glu Phe Thr Leu Ala Ile Ser Asn Leu Glu Ser
65                  70                  75                  80

Glu Asp Phe Thr Val Tyr Phe Cys Leu Gln Tyr Asn Asn Trp Trp Thr
                85                  90                  95

Phe Gly Gln Gly Thr Arg Val Asp Ile Lys
            100                 105

<210> SEQ ID NO 152
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 153
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Val Met Thr Gln Thr Pro Leu Ser Leu Ser Val Thr Pro Gly
1               5                   10                  15

Gln Pro Ala Ser Ile Ser Cys Lys Ser Ser Glu Ser Leu Arg Gln Ser
            20                  25                  30
```

Asn Gly Lys Thr Ser Leu Tyr Trp Tyr Arg Gln Lys Pro Gly Gln Ser
            35                  40                  45

Pro Gln Leu Leu Val Phe Glu Val Ser Asn Arg Phe Ser Gly Val Ser
 50                  55                  60

Asp Arg Phe Val Gly Ser Gly Ser Gly Thr Asp Phe Thr Leu Arg Ile
 65                  70                  75                  80

Ser Arg Val Glu Ala Glu Asp Val Gly Phe Tyr Tyr Cys Met Gln Ser
                 85                  90                  95

Lys Asp Phe Pro Leu Thr Phe Gly Gly Gly Thr Lys Val Asp Leu Lys
            100                 105                 110

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Leu Thr Gln Ser Pro Ser Phe Leu Ser Ala Ser Val Gly
 1               5                  10                  15

Asp Lys Val Thr Ile Thr Cys Arg Ala Ser Gln Gly Val Arg Asn Glu
             20                  25                  30

Leu Ala Trp Tyr Gln Gln Lys Pro Gly Lys Ala Pro Asn Leu Leu Ile
         35                  40                  45

Tyr Tyr Ala Ser Thr Leu Gln Ser Gly Val Pro Ser Arg Phe Ser Ala
 50                  55                  60

Thr Gly Ser Gly Thr His Phe Thr Leu Thr Val Ser Ser Leu Gln Pro
 65                  70                  75                  80

Glu Asp Phe Ala Thr Tyr Phe Cys Gln His Met Ser Ser Tyr Pro Leu
                 85                  90                  95

Thr Phe Gly Gly Gly Thr Lys Val Glu Ile Lys
            100                 105

<210> SEQ ID NO 155
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Val Met Thr Gln Ser Pro Ser Ser Val Ser Ala Ser Val Gly
 1               5                  10                  15

Asp Arg Val Thr Ile Thr Cys Arg Ala Ser Gln Asn Ile Arg Asp Tyr
             20                  25                  30

Leu Asn Trp Tyr Gln His Lys Pro Gly Ser Pro Arg Leu Leu Ile
         35                  40                  45

Tyr Ala Ala Ser Thr Leu Gln Thr Gly Val Pro Ser Arg Phe Ser Gly
     50                  55                  60

Ser Gly Ser Gly Asn Leu Phe Thr Leu Thr Ile Thr Asn Leu Gln Pro
 65                  70                  75                  80

Glu Asp Phe Ala Thr Tyr Tyr Cys Gln Glu Asn Tyr Asn Thr Ile Pro
                 85                  90                  95

Ser Leu Ser Phe Gly Gln Gly Thr Lys Val Asp Ile Arg
            100                 105

```
<210> SEQ ID NO 156
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Ile Val Met Thr Gln Ser Pro Ala Thr Leu Ser Val Ser Leu Gly
1               5                   10                  15

Glu Arg Ala Thr Leu Ser Cys Arg Thr Ser Gln Asn Val Ala Tyr Asn
            20                  25                  30

Phe Ala Trp Tyr Gln Gln Lys Pro Gly Gln Ala Pro Arg Leu Leu Ile
        35                  40                  45

Tyr Glu Ala Ser Ser Arg Ala Thr Gly Thr Pro Ala Arg Phe Ser Gly
50                  55                  60

Ser Gly Phe Gly Thr Glu Phe Thr Leu Thr Ile Ser Ser Met Gln Ser
65                  70                  75                  80

Glu Asp Phe Ala Val Tyr Tyr Cys Gln Gln Tyr Asn Asn Trp Pro Ser
                85                  90                  95

Pro Phe Thr Phe Gly Pro Gly Thr Lys Val His Ile Lys
            100                 105

<210> SEQ ID NO 157
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Phe Val Leu Thr Gln Ser Pro His Ser Leu Ser Val Thr Pro Gly
1               5                   10                  15

Glu Ser Ala Ser Ile Ser Cys Lys Ser Ser His Ser Leu Ile His Gly
            20                  25                  30

Asp Arg Asn Asn Tyr Leu Ala Trp Tyr Val Gln Lys Pro Gly Arg Ser
        35                  40                  45

Pro Gln Leu Leu Ile Tyr Leu Ala Ser Ser Arg Ala Ser Gly Val Pro
    50                  55                  60

Asp Arg Phe Ser Gly Ser Gly Ser Asp Lys Asp Phe Thr Leu Lys Ile
65                  70                  75                  80

Ser Arg Val Glu Thr Glu Asp Val Gly Thr Tyr Tyr Cys Met Gln Gly
                85                  90                  95

Arg Glu Ser Pro Trp Thr Phe Gly Gln Gly Thr Lys Val Asp Ile Lys
            100                 105                 110

<210> SEQ ID NO 158
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
```

```
              20                  25                  30

Tyr Gln Gln His Ala Gly Lys Ala Pro Lys Leu Val Ile Tyr Asp Val
                35                  40                  45

Asn Lys Arg Pro Ser Gly Val Pro Asp Arg Phe Ser Gly Ser Lys Ser
         50                  55                  60

Gly Asn Thr Ala Ser Leu Thr Val Ser Gly Leu Gln Thr Asp Asp Glu
 65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu
            100                 105

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ser Tyr Val Leu Thr Gln Pro Ser Asp Ile Ser Val Ala Pro Gly Glu
 1               5                  10                  15

Thr Ala Arg Ile Ser Cys Gly Glu Lys Ser Leu Gly Ser Arg Ala Val
                20                  25                  30

Gln Trp Tyr Gln His Arg Ala Gly Gln Ala Pro Ser Leu Ile Ile Tyr
                35                  40                  45

Asn Asn Gln Asp Arg Pro Ser Gly Ile Pro Glu Arg Phe Ser Gly Ser
         50                  55                  60

Pro Asp Ser Pro Phe Gly Thr Thr Ala Thr Leu Thr Ile Thr Ser Val
 65                  70                  75                  80

Glu Ala Gly Asp Glu Ala Asp Tyr Tyr Cys His Ile Trp Asp Ser Arg
                85                  90                  95

Val Pro Thr Lys Trp Val Phe Gly Gly Gly Thr Thr Leu Thr Val Leu
            100                 105                 110

<210> SEQ ID NO 160
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Tyr Glu Leu Thr Gln Glu Thr Gly Val Ser Val Ala Leu Gly Arg
 1               5                  10                  15

Thr Val Thr Ile Thr Cys Arg Gly Asp Ser Leu Arg Ser His Tyr Ala
                20                  25                  30

Ser Trp Tyr Gln Lys Lys Pro Gly Gln Ala Pro Ile Leu Leu Phe Tyr
                35                  40                  45

Gly Lys Asn Asn Arg Pro Ser Gly Val Pro Asp Arg Phe Ser Gly Ser
         50                  55                  60

Ala Ser Gly Asn Arg Ala Ser Leu Thr Ile Ser Gly Ala Gln Ala Glu
 65                  70                  75                  80

Asp Asp Ala Glu Tyr Tyr Cys Ser Ser Arg Asp Lys Ser Gly Ser Arg
                85                  90                  95

Leu Ser Val Phe Gly Gly Gly Thr Lys Leu Thr Val Leu
```

<210> SEQ ID NO 161
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Ser Ala Leu Thr Gln Pro Pro Ser Ala Ser Gly Ala Pro Gly Gln
1               5                   10                  15

Arg Val Thr Ile Ser Cys Ser Gly Gly Pro Ser Asn Val Gly Gly Asn
            20                  25                  30

Tyr Val Tyr Trp Tyr Arg Gln Phe Pro Gly Thr Ala Pro Thr Leu Leu
        35                  40                  45

Ile Leu Arg Asp Asp Gln Arg Pro Ser Gly Val Pro Asp Arg Phe Ser
    50                  55                  60

Ala Ser Lys Ser Gly Asn Ser Ala Ser Leu Ala Ile Ser Gly Leu Arg
65                  70                  75                  80

Pro Asp Asp Glu Gly Phe Tyr Phe Cys Ala Thr Tyr Asp Ser Asp Gly
                85                  90                  95

Ser Ile Arg Leu Phe Gly Gly Gly Thr Ala Leu Thr Val Leu
            100                 105                 110

<210> SEQ ID NO 162
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Ser Val Leu Thr Gln Ser Ala Ser Val Ser Gly Ser Leu Gly Gln
1               5                   10                  15

Ser Val Thr Ile Ser Cys Thr Gly Pro Asn Ser Val Cys Cys Ser His
            20                  25                  30

Lys Ser Ile Ser Trp Tyr Gln Trp Pro Pro Gly Arg Ala Pro Thr Leu
        35                  40                  45

Ile Ile Tyr Glu Asp Asn Glu Arg Ala Pro Gly Ile Ser Pro Arg Phe
    50                  55                  60

Ser Gly Tyr Lys Ser Tyr Trp Ser Ala Tyr Leu Thr Ile Ser Asp Leu
65                  70                  75                  80

Arg Pro Glu Asp Glu Thr Thr Tyr Tyr Cys Cys Ser Tyr Thr His Asn
                85                  90                  95

Ser Gly Cys Val Phe Gly Thr Gly Thr Lys Val Ser Val Leu
            100                 105                 110

<210> SEQ ID NO 163
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
                100                 105                 110

<210> SEQ ID NO 164
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ser Tyr Glu Leu Thr Gln Pro Pro Ser Val Ser Val Ser Pro Gly Gln
1               5                   10                  15

Thr Ala Thr Ile Thr Cys Ser Gly Ala Ser Thr Asn Val Cys Trp Tyr
            20                  25                  30

Gln Val Lys Pro Gly Gln Ser Pro Glu Val Val Ile Phe Glu Asn Tyr
        35                  40                  45

Lys Arg Pro Ser Gly Ile Pro Asp Arg Phe Ser Gly Ser Lys Ser Gly
    50                  55                  60

Ser Thr Ala Thr Leu Thr Ile Arg Gly Thr Gln Ala Ile Asp Glu Ala
65                  70                  75                  80

Asp Tyr Tyr Cys Gln Val Trp Asp Ser Phe Ser Thr Phe Val Phe Gly
                85                  90                  95

Ser Gly Thr Gln Val Thr Val Leu
                100

<210> SEQ ID NO 165
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Tyr Asp Val Gly Ser Tyr
            20                  25                  30

Asn Leu Val Ser Trp Tyr Gln Gln His Pro Gly Lys Val Pro Lys Tyr
        35                  40                  45

Ile Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Thr Tyr Tyr Cys Cys Ser Tyr Ala Gly Ser
                85                  90                  95

```
Ser Ile Ile Phe Phe Gly Gly Gly Thr Lys Leu Thr Val Ile
                100                 105                 110

<210> SEQ ID NO 166
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Ser Ala Leu Thr Gln Pro Ala Ser Val Ser Gly Ser Pro Gly Gln
1               5                   10                  15

Ser Ile Thr Ile Ser Cys Thr Gly Thr Lys Tyr Asp Val Gly Ser His
                20                  25                  30

Asp Leu Val Ser Trp Tyr Gln Gln Tyr Pro Gly Lys Val Pro Lys Tyr
            35                  40                  45

Met Ile Tyr Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Cys Ser Phe Gly Gly Ser
                85                  90                  95

Ala Thr Val Val Cys Gly Gly Gly Thr Lys Val Thr Val Leu
                100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Ser Val Leu Thr Gln Pro Pro Ser Val Ser Ala Ala Pro Gly Gln
1               5                   10                  15

Lys Val Thr Ile Ser Cys Ser Gly Asn Thr Ser Asn Ile Gly Asn Asn
                20                  25                  30

Phe Val Ser Trp Tyr Gln Gln Arg Pro Gly Arg Ala Pro Gln Leu Leu
            35                  40                  45

Ile Tyr Glu Thr Asp Lys Arg Pro Ser Gly Ile Pro Asp Arg Phe Ser
    50                  55                  60

Ala Ser Lys Ser Gly Thr Ser Gly Thr Leu Ala Ile Thr Gly Leu Gln
65                  70                  75                  80

Thr Gly Asp Glu Ala Asp Tyr Tyr Cys Ala Thr Trp Ala Ala Ser Leu
                85                  90                  95

Ser Ser Ala Arg Val Phe Gly Thr Gly Thr Lys Val Ile Val Leu
                100                 105                 110
```

```
<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Gly Gly His His His His His His
1               5
```

UNITED STATES PATENT AND TRADEMARK OFFICE
CERTIFICATE OF CORRECTION

| | | |
|---|---|---|
| PATENT NO. | : 11,161,895 B2 | Page 1 of 1 |
| APPLICATION NO. | : 16/337264 | |
| DATED | : November 2, 2021 | |
| INVENTOR(S) | : Barton F. Haynes et al. | |

It is certified that error appears in the above-identified patent and that said Letters Patent is hereby corrected as shown below:

In the Claims

At Column 188, Claim Number 24, Line Number 21 should read: 24. The method of claim 2, wherein broadly neutralizing anti- At Column 188, Claim 26, Line Number 30 should read: 26. The method of claim 15, further comprising step (e):

Signed and Sealed this
Twenty-fourth Day of January, 2023

Katherine Kelly Vidal
*Director of the United States Patent and Trademark Office*